US012357707B2

(12) United States Patent
Wood et al.

(10) Patent No.: US 12,357,707 B2
(45) Date of Patent: Jul. 15, 2025

(54) COMPOSITIONS AND METHODS FOR TREATING LAMINOPATHIES

(71) Applicant: Encoded Therapeutics, Inc., South San Francisco, CA (US)

(72) Inventors: Sirika Wood, South San Francisco, CA (US); Kartik Ramamoorthi, South San Francisco, CA (US); Stephanie Tagliatela, South San Francisco, CA (US); Anne Tanenhaus, South San Francisco, CA (US)

(73) Assignee: Encoded Therapeutics, Inc., South San Francisco, CA (US)

( * ) Notice: Subject to any disclaimer, the term of this patent is extended or adjusted under 35 U.S.C. 154(b) by 861 days.

(21) Appl. No.: 17/433,927

(22) PCT Filed: Feb. 28, 2020

(86) PCT No.: PCT/US2020/020520
§ 371 (c)(1),
(2) Date: Aug. 25, 2021

(87) PCT Pub. No.: WO2020/176896
PCT Pub. Date: Sep. 3, 2020

(65) Prior Publication Data

US 2022/0193264 A1 Jun. 23, 2022

Related U.S. Application Data

(60) Provisional application No. 62/812,021, filed on Feb. 28, 2019.

(51) Int. Cl.
*A61K 48/00* (2006.01)
*C07K 14/78* (2006.01)
*C12N 15/86* (2006.01)

(52) U.S. Cl.
CPC .......... *A61K 48/0058* (2013.01); *C07K 14/78* (2013.01); *C12N 15/86* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| | | | | |
|---|---|---|---|---|
| 9,856,473 | B2 | 1/2018 | Bennett et al. | |
| 2008/0131375 | A1* | 6/2008 | Gordon | C12Q 1/6883 424/9.2 |
| 2020/0347408 | A1* | 11/2020 | Stewart | C07K 14/47 |
| 2022/0133911 | A1* | 5/2022 | Wilson | A01K 67/0278 424/94.5 |

FOREIGN PATENT DOCUMENTS

WO WO2013/123503 8/2013

OTHER PUBLICATIONS

Kang et al., Laminopathies; Mutations on single gene and various human genetic diseases. BMB Rep. (2018), 51: 327-337 (Year: 2018).*
Patil et al., Role of A- and B-type lamins in nuclear structure-function relationships. Biol. Cell (2021), 113: 295-310 (Year: 2021).*
Bollati et al., Structures of the lamin A/C R335W and E347K mutants: Implications for dilated cardiolaminopathies. Biochemical and Biophysical Research Communications (2012), 418: 217-221 (Year: 2012).*
Sagelius et al., Targeted transgenic expression of the mutation causing Hutchinson-Gilford progeria syndrome leads to proliferative and degenerative epidermal disease. Journal of Cell Science (2008), 121; 969-978 (Year: 2008).*
Liu et al., Targeted Gene Correction of Laminopathy-Associated LMNA Mutations in Patient-Specific iPSCs. Cell Stem Cell (2011), 8: 688-694 (Year: 2011).*
Luo et al., Normal and aberrant splicing of LMNA. J Med Genet (2014), 51: 215-223 (Year: 2014).*
*Homo sapiens* lamin A/C (LMNA), RefSeqGene (LRG_254) on chromosome 1, NCBI Reference Sequence: NG_008692.2, published Jan. 24, 2018, https://www.ncbi.nlm.nih.gov/nuccore/365906263, [retrieved Aug. 15, 2024] (Year: 2018).*
Human DNA sequence from clone RP11-54H19 on chromosome 1, complete sequence GenBank: AL135927.14, https://www.ncbi.nlm.nih.gov/nuccore/AL135927.14, [retrieved Aug. 15, 2024] (Year: 2013).*
Fisher et al., Induction and apoptotic regression of lung adenocarcinomas by regulation of a K-Ras transgene in the presence and absence of tumor suppressor genes. Genes and Development (2001), 15: 3249-3262 (Year: 2001).*
PEGFP-C2, https://www.snapgene.com/plasmids/fluorescent_protein_genes_and_plasmids/pEGFP-C2, [retrieved Aug. 16, 2024] (Year: 2024).*
Benarroch et al., Preclinical advances of therapies for laminopathies. Journal of Clinical Medicine (2021), 10: 4834, pp. 1-30 (Year: 2021).*
PCT International Search Report for PCT/US2020/020520, dated Jun. 5, 2020 (5 pages).
Lin, F., et al., "Structural Organization of the Human Gene Encoding Nuclear Lamin A and Nuclear Lamin C", The Journal of Biological Chemistry, vol. 268: 16321-16326 (1993).

(Continued)

*Primary Examiner* — Abigail Vanhorn
*Assistant Examiner* — Catherine Konopka
(74) *Attorney, Agent, or Firm* — White & Case LLP

(57) ABSTRACT

The present disclosure provides compositions and methods for treating, preventing, or inhibiting laminopathies. In one aspect, the disclosure provides nucleic acid constructs and/or vectors comprising a nucleotide sequence encoding lamin A and/or lamin C.

29 Claims, 16 Drawing Sheets

Specification includes a Sequence Listing.

(56) References Cited

OTHER PUBLICATIONS

Lin, F., et al., "Expression of Nuclear Lamins in Human Tissues and Cancer Cell Lines and Transcription from the Promoters of the Lamin A/C and B1 Genes", Experimental Cell Research, vol. 236: 378-384 (1997).

Liu, G-H., et al., "Targeted Gene Correction of Laminopathy-Associated LMNA Mutations in Patient-Specific iPSCs", Cell Stem Cell, vol. 8: 688-694 (2011).

Sagelius, H., et al., "Targeted transgenic expression of the mutation causing Hutchinson-Gilford progeria syndrome leads to proliferative and degenerative epidermal disease", Journal of Cell Science, vol. 121: 969-978 (2008).

Tsai, J-Y., et al., "Cardiac Myocyte-specific Expression of LMNAD300N Activates MMP2 and Induces Severe Interstitial Fibrosis and Cardiac Systolic Dysfunction Leading to Premature Death in Mice", Circulation, vol. 126, Conference Abstract 17773 (2012).

Wojtanik, K.M., "The role of LMNA in adipose: a novel mouse model of lipodystrophy based on the Dunnigan-type familial partial lipodystrophy mutation", Journal of Lipid Research, vol. 50: 1068-1079 (2009).

Gonzalez-Cruz, R. D. et al., "The Emerging Role of Lamin C as an Important LMNA Isoform in Mechanophenotype," Frontiers in Cell and Developmental Biology, vol. 6(151) (Nov. 2018).

Hocquemiller, M. et al., "Adeno-Associated Virus-Based Gene Therapy for CNS Diseases," Human Gene Therapy, vol. 27(7): 478-496 (Jul. 2016).

Supplementary EP Search Report, EP 20 76 2666, dated Nov. 19, 2022.

Varga, R. et al., "Progressive vascular smooth muscle cell defects in a mouse model of Hutchinson-Gilford progeria syndrome," Proceedings of the National Academy of Sciences, vol. 103(9) : 3250-3255 (Feb. 2006).

* cited by examiner

SEQUENCE LISTING

```
<160> NUMBER OF SEQ ID NOS: 102

<210> SEQ ID NO 1
<211> LENGTH: 1995
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atggagaccc cgtcccagcg gcgcgccacc cgcagcgggg cgcaggccag ctccactccg     60

ctgtcgccca cccgcatcac ccggctgcag gagaaggagg acctgcagga gctcaatgat    120

cgcttggcgg tctacatcga ccgtgtgcgc tcgctggaaa cggagaacgc agggctgcgc    180

cttcgcatca ccgagtctga agaggtggtc agccgcgagg tgtccggcat caaggccgcc    240

tacgaggccg agctcgggga tgcccgcaag acccttgact cagtagccaa ggagcgcgcc    300

cgcctgcagc tggagctgag caaagtgcgt gaggagttta aggagctgaa agcgcgcaat    360

accaagaagg agggtgacct gatagctgct caggctcggc tgaaggacct ggaggctctg    420

ctgaactcca aggaggccgc actgagcact gctctcagtg agaagcgcac gctggagggc    480

gagctgcatg atctgcgggg ccaggtggcc aagcttgagg cagccctagg tgaggccaag    540

aagcaacttc aggatgagat gctgcggcgg gtggatgctg agaacaggct gcagaccatg    600

aaggaggaac tggacttcca gaagaacatc tacagtgagg agctgcgtga gaccaagcgc    660

cgtcatgaga cccgactggt ggagattgac aatgggaagc agcgtgagtt tgagagccgg    720

ctggcggatg cgctgcagga actgcgggcc cagcatgagg accaggtgga gcagtataag    780

aaggagctgg agaagactta ttctgccaag ctggacaatg ccaggcagtc tgctgagagg    840

aacagcaacc tggtgggggc tgcccacgag gagctgcagc agtcgcgcat ccgcatcgac    900

agcctctctg cccagctcag ccagctccag aagcagctgg cagccaagga ggcgaagctt    960

cgagacctgg aggactcact ggcccgtgag cgggacacca gccggcggct gctggcggaa   1020

aaggagcggg agatggccga gatgcgggca aggatgcagc agcagctgga cgagtaccag   1080

gagcttctgg acatcaagct ggccctggac atggagatcc acgcctaccg caagctcttg   1140

gagggcgagg aggagaggct acgcctgtcc cccagcccta cctcgcagcg cagccgtggc   1200

cgtgcttcct ctcactcatc ccagacacag ggtgggggca gcgtcaccaa aaagcgcaaa   1260

ctggagtcca ctgagagccg cagcagcttc tcacagcacg cacgcactag cgggcgcgtg   1320

gccgtggagg aggtggatga ggagggcaag tttgtccggc tgcgcaacaa gtccaatgag   1380

gaccagtcca tgggcaattg gcagatcaag cgccagaatg gagatgatcc cttgctgact   1440

taccggttcc caccaaagtt caccctgaag gctgggcagg tggtgacgat ctgggctgca   1500

ggagctgggg ccacccacag cccccctacc gacctggtgt ggaaggcaca gaacacctgg   1560

ggctgcggga acagcctgcg tacggctctc atcaactcca ctggggaaga agtggccatg   1620

cgcaagctgg tgcgctcagt gactgtggtt gaggacgacg aggatgagga tggagatgac   1680

ctgctccatc accaccacgg ctcccactgc agcagctcgg gggaccccgc tgagtacaac   1740
```

```
ctgcgctcgc gcaccgtgct gtgcgggacc tgcgggcagc ctgccgacaa ggcatctgcc   1800

agcggctcag gagcccaggt gggcggaccc atctcctctg gctcttctgc ctccagtgtc   1860

acggtcactc gcagctaccg cagtgtgggg ggcagtgggg gtggcagctt cggggacaat   1920

ctggtcaccc gctcctacct cctgggcaac tccagccccc gaacccagag cccccagaac   1980

tgcagcatca tgtaa                                                    1995


<210> SEQ ID NO 2
<211> LENGTH: 1719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

atggagaccc cgtcccagcg gcgcgccacc cgcagcgggg cgcaggccag ctccactccg     60

ctgtcgccca cccgcatcac ccggctgcag gagaaggagg acctgcagga gctcaatgat    120

cgcttggcgg tctacatcga ccgtgtgcgc tcgctggaaa cggagaacgc agggctgcgc    180

cttcgcatca ccgagtctga agaggtggtc agccgcgagg tgtccggcat caaggccgcc    240

tacgaggccg agctcgggga tgcccgcaag acccttgact cagtagccaa ggagcgcgcc    300

cgcctgcagc tggagctgag caaagtgcgt gaggagttta aggagctgaa agcgcgcaat    360

accaagaagg agggtgacct gatagctgct caggctcggc tgaaggacct ggaggctctg    420

ctgaactcca aggaggccgc actgagcact gctctcagtg agaagcgcac gctggagggc    480

gagctgcatg atctgcgggg ccaggtggcc aagcttgagg cagccctagg tgaggccaag    540

aagcaacttc aggatgagat gctgcggcgg gtggatgctg agaacaggct gcagaccatg    600

aaggaggaac tggacttcca gaagaacatc tacagtgagg agctgcgtga gaccaagcgc    660

cgtcatgaga cccgactggt ggagattgac aatgggaagc agcgtgagtt tgagagccgg    720

ctggcggatg cgctgcagga actgcgggcc cagcatgagg accaggtgga gcagtataag    780

aaggagctgg agaagactta ttctgccaag ctggacaatg ccaggcagtc tgctgagagg    840

aacagcaacc tggtgggggc tgcccacgag gagctgcagc agtcgcgcat ccgcatcgac    900

agcctctctg cccagctcag ccagctccag aagcagctgg cagccaagga ggcgaagctt    960

cgagacctgg aggactcact ggcccgtgag cgggacacca gccggcggct gctggcggaa   1020

aaggagcggg agatggccga gatgcgggca aggatgcagc agcagctgga cgagtaccag   1080

gagcttctgg acatcaagct ggccctggac atggagatcc acgcctaccg caagctcttg   1140

gagggcgagg aggagaggct acgcctgtcc cccagcccta cctcgcagcg cagccgtggc   1200

cgtgcttcct ctcactcatc ccagacacag ggtgggggca gcgtcaccaa aaagcgcaaa   1260

ctggagtcca ctgagagccg cagcagcttc tcacagcacg cacgcactag cgggcgcgtg   1320

gccgtggagg aggtggatga ggagggcaag tttgtccggc tgcgcaacaa gtccaatgag   1380

gaccagtcca tgggcaattg gcagatcaag cgccagaatg gagatgatcc cttgctgact   1440

taccggttcc caccaaagtt caccctgaag gctgggcagg tggtgacgat ctgggctgca   1500

ggagctgggg ccacccacag cccccctacc gacctggtgt ggaaggcaca gaacacctgg   1560

ggctgcggga acagcctgcg tacggctctc atcaactcca ctggggaaga agtggccatg   1620

cgcaagctgg tgcgctcagt gactgtggtt gaggacgacg aggatgagga tggagatgac   1680

ctgctccatc accaccacgt gagtggtagc cgccgctga                          1719
```

<210> SEQ ID NO 3
<211> LENGTH: 3566
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 3
atggagaccc cgtcccagcg gcgcgccacc cgcagcgggg cgcaggccag ctccactccg 60
ctgtcgccca cccgcatcac ccggctgcag gagaaggagg acctgcagga gctcaatgat 120
cgcttggcgg tctacatcga ccgtgtgcgc tcgctggaaa cggagaacgc agggctgcgc 180
cttcgcatca ccgagtctga agaggtggtc agccgcgagg tgtccggcat caaggccgcc 240
tacgaggccg agctcgggga tgcccgcaag acccttgact cagtagccaa ggagcgcgcc 300
cgcctgcagc tggagctgag caaagtgcgt gaggagttta aggagctgaa agcgcgcaat 360
accaagaagg agggtgacct gatagctgct caggctcggc tgaaggacct ggaggctctg 420
ctgaactcca aggaggccgc actgagcact gctctcagtg agaagcgcac gctggagggc 480
gagctgcatg atctgcgggg ccaggtggcc aagcttgagg cagccctagg tgaggccaag 540
aagcaacttc aggatgagat gctgcggcgg gtggatgctg agaacaggct gcagaccatg 600
aaggaggaac tggacttcca gaagaacatc tacagtgagg agctgcgtga gaccaagcgc 660
cgtcatgaga cccgactggt ggagattgac aatgggaagc agcgtgagtt tgagagccgg 720
ctggcggatg cgctgcagga actgcgggcc cagcatgagg accaggtgga gcagtataag 780
aaggagctgg agaagactta ttctgccaag ctggacaatg ccaggcagtc tgctgagagg 840
aacagcaacc tggtgggggc tgcccacgag gagctgcagc agtcgcgcat ccgcatcgac 900
agcctctctg cccagctcag ccagctccag aagcagctgg cagccaagga ggcgaagctt 960
cgagacctgg aggactcact ggcccgtgag cgggacacca gccggcggct gctggcggaa 1020
aaggagcggg agatggccga gatgcgggca aggatgcagc agcagctgga cgagtaccag 1080
gagcttctgg acatcaagct ggccctggac atggagatcc acgcctaccg caagctcttg 1140
gagggcgagg aggagaggct acgcctgtcc cccagcccta cctcgcagcg cagccgtggc 1200
cgtgcttcct ctcactcatc ccagacacag ggtgggggca gcgtcaccaa aaagcgcaaa 1260
ctggagtcca ctgagagccg cagcagcttc tcacagcacg cacgcactag cgggcgcgtg 1320
gccgtggagg aggtggatga ggagggcaag tttgtccggc tgcgcaacaa gtccaatgag 1380
gaccagtcca tgggcaattg gcagatcaag cgccagaatg gagatgatcc cttgctgact 1440
taccggttcc caccaaagtt caccctgaag gctgggcagg tggtgacggt gagtggcagg 1500
gcgcttggga ctctggggag gccttgggtg gcgatgggag cgctggggta agtgtccttt 1560
tctcctctcc agatctgggc tgcaggagct ggggccaccc acagcccccc taccgacctg 1620
gtgtggaagg cacagaacac ctggggctgc gggaacagcc tgcgtacggc tctcatcaac 1680
tccactgggg aagtaagtag gcctgggcct ggctgcttgc tggacgaggc tccccctgat 1740
ggccaacatc ggagccagct gcccccaacc caagtttgcc aattcagggc ccctttctag 1800
agctctctgt tgcaggctcc agacttctcc acccagtagg caaaccaaaa gatgcttcct 1860
caacagcaca aggggtggaa gttagacagt gaggattgtt aaaggcagag ccatactcct 1920
acccggagag cttgacagtg tccctctggg gtggaaatga gttccttagc tccatcacca 1980
cagaggacag agtaagcagc aggccggaca aagggcaggc cacaagaaaa gttgcaggtg 2040
gtcactgggg tagacatgct gtacaaccct tccctggccc tgacccttgg acctggttcc 2100
atgtccccac caggaagtgg ccatgcgcaa gctggtgcgc tcagtgactg tggttgagga 2160
cgacgaggat gaggatggag atgacctgct ccatcaccac cacgtgagtg gtagccgccg 2220
ctgaggccga gcctgcactg gggccaccca gccaggcctg gggcagcct ctccccagcc 2280 tccccgtgcc aaaaatcttt tcattaaaga atgttttgga actttactcg ctggcctggc 2340
ctttcttctc tctcctccct ataccttgaa cagggaaccc aggtgtctgg gtgccctact 2400
ctggtaagga agggagtggg aactttctga tgccatggaa tattcctgtg ggagcagtgg 2460
acaagggtct ggatttgtct tctgggaaag ggaggggagg acagacgtgg ggcatgcccg 2520
ccctgcctct ctcccccatt cttgttgcat gcatatcctc tcatttccct catttttcct 2580
gcaagaatgt tctctctcat tcctgaccgc ccctccactc caattaatag tgcatgcctg 2640
ctgccctaca agcttgctcc cgttctctct tcttttcctc ttaagctcag agtagctaga 2700
acagagtcag agtcactgct ctggttctct gtccccaagt cttcctgagc cttctcccct 2760
tttatgtctt ccctctcctc ctccgggccc ctagcctccc aaacccccat tgcccgctgg 2820
ctccttgggc acagaaccac accttcctgc ctggcggctg ggagcctgca ggagcctgga 2880
gcctggttgg gcctgagtgg tcagtcccag actcgccgtc ccgcctgagc cttgtctccc 2940
ttcccagggc tcccactgca gcagctcggg ggaccccgct gagtacaacc tgcgctcgcg 3000
caccgtgctg tgcgggacct gcgggcagcc tgccgacaag gcatctgcca gcggctcagg 3060
agcccaggtg ggcggaccca tctcctctgg ctcttctgcc tccagtgtca cggtcactcg 3120
cagctaccgc agtgtggggg gcagtggggg tggcagcttc ggggacaatc tggtcacccg 3180
ctcctacctc ctgggcaact ccagcccccg aacccaggtg agttgtctct gctttgtctc 3240
caaatcctgc aggcgggtcc ctggtcatcg aggggtagga cgaggtggcc ttgcaggggg 3300
gagagcctgc cttctcttcc gcagcccggg ggagtgggag cctcctcccc acagcctgag 3360
tcctagacag cccacctctg catcctgccc ctcttgtctg agccccagac tggagggcag 3420
gggcagggct ggagtgtgag ggatggggga gatgctacct cccttctagg ggccagggga 3480
gggagggtct gggtccaggc cctgctgctc acacctctct cctctgtttt ctctcttaga 3540
gcccccagaa ctgcagcatc atgtaa 3566

<210> SEQ ID NO 4
<211> LENGTH: 3160
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
atggagaccc cgtcccagcg gcgcgccacc cgcagcgggg cgcaggccag ctccactccg 60
ctgtcgccca cccgcatcac ccggctgcag gagaaggagg acctgcagga gctcaatgat 120
cgcttggcgg tctacatcga ccgtgtgcgc tcgctggaaa cggagaacgc agggctgcgc 180
cttcgcatca ccgagtctga agaggtggtc agccgcgagg tgtccggcat caaggccgcc 240
tacgaggccg agctcgggga tgcccgcaag acccttgact cagtagccaa ggagcgcgcc 300
cgcctgcagc tggagctgag caaagtgcgt gaggagttta aggagctgaa agcgcgcaat 360
accaagaagg agggtgacct gatagctgct caggctcggc tgaaggacct ggaggctctg 420
ctgaactcca aggaggccgc actgagcact gctctcagtg agaagcgcac gctggagggc 480

-continued

```
gagctgcatg atctgcgggg ccaggtggcc aagcttgagg cagccctagg tgaggccaag    540
aagcaacttc aggatgagat gctgcggcgg gtggatgctg agaacaggct gcagaccatg    600
aaggaggaac tggacttcca gaagaacatc tacagtgagg agctgcgtga gaccaagcgc    660
cgtcatgaga cccgactggt ggagattgac aatgggaagc agcgtgagtt tgagagccgg    720
ctggcggatg cgctgcagga actgcgggcc cagcatgagg accaggtgga gcagtataag    780
aaggagctgg agaagactta ttctgccaag ctggacaatg ccaggcagtc tgctgagagg    840
aacagcaacc tggtgggggc tgcccacgag gagctgcagc agtcgcgcat ccgcatcgac    900
agcctctctg cccagctcag ccagctccag aagcagctgg cagccaagga ggcgaagctt    960
cgagacctgg aggactcact ggcccgtgag cgggacacca gccggcggct gctggcggaa   1020
aaggagcggg agatggccga gatgcgggca aggatgcagc agcagctgga cgagtaccag   1080
gagcttctgg acatcaagct ggccctggac atggagatcc acgcctaccg caagctcttg   1140
gagggcgagg aggagaggct acgcctgtcc cccagcccta cctcgcagcg cagccgtggc   1200
cgtgcttcct ctcactcatc ccagacacag ggtgggggca gcgtcaccaa aaagcgcaaa   1260
ctggagtcca ctgagagccg cagcagcttc tcacagcacg cacgcactag cgggcgcgtg   1320
gccgtggagg aggtggatga ggagggcaag tttgtccggc tgcgcaacaa gtccaatgag   1380
gaccagtcca tgggcaattg gcagatcaag cgccagaatg gagatgatcc cttgctgact   1440
taccggttcc caccaaagtt caccctgaag gctgggcagg tggtgacgat ctgggctgca   1500
ggagctgggg ccacccacag ccccccctacc gacctggtgt ggaaggcaca gaacacctgg   1560
ggctgcggga acagcctgcg tacggctctc atcaactcca ctggggaagt aagtaggcct   1620
gggcctggct gcttgctgga cgaggctccc cctgatggcc aacatcggag ccagctgccc   1680
ccaacccaag tttgccaatt cagggcccct ttctagagct ctctgttgca ggctccagac   1740
ttctccaccc agtaggcaaa ccaaaagatg cttcctcaac agcacaaggg gtggaagtta   1800
gacagtgagg attgttaaag gcagagccat actcctaccc ggagagcttg acagtgtccc   1860
tctggggtgg aaatgagttc cttagctcca tcaccacaga ggacagagta agcagcaggc   1920
cggacaaagg gcaggccaca agaaaagttg caggtggtca ctggggtaga catgctgtac   1980
aacccttccc tggccctgac ccttggacct ggttccatgt ccccaccagg aagtggccat   2040
gcgcaagctg gtgcgctcag tgactgtggt tgaggacgac gaggatgagg atggagatga   2100
cctgctccat caccaccacg tgagtggtag ccgccgctga ggccgagcct gcactggggc   2160
cacccagcca ggcctggggg cagcctctcc ccagcctccc cgtgccaaaa atcttttcat   2220
taaagaatgt tttggaactt tactcgctgg cctggccttt cttctctctc ctccctatac   2280
cttgaacagg gaacccaggt gtctgggtgc cctactctgg taaggaaggg agtgggaact   2340
ttctgatgcc atggaatatt cctgtgggag cagtggacaa gggtctggat ttgtcttctg   2400
ggaaagggag gggaggacag acgtggggca tgcccgccct gcctctctcc cccattcttg   2460
ttgcatgcat atcctctcat ttccctcatt tttcctgcaa gaatgttctc tctcattcct   2520
gaccgcccct ccactccaat taatagtgca tgcctgctgc cctacaagct tgctcccgtt   2580
ctctcttctt ttcctcttaa gctcagagta gctagaacag agtcagagtc actgctctgg   2640
ttctctgtcc ccaagtcttc ctgagccttc tccccttta tgtcttccct ctcctcctcc   2700
gggcccctag cctcccaaac ccccattgcc cgctggctcc ttgggcacag aaccacacct   2760
tcctgcctgg cggctgggag cctgcaggag cctggagcct ggttgggcct gagtggtcag   2820
```

tcccagactc gccgtcccgc ctgagccttg tctcccttcc cagggctccc actgcagcag 2880
ctcgggggac cccgctgagt acaacctgcg ctcgcgcacc gtgctgtgcg ggacctgcgg 2940
gcagcctgcc gacaaggcat ctgccagcgg ctcaggagcc caggtgggcg gacccatctc 3000
ctctggctct tctgcctcca gtgtcacggt cactcgcagc taccgcagtg tgggggggcag 3060 tgggggtggc agcttcgggg acaatctggt cacccgctcc tacctcctgg gcaactccag 3120
cccccgaacc cagagccccc agaactgcag catcatgtaa 3160

<210> SEQ ID NO 5
<211> LENGTH: 2736
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5
atggagaccc cgtcccagcg gcgcgccacc cgcagcgggg cgcaggccag ctccactccg 60
ctgtcgccca cccgcatcac ccggctgcag gagaaggagg acctgcagga gctcaatgat 120
cgcttggcgg tctacatcga ccgtgtgcgc tcgctggaaa cggagaacgc agggctgcgc 180
cttcgcatca ccgagtctga agaggtggtc agccgcgagg tgtccggcat caaggccgcc 240
tacgaggccg agctcgggga tgcccgcaag acccttgact cagtagccaa ggagcgcgcc 300
cgcctgcagc tggagctgag caaagtgcgt gaggagttta aggagctgaa agcgcgcaat 360
accaagaagg agggtgacct gatagctgct caggctcggc tgaaggacct ggaggctctg 420
ctgaactcca aggaggccgc actgagcact gctctcagtg agaagcgcac gctggagggc 480
gagctgcatg atctgcgggg ccaggtggcc aagcttgagg cagccctagg tgaggccaag 540
aagcaacttc aggatgagat gctgcggcgg gtggatgctg agaacaggct gcagaccatg 600
aaggaggaac tggacttcca gaagaacatc tacagtgagg agctgcgtga gaccaagcgc 660
cgtcatgaga cccgactggt ggagattgac aatgggaagc agcgtgagtt tgagagccgg 720
ctggcggatg cgctgcagga actgcgggcc cagcatgagg accaggtgga gcagtataag 780
aaggagctgg agaagactta ttctgccaag ctggacaatg ccaggcagtc tgctgagagg 840
aacagcaacc tggtgggggc tgcccacgag gagctgcagc agtcgcgcat ccgcatcgac 900
agcctctctg cccagctcag ccagctccag aagcagctgg cagccaagga ggcgaagctt 960
cgagacctgg aggactcact ggcccgtgag cgggacacca gccggcggct gctggcggaa 1020
aaggagcggg agatggccga gatgcgggca aggatgcagc agcagctgga cgagtaccag 1080
gagcttctgg acatcaagct ggccctggac atggagatcc acgcctaccg caagctcttg 1140
gagggcgagg aggagaggct acgcctgtcc cccagcccta cctcgcagcg cagccgtggc 1200
cgtgcttcct ctcactcatc ccagacacag ggtgggggca gcgtcaccaa aaagcgcaaa 1260
ctggagtcca ctgagagccg cagcagcttc tcacagcacg cacgcactag cgggcgcgtg 1320
gccgtggagg aggtggatga ggagggcaag tttgtccggc tgcgcaacaa gtccaatgag 1380
gaccagtcca tgggcaattg gcagatcaag cgccagaatg gagatgatcc cttgctgact 1440
taccggttcc caccaaagtt caccctgaag gctgggcagg tggtgacgat ctgggctgca 1500
ggagctgggg ccacccacag ccccccctacc gacctggtgt ggaaggcaca gaacacctgg 1560
ggctgcggga acagcctgcg tacggctctc atcaactcca ctggggaaga agtggccatg 1620
cgcaagctgg tgcgctcagt gactgtggtt gaggacgacg aggatgagga tggagatgac 1680

-continued ctgctccatc accaccacgt gagtggtagc cgccgctgag gccgagcctg cactggggcc 1740
acccagccag gcctgggggc agcctctccc cagcctcccc gtgccaaaaa tcttttcatt 1800
aaagaatgtt ttggaacttt actcgctggc ctggcctttc ttctctctcc tccctatacc 1860
ttgaacaggg aacccaggtg tctgggtgcc ctactctggt aaggaaggga gtgggaactt 1920
tctgatgcca tggaatattc ctgtgggagc agtggacaag ggtctggatt tgtcttctgg 1980
gaaagggagg ggaggacaga cgtggggcat gcccgccctg cctctctccc ccattcttgt 2040
tgcatgcata tcctctcatt tccctcattt ttcctgcaag aatgttctct ctcattcctg 2100
accgcccctc cactccaatt aatagtgcat gcctgctgcc ctacaagctt gctcccgttc 2160
tctcttcttt tcctcttaag ctcagagtag ctagaacaga gtcagagtca ctgctctggt 2220
tctctgtccc caagtcttcc tgagccttct cccctttttat gtcttccctc tcctcctccg 2280
ggcccctagc ctcccaaacc cccattgccc gctggctcct tgggcacaga accacacctt 2340
cctgcctggc ggctgggagc ctgcaggagc ctggagcctg gttgggcctg agtggtcagt 2400
cccagactcg ccgtcccgcc tgagccttgt ctcccttccc agggctccca ctgcagcagc 2460
tcgggggacc ccgctgagta caacctgcgc tcgcgcaccg tgctgtgcgg gacctgcggg 2520
cagcctgccg acaaggcatc tgccagcggc tcaggagccc aggtgggcgg acccatctcc 2580
tctggctctt ctgcctccag tgtcacggtc actcgcagct accgcagtgt ggggggcagt 2640
gggggtggca gcttcgggga caatctggtc acccgctcct acctcctggg caactccagc 2700
ccccgaaccc agagccccca gaactgcagc atcatg 2736

<210> SEQ ID NO 6
<211> LENGTH: 2321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
gtgatgcggt tttggcagta catcaatggg cgtggatagc ggtttgactc acggggattt 60
ccaagtctcc accccattga cgtcaatggg agtttgtttt ggcaccaaaa tcaacgggac 120
tttccaaaat gtcgtaacaa ctccgcccca ttgacgcaaa tgggcggtag gcgtgtacgg 180
tgggaggtct atataagcag agctggtacc gtgtgtatgc tcaggggctg ggaaaggagg 240
ggagggagct ccggctcagg aattcgccac catggagacc ccgtcccagc ggcgcgccac 300
ccgcagcggg gcgcaggcca gctccactcc gctgtcgccc acccgcatca cccggctgca 360
ggagaaggag gacctgcagg agctcaatga tcgcttggcg gtctacatcg accgtgtgcg 420
ctcgctggaa acggagaacg cagggctgcg ccttcgcatc accgagtctg aagaggtggt 480
cagccgcgag gtgtccggca tcaaggccgc ctacgaggcc gagctcgggg atgcccgcaa 540
gacccttgac tcagtagcca aggagcgcgc ccgcctgcag ctggagctga gcaaagtgcg 600
tgaggagttt aaggagctga aagcgcgcaa taccaagaag gagggtgacc tgatagctgc 660
tcaggctcgg ctgaaggacc tggaggctct gctgaactcc aaggaggccg cactgagcac 720
tgctctcagt gagaagcgca cgctggaggg cgagctgcat gatctgcggg gccaggtggc 780
caagcttgag gcagccctag gtgaggccaa gaagcaactt caggatgaga tgctgcggcg 840
ggtggatgct gagaacaggc tgcagaccat gaaggaggaa ctggacttcc agaagaacat 900
ctacagtgag gagctgcgtg agaccaagcg ccgtcatgag acccgactgg tggagattga 960

-continued

```
caatgggaag cagcgtgagt ttgagagccg gctggcggat gcgctgcagg aactgcgggc   1020

ccagcatgag gaccaggtgg agcagtataa gaaggagctg gagaagactt attctgccaa   1080

gctggacaat gccaggcagt ctgctgagag gaacagcaac ctggtggggg ctgcccacga   1140

ggagctgcag cagtcgcgca tccgcatcga cagcctctct gcccagctca gccagctcca   1200

gaagcagctg gcagccaagg aggcgaagct tcgagacctg gaggactcac tggcccgtga   1260

gcgggacacc agccggcggc tgctggcgga aaaggagcgg gagatggccg agatgcgggc   1320

aaggatgcag cagcagctgg acgagtacca ggagcttctg gacatcaagc tggccctgga   1380

catggagatc cacgcctacc gcaagctctt ggagggcgag gaggagaggc tacgcctgtc   1440

ccccagccct acctcgcagc gcagccgtgg ccgtgcttcc tctcactcat cccagacaca   1500

gggtgggggc agcgtcacca aaaagcgcaa actggagtcc actgagagcc gcagcagctt   1560

ctcacagcac gcacgcacta gcgggcgcgt ggccgtggag gaggtggatg aggagggcaa   1620

gtttgtccgg ctgcgcaaca agtccaatga ggaccagtcc atgggcaatt ggcagatcaa   1680

gcgccagaat ggagatgatc ccttgctgac ttaccggttc ccaccaaagt tcaccctgaa   1740

ggctgggcag gtggtgacga tctgggctgc aggagctggg gccacccaca gcccccctac   1800

cgacctggtg tggaaggcac agaacacctg ggggctgcggg aacagcctgc gtacggctct  1860

catcaactcc actggggaag aagtggccat gcgcaagctg gtgcgctcag tgactgtggt   1920

tgaggacgac gaggatgagg atggagatga cctgctccat caccaccacg gctcccactg   1980

cagcagctcg gggaccccg ctgagtacaa cctgcgctcg cgcaccgtgc tgtgcgggac   2040

ctgcgggcag cctgccgaca aggcatctgc cagcggctca ggagcccagg tgggcggacc   2100

catctcctct ggctcttctg cctccagtgt cacggtcact cgcagctacc gcagtgtggg   2160

gggcagtggg ggtggcagct tcggggacaa tctggtcacc cgctcctacc tcctgggcaa   2220

ctccagcccc cgaacccaga gcccccagaa ctgcagcatc atgtaaacta gtaataaaag   2280

atctttattt tcattagatc tgtgtgttgg ttttttgtgt g                       2321
```

<210> SEQ ID NO 7
<211> LENGTH: 2045
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
gtgatgcggt tttggcagta catcaatggg cgtggatagc ggtttgactc acggggattt     60

ccaagtctcc accccattga cgtcaatggg agtttgtttt ggcaccaaaa tcaacgggac    120

tttccaaaat gtcgtaacaa ctccgcccca ttgacgcaaa tgggcggtag gcgtgtacgg    180

tgggaggtct atataagcag agctggtacc gtgtgtatgc tcaggggctg ggaaaggagg    240

ggagggagct ccggctcagg aattcgccac catggagacc ccgtcccagc ggcgcgccac    300

ccgcagcggg gcgcaggcca gctccactcc gctgtcgccc acccgcatca cccggctgca    360

ggagaaggag gacctgcagg agctcaatga tcgcttggcg gtctacatcg accgtgtgcg    420

ctcgctggaa acggagaacg cagggctgcg ccttcgcatc accgagtctg aagaggtggt    480

cagccgcgag gtgtccggca tcaaggccgc ctacgaggcc gagctcgggg atgcccgcaa    540

gacccttgac tcagtagcca aggagcgcgc ccgcctgcag ctggagctga gcaaagtgcg    600

tgaggagttt aaggagctga aagcgcgcaa taccaagaag gagggtgacc tgatagctgc    660
```

-continued

```
tcaggctcgg ctgaaggacc tggaggctct gctgaactcc aaggaggccg cactgagcac    720

tgctctcagt gagaagcgca cgctggaggg cgagctgcat gatctgcggg gccaggtggc    780

caagcttgag gcagccctag gtgaggccaa gaagcaactt caggatgaga tgctgcggcg    840

ggtggatgct gagaacaggc tgcagaccat gaaggaggaa ctggacttcc agaagaacat    900

ctacagtgag gagctgcgtg agaccaagcg ccgtcatgag acccgactgg tggagattga    960

caatgggaag cagcgtgagt ttgagagccg gctggcggat gcgctgcagg aactgcgggc   1020

ccagcatgag gaccaggtgg agcagtataa gaaggagctg gagaagactt attctgccaa   1080

gctggacaat gccaggcagt ctgctgagag gaacagcaac ctggtggggg ctgcccacga   1140

ggagctgcag cagtcgcgca tccgcatcga cagcctctct gcccagctca gccagctcca   1200

gaagcagctg gcagccaagg aggcgaagct tcgagacctg gaggactcac tggcccgtga   1260

gcgggacacc agccggcggc tgctggcgga aaaggagcgg gagatggccg agatgcgggc   1320

aaggatgcag cagcagctgg acgagtacca ggagcttctg gacatcaagc tggccctgga   1380

catggagatc cacgcctacc gcaagctctt ggagggcgag gaggagaggc tacgcctgtc   1440

ccccagccct acctcgcagc gcagccgtgg ccgtgcttcc tctcactcat cccagacaca   1500

gggtgggggc agcgtcacca aaaagcgcaa actggagtcc actgagagcc gcagcagctt   1560

ctcacagcac gcacgcacta gcgggcgcgt ggccgtggag gaggtggatg aggagggcaa   1620

gtttgtccgg ctgcgcaaca agtccaatga ggaccagtcc atgggcaatt ggcagatcaa   1680

gcgccagaat ggagatgatc ccttgctgac ttaccggttc ccaccaaagt tcaccctgaa   1740

ggctgggcag gtggtgacga tctgggctgc aggagctggg gccacccaca gcccccctac   1800

cgacctggtg tggaaggcac agaacacctg ggctgcgggg aacagcctgc gtacggctct   1860

catcaactcc actggggaag aagtggccat gcgcaagctg gtgcgctcag tgactgtggt   1920

tgaggacgac gaggatgagg atggagatga cctgctccat caccaccacg tgagtggtag   1980

ccgccgctga actagtaata aaagatcttt attttcatta gatctgtgtg ttggtttttt   2040

gtgtg                                                               2045
```

<210> SEQ ID NO 8
<211> LENGTH: 3892
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
gtgatgcggt tttggcagta catcaatggg cgtggatagc ggtttgactc acggggattt     60

ccaagtctcc accccattga cgtcaatggg agtttgtttt ggcaccaaaa tcaacgggac    120

tttccaaaat gtcgtaacaa ctccgcccca ttgacgcaaa tgggcggtag gcgtgtacgg    180

tgggaggtct atataagcag agctggtacc gtgtgtatgc tcaggggctg ggaaaggagg    240

ggagggagct ccggctcagg aattcgccac catggagacc ccgtcccagc ggcgcgccac    300

ccgcagcggg gcgcaggcca gctccactcc gctgtcgccc acccgcatca cccggctgca    360

ggagaaggag gacctgcagg agctcaatga tcgcttggcg gtctacatcg accgtgtgcg    420

ctcgctggaa acggagaacg cagggctgcg ccttcgcatc accgagtctg aagaggtggt    480

cagccgcgag gtgtccggca tcaaggccgc ctacgaggcc gagctcgggg atgcccgcaa    540

gacccttgac tcagtagcca aggagcgcgc ccgcctgcag ctggagctga gcaaagtgcg    600
```

-continued

```
tgaggagttt aaggagctga aagcgcgcaa taccaagaag gagggtgacc tgatagctgc    660
tcaggctcgg ctgaaggacc tggaggctct gctgaactcc aaggaggccg cactgagcac    720
tgctctcagt gagaagcgca cgctggaggg cgagctgcat gatctgcggg gccaggtggc    780
caagcttgag gcagccctag gtgaggccaa gaagcaactt caggatgaga tgctgcggcg    840
ggtggatgct gagaacaggc tgcagaccat gaaggaggaa ctggacttcc agaagaacat    900
ctacagtgag gagctgcgtg agaccaagcg ccgtcatgag acccgactgg tggagattga    960
caatgggaag cagcgtgagt ttgagagccg gctggcggat gcgctgcagg aactgcgggc   1020
ccagcatgag gaccaggtgg agcagtataa gaaggagctg gagaagactt attctgccaa   1080
gctggacaat gccaggcagt ctgctgagag gaacagcaac ctggtggggg ctgcccacga   1140
ggagctgcag cagtcgcgca tccgcatcga cagcctctct gcccagctca gccagctcca   1200
gaagcagctg gcagccaagg aggcgaagct tcgagacctg gaggactcac tggcccgtga   1260
gcgggacacc agccggcggc tgctggcgga aaaggagcgg gagatggccg agatgcgggc   1320
aaggatgcag cagcagctgg acgagtacca ggagcttctg gacatcaagc tggccctgga   1380
catggagatc cacgcctacc gcaagctctt ggagggcgag gaggagaggc tacgcctgtc   1440
ccccagccct acctcgcagc gcagccgtgg ccgtgcttcc tctcactcat cccagacaca   1500
gggtgggggc agcgtcacca aaaagcgcaa actggagtcc actgagagcc gcagcagctt   1560
ctcacagcac gcacgcacta gcgggcgcgt ggccgtggag gaggtggatg aggagggcaa   1620
gtttgtccgg ctgcgcaaca agtccaatga ggaccagtcc atgggcaatt ggcagatcaa   1680
gcgccagaat ggagatgatc ccttgctgac ttaccggttc ccaccaaagt tcaccctgaa   1740
ggctgggcag gtggtgacgg tgagtggcag ggcgcttggg actctgggga ggccttgggt   1800
ggcgatggga gcgctggggt aagtgtcctt ttctcctctc cagatctggg ctgcaggagc   1860
tggggccacc cacagccccc ctaccgacct ggtgtggaag gcacagaaca cctggggctg   1920
cgggaacagc ctgcgtacgg ctctcatcaa ctccactggg gaagtaagta ggcctgggcc   1980
tggctgcttg ctggacgagg ctccccctga tggccaacat cggagccagc tgccccccaac   2040
ccaagtttgc caattcaggg cccctttcta gagctctctg ttgcaggctc cagacttctc   2100
cacccagtag gcaaaccaaa agatgcttcc tcaacagcac aaggggtgga agttagacag   2160
tgaggattgt taaaggcaga gccatactcc tacccggaga gcttgacagt gtccctctgg   2220
ggtggaaatg agttccttag ctccatcacc acagaggaca gagtaagcag caggccggac   2280
aaagggcagg ccacaagaaa agttgcaggt ggtcactggg gtagacatgc tgtacaaccc   2340
ttccctggcc ctgacccttg gacctggttc catgtcccca ccaggaagtg gccatgcgca   2400
agctggtgcg ctcagtgact gtggttgagg acgacgagga tgaggatgga gatgacctgc   2460
tccatcacca ccacgtgagt ggtagccgcc gctgaggccg agcctgcact ggggccaccc   2520
agccaggcct gggggcagcc tctccccagc ctccccgtgc caaaaatctt ttcattaaag   2580
aatgttttgg aactttactc gctggcctgg cctttcttct ctctcctccc tataccttga   2640
acagggaacc caggtgtctg ggtgccctac tctggtaagg aagggagtgg gaactttctg   2700
atgccatgga atattcctgt gggagcagtg gacaagggtc tggatttgtc ttctgggaaa   2760
gggaggggag gacagacgtg gggcatgccc gccctgcctc tctcccccat tcttgttgca   2820
tgcatatcct ctcatttccc tcatttttcc tgcaagaatg ttctctctca ttcctgaccg   2880
cccctccact ccaattaata gtgcatgcct gctgccctac aagcttgctc ccgttctctc   2940
ttcttttcct cttaagctca gagtagctag aacagagtca gagtcactgc tctggttctc   3000
```

-continued

```
tgtccccaag tcttcctgag ccttctcccc ttttatgtct tccctctcct cctccgggcc   3060

cctagcctcc caaaccccca ttgcccgctg gctccttggg cacagaacca caccttcctg   3120

cctggcggct gggagcctgc aggagcctgg agcctggttg ggcctgagtg gtcagtccca   3180

gactcgccgt cccgcctgag ccttgtctcc cttcccaggg ctcccactgc agcagctcgg   3240

gggaccccgc tgagtacaac ctgcgctcgc gcaccgtgct gtgcgggacc tgcgggcagc   3300

ctgccgacaa ggcatctgcc agcggctcag gagcccaggt gggcggaccc atctcctctg   3360

gctcttctgc ctccagtgtc acggtcactc gcagctaccg cagtgtgggg ggcagtgggg   3420

gtggcagctt cggggacaat ctggtcaccc gctcctacct cctgggcaac tccagccccc   3480

gaacccaggt gagttgtctc tgctttgtct ccaaatcctg caggcgggtc cctggtcatc   3540

gaggggtagg acgaggtggc cttgcagggg ggagagcctg ccttctcttc cgcagcccgg   3600

gggagtggga gcctcctccc cacagcctga gtcctagaca gcccacctct gcatcctgcc   3660

cctcttgtct gagccccaga ctggagggca ggggcagggc tggagtgtga gggatggggg   3720

agatgctacc tcccttctag gggccagggg agggagggtc tgggtccagg ccctgctgct   3780

cacacctctc tcctctgttt tctctcttag agcccccaga actgcagcat catgtaaact   3840

agtaataaaa gatctttatt ttcattagat ctgtgtgttg gtttttgtg tg            3892
```

<210> SEQ ID NO 9
<211> LENGTH: 3486
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gtgatgcggt tttggcagta catcaatggg cgtggatagc ggtttgactc acggggattt     60

ccaagtctcc accccattga cgtcaatggg agtttgtttt ggcaccaaaa tcaacgggac    120

tttccaaaat gtcgtaacaa ctccgcccca ttgacgcaaa tgggcggtag gcgtgtacgg    180

tgggaggtct atataagcag agctggtacc gtgtgtatgc tcaggggctg ggaaaggagg    240

ggagggagct ccggctcagg aattcgccac catggagacc ccgtcccagc ggcgcgccac    300

ccgcagcggg gcgcaggcca gctccactcc gctgtcgccc acccgcatca cccggctgca    360

ggagaaggag gacctgcagg agctcaatga tcgcttggcg gtctacatcg accgtgtgcg    420

ctcgctggaa acggagaacg cagggctgcg ccttcgcatc accgagtctg aagaggtggt    480

cagccgcgag gtgtccggca tcaaggccgc ctacgaggcc gagctcgggg atgcccgcaa    540

gacccttgac tcagtagcca aggagcgcgc ccgcctgcag ctggagctga gcaaagtgcg    600

tgaggagttt aaggagctga aagcgcgcaa taccaagaag gagggtgacc tgatagctgc    660

tcaggctcgg ctgaaggacc tggaggctct gctgaactcc aaggaggccg cactgagcac    720

tgctctcagt gagaagcgca cgctggaggg cgagctgcat gatctgcggg gccaggtggc    780

caagcttgag gcagccctag gtgaggccaa gaagcaactt caggatgaga tgctgcggcg    840

ggtggatgct gagaacaggc tgcagaccat gaaggaggaa ctggacttcc agaagaacat    900

ctacagtgag gagctgcgtg agaccaagcg ccgtcatgag acccgactgg tggagattga    960

caatgggaag cagcgtgagt ttgagagccg gctggcggat gcgctgcagg aactgcgggc   1020

ccagcatgag gaccaggtgg agcagtataa gaaggagctg gagaagactt attctgccaa   1080

gctggacaat gccaggcagt ctgctgagag gaacagcaac ctggtggggg ctgcccacga   1140
```

```
ggagctgcag cagtcgcgca tccgcatcga cagcctctct gcccagctca gccagctcca   1200
gaagcagctg gcagccaagg aggcgaagct tcgagacctg gaggactcac tggcccgtga   1260
gcgggacacc agccggcggc tgctggcgga aaaggagcgg gagatggccg agatgcgggc   1320
aaggatgcag cagcagctgg acgagtacca ggagcttctg gacatcaagc tggccctgga   1380
catggagatc cacgcctacc gcaagctctt ggagggcgag gaggagaggc tacgcctgtc   1440
ccccagccct acctcgcagc gcagccgtgg ccgtgcttcc tctcactcat cccagacaca   1500
gggtgggggc agcgtcacca aaaagcgcaa actggagtcc actgagagcc gcagcagctt   1560
ctcacagcac gcacgcacta gcgggcgcgt ggccgtggag gaggtggatg aggagggcaa   1620
gtttgtccgg ctgcgcaaca agtccaatga ggaccagtcc atgggcaatt ggcagatcaa   1680
gcgccagaat ggagatgatc ccttgctgac ttaccggttc ccaccaaagt tcaccctgaa   1740
ggctgggcag gtggtgacga tctgggctgc aggagctggg gccacccaca gcccccctac   1800
cgacctggtg tggaaggcac agaacacctg ggctgcgggg aacagcctgc gtacggctct   1860
catcaactcc actggggaag taagtaggcc tgggcctggc tgcttgctgg acgaggctcc   1920
ccctgatggc caacatcgga gccagctgcc cccaacccaa gtttgccaat tcagggcccc   1980
tttctagagc tctctgttgc aggctccaga cttctccacc cagtaggcaa accaaaagat   2040
gcttcctcaa cagcacaagg ggtggaagtt agacagtgag gattgttaaa ggcagagcca   2100
tactcctacc cggagagctt gacagtgtcc ctctggggtg gaaatgagtt ccttagctcc   2160
atcaccacag aggacagagt aagcagcagg ccggacaaag ggcaggccac aagaaaagtt   2220
gcaggtggtc actggggtag acatgctgta caacccttcc ctggccctga cccttggacc   2280
tggttccatg tccccaccag gaagtggcca tgcgcaagct ggtgcgctca gtgactgtgg   2340
ttgaggacga cgaggatgag gatggagatg acctgctcca tcaccaccac gtgagtggta   2400
gccgccgctg aggccgagcc tgcactgggg ccacccagcc aggcctgggg gcagcctctc   2460
cccagcctcc ccgtgccaaa aatcttttca ttaaagaatg ttttggaact ttactcgctg   2520
gcctggcctt tcttctctct cctccctata ccttgaacag ggaacccagg tgtctgggtg   2580
ccctactctg gtaaggaagg gagtgggaac tttctgatgc catggaatat tcctgtggga   2640
gcagtggaca agggtctgga tttgtcttct gggaaaggga ggggaggaca gacgtggggc   2700
atgcccgccc tgcctctctc ccccattctt gttgcatgca tatcctctca tttccctcat   2760
ttttcctgca agaatgttct ctctcattcc tgaccgcccc tccactccaa ttaatagtgc   2820
atgcctgctg ccctacaagc ttgctcccgt tctctcttct tttcctctta agctcagagt   2880
agctagaaca gagtcagagt cactgctctg gttctctgtc cccaagtctt cctgagcctt   2940
ctcccctttt atgtcttccc tctcctcctc cgggccccta gcctcccaaa cccccattgc   3000
ccgctggctc cttgggcaca gaaccacacc ttcctgcctg gcggctggga gcctgcagga   3060
gcctggagcc tggttgggcc tgagtggtca gtcccagact cgccgtcccg cctgagcctt   3120
gtctcccttc ccagggctcc cactgcagca gctcgggga ccccgctgag tacaacctgc   3180
gctcgcgcac cgtgctgtgc gggacctgcg ggcagcctgc cgacaaggca tctgccagcg   3240
gctcaggagc ccaggtgggc ggacccatct cctctggctc ttctgcctcc agtgtcacgg   3300
tcactcgcag ctaccgcagt gtgggggca gtgggggtgg cagcttcggg gacaatctgg   3360
tcacccgctc ctacctcctg ggcaactcca gcccccgaac ccagagcccc cagaactgca   3420
gcatcatgta aactagtaat aaaagatctt tattttcatt agatctgtgt gttggttttt   3480
```

```
tgtgtg                                                            3486

<210> SEQ ID NO 10
<211> LENGTH: 3065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

gtgatgcggt tttggcagta catcaatggg cgtggatagc ggtttgactc acggggattt     60

ccaagtctcc accccattga cgtcaatggg agtttgtttt ggcaccaaaa tcaacgggac    120

tttccaaaat gtcgtaacaa ctccgcccca ttgacgcaaa tgggcggtag gcgtgtacgg    180

tgggaggtct atataagcag agctggtacc gtgtgtatgc tcaggggctg ggaaaggagg    240

ggagggagct ccggctcagg aattcgccac catggagacc ccgtcccagc ggcgcgccac    300

ccgcagcggg gcgcaggcca gctccactcc gctgtcgccc acccgcatca cccggctgca    360

ggagaaggag gacctgcagg agctcaatga tcgcttggcg gtctacatcg accgtgtgcg    420

ctcgctggaa acggagaacg cagggctgcg ccttcgcatc accgagtctg aagaggtggt    480

cagccgcgag gtgtccggca tcaaggccgc ctacgaggcc gagctcgggg atgcccgcaa    540

gacccttgac tcagtagcca aggagcgcgc ccgcctgcag ctggagctga gcaaagtgcg    600

tgaggagttt aaggagctga aagcgcgcaa taccaagaag gagggtgacc tgatagctgc    660

tcaggctcgg ctgaaggacc tggaggctct gctgaactcc aaggaggccg cactgagcac    720

tgctctcagt gagaagcgca cgctggaggg cgagctgcat gatctgcggg gccaggtggc    780

caagcttgag gcagccctag gtgaggccaa gaagcaactt caggatgaga tgctgcggcg    840

ggtggatgct gagaacaggc tgcagaccat gaaggaggaa ctggacttcc agaagaacat    900

ctacagtgag gagctgcgtg agaccaagcg ccgtcatgag acccgactgg tggagattga    960

caatgggaag cagcgtgagt ttgagagccg gctggcggat gcgctgcagg aactgcgggc   1020

ccagcatgag gaccaggtgg agcagtataa gaaggagctg gagaagactt attctgccaa   1080

gctggacaat gccaggcagt ctgctgagag gaacagcaac ctggtggggg ctgcccacga   1140

ggagctgcag cagtcgcgca tccgcatcga cagcctctct gcccagctca gccagctcca   1200

gaagcagctg gcagccaagg aggcgaagct tcgagacctg gaggactcac tggcccgtga   1260

gcgggacacc agccggcggc tgctggcgga aaaggagcgg gagatggccg agatgcgggc   1320

aaggatgcag cagcagctgg acgagtacca ggagcttctg gacatcaagc tggccctgga   1380

catggagatc cacgcctacc gcaagctctt ggagggcgag gaggagaggc tacgcctgtc   1440

ccccagccct acctcgcagc gcagccgtgg ccgtgcttcc tctcactcat cccagacaca   1500

gggtgggggc agcgtcacca aaaagcgcaa actggagtcc actgagagcc gcagcagctt   1560

ctcacagcac gcacgcacta gcgggcgcgt ggccgtggag gaggtggatg aggagggcaa   1620

gtttgtccgg ctgcgcaaca agtccaatga ggaccagtcc atgggcaatt ggcagatcaa   1680

gcgccagaat ggagatgatc ccttgctgac ttaccggttc ccaccaaagt tcaccctgaa   1740

ggctgggcag gtggtgacga tctgggctgc aggagctggg gccacccaca gcccccctac   1800

cgacctggtg tggaaggcac agaacacctg ggctgcgggg aacagcctgc gtacggctct   1860

catcaactcc actggggaag aagtggccat gcgcaagctg gtgcgctcag tgactgtggt   1920

tgaggacgac gaggatgagg atggagatga cctgctccat caccaccacg tgagtggtag   1980
```

-continued ccgccgctga ggccgagcct gcactggggc cacccagcca ggcctggggg cagcctctcc 2040
ccagcctccc cgtgccaaaa atcttttcat taaagaatgt tttggaactt tactcgctgg 2100
cctggccttt cttctctctc ctccctatac cttgaacagg gaacccaggt gtctgggtgc 2160
cctactctgg taaggaaggg agtgggaact ttctgatgcc atggaatatt cctgtgggag 2220
cagtggacaa gggtctggat ttgtcttctg ggaaagggag gggaggacag acgtggggca 2280
tgcccgccct gcctctctcc cccattcttg ttgcatgcat atcctctcat ttccctcatt 2340
tttcctgcaa gaatgttctc tctcattcct gaccgcccct ccactccaat taatagtgca 2400
tgcctgctgc cctacaagct tgctcccgtt ctctcttctt ttcctcttaa gctcagagta 2460
gctagaacag agtcagagtc actgctctgg ttctctgtcc ccaagtcttc ctgagccttc 2520 tccccttta tgtcttccct ctcctcctcc gggcccctag cctcccaaac ccccattgcc 2580
cgctggctcc ttgggcacag aaccacacct tcctgcctgg cggctgggag cctgcaggag 2640
cctggagcct ggttgggcct gagtggtcag tcccagactc gccgtcccgc ctgagccttg 2700
tctcccttcc cagggctccc actgcagcag ctcgggggac cccgctgagt acaacctgcg 2760
ctcgcgcacc gtgctgtgcg ggacctgcgg gcagcctgcc gacaaggcat ctgccagcgg 2820
ctcaggagcc caggtgggcg gacccatctc ctctggctct tctgcctcca gtgtcacggt 2880
cactcgcagc taccgcagtg tggggggcag tgggggtggc agcttcgggg acaatctggt 2940
cacccgctcc tacctcctgg gcaactccag cccccgaacc cagagccccc agaactgcag 3000
catcatgtaa actagtaata aaagatcttt attttcatta gatctgtgtg ttggtttttt 3060
gtgtg 3065

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
aataaaagat ctttattttc attagatctg tgtgttggtt ttttgtgtg 49

<210> SEQ ID NO 12
<211> LENGTH: 664
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 12

Met Glu Thr Pro Ser Gln Arg Arg Ala Thr Arg Ser Gly Ala Gln Ala
1 5 10 15

Ser Ser Thr Pro Leu Ser Pro Thr Arg Ile Thr Arg Leu Gln Glu Lys
20 25 30

Glu Asp Leu Gln Glu Leu Asn Asp Arg Leu Ala Val Tyr Ile Asp Arg
35 40 45

Val Arg Ser Leu Glu Thr Glu Asn Ala Gly Leu Arg Leu Arg Ile Thr
50 55 60

Glu Ser Glu Glu Val Val Ser Arg Glu Val Ser Gly Ile Lys Ala Ala
65 70 75 80

Tyr Glu Ala Glu Leu Gly Asp Ala Arg Lys Thr Leu Asp Ser Val Ala
85 90 95

-continued

```
Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510
```

```
Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
    530                 535                 540

Arg Ser Val Thr Val Val Glu Asp Asp Glu Asp Glu Asp Gly Asp Asp
545                 550                 555                 560

Leu Leu His His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Val Gly
        595                 600                 605

Gly Pro Ile Ser Ser Gly Ser Ser Ala Ser Ser Val Thr Val Thr Arg
    610                 615                 620

Ser Tyr Arg Ser Val Gly Gly Ser Gly Gly Gly Ser Phe Gly Asp Asn
625                 630                 635                 640

Leu Val Thr Arg Ser Tyr Leu Leu Gly Asn Ser Ser Pro Arg Thr Gln
                645                 650                 655

Ser Pro Gln Asn Cys Ser Ile Met
            660


<210> SEQ ID NO 13
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205
```

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
    530                 535                 540

Arg Ser Val Thr Val Val Glu Asp Asp Glu Asp Glu Asp Gly Asp Asp
545                 550                 555                 560

Leu Leu His His His His Val Ser Gly Ser Arg Arg
                565                 570

<210> SEQ ID NO 14
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 14

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415
```

-continued

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr

<210> SEQ ID NO 15
<211> LENGTH: 55
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Arg Phe Pro Pro Lys Phe Thr Leu Lys Ala Gly Gln Val Val Thr Ile
1               5                   10                  15

Trp Ala Ala Gly Ala Gly Ala Thr His Ser Pro Pro Thr Asp Leu Val
            20                  25                  30

Trp Lys Ala Gln Asn Thr Trp Gly Cys Gly Asn Ser Leu Arg Thr Ala
        35                  40                  45

Leu Ile Asn Ser Thr Gly Glu
    50                  55

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Glu Val Ala Met Arg Lys Leu Val Arg Ser Val Thr Val Val Glu Asp
1               5                   10                  15

Asp Glu Asp Glu Asp Gly Asp Asp Leu Leu His His His His Val Ser
            20                  25                  30

Gly Ser Arg Arg
        35

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Glu Val Ala Met Arg Lys Leu Val Arg Ser Val Thr Val Val Glu Asp
1               5                   10                  15

Asp Glu Asp Glu Asp Gly Asp Asp Leu Leu His His His His
            20                  25                  30

<210> SEQ ID NO 18
<211> LENGTH: 90
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 18

```
Gly Ser His Cys Ser Ser Ser Gly Asp Pro Ala Glu Tyr Asn Leu Arg
1               5                   10                  15

Ser Arg Thr Val Leu Cys Gly Thr Cys Gly Gln Pro Ala Asp Lys Ala
            20                  25                  30

Ser Ala Ser Gly Ser Gly Ala Gln Val Gly Gly Pro Ile Ser Ser Gly
        35                  40                  45

Ser Ser Ala Ser Ser Val Thr Val Thr Arg Ser Tyr Arg Ser Val Gly
    50                  55                  60

Gly Ser Gly Gly Gly Ser Phe Gly Asp Asn Leu Val Thr Arg Ser Tyr
65                  70                  75                  80

Leu Leu Gly Asn Ser Ser Pro Arg Thr Gln
                85                  90
```

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

```
Ser Pro Gln Asn Cys Ser Ile Met
1               5
```

<210> SEQ ID NO 20
<211> LENGTH: 535
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160
```

```
Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Thr Ala
        515                 520                 525

Leu Ile Asn Ser Thr Gly Glu
    530                 535
```

<210> SEQ ID NO 21
<211> LENGTH: 646
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 21

Met Glu Thr Pro Ser Gln Arg Arg Ala Thr Arg Ser Gly Ala Gln Ala
1 5 10 15

Ser Ser Thr Pro Leu Ser Pro Thr Arg Ile Thr Arg Leu Gln Glu Lys
20 25 30

Glu Asp Leu Gln Glu Leu Asn Asp Arg Leu Ala Val Tyr Ile Asp Arg
35 40 45

Val Arg Ser Leu Glu Thr Glu Asn Ala Gly Leu Arg Leu Arg Ile Thr
50 55 60

Glu Ser Glu Glu Val Val Ser Arg Glu Val Ser Gly Ile Lys Ala Ala
65 70 75 80

Tyr Glu Ala Glu Leu Gly Asp Ala Arg Lys Thr Leu Asp Ser Val Ala
85 90 95

Lys Glu Arg Ala Arg Leu Gln Leu Glu Leu Ser Lys Val Arg Glu Glu
100 105 110

Phe Lys Glu Leu Lys Ala Arg Asn Thr Lys Lys Glu Gly Asp Leu Ile
115 120 125

Ala Ala Gln Ala Arg Leu Lys Asp Leu Glu Ala Leu Leu Asn Ser Lys
130 135 140

Glu Ala Ala Leu Ser Thr Ala Leu Ser Glu Lys Arg Thr Leu Glu Gly
145 150 155 160

Glu Leu His Asp Leu Arg Gly Gln Val Ala Lys Leu Glu Ala Ala Leu
165 170 175

Gly Glu Ala Lys Lys Gln Leu Gln Asp Glu Met Leu Arg Arg Val Asp
180 185 190

Ala Glu Asn Arg Leu Gln Thr Met Lys Glu Glu Leu Asp Phe Gln Lys
195 200 205

Asn Ile Tyr Ser Glu Glu Leu Arg Glu Thr Lys Arg Arg His Glu Thr
210 215 220

Arg Leu Val Glu Ile Asp Asn Gly Lys Gln Arg Glu Phe Glu Ser Arg
225 230 235 240

Leu Ala Asp Ala Leu Gln Glu Leu Arg Ala Gln His Glu Asp Gln Val
245 250 255

Glu Gln Tyr Lys Lys Glu Leu Glu Lys Thr Tyr Ser Ala Lys Leu Asp
260 265 270

Asn Ala Arg Gln Ser Ala Glu Arg Asn Ser Asn Leu Val Gly Ala Ala
275 280 285

His Glu Glu Leu Gln Gln Ser Arg Ile Arg Ile Asp Ser Leu Ser Ala
290 295 300

Gln Leu Ser Gln Leu Gln Lys Gln Leu Ala Ala Lys Glu Ala Lys Leu
305 310 315 320

Arg Asp Leu Glu Asp Ser Leu Ala Arg Glu Arg Asp Thr Ser Arg Arg
325 330 335

Leu Leu Ala Glu Lys Glu Arg Glu Met Ala Glu Met Arg Ala Arg Met
340 345 350

Gln Gln Gln Leu Asp Glu Tyr Gln Glu Leu Leu Asp Ile Lys Leu Ala
355 360 365

Leu Asp Met Glu Ile His Ala Tyr Arg Lys Leu Leu Glu Gly Glu Glu
370 375 380

Glu Arg Leu Arg Leu Ser Pro Ser Pro Thr Ser Gln Arg Ser Arg Gly
385 390 395 400

```
Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
    530                 535                 540

Arg Ser Val Thr Val Val Glu Asp Asp Glu Asp Glu Asp Gly Asp Asp
545                 550                 555                 560

Leu Leu His His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Val Gly
        595                 600                 605

Gly Pro Ile Ser Ser Gly Ser Ser Ala Ser Ser Val Thr Val Thr Arg
    610                 615                 620

Ser Tyr Arg Ser Val Gly Gly Ser Gly Gly Gly Ser Phe Gly Asp Asn
625                 630                 635                 640

Leu Val Thr Arg Ser Tyr
                645
```

<210> SEQ ID NO 22

<400> SEQUENCE: 22

000

<210> SEQ ID NO 23

<400> SEQUENCE: 23

000

<210> SEQ ID NO 24
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Gly Ser His Cys Ser Ser Ser Gly Asp Pro Ala Glu Tyr Asn Leu Arg
1               5                   10                  15

Ser Arg Thr Val Leu Cys Gly Thr Cys Gly Gln Pro Ala Asp Lys Ala
            20                  25                  30
```

```
Ser Ala Ser Gly Ser Gly Ala Gln Val Gly Gly Pro Ile Ser Ser Gly
        35                  40                  45

Ser Ser Ala Ser Ser Val Thr Val Thr Arg Ser Tyr Arg Ser Val Gly
    50                  55                  60

Gly Ser Gly Gly Gly Ser Phe Gly Asp Asn Leu Val Thr Arg Ser Tyr
65                  70                  75                  80

Leu Leu Gly Asn Ser Ser Pro Arg Thr Gln Ser Pro Gln Asn Cys Ser
                85                  90                  95

Ile Met
```

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
gtaaggtaag aattgaattt ctcagttgaa ggatgcttac actcttgtcc atctag 56

<210> SEQ ID NO 31
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
gtgtgtatgc tcaggggctg ggaaaggagg ggagggagct ccggctcag 49

<210> SEQ ID NO 32
<211> LENGTH: 266

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gtgatgcggt tttggcagta catcaatggg cgtggatagc ggtttgactc acggggattt 60
ccaagtctcc accccattga cgtcaatggg agtttgtttt ggcaccaaaa tcaacgggac 120
tttccaaaat gtcgtaacaa ctccgcccca ttgacgcaaa tgggcggtag gcgtgtacgg 180
tgggaggtct atataagcag agctggtacc gtaaggtaag aattgaattt ctcagttgaa 240
ggatgcttac actcttgtcc atctag 266

<210> SEQ ID NO 33
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gtgatgcggt tttggcagta catcaatggg cgtggatagc ggtttgactc acggggattt 60
ccaagtctcc accccattga cgtcaatggg agtttgtttt ggcaccaaaa tcaacgggac 120
tttccaaaat gtcgtaacaa ctccgcccca ttgacgcaaa tgggcggtag gcgtgtacgg 180
tgggaggtct atataagcag agctggtacc gtgtgtatgc tcaggggctg ggaaaggagg 240
ggagggagct ccggctcag 259

<210> SEQ ID NO 34
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gtgatgacgt gtcccataag gcccctcggt ctaaggcttc cctatttcct ggttcgccgg 60
cggccatttt gggtggaagc gatagctgag tggcggcggc tgctgattgt gttctag 117

<210> SEQ ID NO 35
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gtgatgacgt gtcccatact tccgggtcag gtgggccggc tgtcttgacc ttctttgcgg 60
ctcggccatt ttgtcccagt cagtccggag gctgcggctg cagaagtacc gcctgcg 117

<210> SEQ ID NO 36
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
gtgatgacgt gtcccatatt ttcatctcgc gagacttgtg agcggccatc ttggtcctgc    60

cctgacagat tctcctatcg gggtcacagg gacgctaaga ttgctacctg gactttc     117
```

<210> SEQ ID NO 37
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
gtgatgacgt gtcccatggc ctcattggat gagaggtccc acctcacggc ccgaggcggg    60

gcttctttgc gcttaaaagc cgagccgggc caatgttcaa atgcgcagct cttagtc      117
```

<210> SEQ ID NO 38
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
gtgatgacgt gtcccatccc ccctccaccc cctagcccgc ggagcacgct gggatttggc    60

gcccccctcc tcggtgcaac ctatataagg ctcacagtct gcgctcctgg tacacgc      117
```

<210> SEQ ID NO 39
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
cccccctcca cccccctagcc cgcggagcac gctgggattt ggcgcccccc tcctcggtgc    60

aacctatata aggctcacag tctgcgctcc tggtacacgc                          100
```

<210> SEQ ID NO 40
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
ggcctcattg gatgagaggt cccacctcac ggcccgaggc ggggcttctt tgcgcttaaa    60

agccgagccg ggccaatgtt caaatgcgca gctcttagtc                         100
```

<210> SEQ ID NO 41
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
gggtggggcc cgcgcgtata aaggggggcgc aggcgggctg ggcgttccac aggccaagtg    60

cgctgtgctc gaggggtgcc ggccaggcct gagcgagcga                         100
```

<210> SEQ ID NO 42
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42
ggtgcgatat tcggattggc tggagtcggc catcacgctc cagctacgcc acttcctttt 60
cgtggcacta taaagggtgc tgcacggcgc ttgcatctct 100

<210> SEQ ID NO 43
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43
acttccgggt caggtgggcc ggctgtcttg accttctttg cggctcggcc attttgtccc 60
agtcagtccg gaggctgcgg ctgcagaagt accgcctgcg 100

<210> SEQ ID NO 44
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44
gctgagcgcg cgcgatgggg cgggaggttt ggggtcaagg agcaaactct gcacaagatg 60
gcggcggtag cggcagtggc ggcgcgtagg aggcggtgag 100

<210> SEQ ID NO 45
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45
attttcatct cgcgagactt gtgagcggcc atcttggtcc tgccctgaca gattctccta 60
tcggggtcac agggacgcta agattgctac ctggactttc 100

<210> SEQ ID NO 46
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46
tgggaccccc ggaaggcgga agttctaggg cggaagtggc cgagaggaga ggagaatggc 60
ggcggaaggc tggatttggc gttggggctg gggccggcgg 100

<210> SEQ ID NO 47
<211> LENGTH: 100

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 47
aaggcccctc ggtctaaggc ttccctattt cctggttcgc cggcggccat tttgggtgga 60
agcgatagct gagtggcggc ggctgctgat tgtgttctag 100

<210> SEQ ID NO 48
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48
agtgacccgg aagtagaagt ggcccttgca ggcaagagtg ctggagggcg gcagcggcga 60
ccggagcggt aggagcagca atttatccgt gtgcagcccc 100

<210> SEQ ID NO 49
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 49
gggaggggcg cgctggggag cttcggcgca tgcgcgctga ggcctgcctg accgaccttc 60
agcagggctg tggctaccat gttctctcgc gcgggtgtcg 100

<210> SEQ ID NO 50
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50
actgcgcacg cgcgcggtcg caccgattca cgccccccttc cggcgcctag agcaccgctg 60
ccgccatgtt gaggggggga ccgcgaccag ctgggcccct 100

<210> SEQ ID NO 51
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 51
ccctcgaggg gcggagcaaa aagtgaggca gcaacgcctc cttatcctcg ctcccgcttt 60
cagttctcaa taaggtccga tgttcgtgta taaatgctcg 100

<210> SEQ ID NO 52
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52
cttggtgacc aaatttgaaa aaaaaaaaaa accgcgccaa ctcatgttgt tttcaatcag 60
gtccgccaag tttgtattta aggaactgtt tcagttcata 100

<210> SEQ ID NO 53
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53
ggctgagcta tcctattggc tatcgggaca aaatttgctt gagccaatca aagtgctccg 60
tggacaatcg ccgttctgtc tataaaaagg tgaagcagcg 100

<210> SEQ ID NO 54
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 54
ggaagtgcca gaccggaggt gcgtcattca ccggcgacgc cgatacggtt cctccaccga 60
ggcccatgcg aagctttcca ctatggcttc cagcactgtc 100

<210> SEQ ID NO 55
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 55
ccctcgaggg gcggagcaaa aagtgaggca gcaacgcctc cttatcctcg ctcccgcttt 60
cagttctcaa taaggtccga tgttcgtgta taaatgctcg 100

<210> SEQ ID NO 56
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 56
cttggtgacc aaatttgaaa aaaaaaaaaa accgcgccaa ctcatgttgt tttcaatcag 60
gtccgccaag tttgtattta aggaactgtt tcagttcata 100

<210> SEQ ID NO 57
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 57

-continued ggctgagcta tcctattggc tatcgggaca aaatttgctt gagccaatca aagtgctccg 60
tggacaatcg ccgttctgtc tataaaaagg tgaagcagcg 100

<210> SEQ ID NO 58
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 58
ggaagtgcca gaccggaggt gcgtcattca ccggcgacgc cgatacggtt cctccaccga 60
ggcccatgcg aagctttcca ctatggcttc cagcactgtc 100

<210> SEQ ID NO 59
<211> LENGTH: 204
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 59
gtgatgcggt tttggcagta catcaatggg cgtggatagc ggtttgactc acggggattt 60
ccaagtctcc accccattga cgtcaatggg agtttgtttt ggcaccaaaa tcaacgggac 120
tttccaaaat gtcgtaacaa ctccgcccca ttgacgcaaa tgggcggtag gcgtgtacgg 180
tgggaggtct atataagcag agct 204

<210> SEQ ID NO 60
<211> LENGTH: 278
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 60
tcgaggtgag ccccacgttc tgcttcactc tccccatctc ccccccctcc ccacccccaa 60
ttttgtattt atttattttt taattatttt gtgcagcgat gggggcgggg gggggggggg 120
ggcgcgcgcc aggcggggcg gggcggggcg aggggcgggg cggggcgagg cggagaggtg 180
cggcggcagc caatcagagc ggcgcgctcc gaaagtttcc ttttatggcg aggcggcggc 240
ggcggcggcc ctataaaaag cgaagcgcgc ggcgggcg 278

<210> SEQ ID NO 61
<211> LENGTH: 305
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 61
gcgttacata acttacggta aatggcccgc ctggctgacc gcccaacgac ccccgcccat 60
tgacgtcaat aatgacgtat gttcccatag taacgccaat agggactttc cattgacgtc 120
aatgggtgga gtatttacgg taaactgccc acttggcagt acatcaagtg tatcatatgc 180
caagtacgcc ccctattgac gtcaatgacg gtaaatggcc cgcctggcat tatgcccagt 240
acatgacctt atgggacttt cctacttggc agtacatcta cgtattagtc atcgctatta 300
ccatg 305

<210> SEQ ID NO 62
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
gtacttatat aagggggtgg gggcgcgttc gtcctcagtc gcgatcgaac actcgagccg 60
agcagacgtg cctacggacc 80

<210> SEQ ID NO 63
<211> LENGTH: 279
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63
ggggaggctg ctggtgaata ttaaccaagg tcaccccagt tatcggagga gcaaacaggg 60
gctaagtcca cgctagcgtc tgtctgcaca tttcgtagag cgagtgttcc gatactctaa 120
tctccctagg caaggttcat atttgtgtag gttacttatt ctccttttgt tgactaagtc 180
aataatcaga atcagcaggt ttggagtcag cttggcaggg atcagcagcc tgggttggaa 240
ggagggggta taaaagcccc ttcaccagga gaagccgtc 279

<210> SEQ ID NO 64
<211> LENGTH: 262
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64
gtttgctgct tgcaatgttt gcccatttta gggtggacac aggacgctgt ggtttctgag 60
ccagggctag cgggcgactc agatcccagc cagtggactt agcccctgtt tgctcctccg 120
ataactgggg tgaccttggt taatattcac cagcagcctc ccccgttgcc cctctggatc 180
cactgcttaa atacggacga ggacagggcc ctgtctcctc agcttcaggc accaccactg 240
acctgggaca gtgaatcgcc ac 262

<210> SEQ ID NO 65
<211> LENGTH: 203
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65
tgatgcggtt ttggcagtac atcaatgggc gtggatagcg gtttgactca cggggatttc 60
caagtctcca ccccattgac gtcaatggga gtttgttttg gcaccaaaat caacgggact 120
ttccaaaatg tcgtaacaac tccgccccat tgacgcaaat gggcggtagg cgtgtacggt 180
gggaggtcta tataagcaga gct 203

<210> SEQ ID NO 66
<211> LENGTH: 251
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 66
gtttgctgct tgcaatgttt gcccatttta gggtggacac aggacgctgt ggtttctgag 60
ccagggggcg actcagatcc cagccagtgg acttagcccc tgtttgctcc tccgataact 120
ggggtgacct tggttaatat tcaccagcag cctcccccgt tgcccctctg gatccactgc 180
ttaaatacgg acgaggacag ggccctgtct cctcagcttc aggcaccacc actgacctgg 240
gacagtgaat c 251

<210> SEQ ID NO 67
<211> LENGTH: 304
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 67
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catg 304

<210> SEQ ID NO 68
<211> LENGTH: 1643
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 68
gttacataac ttacggtaaa tggcccgcct ggctgaccgc ccaacgaccc ccgcccattg 60
acgtcaataa tgacgtatgt tcccatagta acgccaatag ggactttcca ttgacgtcaa 120
tgggtggagt atttacggta aactgcccac ttggcagtac atcaagtgta tcatatgcca 180
agtacgcccc ctattgacgt caatgacggt aaatggcccg cctggcatta tgcccagtac 240
atgaccttat gggactttcc tacttggcag tacatctacg tattagtcat cgctattacc 300
atgggtcgag gtgagcccca cgttctgctt cactctcccc atctcccccc cctccccacc 360
cccaattttg tatttattta tttttaatt attttgtgca gcgatggggg cggggggggg 420
gggggcgcgc gccaggcggg gcggggcggg gcgaggggcg gggcggggcg aggcggagag 480
gtgcggcggc agccaatcag agcggcgcgc tccgaaagtt tccttttatg gcgaggcggc 540
ggcggcggcg gccctataaa aagcgaagcg cgcggcgggc gggagtcgct gcgttgcctt 600
cgccccgtgc cccgctccgc gccgcctcgc gccgcccgcc ccggctctga ctgaccgcgt 660
tactcccaca ggtgagcggg cgggacggcc cttctcctcc gggctgtaat tagcgcttgg 720

-continued

```
tttaatgacg gctcgtttct tttctgtggc tgcgtgaaag ccttaaaggg ctccgggagg    780

gccctttgtg cggggggggag cggctcgggg ggtgcgtgcg tgtgtgtgtg cgtggggagc    840

gccgcgtgcg gcccgcgctg cccggcggct gtgagcgctg cgggcgcggc gcggggcttt    900

gtgcgctccg cgtgtgcgcg aggggagcgc ggccgggggc ggtgccccgc ggtgcggggg    960

ggctgcgagg ggaacaaagg ctgcgtgcgg ggtgtgtgcg tgggggggtg agcagggggt   1020

gtgggcgcgg cggtcgggct gtaacccccc cctgcacccc cctccccgag ttgctgagca   1080

cggcccggct tcgggtgcgg ggctccgtgc ggggcgtggc gcggggctcg ccgtgccggg   1140

cgggggggtgg cggcaggtgg gggtgccggg cggggcgggg ccgcctcggg ccggggaggg   1200

ctcgggggag gggcgcggcg gccccggagc gccggcggct gtcgaggcgc ggcgagccgc   1260

agccattgcc ttttatggta atcgtgcgag agggcgcagg gacttccttt gtcccaaatc   1320

tggcggagcc gaaatctggg aggcgccgcc gcaccccctc tagcgggcgc gggcgaagcg   1380

gtgcggcgcc ggcaggaagg aaatgggcgg ggagggcctt cgtgcgtcgc cgcgccgccg   1440

tccccttctc catctccagc ctcggggctg ccgcaggggg acggctgcct tcgggggggga   1500

cggggcaggg cggggttcgg cttctggcgt gtgaccggcg gctctagagc ctctgctaac   1560

catgttcatg ccttcttctt tttcctacag ctcctgggca acgtgctggt tgttgtgctg   1620

tctcatcatt ttggcaaaga att                                           1643
```

<210> SEQ ID NO 69
<211> LENGTH: 231
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
gctccggtgc ccgtcagtgg gcagagcgca catcgcccac agtccccgag aagttggggg     60

gaggggtcgg caattgaacc ggtgcctaga gaaggtggcg cggggtaaac tgggaaagtg    120

atgtcgtgta ctggctccgc ctttttcccg agggtggggg agaaccgtat ataagtgcag    180

tagtcgccgt gaacgttctt tttcgcaacg ggtttgccgc cagaacacag g             231
```

<210> SEQ ID NO 70
<211> LENGTH: 15342
<212> TYPE: DNA
<213> ORGANISM: Homo sapiens

<400> SEQUENCE: 70

```
gtgagttcgc ccaggtggct gcgtgcctgg cggggagtgg agagggcggc gggccggcgc     60

ccctggccgg ccgcaggaag ggagtgagag ggcctggagg ccgataactt tgccatagtc    120

tcctccctcc ccggaactgc ccccagcggg tgactggcag tgtcaagggg aattgtcaag    180

acaggacaga gagggaagtg gtggtctctg ggagagggtc ggggaggata taaggaatgg    240

tgggggtatc agggacaagt tggggctggg gccggcctga attcggtcag attgggattt    300

gccaactatt tggagccggg gggaggggct tgagcaaaac agaactagcc ctgccagctc    360

gaagaactct gggcacccag gacacatcgg agtggcagaa agggtcctgt tagaactttg    420

ttagcgggct tggcactgtg ctagctttgc ccaagctggc tctgaacaca tgatgcccac    480

taagacataa ctctcaagtt ggcatctgtc cagcgtgttg gagcgaggtc aggaaggcag    540

ggcaatcccc cttttccctc ccaagggctt ggcggtggcc ccccctcagc atgaccttgt    600
```

-continued

```
cctgggttct aagggttggg aagttctccc tcactctgcc actctgcgtg tctgggacct    660
tccttgggct ctgacaggcc caccaaaaga gctccgggag atgagagatc ggctcccccg    720
cagctcccac agcccttggc ctgcttggcc caggaatgca agggagggag ggaggcagag    780
ggcagaggct cccagctcag gaagttgtgt tatgcccagg tctggccgca ctcctccctt    840
ggccctctgc ctagtgtctt cgagggttgg gggcactgtc cttccctcct tggggtgagc    900
cactttcatt ttcccagcgg ggccaggcag tctttgctcg ggcccatcct cttagctgct    960
gacgttttga tctttgtctt attgaagtgc tggaatacag tgacattttt gaaatccagc   1020
cgttggaaga ttcaggccac tcccacttta cccacccctg ccccacccta ccccacccta   1080
ctcaactgca ccttcttctt ttctaaaaaa gcctttggga gcttggaagt ataggccctc   1140
tcttccagcc ccatcaaaat ttgtttccct tcttcctgcc ttccctttct ctatgcagac   1200
ccaggccaag agcactaagg gtgcttggag atccgtaaag ggctgttggc tttgacttct   1260
tctctctctt ttatcatcta ctccaaactt ctgctcttcc tagaaccctt tgctaggtgt   1320
ggttttgttg cccaggctgg agtgcaatgg cacaatctcg gctcactgca acctccgcct   1380
cccaggttca agtgattctc ctgcctcagc ctcccgaata gctgagatta caggcatgtg   1440
ccaccatgcc gggctaattt tgtatttcta gtagagatgg ggtttctcca tgttcgtcag   1500
gctagtcttg aactcccaac ctcaggtgat ccacccgcct cagcctccca aagtgctagg   1560
attacaggca tgagccacca cgctgggccc atcacccttc tttctgaaga gtcaatggaa   1620
gttgtgtgta ggaagacagg cttaacggtt ttttttgag acagggtctt actctgtcac   1680
ccagactgga gtgaagtggt gcgatcttgg ctcaccacaa cctctgcctc ccaggctcaa   1740
aagattctcc tgcctcagcc tcctgagtag ctgggattat aagtgtgtgc caccacacat   1800
ggctattttt ttttttttt tttttttaa tttttagtag agatggggtt tcaccatgtt   1860
ggctaggctg gtctcaaact cctgacttca aatgatccac ctgcctcggc ctcccaaagt   1920
gctgggatta caggtgtgag ctaccatgcc cggccatcaa cctttatttt gttttttga   1980
gacggagtct tgctttgttg cccaggctgg agtacagtag tgtgacctca ggtcactgca   2040
acctctgcct cccaggttca agccatgctc ctgcctcagc ctcccaagta gctgggacta   2100
taggtgcctg ccaccacgcc cggctacttt ttatattttt agtagagacg gggtttcacc   2160
atgttggcca gggtgatctc gaactcctga cctcaagtga tctgcctgcc tcagcctccc   2220
aaagtgttgg gattagagac gggagccact gcgcctggct tcttttttc ttgagatagg   2280
gtttcactct gttacccagg ctggagtgca gtggcaaggt catggctcac tgcagcctct   2340
acctctctgg ctcaagccat cctcccgcct cagcctcctg agtagctggg accacaggca   2400
ggcaccacca cccacagcta atgtttttgt attattttgt agagatgggg ttttgccatg   2460
ttgcccacag tcttgaactc ctgggttcat tctgctgaaa gagaccacac ctgtcctttt   2520
ctttatttt attatatttt tcagagacag ggccttgccc tgttgctcag gctagagtgc   2580
aatggtacaa tcataacttg ctgcagcctg gaactcctcc tgggctcaag cgatcctacc   2640
gtctcacctt ccggaatagc tgagactaag ggcaggcacc accacgcttg gctaattttt   2700
ttttttttt ttttttttt gctttttgtt tgtaaagatg gaaacttgct atgttgctca   2760
gctggttccg aagttttggc ctcaagcaat cctcctgcct cggcctccgg aagcactggg   2820
attacaggca taagccacca ggcctgacgc caggcctgtc ttttttctac tagtgatatg   2880
aacaatttag ttagcaagac agataggaag caaggaaggg gagacccaga gaattcgttg   2940
cattctaaac tagtccactc atctaccaaa gccctgtgaa ggacattttt agcagtttta   3000
```

```
gcagttttct ggtcaaaact ttgatcgaga aacagattga gtggattcga tattctcttg   3060
ctcacccagc cacgccagtt tgtctcctct gcctcctagt gcagctgtcc aggcctggga   3120
caccaggcgg gtatgtgcgc atgtggggca gggcggaggt ggtgtgtgta cttgttatat   3180
ttagccacct ccctctgttc tcccccactg atcctggctg gaaaggctgg gcttccggaa   3240
aagagaggtg gatttgcaca cctggatccc aagctgatag aaagtggggt gaagacaaag   3300
gggactcaga ctggggtgtc tgtcctcttc tatgcccaca gtaggaggag ccaggattgg   3360
ttactccctg ctgggtctgc tgtgctcaga gtgaggtaga gaagtgggta gagtaaagaa   3420
tttgggagag gaaaaaaggc attttcccaa cccctcccac caaagcctag agagaaggtg   3480
ttgtctggtt taatgtttaa ttagagctca gagttcaggg ccagatttgg agttgggatg   3540
gaaagttgtt tttaagaccc tgtagcaatt tttgacccag cctgggtacc tcaaccacac   3600
tcaggagttt gggggacctt ctgttgggct ggattatagg ctccaagaag aaaccccttt   3660
cgccaatact ctctctctct tcttttttttg agacagggtc ttgttctgtt gcccaggctg   3720
gggtgcagtg gcatgatcac agctcactgc aacgtcagcc tcacaggctc tggtgattct   3780
cccacctcag cctcctgagt agctgggatt acaagtgtgt gccaccatgc ccagctaatt   3840
tttttttct ttttttttt ttgagacgga gtcttgttct gttgccaggc tggagtgcag   3900
tggtgcgatc tcggctcatt gcaacctcca cctcccaggt tcaagcgatt ctcctgcctc   3960
agcctcccga gtagctggga ctacaggcac atgccatcac gcccagttaa tttttgtatt   4020
tttagtagag ttggggtttc accatgttgg ccaggatggt cttgatctct tgacctcgtg   4080
atccgtccac cttggcctcc caaagtgctg ggattacagg tgtgagccac cgtacccggc   4140
cactaatttt tatatatttt gtagagatgg ggtttcaccg tgttgcccaa gctggtctcg   4200
aactcctagg ctcaagtaat ccacctgcct tggccttggc ctcccaaagt gctgggatgt   4260
ataggcatga gctaccgcac ctggtacccc ctgccccttc tctgtctctt tctagtctgt   4320
agcccaaggg atttggatac ccaagtgcag gcagaatggg aaggttgtaa gcaccaggga   4380
agcctgtctg gagtccaggc ttgcagctgg gccccacccc aggcaaggca gctgggtgga   4440
tgactcagat gctgcccccc tccctcccac cctggtggct ttacagaaga cagcaggaga   4500
cagggtggag acagcagttg tcttaaaggg aggagtggtg gtctgaatgt ctacctcttc   4560
tgccccccctc cccattgcat cctggagtcc cttgcctggc tccttcctga gaccctctgg   4620
tggtgtctgg acacatagct ctctctggac aggtaacatg cacaagtaat tagaatccag   4680
agttgagttc agagttatgg attgggctgc aggatagtgc cagggtctgt gccttcccat   4740
gtgaaactga tggaggaagg ctgagtcaga agtggggaga tccgaggccc acaaagcaga   4800
agcgctactt ccactccaaa aaggccctgg tgcttgacaa cttcctggat tgcccactgt   4860
tgcagcccca gtgtggacag gcagggagat gcaggctcca gttcatgtag gctctgatca   4920
agacaagaac agcaaaggcc acagaggcac agatgcttgt cccatgtcac acaataaagg   4980
ggtcagcact tgatcacagg ccttatgact tccagctggg tgtgctctta ccattaagcc   5040
tcacttctct agcttggggg acaggttgga gggaggatct agagggtgag gtaaggtgaa   5100
gtcaggtagc tgaggctcac ttctgcagcc tggaaactct gctctggggc cagtgacacc   5160
ttagtgctct atggccatac ttcgtggctc atgcctgtaa tcccagtgct ttgggaggct   5220
aaggcaggag gatcacttga ggccaggagt ttgagaccag tctgggcaac atagcaagac   5280
ccccttctgt acaaaaaaat tagccggtca acacctgtag tccagctgct tgggaagctg   5340
```

```
aggcgggagg atcacctgaa gccaggagtt tgaggctatt gtgagctatg actgcactac   5400
tgcactctag cctgggagag agaaagaccc tgtctctgaa aaagaaaaaa acaaaacaaa   5460
actctgctgt cctgcagggc ctgttagcat atgatcgata gcctttgctc cagcctatac   5520
ctggacccag gacccctgcc agcccctcaa tcgtgagacg gtcagagctc tgggaggctg   5580
gtgattcttg tcttgagact atcttgagac ttgtcatggg aattgtccac ccggattgaa   5640
aggaagctgt gccttttggc agacccatta ggttaatggg gttggagacc tttgaggatg   5700
catgggccct gggctttatc tgagggtatc tcctggtgtt acctctccaa ccctccacca   5760
ccaaatccat tctttttttt tttttttttt tttttttgac agtctcgctc cctggcccag   5820
gctggagtgc agtggcatga tcttggctta ctgcaatctc cacctcccag gctcaagtga   5880
tcctcccacc tcagcctccc aagaagctgg gactataggc acgtgccaca tgctcggcta   5940
atttttctat ttttagtaga gaccaggttt caccatgtta ctcaggctgg tcttgaactc   6000
tggggcttaa gcagtccacc caccttgacc tcccaaagtg ctgagagcca ctgagcctag   6060
cccaaatcca cgttctgatt caaagggaaa gaagaagggt gcagctaaac ctggggggtg   6120
agaagtactt aaaaagccca agagaaacaa aagagagaat aattcctcac taggaccccc   6180
tattgccttc ccactattgg tgcccttgct tggcacttcc cctggcctcc aggagtctga   6240
gacttactct tccatggatg tgcccattgc ccccacttcc aggtccaccc cccagtgatt   6300
cggtagctta gtgtctgcgc tgaagcccag gacagctgga tggacaactg gtagatccct   6360
tcacctacca actgtgcttt ctgctcccct ccccccttgct tccctcctcc ccagcccctc   6420
gccaccccta gcagctgcag cagccaagac caagtcttca gagacccaga cacaagggca   6480
gggttcattc cattctcacc tccttggggt cccagtgtac tgataggccg aactctaata   6540
ttataggaga tctctggaag attgcagggt ctcttatccc tcaataaggg gcaaggcaag   6600
ccgggcgcag tggctcacgc ctgtaatccc agcactttga gaagccgagg ggaacagatc   6660
acttcaggtc aggagttaag agaccagcct ggccaacatg gtgaaaccct gtctctacta   6720
aaaatacaaa aattaaccag aaatcgcttg aacccaggag gcagatgttg cagtgagccg   6780
agatcacgcc actgcactcc agccagggcg acagagcaag attccgtctc aaaaaaataa   6840
tactaataat aaataaataa ataaggggca aggtagtcca ccaacaaaat gacaggcagt   6900
gtgatatagt ggacacccta gccctcggtg cccttagttc tgtgtgtggc cctttcacta   6960
aattgctgtg tgaccttgag caaatcgcct cccctttctg gctttcctta gctgtaaaag   7020
aaagggattg gagcggaaag tctccagaga ccttttaggt tccaaagtag tacagtgacc   7080
cacaaagtga gaaaacagtc ttctaaaata ccaagttatt aatagtaaaa tcaaatataa   7140
ataatgtgaa tatagttaat agctaatgtt gttctcaata gaaatgtttc ccacaagctg   7200
tggaattaaa catactacca catttctcta tttccccgtg aaagtttgtt agaaatggtt   7260
aaattgtgac attaccctct tggcaaatgt tttgttttca ttgctactag gaaagggcaa   7320
ctcgttttcg atgcctctcc cttctggacg gtggaaaggg ctgtgtcata gagtaggaac   7380
gggagatgcg gcacaggaat ggctcccatt gacccgggtt gggggctagg gcgaaggcct   7440
aggagaggca gaactgttac cttagagctg gccaggatta gagaacagtg cctggaaccg   7500
gggggagggg cacggtgacc ttgggctgcc caccttctac ccttccagca cccatactgg   7560
ctcccccaac ctgcggctgg gctgggagga ggtcttggcc cctaccaatc ccttaaggaa   7620
ggggaaagag tttgggaagg ggagtcctcc cttcacccct gcctccccca agttgtgaga   7680
gaggaagccg gaatcctgcc tgctgaagcc aggaataatt ctggctgaga tcccaggccc   7740
```

-continued

```
ggcaggggcg ctgagtcatg gtagagggca gagtggagag tggacaggag accctaagct   7800
tgtccagtca gaaaagcaga ggctgagggg tggccttttc ttgagaacta cattcaagtt   7860
gcagcaagaa ggacagtggt ctgaatttga cggggacaaa tggaagggag ataggacaca   7920
tgagttcctt taggtctggc tcaggggagc tagacttcat ttcaaggggt ctaggttctg   7980
ggcagttgag aaggaggcta tttggggtca ccaaggctcc cctttcttcc caaagctcta   8040
acactgccac cttctgctgg ctaggagaga gctgtgtctt ctgaggctag agctggaatg   8100
cagtgagacc agactgccta ggtcctccct cacttcttct cctgaccttg ggtgtggct    8160
cccactctct cccagtgtcc tcagggttaa taactatgtg ccaccagata gagagttaag   8220
gggctgctga attggcttct tgtgaaggga atcccctaaa tgtccctcgt tttggtcact   8280
ggcctccctc ccgcccctt caggacattc tactatcttc ttaggccatc cctccctcct    8340
ccaggcacta cttcttttgc tctatcccca agccccaccc ctgcattttt gtgacaacac   8400
cggaatgatt tctagagaga gaggccagga agaaggaaag tggcacttgg caggagacct   8460
tgcaggggc ggctggtgag gaagccagcc gcccattgtc caggacccca gtgccctggc    8520
ctccggcctc aggcttctcc tgcctctgta caatgccacg ttgatacgcc cagcagctgt   8580
gactcaggcc tggcccctg ccaggcccag cacttctact ggagttgcgt ctgaacatgt    8640
caacaggctt cctatccctc tctcagcacc agttctcccc acttcagccc ctccctctgc   8700
ctggaattaa aacctggctt tgtcttaggg aaggacagct gggagcctag tggctctggt   8760
aggggatctg agaggcctca gaccctaggc atatttggct gtttggcagg tgtcacgccc   8820
aagggaagcg tgtggaagca gagccatgcc tgctgtgggt gcacatgccc gcgtgaggga   8880
gtcggggtgt ttcatcctgg ggcacctgtg ggcttttgag gtgtatgata ttcagaactt   8940
cacaggttgg ggtttgggga aggctcaagg ggcttctaag tccctggaac agctgccccc   9000
ctcagttcct ctctctctct ctcttttttt ttgagatgga gtctcgctct gttgcccagg   9060
ctagaatgca gtggcgcgat cttggctcac tgcaaactcc gcctcctggg ttcaagtgat   9120
tctcctgcct cagcctccca agtagctggg actataggtg cccgccacca tgcctggcta   9180
atttttgtat ttttagtaga aatggggttt caccatgctg gccaggatgg tctcaaactc   9240
ctgacctcgt gatccaccca ccttggcctc ccaaagtgct gggattacag gcgtgagcca   9300
ctgcgcccag cctcagttcc tctctttaag gtctcctttc cagagaggga tagcacctca   9360
aatgccaggg aggggaattc tccacatcct gcccttaccc gagttgtggc agacccacag   9420
actagccaag aaaccaagca gtggttactt tgccgggttg gggggaggt aggggctatc    9480
aaacctcatg attggccgca cacaaaggtg tgagtatgtg tatatttgag ggtgggtggg   9540
agtggcactt tcactaggcc tccgtatcac tctctgactg gggtatctcc cagcaagcga   9600
gacagaggca gacacgcttc ccagactgtc ttactgggtc tctctgtgtt attctctgca   9660
gtgtctgtgt gtatcgtgcc attttctatg ttttgcacca atctgctgtg agtgtcctca   9720
ggtgacctgg gggcaggttt ttagtgcctg agcctacccg tctccaggct ttagtttccc   9780
cctgtaaaag tataggagtt ggttcaagag aaggttcctc tagaagcctt gagcctgtga   9840
accgtctagt ctccgggtat ttgtgggaca cacagaaaaa gccccacgac ccaacaggta   9900
gaacactggc tgaaatcagc agggcagagc tgagacaggc tcaagtaggc tgaggggtag   9960
ggaggttttg ggtgaatggg agggagggac agagagaagg aggatatatt gcagtaggag  10020
gagttgctgg aacaaaagga ggggtggtag gagtggcttg ggtggcagc agaagacgcc   10080
```

ctgtcacatg gcgggaagtc agcctgggca gaggtctagg tgtccaggag ggcctgggtg 10140
tggtggctca cgcctgtaat cccaggactt tgggaggctg atgcaggagg atcacgtgag 10200
gtcaggagtt caagaccagc ctggccaaca tggcgaaacc ctatctctac taaaaatgcc 10260
aaaaattagc tgggtgtggt ggcaggcgcc tgtaatccca gctactctgg aggctgaggc 10320
acaagaattg cttgaacctg ggaggtggag gttgcaggga gccgagatcg cgccactcta 10380
ctctagcctg ggcaacacag tgagactctg tctcaaaaat aataataata ggggctgggc 10440
gcggtggctc atgactgtaa tcccagcatt ttgggaggtg gaggcgggtg gatcacctga 10500
ggtcaggagt ccgagaccag cctggccaac atggcaaaac tccgtctcta ctaaaaatag 10560
aaaaattagc taggcatggt ggtgcaggcc tgtaatccag ctactcggga ggctgagaag 10620
caggagaatc acttgaacct gggaggtgaa ggttgcagtg agatcacctg ggcgacagaa 10680
tgagactcca cctcaaaata ataataatag taataataat aaatgaaaaa ttttaaaatt 10740
aaacaattaa aaattttaaa ttaaaattaa acaaattaga tgcccaggag gatacaggag 10800
agcatttgcc accaggcgga ctccctgtac ccacccggcc acagggggcg atgttcctgg 10860
gagacaggaa atgcccaggg gctgggagac cctctgctct tctgctccct tcctgtgtgc 10920
tgcctggcaa tggggaactc tgagggctgg tgagcagggc tgctgaggag tgggtctaag 10980
gagtccctgc agggctgggc cagctcctcc acctcccctt tgtcttcccc tcccacttgt 11040
tatttttagc tacagtgtct gtccctcttg cttctccccc agattgggag aggaaacgga 11100
ggcctctccc tccgggccta gcctgttgcc cccagcaacc gggcccaaac aggcctgtgg 11160
ccggccctgg cttccatatc tggcatcaga gttgggctga gcagggtgac tcagagggtg 11220
ggtcagcgcc tggcccggtg cccacctagc ccctttgctg tgctggtgcc tttcttcccc 11280
aaacagcccc aagggcccgg gcctgctgca gctggggagc cggacttcct tgtcccacca 11340
ggcacagctc ttcagacccc tgccttgggt cacatttgca agtgccaact ctcatttcta 11400
ccttattctt ttcctctctg ttcccctccc cacccccctct cttccctctt tctgagatca 11460
gatttgccag tgatgggaag agttagaaac aggatgccca gcccttctcg cctcaagagg 11520
ccactgggat gcagccactc ctgtgcttgg ggaacctgga ggatgcaagg gaaaggactg 11580
gcactctgct ggcacagcac ccggcctggg gcaggacacg ggcgaagcca gggtctcccc 11640
tgtgagcact agaggatttc ccgacccctg cccgggtatt gtgtgcctga gcatgagtca 11700
cctgaggggc ccaggttccc acccttccca gctcctctgg cctgccccac cctgtcctcc 11760
ctgccaaccc agcacgggga cggcactcag cgtgtgctca gctttcctga tgccaacccc 11820
cagtggagtg ggctgcacca ccaccctggg accgaatgcc tggctagggt ctactttggt 11880
ccctgctagg tctgaggacc cctcctagga aggaaatggc acttgggggc gggggcaggg 11940
aggagggagg agagacactg ggctctactg taccccctagt catctcttgg ggtgtgcgtg 12000
tggctccctg gccacagagc tcccaaggtc tgagtcatga gcccatgggt gatagtggct 12060
tcttccccgc agatgggagc tccccgtgcc taagaaaacc acaaaggttc ttcctcactt 12120
ccctctctgc tcgtggtttt tctcatctgc agggtgtgtc ttagtccttt aatctcctct 12180
ctttgcagtg ctagtcaaaa cctccaccag ggaaagacaa ataacccccct tactgttttt 12240
tttttttttt tttttttttt ttgagatgga gtctcgctct gtcacccatg ctgtagtgca 12300
gtggcacaat ctcggctcac tgcaacctcc gcctcccaag ttcaagtgat cctcctacct 12360
cagcctcctc agtagctggg actacaggtg cacaccaccg tacccagcta aatttttttt 12420
tttttttttt gagatagagt ctcactctgt cacccaggct ggagtacagt ggtacaatct 12480

-continued

```
caactcacta caatctccgc ctcccaggct caagcaattc tcgtgtctca gcctcccaag  12540
ttgctgggac tatggacgtg caccaccttg cccgactaat tttgtattt ttgatagagt  12600
cagagtttca ccatgttggc aggctggtct cgaactcctg gcctcaagtg atccacctgc  12660
cttggcctcc caaagtgctg ggattacagg tgtgagccac cacactcagc cagcccccctt  12720
actttccttg gagaccatat actgtggctt gtgccaaagt ggtacagcat ggatttccag  12780
ctcccctatc tacttgctgc gggaccctag atatagcttt ctgtgcctat ttcctcaatt  12840
gcataggaat agcacctatc gcatagggta gctgtgaaga tgacgtgagt taacataata  12900
tttagagcag tgcttggtac ctaataagct ctatataagt gtttgctatt atattattat  12960
tatcactgcc accaccgctt ttgcaagcag cagaaggtga agaggttaga ctgaagaaaa  13020
aacttctgtg ctcatcagcc cataagctcg cagagcacag ggatcatgca tctatgtttt  13080
cctcagtcag tgtctgccag gcactggcaa ggaaaggctg ttaccagggg gaactccagg  13140
aattcctcct ggcacctaag gaggctgggg agacaggact agggaaaagg tgcccttgag  13200
acaccttctg aaatcatccc attgccttcc agcttctttc agctcaggct ggctggtcag  13260
ggaaacgctt tgtgccatag tgtctgccct cttcctcctc ctggcttctc cattctctct  13320
ggaacttgtg gcttaggaaa gcagtgaggt ggaggaggag gaaccctaga tcagcagcta  13380
gaattgactg gaatgctgct gctggctttc ggtaattgac actgggccat tcaccttcct  13440
cctttgcacc tcagtttcct catctataaa agggagaggg ttgagctgaa tcaactctaa  13500
gctccttcta gttctctaaa ttctgagagc ctcctagtac agccagcagc agccattagc  13560
cttcagggta gagaggcctc ttctgggaag ccccagccag cctgggggtc agcccaagga  13620
gctcggaatc taagttgccc cagttgcttc actttaccag cggtttttct tcatttttccc  13680
tcctccccct gcagctgctt cagcttcgga aaagttctga agtcatggaa agttggggct  13740
gtgctcccag ccaggggcta ggccggatgg cagccaaaac ctgagctggg ttttgacttt  13800
atttttagct tttctgactg agacagagga gggaatacat tctccggttc tggaaggggc  13860
tcttttttgc aggagacaga cacttacatt aaacaacttg ttctgaggtg tggccagagg  13920
cctggactga gcaagtgtgc aggctggggg agcttcctct ggcttctcat gtccttcccc  13980
tgcccctctg agtgtcactc tatcctcctc cctgcctggt ggggggaggt gggggtgact  14040
cctttttgg actctcctaa gcagaacact gcctgggtct cgtcctccag agcttctgca  14100
aatctagcct tccctatccc tcttcacagt gaattgctgg gcctcttgga gtttaggact  14160
tttgtggtag aagaaaaatg ttggcagggc tgcttttctc ctttccagga tagatttttc  14220
cttctgccca cgcttggttt tcctttttc catctgctgt ggtgggctca tgcttaagca  14280
ctgatgagtt acagatggca gctggaacca ggtcctctgg atctttccct ccgctccctg  14340
ggtctgctgc tttctctcac cctatatttg tgaagcaatt gtaacatcta gaaagttctt  14400
gggttctctg gaggttttta agaaaatagg acctttctat ttctccagtc cactagcaaa  14460
aataatcagg ggcccagaaa aggtgaggga ggtggcagag gcagcgctgt tcgactggtt  14520
atagctaaag ctttacccac tttgaggagc agggaggctt aaagctgggg cccagatgga  14580
cctggaggcc tgggatccac atctggaacc agatgctgag gctatggtag atgggtaggg  14640
ctcagccttc tcccagggca cggatgaggc aggagggagg gaggcaggga cccctctgtt  14700
cagtgcagat cagggcaccc agactgggtc ctgagaaagg aaagggtcaa tattgtgcct  14760
ggtcatcctt gtctgaggtc cctctgagct ctaaccagac tttccttccc cacagtccca  14820
```

-continued

```
catgtgtaaa agggactagg agaggtgacc agtacctttg gggctcagat cgagaagtgc  14880

tagggacatg tgggccatga gcttagttgt caggctcctc agagggaggg aagcttggcc  14940

aaagggaagt gagtagagtc cagggagaag gctaagtaag gccctgtgtg ggaaggggca  15000

ggagacaaag gtacccctgt ctctttggga aagaatggga ggagagagag ggaaaagcat  15060

tcatatcacg gggtagagct ctgcccttgg ccccaggcac gttcctgagc cctgagtcat  15120

gggaagggtg gagaagcagg aagggggttt tcaaggacct tggggaggtg ggagcccagc  15180

cccagaggca agcagatgca aaccaaccta atgcaaggat gccctctcct ggtaattgca  15240

ggcatagcag cgccagcccc catggctgac ctcctgggag cctggcactg tctaggcaca  15300

cagactcctt ctcttaaatc tactctcccc tctcttcttt ag                      15342
```

<210> SEQ ID NO 71
<211> LENGTH: 3629
<212> TYPE: DNA
<213> ORGANISM: Homo sapiens

<400> SEQUENCE: 71

```
gtgaggccac cctgcagggc ccacccatgg ccccacctaa cacatgtaca ctcactcttc     60

tacctaggcc ctcccccatg tggtgcctgg tctgacctgt cacctgattt cagagccatt    120

cacctgtcct agagtcattt tacccactga ggtcacatct tatcctaatt tggctgccaa    180

tgggatctac cacagtgaat ttaaaataat ccaggaggcc gggcatggtg gttcacgcct    240

gtaatcccag cactttagga ggccgaggtg ggccgatcac gaggtcagga gatcgagatc    300

atcctgacta acatggtgaa accccgtctc tactaaaaat acaaaaaatt agcctggcat    360

ggtggcgggc gcctgtagtc ccaactactc gggaggctga ggcaggagaa tggcgtgagc    420

ctgcgaggca gagcttgcag tgagctgaga tcatgccact gcactccagc ctgggcaaca    480

gagtgagact ccgtctcaaa aaaataataa taataataat aaaaataatc caggccatgt    540

gtggtggctc atgcctgtaa tcccagcatt ttgggaggcc aaggaggcag gattgcttga    600

gtccaggagt ttgagaccag cctgggcaac acagacccca tctctagaaa ataaaaattt    660

aaagaaatta gctgggcatg gtggtgtgca cctatagtcc cagctacttg ggaggctgag    720

gcaggaggat ggcttgaacc tgagaggtcg aggatacagt gagctgtgat tgcaccactg    780

cacttcagcc tgggtgacag agggaaaccc tgtctctaca taaataaata cataaaataa    840

aataatccac aagccatttc tacttaactt tgcaatgaac tgtacctgac cctagatccc    900

tcccagtttg gccctccggt atacaagggc ctcctatagg cccttgtgat ttctctgggg    960

aaaaggagga ctggagttga tcatttattg aggccatcag aagcggatgg ctaattacat   1020

atgggacatg tgttaataat gctttgtgta tatagagtgg cctttacttt caaaacactc   1080

ttctccaatt tatcatgtta aaagctagga attgggctgg gtgcagtggc tcacgcctat   1140

aatcccagca ctttgggagg ccaaggcggg tggatcattt gaggtcagga gtttgagacc   1200

agtctgacca acatggttaa actccgtctc tactaaaaat acaaaattag ccaggcgtgg   1260

tggcacacac ctgtagtccc aacaactact tgtgaggctg aggcaggaaa atcatttgaa   1320

cccaggatca gaggttgtgg tgaactgaga ttgcaccatt gcactccagc ctgggcaaca   1380

agagcaaaac tctatctcaa aaaaaataaa aaatagccag gcacggtggc tcatgcctgt   1440

aatcctagca ctttgggagg cagaggtggg cagatcacct gaggttagga gttcgagact   1500

agcctggcca acatggtgaa accccatctc tactacaaat acaaaaatta gctaggcatg   1560

gtggcagcca cctgtaatcc cagctacttg ggaggctgag gcaggagaat cgcttgaacc   1620
```

-continued

```
cgggaggtgg aggttgcagt gagccaagat cgggtcacag cactccagcc taggcaacag   1680

agcgagactc catctcaaaa aaacataaat aaataaaaat aaaaataaat aataaataaa   1740

agctaagaat caaagaagca gtttattcct aatttcacag tctcatctgt tcatagtggg   1800

gccaggatta gagtcagtgg ccaagcttcc atcctgggtt ctttcccttc ccaggcccta   1860

ccatcatagt ataccaggga aagacctgga gaagccagca ggttgaccac cgaaccaagg   1920

ctgggccacc ttcctcctgg gtctggtctc cagcctccca gttgtaccct tcccccagcc   1980

cttcctggat gcactgatca gcctgtgctt ccttgccctg tttttcttta taaatagagc   2040

catgttctcc tctctctctc tctctttttt tttttttttt ttttgagatg gagtcttact   2100

ctgtcaccca ggctggagtg caatggcacg atctcagctc actgcaacct ctgtctccca   2160

ggttcaagca attctcctgc ctcagcctcc cgagtagctg ggattacagg tgcccaccac   2220

catgcccagc tactttttgg atttttagta gagacagggt ttcaccatgt tggtcaggct   2280

ggtcttgaac tcctgacctt aggtgttctg cccgcctcag cctcccaaag tgctgggatt   2340

acaggcgtga gccaccacgc ctggcaagac gtgttctctc tatgttgttg aggctggtct   2400

tgaactcctg gctgcaagag atcttcctgc ctcagcctcc caatgtgctg ggattatagg   2460

catgagccac cacacttagc ccagcctgtg ctttcttaaa tgaaaatcta agcatacggc   2520

tgggtgtggt ggctcacgcc tgtaatccca gcattttggg aggccaaggt gggcagatca   2580

cgaggtcagg agatcgagac tatcctggcc aacatggtga aaccctgtct ctactaaaga   2640

tacaaaaatt agctgggtgt ggtggcccat gtctgtagtc ccagctactc gggagactga   2700

ggcaggagaa tggcatgaac ctgggaggca gagcttgcag tgagctgaga tcgcgccact   2760

gctctccagc ctaggtgaca gagcgagact ccatctcaaa aaaaaaataa aaataaaaaa   2820

aagaaaatct aagcgtggtg ctcccctgct caaacatcct caggttcttt tcatggcaga   2880

taagggcatc tcttcatgag ccagcccctg cctactgacc cagccacctc tcccatccct   2940

tcccaccccg tacttcaggc ttcagcagta ctgatctttc caaagacccc agaacacaca   3000

tgccttcata cctctgtgcc tgtacatgct tgtttctgcc cttgaaatca tgacagtagc   3060

tctctgtagg ccccgctagc ctgtcccttg ggtcttagcc tcttggaggc cttcccagag   3120

ccccccaaaa gtaccccagg catactttgg ttccttctct catgtcccct cagtactttg   3180

cacatacctc ctttatagca gttgctatgt tgtgccagag aagggagtcc tgtggctggg   3240

gggcatatat cttttctttt tgagacagag tctagctgtg tcacccaggc tggagtgcag   3300

tagtgcgatc tcggctcact gcaacctcca cctcctggat tcaagcgatt cttgtgcctc   3360

agcctcctga gtagctggga ctacaggcgt gtgccaccat catgcctggc tacttttttg   3420

tattagatat atattttctc tcttagcaca gtacctacca agagtgagtg agtagatgtc   3480

ctgacccctg caggcatcca aggccctcct tccctggacc tgtttccaca tgtgtgaagg   3540

ggtgcacagg cagcagccca cctctcagct tccttccagt tcttgtgttc tgtgacccct   3600

tttcctcatc tctgcctgct tcctcacag                                     3629
```

<210> SEQ ID NO 72
<211> LENGTH: 276
<212> TYPE: DNA
<213> ORGANISM: Homo sapiens

<400> SEQUENCE: 72

```
gtggggactg tgctttgcaa gccagagggc tggggctggg tgatgacaga cttgggctgg     60
```

-continued

```
gctagggggg accagctgtg tgcagagctc gccttcctga gtcccttgcc ctagtggaca    120

gggagttggg ggtggccagc actcagctcc caggttaaag tggggctggt agtggctcat    180

ggagtagggc tgggcaggga gccccgcccc tgggtcttgg cctcccagga actaattctg    240

attttggttt ctgtgtcctt cctccaaccc ttccag                              276


<210> SEQ ID NO 73
<211> LENGTH: 211
<212> TYPE: DNA
<213> ORGANISM: Homo sapiens

<400> SEQUENCE: 73

gtgcttgctc tcgattggtt ccctcactgc ctctgccctt ggcagcccta cccttaccca     60

cgctgggcta tgccttctgg ggatcaggca gatggtggca gggagctcag ggtggcccag    120

gacctggggc tgtagcagtg atgcccaact caggcctgtg cctccacccc tcccagtcac    180

cacagtccta accctttgtc ctcccctcca g                                   211


<210> SEQ ID NO 74
<211> LENGTH: 588
<212> TYPE: DNA
<213> ORGANISM: Homo sapiens

<400> SEQUENCE: 74

gtgatacccc acctcacccc tctctccagg ggcctagagt ctgggccgga tgcaggctgg     60

aagcccaggg ttgggggtgg gggtgggggt gggaggttcc tgaggaggag agggatgaaa    120

agtgtcccca caaccacaga gaagggtcgc aggatgtgga gtcagatggc ctgtgtgctg    180

tttctgtaca ctcttacctc accttcactt ctcagggctt tggttttccc attcgaaaat    240

ggaggctgtt cttaatctcc ctaactcaga gttgccacag gactctgcaa tgtgaggtgt    300

taaaagcatc agtatttttc tagttggctg tgctatttgt gacaggagaa aaagtctagc    360

ctcagaacga gaggtttcag ttagacaagg ggaaggactt cccagttgcc agccaagact    420

atgtttagag cttgtgatgt tcagagctgg ctctgatgag ggctctgggg aagctctgat    480

tgcagatcct ggagagagta gccaggtgtc tcctacaccg acccacgtcc ctccttcccc    540

atacttaggg cccttgggag ctcaccaaac cctcccaccc cccttcag                 588


<210> SEQ ID NO 75
<211> LENGTH: 92
<212> TYPE: DNA
<213> ORGANISM: Homo sapiens

<400> SEQUENCE: 75

gtgggctggg gagacgtcgg ggaggtgctg gcagtgtcct ctggccggca actggccttg     60

actagacccc cacttggtct ccctctcccc ag                                   92


<210> SEQ ID NO 76
<211> LENGTH: 484
<212> TYPE: DNA
<213> ORGANISM: Homo sapiens

<400> SEQUENCE: 76

gtaggctcct gctcagggtc taaggggata cagctgcatc agggagagag tggcaagaca     60

gaaggatggc atgtggagag aggaacatcc ttgccctcag agggtggacc agggtgagcc    120

tgtatatctc ctccacactc tggttccagg cctggctcct ggactctttg gctgtgagac    180

cttgagcagg ttatttaacc tctcagagca tcagtttcct catctgtaaa atggggatga    240
```

atactgatcc ctaagtcttt gagttgtcag gaagatgaaa gataaggtat ccgtgtgcct 300
ggtgctgcgt atgtgtccac agatcatggc tattatcccc gggggaaggg cagtgacagg 360
ggtgtgtgta gatggaagga gaggcctcaa ttgcaggcag gcagagggct gggcctttga 420
gcaagataca cccaagagcc tgggtgagcc tccccgacct tcctcttccc tatcttcccg 480
gcag 484

<210> SEQ ID NO 77
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
gtgagtggca gggcgcttgg gactctgggg aggccttggg tggcgatggg agcgctgggg 60
taagtgtcct tttctcctct ccag 84

<210> SEQ ID NO 78
<211> LENGTH: 421
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78
gtaagtaggc ctgggcctgg ctgcttgctg gacgaggctc cccctgatgg ccaacatcgg 60
agccagctgc ccccaaccca agtttgccaa ttcagggccc ctttctagag ctctctgttg 120
caggctccag acttctccac ccagtaggca aaccaaaaga tgcttcctca acagcacaag 180
gggtggaagt tagacagtga ggattgttaa aggcagagcc atactcctac ccggagagct 240
tgacagtgtc cctctggggt ggaaatgagt tccttagctc catcaccaca gaggacagag 300
taagcagcag gccggacaaa gggcaggcca caagaaaagt tgcaggtggt cactggggta 360
gacatgctgt acaacccttc cctggccctg acccttggac ctggttccat gtccccacca 420
g 421

<210> SEQ ID NO 79
<211> LENGTH: 744
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79
gtgagtggta gccgccgctg aggccgagcc tgcactgggg ccacccagcc aggcctgggg 60
gcagcctctc cccagcctcc ccgtgccaaa aatcttttca ttaaagaatg ttttggaact 120
ttactcgctg gcctggcctt tcttctctct cctccctata ccttgaacag ggaacccagg 180
tgtctgggtg ccctactctg gtaaggaagg gagtgggaac tttctgatgc catggaatat 240
tcctgtggga gcagtggaca agggtctgga tttgtcttct gggaaaggga ggggaggaca 300
gacgtggggc atgcccgccc tgcctctctc ccccattctt gttgcatgca tatcctctca 360
tttccctcat ttttcctgca agaatgttct ctctcattcc tgaccgcccc tccactccaa 420
ttaatagtgc atgcctgctg ccctacaagc ttgctcccgt tctctcttct tttcctctta 480
agctcagagt agctagaaca gagtcagagt cactgctctg gttctctgtc cccaagtctt 540
cctgagcctt ctccccttt atgtcttccc tctcctcctc cgggccccta gcctcccaaa 600
cccccattgc ccgctggctc cttgggcaca gaaccacacc ttcctgcctg gcggctggga 660
gcctgcagga gcctggagcc tggttgggcc tgagtggtca gtcccagact cgccgtcccg 720
cctgagcctt gtctcccttc ccag 744

<210> SEQ ID NO 80
<211> LENGTH: 322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80
gtgagttgtc tctgctttgt ctccaaatcc tgcaggcggg tccctggtca tcgaggggta 60
ggacgaggtg gccttgcagg ggggagagcc tgccttctct tccgcagccc gggggagtgg 120
gagcctcctc cccacagcct gagtcctaga cagcccacct ctgcatcctg cccctcttgt 180
ctgagcccca gactggaggg caggggcagg gctggagtgt gagggatggg ggagatgcta 240
cctcccttct aggggccagg ggagggaggg tctgggtcca ggccctgctg ctcacacctc 300
tctcctctgt tttctctctt ag 322

<210> SEQ ID NO 81
<211> LENGTH: 356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81
atggagaccc cgtcccagcg gcgcgccacc cgcagcgggg cgcaggccag ctccactccg 60
ctgtcgccca cccgcatcac ccggctgcag gagaaggagg acctgcagga gctcaatgat 120
cgcttggcgg tctacatcga ccgtgtgcgc tcgctggaaa cggagaacgc agggctgcgc 180
cttcgcatca ccgagtctga agaggtggtc agccgcgagg tgtccggcat caaggccgcc 240
tacgaggccg agctcgggga tgcccgcaag acccttgact cagtagccaa ggagcgcgcc 300
cgcctgcagc tggagctgag caaagtgcgt gaggagttta aggagctgaa agcgcg 356

<210> SEQ ID NO 82
<211> LENGTH: 157
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82
caataccaag aaggagggtg acctgatagc tgctcaggct cggctgaagg acctggaggc 60
tctgctgaac tccaaggagg ccgcactgag cactgctctc agtgagaagc gcacgctgga 120
gggcgagctg catgatctgc ggggccaggt ggccaag 157

<210> SEQ ID NO 83
<211> LENGTH: 126
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 83
cttgaggcag ccctaggtga ggccaagaag caacttcagg atgagatgct gcggcgggtg 60
gatgctgaga acaggctgca gaccatgaag gaggaactgg acttccagaa gaacatctac 120
agtgag 126

<210> SEQ ID NO 84
<211> LENGTH: 171
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 84
gagctgcgtg agaccaagcg ccgtcatgag acccgactgg tggagattga caatgggaag 60
cagcgtgagt ttgagagccg gctggcggat gcgctgcagg aactgcgggc ccagcatgag 120
gaccaggtgg agcagtataa gaaggagctg gagaagactt attctgccaa g 171

<210> SEQ ID NO 85
<211> LENGTH: 126
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 85
ctggacaatg ccaggcagtc tgctgagagg aacagcaacc tggtgggggc tgcccacgag 60
gagctgcagc agtcgcgcat ccgcatcgac agcctctctg cccagctcag ccagctccag 120
aagcag 126

<210> SEQ ID NO 86
<211> LENGTH: 221
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 86
ctggcagcca aggaggcgaa gcttcgagac ctggaggact cactggcccg tgagcgggac 60
accagccggc ggctgctggc ggaaaaggag cgggagatgg ccgagatgcg ggcaaggatg 120
cagcagcagc tggacgagta ccaggagctt ctggacatca agctggccct ggacatggag 180
atccacgcct accgcaagct cttggagggc gaggaggaga g 221

<210> SEQ ID NO 87
<211> LENGTH: 223
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 87
gctacgcctg tcccccagcc ctacctcgca gcgcagccgt ggccgtgctt cctctcactc 60
atcccagaca cagggtgggg gcagcgtcac caaaaagcgc aaactggagt ccactgagag 120
ccgcagcagc ttctcacagc acgcacgcac tagcgggcgc gtggccgtgg aggaggtgga 180
tgaggagggc aagtttgtcc ggctgcgcaa caagtccaat gag 223

<210> SEQ ID NO 88
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88
gaccagtcca tgggcaattg gcagatcaag cgccagaatg gagatgatcc cttgctgact 60
taccggttcc caccaaagtt caccctgaag gctgggcagg tggtgacg 108

<210> SEQ ID NO 89
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89
atctgggctg caggagctgg ggccacccac agccccccta ccgacctggt gtggaaggca 60
cagaacacct ggggctgcgg gaacagcctg cgtacggctc tcatcaactc cactggggaa 120

<210> SEQ ID NO 90
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
gaagtggcca tgcgcaagct ggtgcgctca gtgactgtgg ttgaggacga cgaggatgag 60
gatggagatg acctgctcca tcaccaccac 90

<210> SEQ ID NO 91
<211> LENGTH: 111
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91
gaagtggcca tgcgcaagct ggtgcgctca gtgactgtgg ttgaggacga cgaggatgag 60
gatggagatg acctgctcca tcaccaccac gtgagtggta gccgccgctg a 111

<210> SEQ ID NO 92
<211> LENGTH: 270
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92
ggctcccact gcagcagctc gggggacccc gctgagtaca acctgcgctc gcgcaccgtg 60
ctgtgcggga cctgcgggca gcctgccgac aaggcatctg ccagcggctc aggagcccag 120

-continued gtgggcggac ccatctcctc tggctcttct gcctccagtg tcacggtcac tcgcagctac 180
cgcagtgtgg ggggcagtgg gggtggcagc ttcggggaca atctggtcac ccgctcctac 240
ctcctgggca actccagccc ccgaacccag 270

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
agcccccaga actgcagcat catgtaa 27

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 94
gctcttctgc ctccagtgtc 20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 95
atgatgctgc agttctgggg 20

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 96
cctggtgtgg aaggcacaga ac 22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 97
ggctaccact cacgtggtgg tg 22

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
accaagaagg agggtgacct 20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
agcctgttct cagcatccac 20

<210> SEQ ID NO 100
<211> LENGTH: 952
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100
gagtgggtaa gtgtgaaaaa tctgcatgtg tggctgaaga tgggcacaga cacggtcaag 60
tctgtatgtg agagtgctga actggggttc tgtgtgaaaa tctgcctgag gcggcaggga 120
gaatcactgc cattgcgtga gcaggttgga tgttggccac tctatcagga gcattaggga 180
aggggtgggg actccagacg tgtccccaaa ccagggtggc ctcaagacct tgggagaaca 240
cttgtctgaa gacttgggga acagaaggag accaggcatg gcacttatgc agactgaggc 300
caggacagaa tttcctgaca aaagaaaact gagccatgga gatggacaac agatcccttc 360
cctgggcacc atactgcagc ttttagtccc tagcactggg ggctccagta ctaacagcag 420
gaagatgctc ccagcctggg actgtgtgag ggaggtcaga atgggaagga gaggctgggg 480
aacaggggag gaaagcccat ggttgggagg cggaggacag gcatttggcc tgcaggagaa 540
ggtgaccctc acccatgttt tcagttcacc cttcgggtta aaaataactg aggtaagggc 600
catggcaggg tgggagaggc ggtgtgagaa ggtcctgtct tcccactatc tgctcatcag 660
ccctttgaag gggaggaatg tgcccaagga ctaaaaaaag gccgtggagc cagagaggct 720
ggggcagcag acctttcttg ggcaaatcag ggggccctgc tgtcctcctg tcacctccag 780
agccaaagga tcaaaggagg aggagccagg aggggagaga ggtgggaggg agggtccctc 840
cggaaggact ccaaatttag acagagggtg ggggaaacgg gatataaagg aactggagct 900
ttgaggacag atagagagac tcctgcggcc caggtaagag gaggtttggg gt 952

<210> SEQ ID NO 101
<211> LENGTH: 406
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101
agcagtctgg gctttcacat gacagcatct ggggctgcgg cagagggtcg ggtccgaagc 60
gctgccttat cagcgtcccc agccctggga ggtgacagct ggctggcttg tgtcagcccc 120
tcgggcactc acgtatctcc atccgacggg tttaaaatag caaaactctg aggccacaca 180

-continued

```
atagcttggg cttatatggg ctcctgtggg ggaaggggga gcacggaggg ggccggggcc    240

gctgctgcca aaatagcagc tcacaagtgt tgcattcctc tctgggcgcc gggcacattc    300

ctgctggctc tgcccgcccc ggggtgggcg ccgggggggac cttaaagcct ctgcccccca    360

aggagccctt cccagacagc cgccggcacc caccgctccg tgggac                   406


<210> SEQ ID NO 102
<211> LENGTH: 584
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

gcgttacata acttacggta aatggcccgc ctggctgacc gcccaacgac ccccgcccat     60

tgacgtcaat aatgacgtat gttcccatag taacgccaat agggactttc cattgacgtc    120

aatgggtgga gtatttacgg taaactgccc acttggcagt acatcaagtg tatcatatgc    180

caagtacgcc ccctattgac gtcaatgacg gtaaatggcc cgcctggcat tatgcccagt    240

acatgacctt atgggacttt cctacttggc agtacatcta cgtattagtc atcgctatta    300

ccatggtcga ggtgagcccc acgttctgct tcactctccc catctccccc ccctccccac    360

ccccaatttt gtatttattt atttttttaat tattttgtgc agcgatgggg gcgggggggg    420

gggggggcg cgcgccaggc ggggcggggc ggggcgaggg gcggggcggg gcgaggcgga    480

gaggtgcggc ggcagccaat cagagcggcg cgctccgaaa gtttcctttt atggcgaggc    540

ggcggcggcg gcggccctat aaaaagcgaa gcgcgcggcg ggcg                     584
```

COMPOSITIONS AND METHODS FOR TREATING LAMINOPATHIES

CROSS-REFERENCE TO RELATED APPLICATIONS

This application is a national stage filing under 35 U.S.C. § 371 of International Application No. PCT/US2020/020520, filed on Feb. 28, 2020, which claims the benefit of priority from U.S. Provisional Application No. 62/812,021, filed on Feb. 28, 2019 (now expired). The foregoing applications are incorporated herein by reference in their entirety.

SEQUENCE LISTING

The instant application contains a Sequence Listing, which has been submitted via EFS-Web and is hereby incorporated by reference in its entirety. Said ASCII copy, created on Mar. 9, 2022 is named 1864445-0002-005-301_Seq.txt and is 125,096 bytes in size.

BACKGROUND OF THE DISCLOSURE

The LMNA gene encodes at least three isoforms (lamin A, lamin C, and lamin AΔ10) as a result of normal alternative splicing. The two main isoforms, lamin A and lamin C, are constitutive components of the fibrous nuclear lamina, a complex molecular interface located between the inner membrane of the nuclear envelope and DNA. Lamin A and lamin C have diverse physiological roles, ranging from mechanical nuclear membrane maintenance to gene regulation. Numerous mutations in the LMNA gene give rise to a spectrum of diseases known as laminopathies. These diseases include at least eight well-characterized phenotypes, some of which are confined to the skeletal muscles or skin, while others are multisystemic.

Dilated cardiomyopathy is one of the diseases amongst the large families of LMNA-related diseases. Prevalence of dilated cardiomyopathy ranges from 1:2500 individuals to 1:250 individuals. Dilated cardiomyopathy is characterized by dilation and impaired contraction of the left ventricle or both ventricles and impaired systolic function. Despite being a rare disease, dilated cardiomyopathy represents a serious health burden, often leading to arrhythmias, thromboembolism and sudden death at any stage of disease. There is no specific treatment for dilated cardiomyopathy or the other LMNA-related laminopathies.

There is a need for novel treatments for laminopathies (e.g., dilated cardiomyopathy).

SUMMARY OF THE DISCLOSURE

Provided herein are compositions and methods, that, in some embodiments, may be used for treatment of laminopathies such as dilated cardiomyopathy.

In some embodiments, the disclosure provides a nucleic acid construct comprising a nucleotide sequence encoding (a) a lamin A polypeptide, (b) a lamin C polypeptide, or (c) a lamin A polypeptide and a lamin C polypeptide, or a biologically active variant and/or fragment of any of (a)-(c) operably linked to a regulatory element having less than 500 bp. In some embodiments, the disclosure provides a nucleic acid construct comprising a nucleotide sequence encoding (a) a lamin A polypeptide, (b) a lamin C polypeptide, or (c) a lamin A polypeptide and a lamin C polypeptide, or a biologically active variant and/or fragment of any one of (a)-(c), wherein the nucleotide sequence comprises at least one, but not all, of the non-coding sequences of the LMNA gene. In certain embodiments, the non-coding sequence is an intron. In certain embodiments, the nucleotide sequence comprises at least one, but not all, of the introns corresponding to introns 1-11 of a wild-type human LMNA gene. In certain embodiments, the nucleotide sequence comprises the intron corresponding to intron 10 of the wildtype-human LMNA gene. In certain embodiments, the intron corresponding to intron 10 comprises a nucleotide sequence that is at least 80%, 85%, 90%, 95%, 98%, 99% or 100% identical to the nucleotide sequence of SEQ ID NO: 79, or a fragment thereof. In certain embodiments, the nucleotide sequence comprises the intron corresponding to intron 8 of the wild-type-human LMNA gene. In certain embodiments, the intron corresponding to intron 8 comprises a nucleotide sequence that is at least 80%, 85%, 90%, 95%, 98%, 99% or 100% identical to the nucleotide sequence of SEQ ID NO: 77, or a fragment thereof. In certain embodiments, the nucleotide sequence comprises the intron corresponding to intron 9 of the wildtype-human LMNA gene. In certain embodiments, the intron corresponding to intron 9 comprises a nucleotide sequence that is at least 80%, 85%, 90%, 95%, 98%, 99% or 100% identical to the nucleotide sequence of SEQ ID NO: 78, or a fragment thereof. In certain embodiments, the nucleotide sequence comprises the intron corresponding to intron 11 of the wildtype-human LMNA gene. In certain embodiments, the intron corresponding to intron 11 comprises a nucleotide sequence that is at least 80%, 85%, 90%, 95%, 98%, 99% or 100% identical to the nucleotide sequence of SEQ ID NO: 80, or a fragment thereof. In certain embodiments, the nucleotide sequence comprises the introns corresponding to introns 9 and 10 of the wildtype-human LMNA gene. In certain embodiments, the nucleotide sequence comprises the introns corresponding to introns 8, 9, 10 and 11 of the wildtype-human LMNA gene. In certain embodiments, the nucleic acid construct comprises at least one intron corresponding to introns 8-11 of the wildtype human LMNA gene, and lacks at least one intron corresponding to introns 1-7 of the wildtype human LMNA gene. In certain embodiments, the nucleic acid construct comprises the intron corresponding to intron 10 of the wildtype human LMNA gene, and lacks at least one intron corresponding to introns 1-7 of the wildtype human LMNA gene. In certain embodiments, the nucleic acid construct comprises the introns corresponding to introns 8-11 of the wildtype human LMNA gene, and lacks the introns corresponding to introns 1-7 of the wildtype human LMNA gene. In certain embodiments, the nucleic acid construct comprises the introns corresponding to introns 9 and 10 of the wildtype human LMNA gene, and lacks the introns corresponding to introns 1-8 and 11 of the wildtype human LMNA gene. In certain embodiments, the nucleic acid construct comprises the intron corresponding to intron 10 of the wildtype human LMNA gene, and lacks the introns corresponding to introns 1-9 and 11 of the wildtype human LMNA gene. In certain embodiments, the nucleotide sequence is operably linked to a regulatory element. In certain embodiments, the nucleotide sequence is operably linked to a regulatory element having less than or equal to 400 base pairs (bp), 300 bp, 250 bp, 200 bp, 150 bp, 140 bp, 130 bp, 120 bp, 110 bp, 100 bp, 70 bp, or 50 bp. In certain embodiments, the regulatory element is any one of or combination of: any one of SEQ ID NOs: 30-58, CBA, CMV, SCP, SERpE_TTR, Protol, minCMV, UCL-HLP, CMVe, CAG, or EFS. In certain embodiments, the regulatory element is any one of or combination of SEQ ID NO: 31, SEQ ID NO: 33, CBA, or minCMV. In certain embodiments, the regulatory element is SEQ ID NO: 33. In certain embodiments, the regulatory element is CBA. In certain embodiments, the regulatory element is minCMV. In certain embodiments, the regulatory element is cell-type selective. In certain embodiments, the regulatory element is selectively expressed in cardiomyocytes. In certain embodiments, the nucleic acid construct comprises a nucleotide sequence that is at least 80% identical to the nucleotide sequence of any one of SEQ ID NOs: 1-10, or a codon-optimized variant and/or a fragment thereof. In certain embodiments, the nucleic acid construct comprises a nucleotide sequence that is at least 90% identical to the nucleotide sequence of any one of SEQ ID NOs: 1-10, or a codon-optimized variant and/or a fragment thereof. In certain embodiments, the nucleic acid construct comprises a nucleotide sequence that is at least 95% identical to the nucleotide sequence of any one of SEQ ID NOs: 1-10, or a codon-optimized variant and/or a fragment thereof. In certain embodiments, the nucleic acid construct comprises a nucleotide sequence that is the sequence of any one of SEQ ID NOs: 1-10, or a codon-optimized variant and/or a fragment thereof. In certain embodiments, the nucleotide sequence encodes a lamin A polypeptide comprising an amino acid sequence that is at least 80%, 85%, 90%, 95%, 98%, 99% or 100% identical to the amino acid sequence of SEQ ID NO: 12, or a biologically active fragment thereof. In certain embodiments, the nucleotide sequence encodes a lamin A polypeptide comprising an amino acid sequence that is at least 80%, 85%, 90%, 95%, 98%, 99% or 100% identical to the amino acid sequence of SEQ ID NO: 21, or a biologically active fragment thereof. In certain embodiments, the nucleotide sequence encodes a lamin C polypeptide comprising an amino acid sequence that is at least 80%, 85%, 90%, 95%, 98%, 99% or 100% identical to the amino acid sequence of SEQ ID NO: 13, or a biologically active fragment thereof. In certain embodiments, the nucleotide sequence encodes a lamin A polypeptide comprising an amino acid sequence that is at least 80%, 85%, 90%, 95%, 98%, 99% or 100% identical to the amino acid sequence of SEQ ID NO: 12, or a biologically active fragment thereof, and a lamin C polypeptide comprising an amino acid sequence that is at least 80%, 85%, 90%, 95%, 98%, 99% or 100% identical to the amino acid sequence of SEQ ID NO: 13, or a biologically active fragment thereof. In certain embodiments, the nucleotide sequence encodes a lamin A polypeptide comprising an amino acid sequence that is at least 80%, 85%, 90%, 95%, 98%, 99% or 100% identical to the amino acid sequence of SEQ ID NO: 21, or a biologically active fragment thereof, and a lamin C polypeptide comprising an amino acid sequence that is at least 80%, 85%, 90%, 95%, 98%, 99% or 100% identical to the amino acid sequence of SEQ ID NO: 13, or a biologically active fragment thereof. In certain embodiments, the nucleotide sequence further comprises a polyadenylation signal.

In some embodiments, the disclosure provides for a nucleic acid construct comprising a nucleotide sequence encoding a lamin A polypeptide and a lamin C polypeptide, or a biologically active variant and/or fragment thereof, wherein said construct comprises at least intron 8 or intron 11 of the wildtype-human LMNA gene. In some embodiments, intron 8 comprises a nucleotide sequence that is at least 80%, 85%, 90%, 95%, 98%, 99% or 100% identical to the nucleotide sequence of SEQ ID NO: 77, or a fragment thereof. In some embodiments, intron 11 comprises a nucleotide sequence that is at least 80%, 85%, 90%, 95%, 98%, 99% or 100% identical to the nucleotide sequence of SEQ ID NO: 80, or a fragment thereof. In some embodiments, the nucleotide sequence further comprises intron 10 of the wildtype-human LMNA gene. In some embodiments, intron 10 comprises a nucleotide sequence that is at least 80%, 85%, 90%, 95%, 98%, 99% or 100% identical to the nucleotide sequence of SEQ ID NO: 79, or a fragment thereof. In some embodiments, the nucleotide sequence further comprises intron 9 of the wildtype-human LMNA gene. In some embodiments, intron 9 comprises a nucleotide sequence that is at least 80%, 85%, 90%, 95%, 98%, 99% or 100% identical to the nucleotide sequence of SEQ ID NO: 78, or a fragment thereof. In some embodiments, the nucleotide sequence comprises introns 8 and 11 of the wildtype-human LMNA gene. In some embodiments, the nucleotide sequence comprises intron 8 of the wildtype-human LMNA gene. In some embodiments, the nucleotide sequence comprises intron 11 of the wildtype-human LMNA gene. In some embodiments, the nucleotide sequence further comprises introns 9 and 10 of the wildtype-human LMNA gene. In some embodiments, the nucleotide sequence comprises introns 8, 9, 10 and 11 of the wildtype-human LMNA gene. In some embodiments, the nucleic acid construct lacks at least one intron corresponding to introns 1-7 of the wildtype human LMNA gene. In some embodiments, the nucleic acid construct lacks introns 1-7 of the wildtype human LMNA gene. In some embodiments, the nucleic acid construct further comprises intron 9 of the wildtype human LMNA gene, and lacks at least one intron corresponding to introns 1-7 of the wildtype human LMNA gene. In some embodiments, the nucleic acid construct further comprises intron 10 of the wildtype human LMNA gene, and lacks at least one intron corresponding to introns 1-7 of the wildtype human LMNA gene. In some embodiments, the nucleic acid construct comprises introns 8-11 of the wildtype human LMNA gene, and lacks introns 1-7 of the wildtype human LMNA gene. In some embodiments, the regulatory element has less than or equal to 500 base pairs. In some embodiments, the regulatory element has less than or equal to 900 base pairs. In some embodiments, the regulatory element has less than or equal to 800 base pairs (bp), 700 bp, 600 bp, 500 bp, 400 bp, 300 bp, 250 bp, 200 bp, 150 bp, 140 bp, 130 bp, 120 bp, 110 bp, 100 bp, 70 bp, or 50 bp. In some embodiments, the regulatory element is any one of or combination of: any one of SEQ ID NOs: 30-58, SEQ ID NO: 102, CBA, CMV, SCP, SERpE_TTR, Protol, minCMV, UCL-HLP, CMVe, Myh6, Desmin, cTnT, α-MHC, MLC-2, CAG, or EFS. In some embodiments, the regulatory element is any one of or combination of SEQ ID NO: 31, SEQ ID NO: 33, CBA, or minCMV. In some embodiments, the regulatory element is SEQ ID NO: 33. In some embodiments, the regulatory element is CBA. In some embodiments, the regulatory element is minCMV. In some embodiments, the regulatory element is cell-type selective. In some embodiments, the regulatory element is selectively expressed in cardiomyocytes. In some embodiments, the regulatory element is any one of or combination of Myh6, Desmin, cTnT, α-MHC, or MLC-2. In some embodiments, the regulatory element is cTNT. In some embodiments, the cTNT regulatory element comprises SEQ ID NO: 101. In some embodiments, the nucleic acid construct comprises a nucleotide sequence that is at least 80% identical to the nucleotide sequence of SEQ ID NO: 3 or SEQ ID NO: 8, or a codon-optimized variant and/or a fragment thereof. In some embodiments, the nucleic acid construct comprises a nucleotide sequence that is at least 90% identical to the nucleotide sequence of SEQ ID NO: 3 or SEQ ID NO: 8, or a codon-optimized variant and/or a fragment thereof. In some embodiments, the nucleic acid construct comprises a nucleotide sequence that is at least 95% identical to the nucleotide sequence of SEQ ID NO: 3 or SEQ ID NO: 8, or a codon-optimized variant and/or a fragment thereof. In some embodiments, the nucleic acid construct comprises a nucleotide sequence that is the sequence of SEQ ID NO: 3 or SEQ ID NO: 8, or a codon-optimized variant and/or a fragment thereof. In some embodiments, the nucleotide sequence encodes a lamin A polypeptide comprising an amino acid sequence that is at least 80%, 85%, 90%, 95%, 98%, 99% or 100% identical to the amino acid sequence of SEQ ID NO: 12, or a biologically active fragment thereof, and a lamin C polypeptide comprising an amino acid sequence that is at least 80%, 85%, 90%, 95%, 98%, 99% or 100% identical to the amino acid sequence of SEQ ID NO: 13, or a biologically active fragment thereof. In some embodiments, the nucleotide sequence encodes a lamin A polypeptide comprising an amino acid sequence that is at least 80%, 85%, 90%, 95%, 98%, 99% or 100% identical to the amino acid sequence of SEQ ID NO: 21, or a biologically active fragment thereof, and a lamin C polypeptide comprising an amino acid sequence that is at least 80%, 85%, 90%, 95%, 98%, 99% or 100% identical to the amino acid sequence of SEQ ID NO: 13, or a biologically active fragment thereof. In some embodiments, the nucleotide sequence further comprises a polyadenylation signal.

In some embodiments, the disclosure provides for a nucleotide construct comprising a nucleotide sequence encoding: (a) exons 1-12 of a wild-type LMNA gene; and (b) intron 8 of a wild-type LMNA gene. In some embodiments, the disclosure provides for a nucleotide construct comprising a nucleotide sequence encoding: (a) exons 1-12 of a wild-type LMNA gene; and (b) intron 11 of a wild-type LMNA gene. In some embodiments, the disclosure provides for a nucleotide construct comprising a nucleotide sequence encoding: (a) exons 1-12 of a wild-type LMNA gene; and (b) intron 8 and intron 11 of a wild-type LMNA gene. In some embodiments, the nucleotide sequence further encodes one or more of introns 9 and 10 of a wild-type LMNA gene. In some embodiments, the disclosure provides for a nucleotide construct comprising a nucleotide sequence encoding: (a) exons 1-12 of a wild-type LMNA gene; and (b) introns 8-11 of a wild-type LMNA gene. In some embodiments, the nucleotide sequence is at least 80% identical to the nucleotide sequence of SEQ ID NO: 3 or SEQ ID NO: 8, or a codon-optimized variant and/or a fragment thereof. In some embodiments, the nucleotide sequence is at least 90% identical to the nucleotide sequence of SEQ ID NO: 3 or SEQ ID NO: 8, or a codon-optimized variant and/or a fragment thereof. In some embodiments, the nucleotide sequence is at least 95% identical to the nucleotide sequence of SEQ ID NO: 3 or SEQ ID NO: 8, or a codon-optimized variant and/or a fragment thereof. In some embodiments, the nucleotide sequence is the sequence of SEQ ID NO: 3 or SEQ ID NO: 8, or a codon-optimized variant and/or a fragment thereof. In some embodiments, the nucleotide sequence encodes: a) a lamin A polypeptide having an amino acid sequence that is at least 80%, 85%, 90%, 95%, 98%, 99% or 100% identical to the amino acid sequence of SEQ ID NO: 12, and b) a lamin C polypeptide having an amino acid sequence at least 80%, 85%, 90%, 95%, 98%, 99% or 100% identical to the amino acid sequence of SEQ ID NO: 13. In some embodiments, the nucleotide sequence encodes: a) a lamin A polypeptide having an amino acid sequence that is at least 80%, 85%, 90%, 95%, 98%, 99% or 100% identical to the amino acid sequence of SEQ ID NO: 21, and b) a lamin C polypeptide having an amino acid sequence at least 80%, 85%, 90%, 95%, 98%, 99% or 100% identical to the amino acid sequence of SEQ ID NO: 13. In some embodiments, the nucleotide sequence encodes a polypeptide having the amino acid sequence of any one or more of SEQ ID NO: 12-19, or 21. In some embodiments, the nucleotide sequence does not comprise the nucleotide sequence corresponding to introns 1-7 of a wild-type LMNA gene. In some embodiments, the nucleotide sequence is operably linked to a regulatory element. In some embodiments, the nucleotide sequence is operably linked to a regulatory element having less than 900 bp. In some embodiments, the nucleotide sequence is operably linked to a regulatory element having less than or equal to 900 bp, 800 bp, 700 bp, 600 bp, 500 bp, 400 bp, 300 bp, 250 bp, 200 bp, 150 bp, 140 bp, 130 bp, 120 bp, 110 bp, 100 bp, 70 bp, or 50 bp. In some embodiments, the regulatory element is any one of or combination of any one of SEQ ID NOs: 30-58, SEQ ID NO: 102, CBA, CMV, SCP, SERpE_TTR, Protol, minCMV, UCL-HLP, CMVe, Myh6, Desmin, cTnT, α-MHC, MLC-2, CAG, or EFS.

In some embodiments, the disclosure provides for a viral vector comprising any of the nucleic acid constructs provided herein. In certain embodiments, the viral vector comprises a nucleotide sequence encoding (a) a lamin A polypeptide, (b) a lamin C polypeptide, or (c) a lamin A polypeptide and a lamin C polypeptide, or a biologically active variant and/or fragment of any one of (a)-(c). In certain embodiments, the nucleotide sequence comprises at least one non-coding region of the LMNA gene. In certain embodiments, the non-coding region is an intron. In certain embodiments, the viral vector comprises a nucleotide sequence encoding: (a) exons 1-12 of a wild-type LMNA gene; and (b) intron 10 of a wild-type LMNA gene. In certain embodiments, the viral vector comprises a nucleic acid construct provided herein, wherein the nucleotide sequence further encodes one or more of introns 8, 9, and 11 of a wild-type LMNA gene. In some embodiments, the disclosure provides a viral vector comprising a nucleotide sequence encoding: (a) exons 1-12 of a wild-type LMNA gene; and (b) introns 9 and 10 of a wild-type LMNA gene. In some embodiments, the disclosure provides a viral vector comprising a nucleotide sequence encoding: (a) exons 1-12 of a wild-type LMNA gene; and (b) introns 8-11 of a wild-type LMNA gene. In certain embodiments, the viral vector comprises a nucleotide sequence that is at least 80% identical to the nucleotide sequence of any one of SEQ ID NOs: 1-10, or a codon-optimized variant and/or a fragment thereof. In certain embodiments, the viral vector comprises a nucleotide sequence that is at least 90% identical to the nucleotide sequence of any one of SEQ ID NOs: 1-10, or a codon-optimized variant and/or a fragment thereof. In certain embodiments, the viral vector comprises a nucleotide sequence that is at least 95% identical to the nucleotide sequence of any one of SEQ ID NOs: 1-10, or a codon-optimized variant and/or a fragment thereof. In certain embodiments, the viral vector comprises a nucleotide sequence that is the sequence of any one of SEQ ID NOs: 1-10, or a codon-optimized variant and/or a fragment thereof. In certain embodiments, the viral vector comprises a nucleotide sequence encoding a lamin A polypeptide comprising an amino acid sequence that is at least 80%, 85%, 90%, 95%, 98%, 99% or 100% identical to the amino acid sequence of SEQ ID NO: 12, or a biologically active fragment thereof. In certain embodiments, the viral vector comprises a nucleotide sequence encoding a lamin A polypeptide comprising an amino acid sequence that is at least 80%, 85%, 90%, 95%, 98%, 99% or 100% identical to the amino acid sequence of SEQ ID NO: 21, or a biologically active fragment thereof. In certain embodiments, the viral vector comprises a nucleotide sequence encoding a lamin C polypeptide comprising an amino acid sequence that is at least 80%, 85%, 90%, 95%, 98%, 99% or 100% identical to the amino acid sequence of SEQ ID NO: 13, or a biologically active fragment thereof. In certain embodiments, the viral vector comprises a nucleotide sequence encoding (a) a lamin A polypeptide having an amino acid sequence that is at least 80%, 85%, 90%, 95%, 98%, 99% or 100% identical to the amino acid sequence of SEQ ID NO: 12, and (b) a lamin C polypeptide having an amino acid sequence at least 80%, 85%, 90%, 95%, 98%, 99% or 100% identical to the amino acid sequence of SEQ ID NO: 13. In certain embodiments, the viral vector comprises a nucleotide sequence encoding (a) a lamin A polypeptide having an amino acid sequence that is at least 80%, 85%, 90%, 95%, 98%, 99% or 100% identical to the amino acid sequence of SEQ ID NO: 21, and (b) a lamin C polypeptide having an amino acid sequence at least 80%, 85%, 90%, 95%, 98%, 99% or 100% identical to the amino acid sequence of SEQ ID NO: 13. In certain embodiments, the viral vector comprises a nucleotide sequence encoding a polypeptide having the amino acid sequence of SEQ ID NO: 12-21 or 24. In certain embodiments, the viral vector comprises a nucleotide sequence does not comprise the nucleotide sequence corresponding to introns 1-7 of a wild-type LMNA gene. In certain embodiments, the viral vector comprises a nucleotide sequence that is operably linked to a regulatory element. In certain embodiments, the viral vector comprises a nucleotide sequence that is operably linked to a regulatory element having less than or equal to 400 bp, 300 bp, 250 bp, 200 bp, 150 bp, 140 bp, 130 bp, 120 bp, 110 bp, 100 bp, 70 bp, or 50 bp. In certain embodiments, the viral vector comprises a regulatory element that is any one of or combination of any one of SEQ ID NOs: 30-58, CBA, CMV, SCP, SERpE_TTR, Protol, minCMV, UCL-HLP, CMVe, CAG, or EFS. In certain embodiments, the viral vector comprises a regulatory element that is any one of or combination of SEQ ID NO: 31, SEQ ID NO: 33, CBA, or minCMV. In certain embodiments, the viral vector comprises a regulatory element that is SEQ ID NO: 33. In certain embodiments, the viral vector comprises a regulatory element that is CBA. In certain embodiments, the viral vector comprises a regulatory element that is minCMV. In certain embodiments, the viral vector comprises a regulatory element that is cell-type selective. In certain embodiments, the viral vector comprises a regulatory element that is selectively expressed in neuronal cells, retinal cells, renal cells, skeletal muscle cells, adipocytes, or cardiomyocytes. In certain embodiments, the viral vector comprises a regulatory element that is selectively expressed in cardiomyocytes. In certain embodiments, the viral vector comprises a nucleotide sequence further comprising a polyadenylation signal. In certain embodiments, the viral vector is an adeno-associated virus (AAV) vector. In certain embodiments, the AAV vector is AAV6, AAV9, scAAV6, or scAAV9. In certain embodiments, the AAV vector comprises a nucleotide sequence further comprising a 5' AAV inverted terminal repeat (ITR) sequence and a 3' AAV ITR sequence.

In some embodiments, the disclosure provides for a viral vector comprising a nucleotide sequence encoding a lamin A polypeptide and a lamin C polypeptide, or a biologically active variant and/or fragment thereof, wherein said nucleotide sequence comprises at least intron 8 or intron 11 of the wildtype-human LMNA gene. In some embodiments, the disclosure provides for a viral vector comprising a nucleotide sequence encoding: (a) exons 1-12 of a wild-type LMNA gene; and (b) intron 8 of a wild-type LMNA gene. In some embodiments, the disclosure provides for a viral vector comprising a nucleotide sequence encoding: (a) exons 1-12 of a wild-type LMNA gene; and (b) intron 11 of a wild-type LMNA gene. In some embodiments, the disclosure provides for a viral vector comprising a nucleotide sequence encoding: (a) exons 1-12 of a wild-type LMNA gene; and (b) intron 8 and intron 11 of a wild-type LMNA gene. In some embodiments, the nucleotide sequence further encodes one or more of introns 9 and 10 of a wild-type LMNA gene. In some embodiments, the disclosure provides for a viral vector comprising a nucleotide sequence encoding: (a) exons 1-12 of a wild-type LMNA gene; and (b) introns 8-11 of a wild-type LMNA gene. In some embodiments, the nucleotide sequence is at least 80% identical to the nucleotide sequence of SEQ ID NO: 3 or SEQ ID NO: 8, or a codon-optimized variant and/or a fragment thereof. In some embodiments, the nucleotide sequence is at least 90% identical to the nucleotide sequence of SEQ ID NO: 3 or SEQ ID NO: 8, or a codon-optimized variant and/or a fragment thereof. In some embodiments, the nucleotide sequence is at least 95% identical to the nucleotide sequence of SEQ ID NO: 3 or SEQ ID NO: 8, or a codon-optimized variant and/or a fragment thereof. In some embodiments, the nucleotide sequence is the sequence of SEQ ID NO: 3 or SEQ ID NO: 8, or a codon-optimized variant and/or a fragment thereof. In some embodiments, the nucleotide sequence encodes: a) a lamin A polypeptide having an amino acid sequence that is at least 80%, 85%, 90%, 95%, 98%, 99% or 100% identical to the amino acid sequence of SEQ ID NO: 12, and b) a lamin C polypeptide having an amino acid sequence at least 80%, 85%, 90%, 95%, 98%, 99% or 100% identical to the amino acid sequence of SEQ ID NO: 13. In some embodiments, the nucleotide sequence encodes: a) a lamin A polypeptide having an amino acid sequence that is at least 80%, 85%, 90%, 95%, 98%, 99% or 100% identical to the amino acid sequence of SEQ ID NO: 21, and b) a lamin C polypeptide having an amino acid sequence at least 80%, 85%, 90%, 95%, 98%, 99% or 100% identical to the amino acid sequence of SEQ ID NO: 13. In some embodiments, the nucleotide sequence encodes a polypeptide having the amino acid sequence of any one or more of SEQ ID NO: 12-19, or 21. In some embodiments, the nucleotide sequence does not comprise the nucleotide sequence corresponding to introns 1-7 of a wild-type LMNA gene. In some embodiments, the nucleotide sequence is operably linked to a regulatory element. In some embodiments, the nucleotide sequence is operably linked to a regulatory element having less than 500 bp. In some embodiments, the nucleotide sequence is operably linked to a regulatory element having less than 900 bp. In some embodiments, the nucleotide sequence is operably linked to a regulatory element having less than or equal to 800 bp, 700 bp, 600 bp, 500 bp, 400 bp, 300 bp, 250 bp, 200 bp, 150 bp, 140 bp, 130 bp, 120 bp, 110 bp, 100 bp, 70 bp, or 50 bp. In some embodiments, the regulatory element is any one of or combination of any one of SEQ ID NOs: 30-58, SEQ ID NO: 102, CBA, CMV, SCP, SERpE_TTR, Protol, minCMV, UCL-HLP, CMVe, Myh6, Desmin, cTnT, MLC-2, CAG, or EFS. In some embodiments, the regulatory element is any one of or combination of SEQ ID NO: 31, SEQ ID NO: 33, CBA, or minCMV. In some embodiments, the regulatory element is SEQ ID NO: 33. In some embodiments, the regulatory element is CBA. In some embodiments, the regulatory element is minCMV. In some embodiments, the regulatory element is cell-type selective. In some embodiments, the regulatory element is selectively expressed in neuronal cells, retinal cells, renal cells, skeletal muscle cells, adipocytes, or cardiomyocytes. In some embodiments, the regulatory element is selectively expressed in cardiomyocytes. In some embodiments, the regulatory element is any one of or combination of Myh6, Desmin, cTnT, α-MHC, or MLC-2. In some embodiments, the regulatory element is cTNT. In some embodiments, the cTNT regulatory element comprises SEQ ID NO: 101. In some embodiments, the nucleotide sequence further comprises a polyadenylation signal. In some embodiments, the viral vector is an adeno-associated virus (AAV) vector. In some embodiments, the AAV vector is AAV1, AAV2, AAV5, AAV6, AAV8, AAV9, scAAV1, scAAV2, scAAV5, scAAV6, scAAV8, or scAAV9. In some embodiments, the nucleotide sequence further comprises a 5' AAV inverted terminal repeat (ITR) sequence and a 3' AAV ITR sequence.

In some embodiments, the disclosure provides a viral particle comprising any of the viral vectors as provided herein. In certain embodiments, the viral particle comprises capsid proteins of an AAV. In certain embodiments, the capsid proteins of an AAV is an AAV6 or AAV9.

In some embodiments, the disclosure provides a host cell comprising any of the nucleic acid constructs, viral vectors, or viral particles as provided herein.

In some embodiments, the disclosure provides pharmaceutical composition comprising any of the nucleic acid constructs, viral vectors, viral particles, or host cells as provided herein; and one or more pharmaceutically acceptable excipients.

In some embodiments, the disclosure provides a method for treating a laminopathy in a subject comprising administering a therapeutically effective amount of any of the nucleic acid constructs, viral vectors, viral particles, host cells, or pharmaceutical compositions as provided herein to a subject in need thereof.

In some embodiments, the disclosure provides a method for expressing (a) a lamin A polypeptide, (b) a lamin C polypeptide, or (c) a lamin A polypeptide and a lamin C polypeptide, or a biologically active variant and/or a fragment of any one of (a)-(c) in a subject comprising administering to said subject a therapeutically effective amount of any of the nucleic acid constructs, viral vectors, viral particles, host cells, or pharmaceutical compositions as provided herein.

In some embodiments, the disclosure provides a method for increasing expression of (a) a functional lamin A polypeptide, (b) a functional lamin C polypeptide, or (c) a functional lamin A polypeptide and a functional lamin C polypeptide, or a biologically active variant and/or a fragment of any one of (a)-(c) in a subject comprising administering to said subject a therapeutically effective amount of any of the nucleic acid constructs, viral vectors, viral particles, host cells, or pharmaceutical compositions as provided herein.

In certain embodiments, the subject treated in accordance with any of the methods disclosed herein is suffering from a laminopathy. In certain embodiments, the laminopathy is any one or more of: Charcot-Marie-Tooth disease, Emery-Dreifuss muscular dystrophy, familial partial lipodystrophy, Hutchinson-Gilford progeria syndrome, limb-girdle muscular dystrophy, LA/INA-related congenital muscular dystrophy, mandibuloacral dysplasia, arrhythmogenic right ventricular cardiomyopathy, familial atrial fibrillation, left ventricular noncompaction, or dilated cardiomyopathy. In certain embodiments, the laminopathy is dilated cardiomyopathy. In certain embodiments, any of the nucleic acid constructs, viral vectors, viral particles, host cells, or pharmaceutical compositions provided herein is administered intramyocardially, intravenously, intramuscularly, intrathecally, subcutaneously, systemically, or locally into the myocardium. In certain embodiments, any of the nucleic acid constructs, viral vectors, viral particles, host cells, or pharmaceutical compositions provided herein is administered intravenously or systemically.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10A shows the expression of Lamin A and Lamin C in the heart and liver under the control of a ubiquitous promoter. FIG. 10B shows the expression of Lamin A and Lamin C in the heart and liver under the control of a heart-specific promoter (cTNT).

In FIG. 11A, the construct comprises a CBA promoter, a lamin isoform A/C insert comprising exons 1-12 of lamin A/C, introns 8-11 of lamin A/C, and a polyadenylation sequence signal. In FIG. 11B, the construct comprises a CBA promoter, a lamin isoform A/C insert comprising exons 1-12 of lamin A/C, intron 9 and 10 of lamin A/C, and a polyadenylation sequence signal. In FIG. 11C, the construct comprises a CBA promoter, a lamin isoform A/C insert comprising exons 1-12 of lamin A/C, intron 10 of lamin A/C, and a polyadenylation sequence signal.

DETAILED DESCRIPTION OF THE DISCLOSURE

Figure 1:
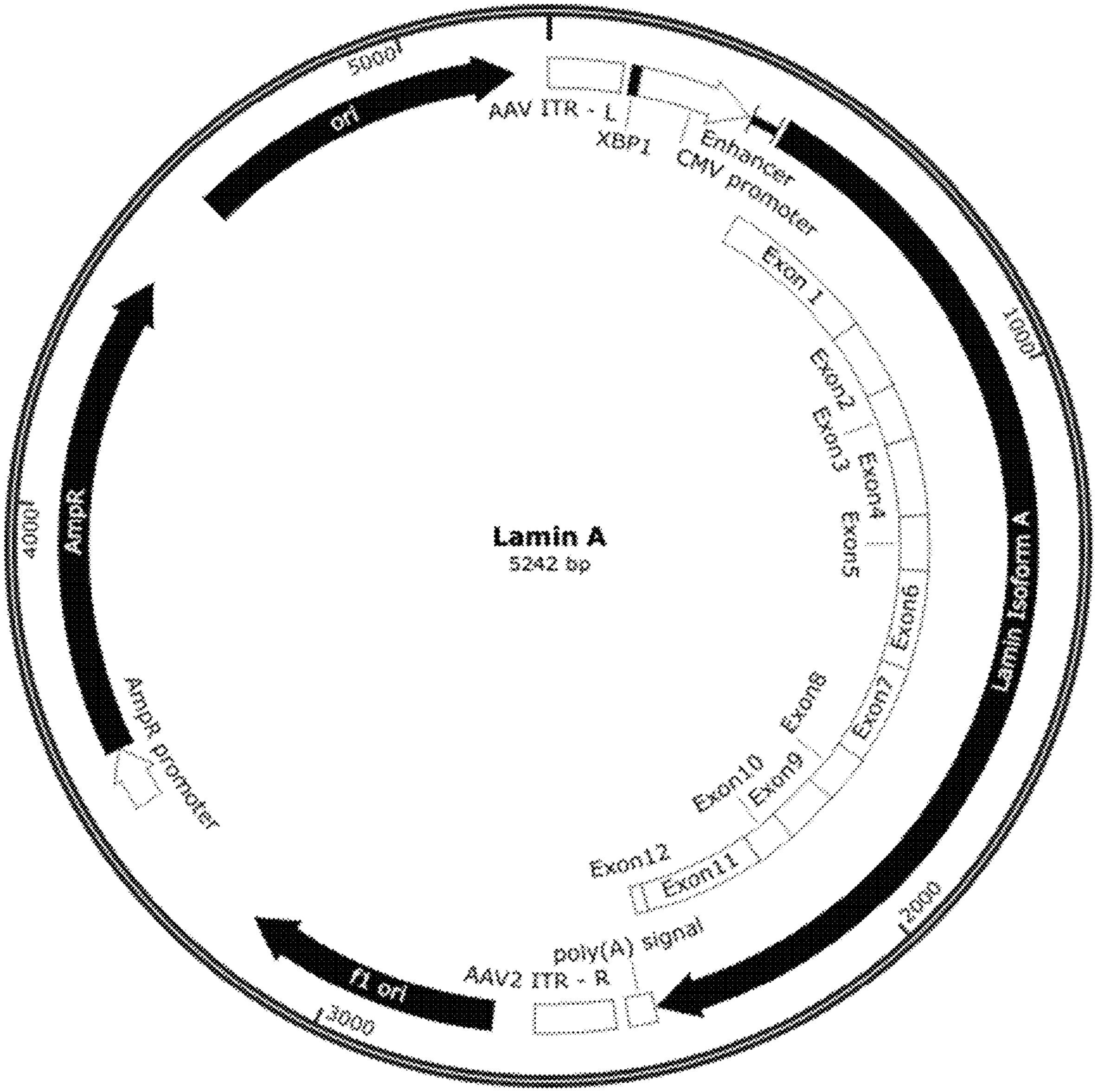
FIG. 1 illustrates a vector map of a full viral vector genome construct for expression of lamin A. The viral vector comprises an adeno-associated viral (AAV) vector comprising a CMV promoter, an enhancer having SEQ ID NO: 31, a lamin isoform A insert comprising exons 1-12 of lamin A, and a polyadenylation sequence signal.
Figure 2:
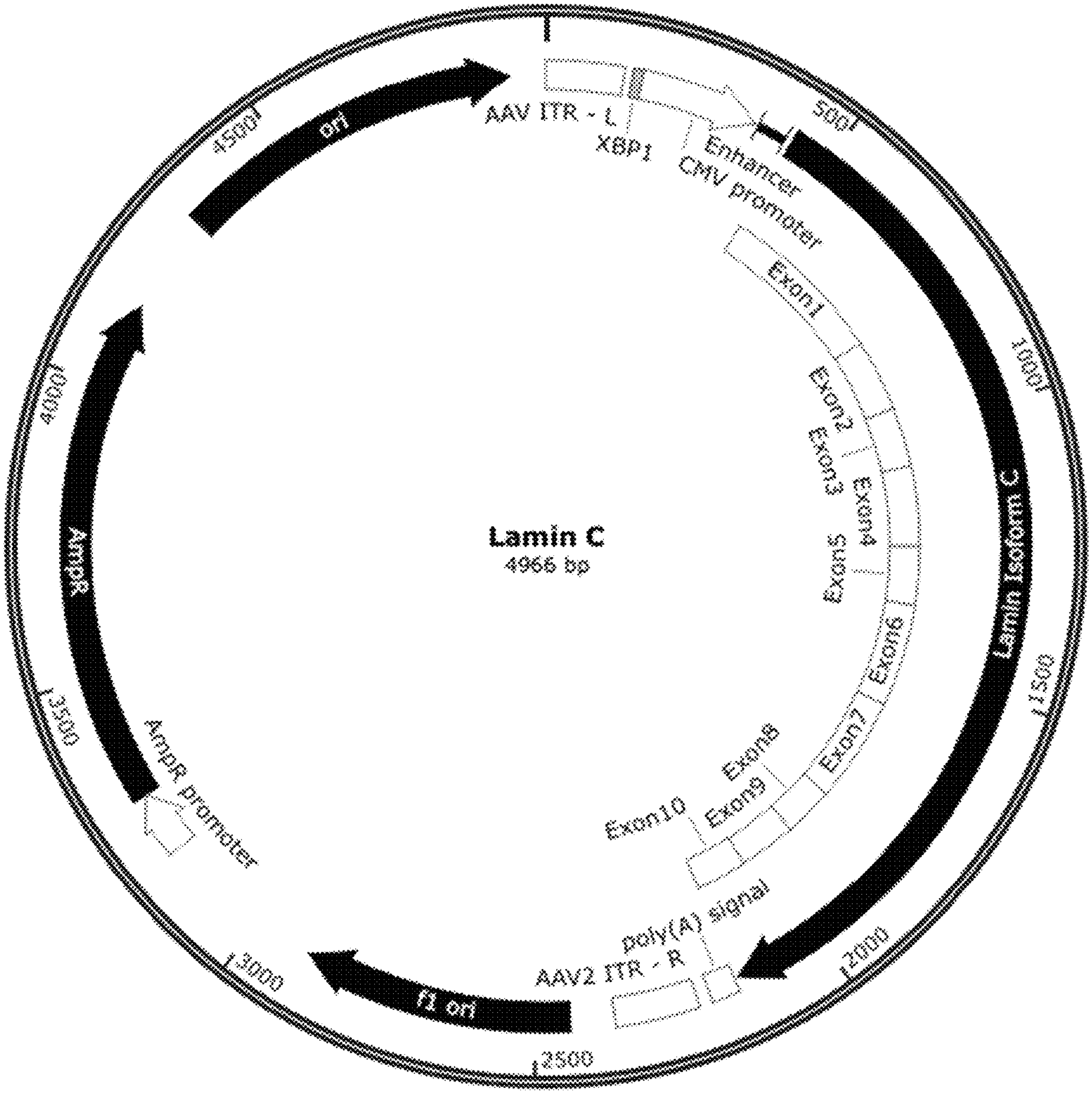
FIG. 2 illustrates a vector map of a full viral vector genome construct for expression of lamin C. The viral vector comprises an adeno-associated viral (AAV) vector comprising a CMV promoter, an enhancer having SEQ ID NO: 31, a lamin isoform C insert comprising exons 1-10 of lamin C, and a polyadenylation sequence signal.
Figure 3:
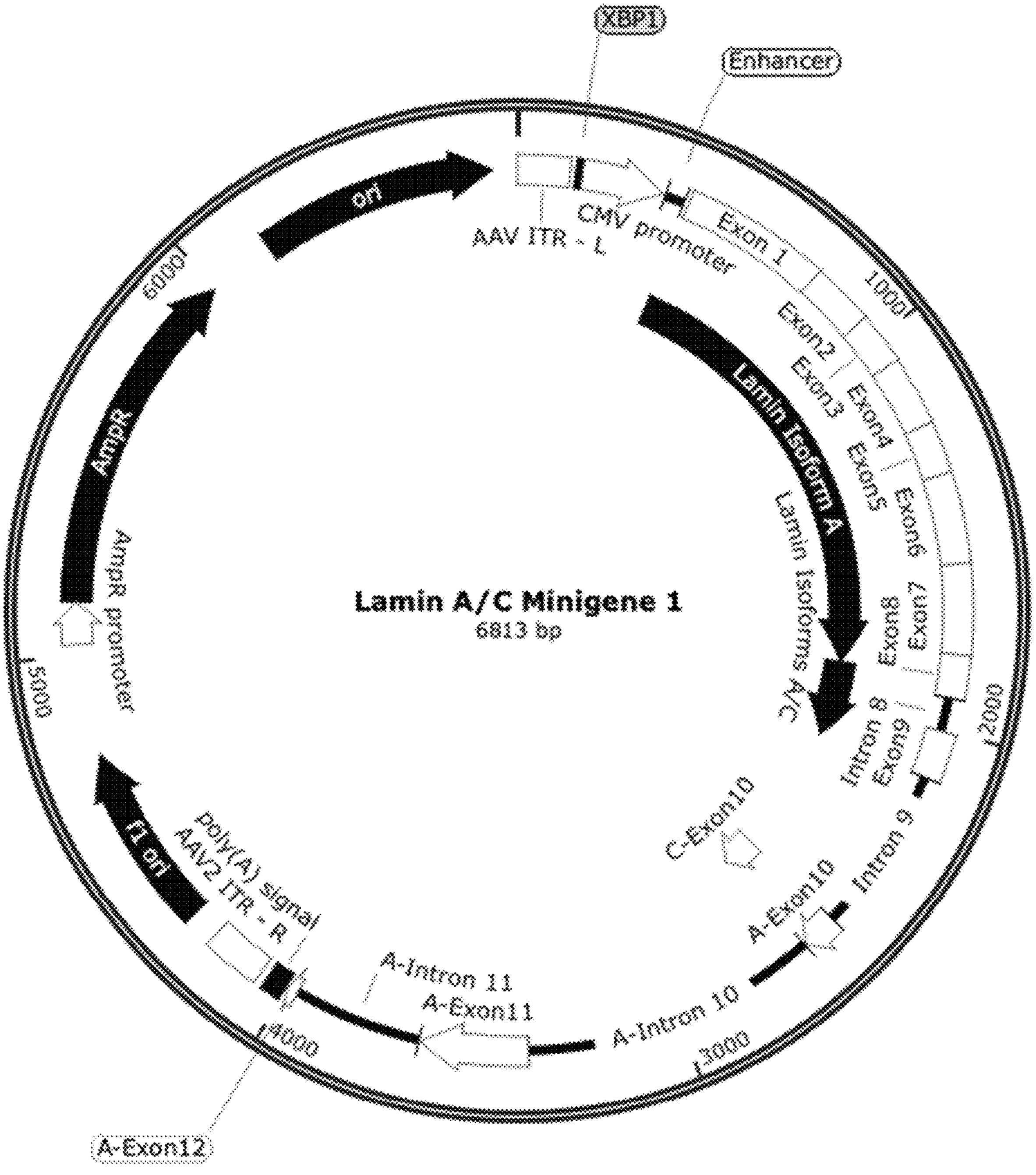
FIG. 3 illustrates a vector map of a full viral vector genome construct (minigene 1) for expression of lamin A and lamin C. The viral vector comprises an adeno-associated viral (AAV) vector comprising a CMV promoter, an enhancer having SEQ ID NO: 31, a lamin isoform A/C insert comprising exons 1-12 of lamin A/C, introns 8-11 of lamin A/C, and a polyadenylation sequence signal.
Figure 4:
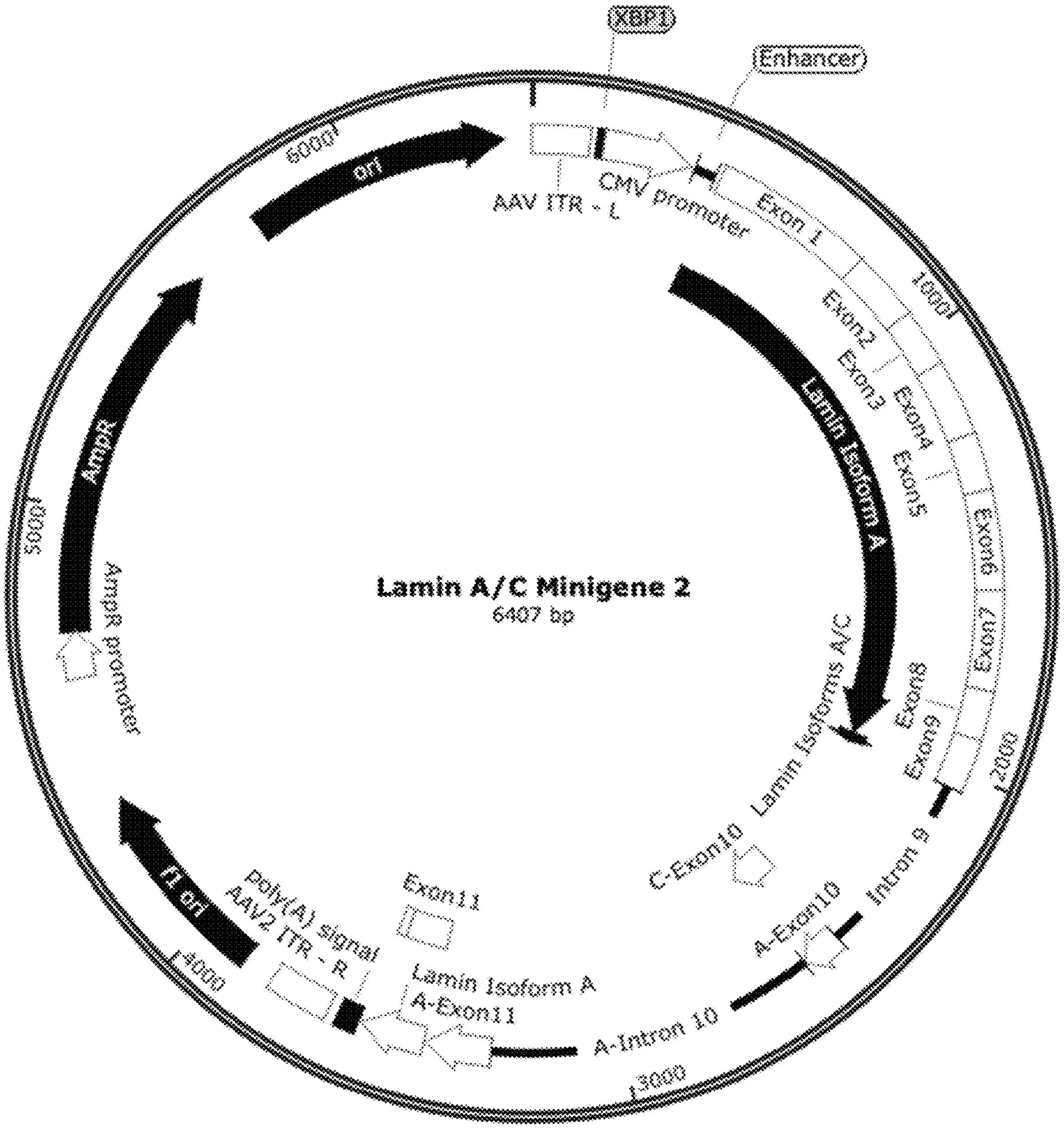
FIG. 4 illustrates a vector map of a full viral vector genome construct (minigene 2) for expression of lamin A and lamin C. The viral vector comprises an adeno-associated viral (AAV) vector comprising a CMV promoter, an enhancer having SEQ ID NO: 31, a lamin isoform A/C insert comprising exons 1-12 of lamin A/C, intron 9 and 10 of lamin A/C, and a polyadenylation sequence signal.
Figure 5:
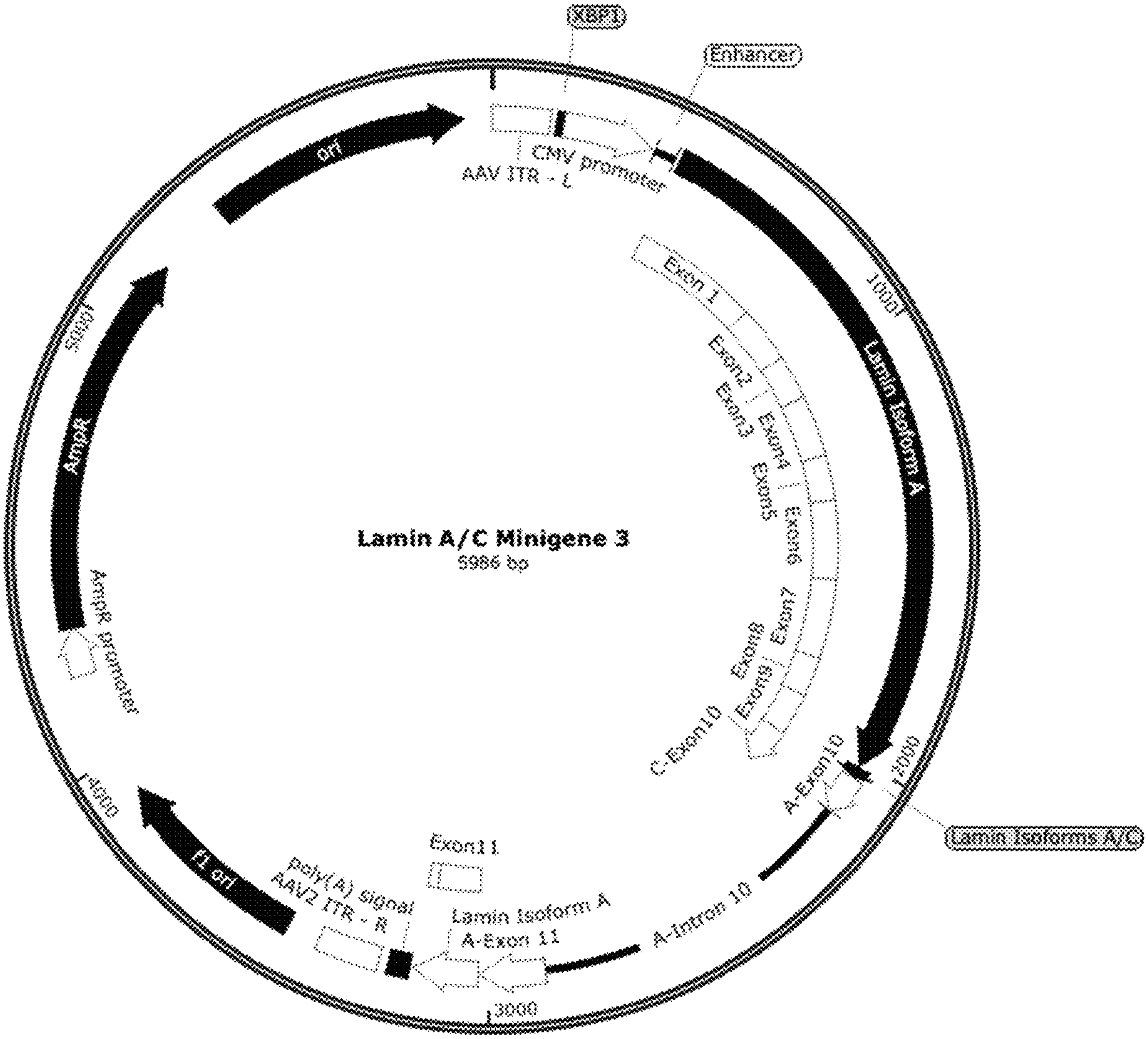
FIG. 5 illustrates a vector map of a full viral vector genome construct (minigene 3) for expression of lamin A and lamin C. The viral vector comprises an adeno-associated viral (AAV) vector comprising a CMV promoter, an enhancer having SEQ ID NO: 31, a lamin isoform A/C insert comprising exons 1-12 of lamin A/C, intron 10 of lamin A/C, and a polyadenylation sequence signal.

Lamin A and lamin C are constitutive components of the fibrous nuclear lamina, a complex molecular interface located between the inner membrane of the nuclear envelope and DNA. Lamin A and lamin C have diverse physiological roles, ranging from mechanical nuclear membrane maintenance to gene regulation. The LMNA gene encodes at least three isoforms (lamin A, lamin C, and lamin AΔ10) as a result of normal alternative splicing. LMNA contains twelve exons, which yield transcripts for lamin C and prelamin A (the precursor to mature lamin A) by alternative splicing of exon 10. Both isoforms are identical for the first 566 amino acids (encoded by exons 1-10), but their carboxyl terminal sequences diverge. Prelamin A contains an extra 98 unique amino acids at the C terminus (encoded by exons 11-12), while lamin C terminates with exon 10 sequences and has 6 unique C-terminal amino acids. Prelamin A is processed to form lamin A, a 646 amino acids long protein. Meanwhile, lamin C is composed of 572 amino acids.

LMNA mutations in humans result in a variety of diseases, including cardiomyopathy, muscular dystrophy, and progeriod disorders. More than 500 disease-causing mutations have been identified, some of which result in diseases such as dilated cardiomyopathy. Dilated cardiomyopathy is characterized by dilation and impaired contraction of the left ventricle or both ventricles and impaired systolic function. The prevalence of dilated cardiomyopathy ranges from 1:2500 individuals to 1:250 individuals. Despite being a rare disease, dilated cardiomyopathy represents a serious health burden, often leading to arrhythmias, thromboembolism and sudden death at any stage of disease. As of 2014, 165 dilated cardiomyopathy associated mutations had been identified in the LMNA gene (Tesson F. Cardiol J. 2014; 21(4):331-42). These mutations included missense/nonsense mutations, splicing mutations, small deletions, small insertions, small indel, gross deletions, or gross insertions. The majority of LMNA mutations leading to dilated cardiomyopathy are autosomal dominant missense mutations found throughout the gene that generate mutated lamin A/C proteins.

The present disclosure contemplates compositions and methods for treating, preventing, or inhibiting dilated cardiomyopathy and other laminopathies. In one aspect, the disclosure provides a viral vector, viral particle, host cell, or pharmaceutical composition comprising a nucleotide sequence encoding (a) a lamin A polypeptide; (b) a lamin C polypeptide; (c) a lamin A and lamin C polypeptide; or a codon-optimized variant and/or fragment of any of the foregoing. In one aspect, the disclosure provides a viral vector, viral particle, host cell, or pharmaceutical composition comprising a nucleotide sequence encoding (a) a biologically active fragment of a lamin A polypeptide; (b) a biologically active fragment of a lamin C polypeptide; (c) a biologically active fragment of a lamin A and a biologically active fragment of a lamin C polypeptide; or a codon-optimized variant and/or fragment of any of the foregoing. In another aspect, the disclosure provides a nucleic acid comprising a nucleotide sequence encoding (a) a lamin A polypeptide; (b) a lamin C polypeptide; (c) a lamin A polypeptide and a lamin C polypeptide, or a codon-optimized variant thereof and/or fragment thereof operably linked to any one of or combination of: SEQ ID NO: 31, SEQ ID NO: 33, CBA, and/or minCMV. In another aspect, the disclosure provides a nucleic acid comprising a nucleotide sequence encoding (a) a biologically active fragment of a lamin A polypeptide; (b) a biologically active fragment of a lamin C polypeptide; (c) a biologically active fragment of a lamin A polypeptide and a biologically active fragment of a lamin C polypeptide, or a codon-optimized variant thereof and/or fragment thereof operably linked to any one of or combination of: SEQ ID NO: 31, SEQ ID NO: 33, CBA, and/or minCMV. In another embodiment, the disclosure provides a method for treating a laminopathy in a subject comprising administering one or more of any of the nucleic acids, viral vectors, viral particles, host cells, or pharmaceutical compositions disclosed herein.

A wide variety of laminopathies may be treated or prevented using the nucleic acids, viral vectors, viral particles, host cells, pharmaceutical compositions, and methods provided herein. Laminopathies that may be treated or prevented using the nucleic acids, viral vectors, viral particles, host cells, pharmaceutical compositions, and methods of the disclosure include but are not limited to Charcot-Marie-Tooth disease, Emery-Dreifuss muscular dystrophy, familial partial lipodystrophy, Hutchinson-Gilford progeria syndrome, limb-girdle muscular dystrophy, LMNA-related congenital muscular dystrophy, mandibuloacral dysplasia, arrhythmogenic right ventricular cardiomyopathy, familial atrial fibrillation, left ventricular noncompaction, and dilated cardiomyopathy.

A. General Techniques

Unless otherwise defined herein, scientific and technical terms recited herein shall have the meanings that are commonly understood by those of ordinary skill in the art. Generally, nomenclature used in connection with, and techniques of, pharmacology, cell and tissue culture, molecular biology, cell and cancer biology, neurobiology, neurochemistry, virology, immunology, microbiology, genetics and protein and nucleic acid chemistry, described herein, are those well-known and commonly used in the art. In case of conflict, the present specification, including definitions, will control.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R.I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Sambrook and Russell, Molecular Cloning: A Laboratory Manual, 3rd. ed., Cold Spring Harbor Laboratory Press, Cold Spring Harbor, N.Y. (2001); Ausubel et al., Current Protocols in Molecular Biology, John Wiley & Sons, N Y (2002); Harlow and Lane Using Antibodies: A Laboratory Manual, Cold Spring Harbor Laboratory Press, Cold Spring Harbor, N.Y. (1998); Coligan et al., Short Protocols in Protein Science, John Wiley & Sons, N Y (2003); Short Protocols in Molecular Biology (Wiley and Sons, 1999).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well known and commonly used in the art. Standard techniques are used for chemical syntheses, and chemical analyses.

B. Definitions

Throughout this specification and embodiments, the word "comprise," or variations such as "comprises" or "comprising," will be understood to imply the inclusion of a stated integer or group of integers but not the exclusion of any other integer or group of integers.

It is understood that wherever embodiments are described herein with the language "comprising," otherwise analogous embodiments described in terms of "consisting of" and/or "consisting essentially of" are also provided.

The term "including" is used to mean "including but not limited to." "Including" and "including but not limited to" are used interchangeably.

Any example(s) following the term "e.g." or "for example" is not meant to be exhaustive or limiting.

Unless otherwise required by context, singular terms shall include pluralities and plural terms shall include the singular.

By way of example, "an element" means one element or more than one element.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g., 1 to 6.1, and ending with a maximum value of 10 or less, e.g., 5.5 to 10.

Where aspects or embodiments of the disclosure are described in terms of a Markush group or other grouping of alternatives, the present disclosure encompasses not only the entire group listed as a whole, but each member of the group individually and all possible subgroups of the main group, but also the main group absent one or more of the group members. The present disclosure also envisages the explicit exclusion of one or more of any of the group members in the disclosure.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Unless otherwise indicated, the term "lamin A" is used herein to refer to prelamin A polypeptides and/or mature lamin A polypeptides. The term covers all lamin A polypeptides formed as a result of posttranslational modifications of prelamin A (e.g. removal of the 18 amino acids from the carboxyl terminus of prelamin A to form mature lamin A). The term includes all biologically active lamin A proteins, fragments or variants thereof.

The term "AAV" is an abbreviation for adeno-associated virus and may be used to refer to the virus itself or a derivative thereof. The term covers all serotypes, subtypes, and both naturally occurring and recombinant forms, except where required otherwise. The abbreviation "rAAV" refers to recombinant adeno-associated virus. The term "AAV" includes AAV1, AAV2, AAV3, AAV4, AAV5, AAV6, AAV7, AAV8, AAV9, AAV10, AAV11, AAV12, rh10, and hybrids thereof, avian AAV, bovine AAV, canine AAV, equine AAV, primate AAV, non-primate AAV, and ovine AAV. The genomic sequences of various serotypes of AAV, as well as the sequences of the native terminal repeats (TRs), Rep proteins, and capsid subunits are known in the art. Such sequences may be found in the literature or in public databases such as GenBank. A "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs). An ITR sequence is a term well understood in the art and refers to relatively short sequences found at the termini of viral genomes which are in opposite orientation. An rAAV vector may either be single-stranded (ssAAV) or self-complementary (scAAV). An "AAV virus" or "AAV viral particle" refers to a viral particle composed of at least one AAV capsid protein and an encapsidated polynucleotide rAAV vector. If the particle comprises a heterologous polynucleotide (i.e., a polynucleotide other than a wild-type AAV genome such as a transgene to be delivered to a mammalian cell), it is typically referred to as an "rAAV viral particle" or simply an "rAAV particle".

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, up to 15%, up to 10%, up to 5%, or up to 1% above and/or below a given value.

The terms "determining", "measuring", "evaluating", "assessing", "assaying", "analyzing", and their grammatical equivalents can be used interchangeably herein to refer to any form of measurement and include determining if an element is present or not (for example, detection). These terms can include both quantitative and/or qualitative determinations. Assessing may be relative or absolute.

An "expression cassette" refers to a nucleic molecule comprising one or more regulatory elements operably linked to a coding sequence (e.g., a gene or genes) for expression.

The term "effective amount" or "therapeutically effective amount" refers to that amount of a composition described herein that is sufficient to affect the intended application, including but not limited to disease treatment, as defined below. The therapeutically effective amount may vary depending upon the intended treatment application (in a cell or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in a target cell. The specific dose will vary depending on the particular composition chosen, the dosing regimen to be followed, whether it is administered in combination with other compounds, timing of administration, the tissue to which it is administered, and the physical delivery system in which it is carried.

A "fragment" of a nucleotide or peptide sequence refers to a fragment of the sequence that is shorter than the full-length or reference DNA or protein sequence.

The term "biologically active" as used herein when referring to a molecule such as a protein, polypeptide, nucleic acid, and/or polynucleotide means that the molecule retains at least one biological activity (either functional or structural) that is substantially similar to a biological activity of the full-length or reference protein, polypeptide, nucleic acid, and/or polynucleotide. For example, a "biologically active" lamin A or lamin C protein, or fragment or variant thereof, would retain at least one activity that is substantially similar to a full-length or reference wild-type lamin A or lamin C protein, respectively.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell but may contain mutations. Mutant progeny that have the same function or biological activity as screened or selected for in the originally transformed cell are included herein.

The term "human derived" as used herein refers to sequences that are found in a human genome (or a human genome build), or sequences homologous thereto. A homologous sequence may be a sequence which has a region with at least 80% sequence identity (e.g., as measured by BLAST) as compared to a region of the human genome. For example, a sequence that has at least 80%, at least 85%, at least 90%, at least 91%, at least 92%, at least 93%, at least 94%, at least 95%, at least 96%, at least 97%, at least 98%, at least 99% or 100% identity to a human sequence is deemed human derived. In some cases, a regulatory element contains a human derived sequence and a non-human derived sequence such that overall the regulatory element has low sequence identity to the human genome, while a part of the regulatory element has 100% sequence identity (or local sequence identity) to a sequence in the human genome.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

The term "in vivo" refers to an event that takes place in a subject's body.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally, at a chromosomal location that is different from its natural chromosomal location, or contains only coding sequences.

As used herein, "operably linked", "operable linkage", "operatively linked", or grammatical equivalents thereof refer to juxtaposition of genetic elements, e.g., a promoter, an enhancer, a polyadenylation sequence, etc., wherein the elements are in a relationship permitting them to operate in the expected manner. For instance, a regulatory element, which can comprise promoter and/or enhancer sequences, is operatively linked to a coding region if the regulatory element helps initiate transcription of the coding sequence. There may be intervening residues between the regulatory element and coding region so long as this functional relationship is maintained.

A "pharmaceutically acceptable carrier" refers to an ingredient in a pharmaceutical formulation or composition, other than an active ingredient, which is nontoxic to a subject. A pharmaceutically acceptable carrier includes, but is not limited to, a buffer, excipient, stabilizer, or preservative.

The terms "pharmaceutical formulation" or "pharmaceutical composition" refer to a preparation which is in such form as to permit the biological activity of an active ingredient contained therein to be effective, and which contains no additional components which are unacceptably toxic to a subject to which the formulation would be administered.

The term "regulatory element" refers to a nucleic acid sequence or genetic element which is capable of influencing (e.g., increasing, decreasing, or modulating) expression of an operably linked sequence, such as a gene. Regulatory elements include, but are not limited to, promoter, enhancer, repressor, silencer, insulator sequences, an intron, UTR, an inverted terminal repeat (ITR) sequence, a long terminal repeat sequence (LTR), stability element, posttranslational response element, or a polyA sequence, or a combination thereof. Regulatory elements can function at the DNA and/or the RNA level, e.g., by modulating gene expression at the transcriptional phase, post-transcriptional phase, or at the translational phase of gene expression; by modulating the level of translation (e.g., stability elements that stabilize mRNA for translation), RNA cleavage, RNA splicing, and/or transcriptional termination; by recruiting transcriptional factors to a coding region that increase gene expression; by increasing the rate at which RNA transcripts are produced, increasing the stability of RNA produced, and/or increasing the rate of protein synthesis from RNA transcripts; and/or by preventing RNA degradation and/or increasing its stability to facilitate protein synthesis. In some embodiments, a regulatory element refers to an enhancer, repressor, promoter, or a combination thereof, particularly an enhancer plus promoter combination or a repressor plus promoter combination. In some embodiments, the regulatory element is derived from a human sequence.

The terms "subject" and "individual" are used interchangeably herein to refer to a vertebrate, preferably a mammal, more preferably a human. The methods described herein can be useful in human therapeutics, veterinary applications, and/or preclinical studies in animal models of a disease or condition.

As used herein, the terms "treat", "treatment", "therapy" and the like refer to obtaining a desired pharmacologic and/or physiologic effect, including, but not limited to, alleviating, delaying or slowing progression, reducing effects or symptoms, preventing onset, preventing reoccurrence, inhibiting, ameliorating onset of a diseases or disorder, obtaining a beneficial or desired result with respect to a disease, disorder, or medical condition, such as a therapeutic benefit and/or a prophylactic benefit. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some cases, for prophylactic benefit, the compositions are administered to a subject at risk of developing a particular disease, or to a subject reporting one or more of the physiological symptoms of a disease, even though a diagnosis of this disease may not have been made. The methods of the present disclosure may be used with any mammal. In some cases, the treatment can result in a decrease or cessation of symptoms. A prophylactic effect includes delaying or eliminating the appearance of a disease or condition, delaying or eliminating the onset of symptoms of a disease or condition, slowing, halting, or reversing the progression of a disease or condition, or any combination thereof.

A "variant" of a nucleotide sequence refers to a sequence having a genetic alteration or a mutation as compared to the most common wild-type DNA sequence (e.g., cDNA or a sequence referenced by its GenBank accession number) or a specified reference sequence.

A "vector" as used herein refers to a nucleic acid molecule that can be used to mediate delivery of another nucleic acid molecule to which it is linked into a cell where it can be replicated or expressed. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Other examples of vectors include plasmids and viral vectors.

In general, "sequence identity" or "sequence homology", which can be used interchangeably, refer to an exact nucleotide-to-nucleotide or amino acid-to-amino acid correspondence of two polynucleotides or polypeptide sequences, respectively. Two or more sequences (polynucleotide or amino acid) can be compared by determining their "percent identity", also referred to as "percent homology". The percent identity to a reference sequence (e.g., nucleic acid or amino acid sequence) may be calculated as the number of exact matches between two optimally aligned sequences divided by the length of the reference sequence and multiplied by 100. Conservative substitutions are not considered as matches when determining the number of matches for sequence identity. It will be appreciated that where the length of a first sequence (A) is not equal to the length of a second sequence (B), the percent identity of A:B sequence will be different than the percent identity of B:A sequence. Sequence alignments, such as for the purpose of assessing percent identity, may be performed by any suitable alignment algorithm or program, including but not limited to the Needleman-Wunsch algorithm (see, e.g., the EMBOSS Needle aligner available on the world wide web at ebi.ac.uk/Tools/psa/emboss_needle/), the BLAST algorithm (see, e.g., the BLAST alignment tool available on the world wide web at blast.ncbi.nlm.nih.gov/Blast.cgi), the Smith-Waterman algorithm (see, e.g., the EMBOSS Water aligner available on the world wide web at ebi.ac.uk/Tools/psa/emboss_water/), and Clustal Omega alignment program (see e.g., the world wide web at clustal.org/omega/ and F. Sievers et al., Mol Sys Biol. 7: 539 (2011)). Optimal alignment may be assessed using any suitable parameters of a chosen algorithm, including default parameters. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin and Altschul, Proc. Natl. Acad. Sci. USA 90:5873-5877 (1993); and Altschul et al., Nucleic Acids Res. 25:3389-3402 (1997).

Unless otherwise indicated, all terms used herein have the same meaning as they would to one skilled in the art and the practice of the present invention will employ, conventional techniques of molecular biology, microbiology, and recombinant DNA technology, which are within the knowledge of those of skill of the art.

C. Nucleic Acid Constructs

1. Lamin Constructs

Provided herein are nucleic acid constructs comprising a nucleotide sequence encoding lamin A, lamin C, lamin A and lamin C (or biologically active variants or fragments thereof), or a codon-optimized variant and/or fragment thereof. In certain embodiments, the nucleic acid construct comprises a nucleotide sequence encoding lamin A (or a biologically active variant or fragment thereof) or a codon-optimized variant and/or fragment thereof. In certain embodiments, the nucleic acid construct comprises a nucleotide sequence encoding lamin C (or a biologically active variant or fragment thereof) or a codon-optimized variant and/or fragment thereof. In certain embodiments, the nucleic acid construct comprises a nucleotide sequence encoding both lamin A and lamin C (or biologically active variants or fragments thereof) or a codon-optimized variant and/or fragment thereof.

In some embodiments, the nucleic acid construct comprises a transgene operably linked to a regulatory element, wherein the transgene encodes (a) lamin A (or a biologically active variant or fragment thereof); (b) lamin C (or a biologically active variant or fragment thereof); (c) both lamin A and lamin C (or biologically active variants or fragments thereof), or a codon-optimized variant and/or fragment thereof. In certain embodiments, the transgene comprises a nucleotide sequence encoding lamin A (or a biologically active variant or fragment thereof) or a codon-optimized variant and/or fragment thereof. In certain embodiments, the transgene comprises a nucleotide sequence encoding lamin C (or a biologically active variant or fragment thereof) or a codon-optimized variant and/or fragment thereof. In certain embodiments, the transgene comprises a nucleotide sequence encoding both lamin A and lamin C (or biologically active variants or fragments thereof) or a codon-optimized variant and/or fragment thereof.

In some cases, the nucleic acid construct comprises a nucleic acid coding sequence which is operatively linked to regulatory components in a manner which permits transcription, translation, and/or expression of a transgene in a target cell (e.g. a cardiomyocyte or myocardiocyte, which terms are used interchangeably herein). The transgene (heterologous nucleic acid sequence) can be derived from any organism. In certain embodiments, the transgene is derived from a human. In certain embodiments, the transgene encodes a mature form of lamin A (or a biologically active variant or fragment thereof). In certain embodiments, the transgene encodes prelamin A (or a biologically active variant or fragment thereof). In certain embodiments, the transgene encodes lamin C (or a biologically active variant or fragment thereof). In certain embodiments, the transgene encodes both lamin A and lamin C (or biologically active variants or fragments thereof). In certain embodiments, the transgene encodes both prelamin A and lamin C (or biologically active variants or fragments thereof). In some embodiments, the transgene encodes a polypeptide comprising an amino acid sequence that is at least 60%, 65%, 70%, 75%, 80%, 82%, 85%, 87%, 90%, 91%, 92%, 93%, 94%, 95%, 96%, 97%, 98%, 99%, or 100% identical to the amino acid sequence of SEQ ID NO: 12, or a biologically active fragment thereof. In some embodiments, the transgene encodes a polypeptide comprising an amino acid sequence that is at least 60%, 65%, 70%, 75%, 80%, 82%, 85%, 87%, 90%, 91%, 92%, 93%, 94%, 95%, 96%, 97%, 98%, 99%, or 100% identical to the amino acid sequence of SEQ ID NO: 21, or a biologically active fragment thereof. In some embodiments, the transgene encodes a polypeptide comprising an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to the amino acid sequence of SEQ ID NO: 13, or a biologically active fragment thereof.

In certain embodiments, the nucleic acid construct may comprise one or more transgenes. In some embodiments, the transgene comprises more than one LMNA splice variant (e.g. both lamin A and lamin C), or fragments derived from more than LMNA splice variant. This may be accomplished using a single nucleic acid construct carrying two or more heterologous sequences, or using a single nucleic acid construct carrying a single sequence which encodes two or more LMNA splice variants (e.g. lamin A and lamin C). In some embodiments, the transgene comprises only one LMNA splice variant (e.g. lamin A or lamin C), or fragments derived from one LMNA splice variant. It is contemplated that two or more nucleic acid constructs each carrying one or more heterologous sequences encoding at least one LMNA splice variant may be used separately or together (e.g., in the same or different viral vector(s)). In some embodiments, in addition to a LMNA gene, splice variant, or fragment thereof, the nucleic acid construct may also encode additional proteins, peptides, RNA, enzymes, or catalytic RNAs.

In certain embodiments, any of the nucleic acid constructs disclosed herein comprises a nucleotide sequence encoding exons 1-12 of a wild-type LMNA gene (e.g. SEQ ID NOs: 81-93) and introns 8-11 of a wild-type LMNA gene (e.g. SEQ ID NOs: 77-80). In certain embodiments, the nucleic acid construct comprises a nucleotide sequence encoding exons 1-12 of a wild-type LMNA gene (e.g. SEQ ID NOs: 81-93) and introns 9 and 10 of a wild-type LMNA gene (e.g. SEQ ID NOs: 78 and 79). In certain embodiments, the nucleic acid construct comprises a nucleotide sequence encoding exons 1-12 of a wild-type LMNA gene e.g. SEQ ID NOs: 81-93) and intron 10 of a wild-type LMNA gene (e.g. SEQ ID NO: 79).

In certain embodiments, the nucleic acid construct comprises a nucleotide sequence that comprises, consists of, or consists essentially of, the nucleic acid sequence of any one of SEQ ID NOs: 1-10, and nucleic acid sequences that are at least 60%, 65%, 70%, 75%, 80%, 82%, 85%, 87%, 90%, 91%, 92%, 93%, 94%, 95%, 96%, 97%, 98%, 99% or 100% identical to any of the foregoing, and fragments of any of the foregoing. In certain embodiments, the nucleic acid construct comprises a nucleotide sequence that is the sequence of any one of SEQ ID NOs: 1-10, or codon-optimized variant and/or a fragment thereof. In certain embodiments, the nucleic acid construct comprises a nucleotide sequence that is at least 60% identical to any one of SEQ ID NOs: 1-10, or codon-optimized variant and/or a fragment thereof. In certain embodiments, the nucleic acid construct comprises a nucleotide sequence that is at least 65% identical to any one of SEQ ID NOs: 1-10, or codon-optimized variant and/or a fragment thereof. In certain embodiments, the nucleic acid construct comprises a nucleotide sequence that is at least 70% identical to any one of SEQ ID NOs: 1-10, or codon-optimized variant and/or a fragment thereof. In certain embodiments, the nucleic acid construct comprises a nucleotide sequence that is at least 75% identical to any one of SEQ ID NOs: 1-10, or codon-optimized variant and/or a fragment thereof. In certain embodiments, the nucleic acid construct comprises a nucleotide sequence that is at least 80% identical to any one of SEQ ID NOs: 1-10, or codon-optimized variant and/or a fragment thereof. In certain embodiments, the nucleic acid construct comprises a nucleotide sequence that is at least 82% identical to any one of SEQ ID NOs: 1-10, or codon-optimized variant and/or a fragment thereof. In certain embodiments, the nucleic acid construct comprises a nucleotide sequence that is at least 85% identical to any one of SEQ ID NOs: 1-10, or codon-optimized variant and/or a fragment thereof. In certain embodiments, the nucleic acid construct comprises a nucleotide sequence that is at least 87% identical to any one of SEQ ID NOs: 1-10, or codon-optimized variant and/or a fragment thereof. In certain embodiments, the nucleic acid construct comprises a nucleotide sequence that is at least 90% identical to any one of SEQ ID NOs: 1-10, or codon-optimized variant and/or a fragment thereof. In certain embodiments, the nucleic acid construct comprises a nucleotide sequence that is at least 91% identical to any one of SEQ ID NOs: 1-10, or codon-optimized variant and/or a fragment thereof. In certain embodiments, the nucleic acid construct comprises a nucleotide sequence that is at least 92% identical to any one of SEQ ID NOs: 1-10, or codon-optimized variant and/or a fragment thereof. In certain embodiments, the nucleic acid construct comprises a nucleotide sequence that is at least 93% identical to any one of SEQ ID NOs: 1-10, or codon-optimized variant and/or a fragment thereof. In certain embodiments, the nucleic acid construct comprises a nucleotide sequence that is at least 94% identical to any one of SEQ ID NOs: 1-10, or codon-optimized variant and/or a fragment thereof. In certain embodiments, the nucleic acid construct comprises a nucleotide sequence that is at least 95% identical to any one of SEQ ID NOs: 1-10, or codon-optimized variant and/or a fragment thereof. In certain embodiments, the nucleic acid construct comprises a nucleotide sequence that is at least 96% identical to any one of SEQ ID NOs: 1-10, or codon-optimized variant and/or a fragment thereof. In certain embodiments, the nucleic acid construct comprises a nucleotide sequence that is at least 97% identical to any one of SEQ ID NOs: 1-10, or codon-optimized variant and/or a fragment thereof. In certain embodiments, the nucleic acid construct comprises a nucleotide sequence that is at least 98% identical to any one of SEQ ID NOs: 1-10, or codon-optimized variant and/or a fragment thereof. In certain embodiments, the nucleic acid construct comprises a nucleotide sequence that is at least 99% identical to any one of SEQ ID NOs: 1-10, or codon-optimized variant and/or a fragment thereof.

In certain embodiments, the nucleic acid construct comprises a nucleotide sequence that is 100% identical to any one of SEQ ID NOs: 1-10, or codon-optimized variant and/or a fragment thereof. In some embodiments, the nucleic acid construct comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 1 that encodes the polypeptide sequence of SEQ ID NO: 12 or 21. In some embodiments, the nucleic acid construct comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 6 that encodes the polypeptide sequence of SEQ ID NO: 12 or 21. In some embodiments, the nucleic acid construct comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 2 that encodes the polypeptide sequence of SEQ ID NO: 13. In some embodiments, the nucleic acid construct comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 7 that encodes the polypeptide sequence of SEQ ID NO: 13. In some embodiments, the nucleic acid construct comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 3 that encodes the polypeptide sequence of any one or more of SEQ ID NOs: 12, 13 or 21. In some embodiments, the nucleic acid construct comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 4 that encodes the polypeptide sequence of any one or more of SEQ ID NOs: 12, 13 or 21. In some embodiments, the nucleic acid construct comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 5 that encodes the polypeptide sequence of any one or more of SEQ ID NOs: 12, 13 or 21. In some embodiments, the nucleic acid construct comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 8 that encodes the polypeptide sequence of any one or more of SEQ ID NOs: 12, 13 or 21. In some embodiments, the nucleic acid construct comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 9 that encodes the polypeptide sequence of any one or more of SEQ ID NOs: 12, 13 or 21. In some embodiments, the nucleic acid construct comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 10 that encodes the polypeptide sequence of any one or more of SEQ ID NOs: 12, 13 or 21.

In certain embodiments, the nucleic acid construct comprises a nucleotide sequence that comprises, consists of, or consists essentially of, the nucleic acid sequence of any one of SEQ ID NOs: 3-5, and/or nucleic acid sequences that are at least 60%, 65%, 70%, 75%, 80%, 82%, 85%, 87%, 90%, 91%, 92%, 93%, 94%, 95%, 96%, 97%, 98%, 99% or 100% identical to any of the foregoing or fragments of any of the foregoing. In certain embodiments, the nucleic acid construct comprises a nucleotide sequence that is the sequence of any one of SEQ ID NOs: 3-5, or a codon-optimized variant and/or a fragment thereof. In certain embodiments, the nucleic acid construct comprises a nucleotide sequence that is at least 60% identical to any one of SEQ ID NOs: 3-5, or a codon-optimized variant and/or a fragment thereof. In certain embodiments, the nucleic acid construct comprises a nucleotide sequence that is at least 65% identical to any one of SEQ ID NOs: 3-5, or a codon-optimized variant and/or a fragment thereof. In certain embodiments, the nucleic acid construct comprises a nucleotide sequence that is at least 70% identical to any one of SEQ ID NOs: 3-5, or a codon-optimized variant and/or a fragment thereof. In certain embodiments, the nucleic acid construct comprises a nucleotide sequence that is at least 75% identical to any one of SEQ ID NOs: 3-5, or a codon-optimized variant and/or a fragment thereof. In certain embodiments, the nucleic acid construct comprises a nucleotide sequence that is at least 80% identical to any one of SEQ ID NOs: 3-5, or a codon-optimized variant and/or a fragment thereof. In certain embodiments, the nucleic acid construct comprises a nucleotide sequence that is at least 82% identical to any one of SEQ ID NOs: 3-5, or a codon-optimized variant and/or a fragment thereof. In certain embodiments, the nucleic acid construct comprises a nucleotide sequence that is at least 85% identical to any one of SEQ ID NOs: 3-5, or a codon-optimized variant and/or a fragment thereof. In certain embodiments, the nucleic acid construct comprises a nucleotide sequence that is at least 87% identical to any one of SEQ ID NOs: 3-5, or a codon-optimized variant and/or a fragment thereof. In certain embodiments, the nucleic acid construct comprises a nucleotide sequence that is at least 90% identical to any one of SEQ ID NOs: 3-5, or a codon-optimized variant and/or a fragment thereof. In certain embodiments, the nucleic acid construct comprises a nucleotide sequence that is at least 91% identical to any one of SEQ ID NOs: 3-5, or codon-optimized variant and/or a fragment thereof. In certain embodiments, the nucleic acid construct comprises a nucleotide sequence that is at least 92% identical to any one of SEQ ID NOs: 3-5, or a codon-optimized variant and/or a fragment thereof. In certain embodiments, the nucleic acid construct comprises a nucleotide sequence that is at least 93% identical to any one of SEQ ID NOs: 3-5, or codon-optimized variant and/or a fragment thereof. In certain embodiments, the nucleic acid construct comprises a nucleotide sequence that is at least 94% identical to any one of SEQ ID NOs: 3-5, or a codon-optimized variant and/or a fragment thereof. In certain embodiments, the nucleic acid construct comprises a nucleotide sequence that is at least 95% identical to any one of SEQ ID NOs: 3-5, or codon-optimized variant and/or a fragment thereof. In certain embodiments, the nucleic acid construct comprises a nucleotide sequence that is at least 96% identical to any one of SEQ ID NOs: 3-5, or a codon-optimized variant and/or a fragment thereof. In certain embodiments, the nucleic acid construct comprises a nucleotide sequence that is at least 97% identical to any one of SEQ ID NOs: 3-5, or a codon-optimized variant and/or a fragment thereof. In certain embodiments, the nucleic acid construct comprises a nucleotide sequence that is at least 98% identical to any one of SEQ ID NOs: 3-5, or a codon-optimized variant and/or a fragment thereof. In certain embodiments, the nucleic acid construct comprises a nucleotide sequence that is at least 99% identical to any one of SEQ ID NOs: 3-5, or a codon-optimized variant and/or a fragment thereof. In certain embodiments, the nucleic acid construct comprises a nucleotide sequence that is 100% identical to any one of SEQ ID NOs: 3-5, or a codon-optimized variant and/or a fragment thereof.

In certain embodiments, the nucleic acid construct comprises a nucleotide sequence encoding a polypeptide that comprises, consists of, or consists essentially of, the amino acid sequence of any one of SEQ ID NOs: 12-21 and 24, and polypeptides that are at least 60%, 65%, 70%, 75%, 80%, 82%, 85%, 87%, 90%, 91%, 92%, 93%, 94%, 95%, 96%, 97%, 98%, 99% or 100% identical to any of the foregoing. In certain embodiments, the nucleic acid construct comprises a nucleotide sequence encoding a polypeptide of any one of SEQ ID NOs: 12-21 and 24, or biologically active variants and/or fragments thereof. In certain embodiments, the nucleic acid construct comprises a nucleotide sequence encoding a polypeptide that is at least 60% identical to any one of SEQ ID NOs: 12-21 and 24, or biologically active variants and/or fragments thereof. In certain embodiments, the nucleic acid construct comprises a nucleotide sequence encoding a polypeptide that is at least 65% identical to any one of SEQ ID NOs: 12-21 and 24, or biologically active variants and/or fragments thereof. In certain embodiments, the nucleic acid construct comprises a nucleotide sequence encoding a polypeptide that is at least 70% identical to any one of SEQ ID NOs: 12-21 and 24, or biologically active variants and/or fragments thereof. In certain embodiments, the nucleic acid construct comprises a nucleotide sequence encoding a polypeptide that is at least 75% identical to any one of SEQ ID NOs: 12-21 and 24, or biologically active variants and/or fragments thereof. In certain embodiments, the nucleic acid construct comprises a nucleotide sequence encoding a polypeptide that is at least 80% identical to any one of SEQ ID NOs: 12-21 and 24, or biologically active variants and/or fragments thereof. In certain embodiments, the nucleic acid construct comprises a nucleotide sequence encoding a polypeptide that is at least 82% identical to any one of SEQ ID NOs: 12-21 and 24, or biologically active variants and/or fragments thereof. In certain embodiments, the nucleic acid construct comprises a nucleotide sequence encoding a polypeptide that is at least 85% identical to any one of SEQ ID NOs: 12-21 and 24, or biologically active variants and/or fragments thereof. In certain embodiments, the nucleic acid construct comprises a nucleotide sequence encoding a polypeptide that is at least 87% identical to any one of SEQ ID NOs:12-21 and 24, or biologically active variants and/or fragments thereof. In certain embodiments, the nucleic acid construct comprises a nucleotide sequence encoding a polypeptide that is at least 90% identical to any one of SEQ ID NOs: 12-21 and 24, or biologically active variants and/or fragments thereof. In certain embodiments, the nucleic acid construct comprises a nucleotide sequence encoding a polypeptide that is at least 91% identical to any one of SEQ ID NOs: 12-21 and 24, or biologically active variants and/or fragments thereof. In certain embodiments, the nucleic acid construct comprises a nucleotide sequence encoding a polypeptide that is at least 92% identical to any one of SEQ ID NOs: 12-21 and 24, or biologically active variants and/or fragments thereof. In certain embodiments, the nucleic acid construct comprises a nucleotide sequence encoding a polypeptide that is at least 93% identical to any one of SEQ ID NOs: 12-21 and 24, or biologically active variants and/or fragments thereof. In certain embodiments, the nucleic acid construct comprises a nucleotide sequence encoding a polypeptide that is at least 94% identical to any one of SEQ ID NOs: 12-21 and 24, or biologically active variants and/or fragments thereof. In certain embodiments, the nucleic acid construct comprises a nucleotide sequence encoding a polypeptide that is at least 95% identical to any one of SEQ ID NOs: 12-21 and 24, or biologically active variants and/or fragments thereof. In certain embodiments, the nucleic acid construct comprises a nucleotide sequence encoding a polypeptide that is at least 96% identical to any one of SEQ ID NOs: 12-21 and 24, or biologically active variants and/or fragments thereof. In certain embodiments, the nucleic acid construct comprises a nucleotide sequence encoding a polypeptide that is at least 97% identical to any one of SEQ ID NOs: 12-21 and 24, or biologically active variants and/or fragments thereof. In certain embodiments, the nucleic acid construct comprises a nucleotide sequence encoding a polypeptide that is at least 98% identical to any one of SEQ ID NOs: 12-21 and 24, or biologically active variants and/or fragments thereof. In certain embodiments, the nucleic acid construct comprises a nucleotide sequence encoding a polypeptide that is at least 99% identical to any one of SEQ ID NOs: 12-21 and 24, or biologically active variants and/or fragments thereof. In certain embodiments, the nucleic acid construct comprises a nucleotide sequence encoding a polypeptide that is 100% identical to any one of SEQ ID NOs: 12-21 and 24, or biologically active variants and/or fragments thereof.

In certain embodiments, the nucleic acid construct comprises a nucleotide sequence encoding lamin A that comprises, consists of, or consists essentially of, an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 12, or biologically active fragments thereof. In certain embodiments, the nucleic acid construct comprises a nucleotide sequence encoding lamin A that comprises, consists of, or consists essentially of, an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 21, or biologically active fragments thereof. In certain embodiments, the nucleic acid construct comprises a nucleotide sequence encoding lamin C that comprises, consists of, or consists essentially of, an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 13, or biologically active fragments thereof. In certain embodiments, the nucleic acid construct comprises a nucleotide sequence encoding lamin A having an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 12 or biologically active fragments thereof, and also encoding lamin C having an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 13 or biologically active fragments thereof. In certain embodiments, the nucleic acid construct comprises a nucleotide sequence encoding lamin A having an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 21 or biologically active fragments thereof, and also encoding lamin C having an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 13 or biologically active fragments thereof. In certain embodiments, the nucleic acid construct comprises a nucleotide sequence encoding lamin A that comprises, consists of, or consists essentially of, the amino acid sequence of SEQ ID NO: 12. In certain embodiments, the nucleic acid construct comprises a nucleotide sequence encoding lamin A that comprises, consists of, or consists essentially of, the amino acid sequence of SEQ ID NO: 21. In certain embodiments, the nucleic acid construct comprises a nucleotide sequence encoding lamin C that comprises, consists of, or consists essentially of, the amino acid sequence of SEQ ID NO: 13. In certain embodiments, the nucleic acid construct comprises a nucleotide sequence encoding lamin A and lamin C that comprises, consists of, or consists essentially of, the amino acid sequence of SEQ ID NO: 12 and/or 13. In certain embodiments, the nucleic acid construct comprises a nucleotide sequence encoding lamin A and lamin C that comprises, consists of, or consists essentially of, the amino acid sequence of SEQ ID NO: 21 and/or 13. In certain embodiments, the nucleic acid construct comprises a nucleotide sequence encoding lamin A having the amino acid sequence of SEQ ID NO: 12, and also encoding lamin C having the amino acid sequence of SEQ ID NO: 13. In certain embodiments, the nucleic acid construct comprises a nucleotide sequence encoding lamin A having the amino acid sequence of SEQ ID NO: 21, and also encoding lamin C having the amino acid sequence of SEQ ID NO: 13.

In some cases, the nucleic acid construct comprises a nucleotide sequence encoding lamin A and/or lamin C, wherein the nucleotide sequence does not comprise one or more, two or more, three or more, four or more, five or more, six or more, seven or more, eight or more, nine or more, ten or more, or eleven or more introns from a wild-type LMNA gene. In certain embodiments, the nucleic acid construct does not comprise the nucleotide sequence corresponding to introns 1-7 of a wild-type LMNA gene (e.g. SEQ ID NOs: 70-76). In certain embodiments, the nucleic acid construct does not comprise the nucleotide sequence corresponding to introns 1-8 and 11 of a wild-type LMNA gene (e.g. SEQ ID NOs: 70-77 and 80). In certain embodiments, the nucleic acid construct does not comprise the nucleotide sequence corresponding to introns 1-9 and 11 of a wild-type LMNA gene (e.g. SEQ ID NOs:70-78 and 80).

In some cases, the nucleic acid construct comprises a nucleotide sequence encoding lamin A and/or lamin C, wherein the nucleotide sequence comprises one or more, two or more, three or more, four or more, five or more, six or more, seven or more, eight or more, nine or more, ten or more, or eleven or more introns (e.g. SEQ ID NOs: 70-80). In certain embodiments, the one or more introns correspond to the introns from a wild-type LMNA gene, e.g., a wild-type human LMNA gene. In other embodiments, the one or more introns are synthetic introns. In particular embodiments, the one or more introns are positioned in the nucleic acid construct such that the nucleotide sequence is capable of encoding both lamin A and lamin C in a splice-dependent manner. In particular embodiments, the one or more introns are positioned in the nucleic acid construct such that the pre-mRNA undergoes alternative splicing to produce mature mRNA encoding lamin A, and/or lamin C. In particular embodiments, the one or more introns are positioned in the nucleic acid construct such that the pre-mRNA undergoes alternative splicing to produce more mature mRNA encoding lamin C than mature mRNA encoding lamin A. In particular embodiments, the one or more introns are positioned in the nucleic acid construct such that the pre-mRNA undergoes alternative splicing to produce more mature mRNA encoding lamin A than mature mRNA encoding lamin C. In certain embodiments, the one or more introns are positioned in the nucleic acid construct such that the pre-mRNA undergoes alternative splicing to produce about the same levels of mature mRNA encoding lamin A and mature mRNA encoding lamin C. In certain embodiments, the nucleic acid construct comprises nucleotide sequences corresponding to introns 8-11 of a wild-type LMNA gene (e.g. SEQ ID NOs: 77-80). In certain embodiments, the nucleic acid construct comprises nucleotide sequences corresponding to introns 9 and 10 of a wild-type LMNA gene (e.g. SEQ ID NOs: 78 and 79). In certain embodiments, the nucleic acid construct comprises the nucleotide sequence corresponding to intron 10 of a wild-type LMNA gene (e.g. SEQ ID NO: 79).

In some embodiments, the nucleic acid construct comprises at least one, but not all, of the endogenous introns of the wild-type human LMNA gene. In some embodiments, the nucleic acid construct comprises at least one intron corresponding to introns 8-11 of the wild-type human LMNA gene (e.g. SEQ ID NOs: 77-80), and lacks at least one intron corresponding to introns 1-7 of the wild-type human LMNA gene (e.g. SEQ ID NOs: 70-76). In some embodiments, the nucleic acid comprises introns corresponding to introns 8-11 of the wild-type human LMNA gene (e.g. SEQ ID NOs: 77-80), and lacks at least one intron corresponding to introns 1-7 of the wild-type human LMNA gene (e.g. SEQ ID NOs: 70-76). In some embodiments, the nucleic acid comprises introns corresponding to introns 8-11 of the human wild-type LMNA gene (e.g. SEQ ID NOs: 77-80), and lacks all of the introns corresponding to introns 1-7 of the human wild-type LMNA gene (e.g. SEQ ID NOs: 70-76). In some embodiments, the nucleic acid comprises introns corresponding to introns 9-10 of the wild-type human LMNA gene (e.g. SEQ ID NOs: 78 and 79), and lacks at least one intron corresponding to introns 1-7 of the wild-type human LMNA gene (e.g. SEQ ID NOs: 70-76). In some embodiments, the nucleic acid comprises introns corresponding to introns 9-10 of the wild-type human LMNA gene (e.g. SEQ ID NOs: 78 and 79), and lacks all of the introns corresponding to introns 1-7 of the wild-type human LMNA gene (e.g. SEQ ID NOs: 70-76). In some embodiments, the nucleic acid comprises introns corresponding to introns 9-10 of the wild-type human LMNA gene (e.g. SEQ ID NOs: 78 and 79), and lacks all of the introns corresponding to introns 1-8 and 11 of the wild-type human LMNA gene (e.g. SEQ ID NOs: 70-77 and 80). In some embodiments, the nucleic acid comprises the intron corresponding to intron 10 of the wild-type human LMNA gene (e.g. SEQ ID NO: 79), and lacks at least one intron corresponding to introns 1-7 of the wild-type human LMNA gene (e.g. SEQ ID NOs: 70-76). In some embodiments, the nucleic acid comprises the intron corresponding to intron 10 of the wild-type human LMNA gene (e.g. SEQ ID NO: 79), and lacks all of the introns corresponding to introns 1-7 of the wild-type human LMNA gene (e.g. SEQ ID NOs: 70-76). In some embodiments, the nucleic acid comprises the intron corresponding to intron 10 of the wild-type human LMNA gene (e.g. SEQ ID NO: 79), and lacks all of the introns corresponding to introns 1-9 and 11 of the wild-type human LMNA gene (e.g. SEQ ID NOs: 70-78 and 80). In some embodiments, the intron corresponding to intron 8 of the wild-type human LMNA gene comprises a nucleotide sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 77, or a fragment thereof. In some embodiments, the intron corresponding to intron 9 of the wild-type human LMNA gene comprises a nucleotide sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 78, or a fragment thereof. In some embodiments, the intron corresponding to intron 10 of the wild-type human LMNA gene comprises a nucleotide sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 79 or a fragment thereof. In some embodiments, the intron corresponding to intron 11 of the wild-type human LMNA gene comprises a nucleotide sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 80 or a fragment thereof.

In some cases, the nucleic acid construct comprises a nucleotide sequence encoding lamin A (or a biologically active fragment or variant thereof) and/or lamin C (or a biologically active fragment or variant thereof), wherein the nucleotide sequence comprises intron 8 of a wild-type LMNA gene. In some cases, the nucleic acid construct comprises a nucleotide sequence encoding lamin A (or a biologically active fragment or variant thereof) and/or lamin C (or a biologically active fragment or variant thereof), wherein the nucleotide sequence comprises intron 9 of a wild-type LMNA gene. In some cases, the nucleic acid construct comprises a nucleotide sequence encoding lamin A (or a biologically active fragment or variant thereof) and/or lamin C (or a biologically active fragment or variant thereof), wherein the nucleotide sequence comprises intron 10 of a wild-type LMNA gene. In some cases, the nucleic acid construct comprises a nucleotide sequence encoding lamin A (or a biologically active fragment or variant thereof) and/or lamin C (or a biologically active fragment or variant thereof), wherein the nucleotide sequence comprises intron 11 of a wild-type LMNA gene. In some cases, the nucleic acid construct comprises a nucleotide sequence encoding lamin A (or a biologically active fragment or variant thereof) and/or lamin C (or a biologically active fragment or variant thereof), wherein the nucleotide sequence comprises introns 9 and 10 of a wild-type LMNA gene. In some cases, the nucleic acid construct comprises a nucleotide sequence encoding lamin A (or a biologically active fragment or variant thereof) and/or lamin C (or a biologically active fragment or variant thereof), wherein the nucleotide sequence comprises introns 8, 9, 10, and 11 of a wild-type LMNA gene.

In certain embodiments, the nucleic acid construct comprises a nucleotide sequence that comprises, consists of, or consists essentially of, the nucleic acid sequence of any one or more of SEQ ID NOs: 77-80, and nucleic acid sequences that are at least 60%, 65%, 70%, 75%, 80%, 82%, 85%, 87%, 90%, 91%, 92%, 93%, 94%, 95%, 96%, 97%, 98%, 99% or 100% identical to any one or more of the foregoing. In certain embodiments, the nucleic acid construct comprises a nucleotide sequence that is the sequence of any one or more of SEQ ID NOs: 77-80, or a biologically active variant and/or a fragment thereof. In certain embodiments, the nucleic acid construct comprises a nucleotide sequence that is at least 60% identical to any one or more of SEQ ID NOs: 77-80, or a biologically active variant and/or a fragment thereof. In certain embodiments, the nucleic acid construct comprises a nucleotide sequence that is at least 65% identical to any one or more of SEQ ID NOs: 77-80, or a biologically active variant and/or a fragment thereof. In certain embodiments, the nucleic acid construct comprises a nucleotide sequence that is at least 70% identical to any one or more of SEQ ID NOs: 77-80, or a biologically active variant and/or a fragment thereof. In certain embodiments, the nucleic acid construct comprises a nucleotide sequence that is at least 75% identical to any one or more of SEQ ID NOs: 77-80, or a biologically active variant and/or a fragment thereof. In certain embodiments, the nucleic acid construct comprises a nucleotide sequence that is at least 80% identical to any one or more of SEQ ID NOs: 77-80, or a biologically active variant and/or a fragment thereof. In certain embodiments, the nucleic acid construct comprises a nucleotide sequence that is at least 82% identical to any one or more of SEQ ID NOs: 77-80, or a biologically active variant and/or a fragment thereof. In certain embodiments, the nucleic acid construct comprises a nucleotide sequence that is at least 85% identical to any one or more of SEQ ID NOs: 77-80, or a biologically active variant and/or a fragment thereof. In certain embodiments, the nucleic acid construct comprises a nucleotide sequence that is at least 87% identical to any one or more of SEQ ID NOs: 77-80, or a biologically active variant and/or a fragment thereof. In certain embodiments, the nucleic acid construct comprises a nucleotide sequence that is at least 90% identical to any one or more of SEQ ID NOs: 77-80, or a biologically active variant and/or a fragment thereof. In certain embodiments, the nucleic acid construct comprises a nucleotide sequence that is at least 91% identical to any one or more of SEQ ID NOs: 77-80, or a biologically active variant and/or a fragment thereof. In certain embodiments, the nucleic acid construct comprises a nucleotide sequence that is at least 92% identical to any one or more of SEQ ID NOs: 77-80, or a biologically active variant and/or a fragment thereof. In certain embodiments, the nucleic acid construct comprises a nucleotide sequence that is at least 93% identical to any one or more of SEQ ID NOs: 77-80, or a biologically active variant and/or a fragment thereof. In certain embodiments, the nucleic acid construct comprises a nucleotide sequence that is at least 94% identical to any one or more of SEQ ID NOs: 77-80, or a biologically active variant and/or a fragment thereof. In certain embodiments, the nucleic acid construct comprises a nucleotide sequence that is at least 95% identical to any one or more of SEQ ID NOs: 77-80, or a biologically active variant and/or a fragment thereof. In certain embodiments, the nucleic acid construct comprises a nucleotide sequence that is at least 96% identical to any one or more of SEQ ID NOs: 77-80, or a biologically active variant and/or a fragment thereof. In certain embodiments, the nucleic acid construct comprises a nucleotide sequence that is at least 97% identical to any one or more of SEQ ID NOs: 77-80, or a biologically active variant and/or a fragment thereof. In certain embodiments, the nucleic acid construct comprises a nucleotide sequence that is at least 98% identical to any one or more of SEQ ID NOs: 77-80, or a biologically active variant and/or a fragment thereof. In certain embodiments, the nucleic acid construct comprises a nucleotide sequence that is at least 99% identical to any one or more of SEQ ID NOs: 77-80, or a biologically active variant and/or a fragment thereof. In certain embodiments, the nucleic acid construct comprises a nucleotide sequence that is 100% identical to any one or more of SEQ ID NOs: 77-80, or a biologically active variant and/or a fragment thereof. 1851 In some embodiments, a transgene of the disclosure comprises a variant of these sequences, wherein such variants can include missense mutations, nonsense mutations, duplications, deletions, and/or additions. In some embodiments, the variant comprises a polynucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to the specific nucleic acid sequence set forth in SEQ ID NO: 3. In some embodiments, the variant comprises a polynucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to the specific nucleic acid sequence set forth in SEQ ID NO: 4. In some embodiments, the variant comprises a polynucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to the specific nucleic acid sequence set forth in SEQ ID NO: 5. In some embodiments, the variant comprises a polynucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to the specific nucleic acid sequence set forth in SEQ ID NO: 6. In some embodiments, the variant comprises a polynucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to the specific nucleic acid sequence set forth in SEQ ID NO: 7. In some embodiments, the variant comprises a polynucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to the specific nucleic acid sequence set forth in SEQ ID NO: 8. In some embodiments, the variant comprises a polynucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to the specific nucleic acid sequence set forth in SEQ ID NO: 9. In some embodiments, the variant comprises a polynucleotide sequence that is at least 60%, at least 65%, at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% identical to the specific nucleic acid sequence set forth in SEQ ID NO: 10.

In some embodiments, the variant comprises a nucleic acid construct comprising a nucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to SEQ ID NO: 1 that encodes the polypeptide sequence of SEQ ID NO: 12 or 21. In some embodiments, the variant comprises a nucleic acid construct comprising a nucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to SEQ ID NO: 6 that encodes the polypeptide sequence of SEQ ID NO: 12 or 21. In some embodiments, the variant comprises a nucleic acid construct comprising a nucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to SEQ ID NO: 2 that encodes the polypeptide sequence of SEQ ID NO: 13. In some embodiments, the variant comprises a nucleic acid construct comprising a nucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to SEQ ID NO: 7 that encodes the polypeptide sequence of SEQ ID NO: 13. In some embodiments, the variant comprises a nucleic acid construct comprising a nucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to SEQ ID NO: 3 that encodes the polypeptide sequence of any one or more of SEQ ID NOs: 12, 13 or 21. In some embodiments, the variant comprises a nucleic acid construct comprising a nucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to SEQ ID NO: 4 that encodes the polypeptide sequence of any one or more of SEQ ID NOs: 12, 13 or 21. In some embodiments, the variant comprises a nucleic acid construct comprising a nucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to SEQ ID NO: 5 that encodes the polypeptide sequence of any one or more of SEQ ID NOs: 12, 13 or 21. In some embodiments, the variant comprises a nucleic acid construct comprising a nucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to SEQ ID NO: 8 that encodes the polypeptide sequence of any one or more of SEQ ID NOs: 12, 13 or 21. In some embodiments, the variant comprises a nucleic acid construct comprising a nucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to SEQ ID NO: 9 that encodes the polypeptide sequence of any one or more of SEQ ID NOs: 12, 13 or 21. In some embodiments, the variant comprises a nucleic acid construct comprising a nucleotide sequence that is at least 60%, at least 65%, at least 70%, at least 75%, at least 80%, at least 82%, at least 85%, at least 87%, at least 89%, at least 90%, at least 91%, at least 92%, at least 93%, at least 94%, at least 95%, at least 96%, at least 97%, at least 98%, or at least 99% identical to SEQ ID NO: 10 that encodes the polypeptide sequence of any one or more of SEQ ID NOs: 12, 13 or 21.

One of ordinary skill in the art will appreciate that nucleic acid sequences complementary to the nucleic acids, and variants of the nucleic acids are also within the scope of this disclosure. Nucleic acid sequences may be single-stranded (coding or antisense) or double-stranded, and may be DNA (genomic or synthetic), cDNA, or RNA molecules. RNA molecules include mRNA molecules. Additional coding or non-coding sequences may, but need not, be present within a nucleic acid sequence of the present disclosure, and a nucleic acid sequence may, but need not, be linked to other molecules and/or support materials. In further embodiments, the nucleic acid sequences of the disclosure can be isolated, recombinant, and/or fused with a heterologous nucleotide sequence. In some embodiments, any of the nucleotides disclosed herein (e.g., SEQ ID NOs: 1-10, or variants or fragments thereof) is codon-optimized (e.g., codon-optimized for human expression). In some embodiments, a transgene encodes a biologically active lamin A and/or lamin C polypeptide with 1, 2, 3, 4, 5, 6, 7, 8, 9, 10, 11, 12, 13, 14, or 15 amino acid substitutions, deletions, and/or additions relative to the wild-type polypeptide (e.g., a polypeptide comprising the amino acid sequence of SEQ ID NO: 12, 13, or 21). In some embodiments, a transgene encodes a biologically active lamin A and/or lamin C polypeptide with 1, 2, 3, 4, or 5 amino acid deletions relative to the wild-type polypeptide (e.g., a polypeptide comprising the amino acid sequence of SEQ ID NO: 12, 13, or 21). In some embodiments, a transgene encodes a biologically active lamin A and/or lamin C polypeptide with 1, 2, 3, 4, or 5 amino acid substitutions relative to the wild-type polypeptide (e.g., a polypeptide comprising the amino acid sequence of SEQ ID NO: 12, 13, or 21). In some embodiments, a transgene encodes a biologically active lamin A and/or lamin C polypeptide with 1, 2, 3, 4, or 5 amino acid insertions relative to the wild-type polypeptide (e.g., a polypeptide comprising the amino acid sequence of SEQ ID NO: 12, 13, or 21).

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure (i.e. codon optimization). For example, a number of amino acids are designated by more than one triplet. Codons that specify the same amino acid, or synonyms (for example, CAU and CAC are synonyms for histidine) may result in "silent" mutations which do not affect the amino acid sequence of the protein. One skilled in the art will appreciate that these variations in one or more nucleotides (up to about 3-5% of the nucleotides) of the nucleic acids encoding a particular protein may exist among members of a given species due to natural allelic variation. Any and all such nucleotide variations and resulting amino acid polymorphisms are within the scope of this disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The nucleic acids/polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence. In other embodiments, nucleic acids of the disclosure also include nucleotide sequences that hybridize under highly stringent conditions to any of the nucleotide sequences set forth in any one of SEQ ID NOs: 1-10 (or variants or fragments thereof), or sequences complementary thereto. One of ordinary skill in the art will readily understand that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

As provided herein, any of the LMNA transgenes or fragments thereof (e.g. a gene encoding lamin A and/or lamin C) disclosed herein may be used to correct or ameliorate gene deficiencies, which may include deficiencies in which normal variant gene products of LMNA are expressed at less than normal levels or deficiencies in which the functional variants are not expressed. In some embodiments, the transgene sequence encodes a single LMNA isoform or biologically active fragment thereof. The disclosure further includes using multiple transgenes, e.g., two or more transgenes encoding two or more LMNA isoforms or biologically active fragments thereof. In a particular embodiment, different LMNA isoforms (e.g. lamin A and/or lamin C or biologically active fragments or variants thereof) may be encoded by the same transgene by utilizing alternative splicing of a single nucleotide sequence. In certain situations, a different transgene may be used to encode different LMNA isoforms or biologically active fragments thereof (e.g. lamin A and/or lamin C or biologically active fragments or variants thereof). Alternatively, multiple different LMNA isoforms (e.g. lamin A and/or lamin C or biologically active fragments or variants thereof) may be encoded by the same transgene. In some embodiments, a single transgene includes the DNA encoding multiple LMNA isoforms (e.g.

lamin A and lamin C or biologically active fragments or variants thereof) with the DNA for each protein or functional fragment thereof separated by one or more internal ribozyme entry site (IRES) or self-cleaving 2A peptides. In some embodiments, this is desirable when the size of the DNA encoding each of the subunits is small, e.g., the total size of the DNA encoding the subunits and the IRES is less than five kilobases. As an alternative to an IRES, the DNA may be separated by one or more sequences encoding a 2A peptide, which self-cleaves in a post-translational event. See, e.g., MX. Donnelly, et al, J. Gen. Virol, 78(Pt 1): 13-21 (January 1997); Furler, S., et al, Gene Ther., 8(11):864-873 (June 2001); Klump H., et al, Gene Ther., 8(10):811-817 (May 2001). This 2A peptide is significantly smaller than an IRES, making it well suited for use when space is a limiting factor. In some embodiments, the one or more self-cleaving 2A peptides are selected from the group consisting of T2A, P2A, E2A, and F2A.

2. Regulatory Elements

In certain embodiments, the lamin A and/or lamin C constructs disclosed herein are part of a nucleic acid construct comprising one or more regulatory elements in addition to the lamin A and/or lamin C sequence. In exemplary embodiments, the lamin A and/or lamin C constructs disclosed herein are part of a nucleic acid construct comprising a promoter situated upstream of the lamin A and/or lamin C construct so as to be capable of driving expression of the lamin A and/or lamin C sequence in a cell.

In one embodiment, a nucleic acid construct disclosed herein comprises a promoter comprising a sequence that is at least 80%, 85%, 90%, 91%, 92%, 93%, 94%, 95%, 96%, 97%, 98%, 99% or 100% identical to any one of SEQ ID NOs: 30-69 or 100-102 (as shown below in Tables 3 and 4). In one embodiment, a nucleic acid construct disclosed herein comprises a promoter having any one of SEQ ID NOs: 30-69 or 100-102 (as shown below in Tables 3 and 4) operably linked to any one of the lamin A and/or lamin C sequences disclosed herein, e.g., a lamin A and/or lamin C sequence comprising any one of SEQ ID NOs: 1-5 (as shown below in Table 1), or a functional fragment thereof. In one embodiment, a nucleic acid construct comprises a promoter comprising a sequence that is at least 80%, 85%, 90%, 91%, 92%, 93%, 94%, 95%, 96%, 97%, 98%, 99% or 100% identical to SEQ ID NO: 102. In one embodiment, a nucleic acid construct comprises a promoter having the sequence of SEQ ID NO: 102. In another embodiment, a nucleic acid construct disclosed herein comprises a regulatory element having a combination of two or more (e.g., two or more, three or more, four or more, five or more, or 2, 3, 4, or 5) of any one of SEQ ID NOs: 30-69 or 100-102 (as shown below in Tables 3 and 4) operably linked to any one of the lamin A and/or lamin C sequences disclosed herein, e.g., a lamin A and/or lamin C sequence comprising any one of SEQ ID NOs: 1-5 (as shown below in Table 1), or a functional fragment thereof.

In certain embodiments, a nucleic acid construct disclosed herein comprises a promoter having any one of SEQ ID NOs: 30-69 or 100-102 (as shown below in Tables 3 and 4) operably linked to any one of the lamin A and/or lamin C sequences disclosed herein, e.g., a lamin A and/or lamin C sequence comprising any one of SEQ ID NOs: 1-5 (as shown below in Table 1), or a functional fragment thereof. In certain embodiments, the promoter sequence produces at least 5-fold, 10-fold, 15-fold, 20-fold, 25-fold, 30-fold, 35-fold, 40-fold, 45-fold, 50-fold, 55-fold, 60-fold, 65-fold, 70-fold, or 75-fold, or at least 20-90 fold, 20-80 fold, 20-70 fold, 20-60 fold, 30-90 fold, 30-80 fold, 30-70 fold, 30-60 fold, 40-90 fold, 40-80 fold, 40-70 fold, 40-60 fold, 50-90 fold, 50-80 fold, 50-70 fold, 50-60 fold, 60-90 fold, 60-80 fold, 60-70 fold, 70-90 fold, 70-80 fold, 80-90 fold greater expression of the lamin A and/or lamin C sequence in a mammalian cell relative to the level of expression of the same lamin A and/or lamin C sequence from the CMV promoter in the same type of mammalian cell. In certain embodiments, the promoter sequence drives expression of the lamin A and/or lamin C sequence in a high percentage of cardiomyocyte cells, e.g., at least 20%, 25%, 30%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or greater, or at least 20-90%, 20-80%, 20-70%, 30-90%, 30-80%, 30-70%, 40-90%, 40-80%, 40-70%, 50-90%, 50-80%, 50-70%, 60-90%, 60-80%, 60-70%, 70-90%, 70-80%, 80-100%, 80-95%, 80-90%, 90-100%, or 90-95% of cardiomyocytes containing the nucleic acid construct express the lamin A and/or lamin C construct. In certain embodiments, the promoter sequence drives expression of the lamin A and/or lamin C sequence in a high percentage of hepatocyte cells, e.g., at least 20%, 25%, 30%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or greater, or at least 20-90%, 20-80%, 20-70%, 30-90%, 30-80%, 30-70%, 40-90%, 40-80%, 40-70%, 50-90%, 50-80%, 50-70%, 60-90%, 60-80%, 60-70%, 70-90%, 70-80%, 80-100%, 80-95%, 80-90%, 90-100%, or 90-95% of hepatocytes containing the nucleic acid construct express the lamin A and/or lamin C construct.

In one embodiment, a nucleic acid construct disclosed herein comprises a promoter having any one of SEQ ID NOs: 30-69 or 100-102 operably linked to a lamin A and/or lamin C sequence comprising (i) any one of SEQ ID NOs: 1-5, (ii) a sequence having at least 60%, 65%, 70%, 75%, 80%, 85%, 90%, 91%, 92%, 93%, 94%, 95%, 96%, 97%, 98%, 99% or 100% identity to any one of SEQ ID NOs: 1-5, or (iii) a functional fragment of any of the foregoing. In certain embodiments, such lamin A and/or lamin C nucleotide sequence encodes a protein having a sequence that is at least 90%, 95%, 98%, 99% or 100% identical to the wild type lamin A and/or lamin C protein sequence (e.g., SEQ ID NOs: 12, 13, and/or 21). In certain embodiments, such lamin A and/or lamin C sequence encodes a full length lamin A and/or lamin C protein, e.g., having one or more of SEQ ID NOs: 12, 13 and/or 21.

In one embodiment, a nucleic acid construct of the disclosure comprises a promoter having SEQ ID NO: 33 operably linked to a lamin A and/or lamin C sequence comprising (i) any one of SEQ ID NOs: 1-5, (ii) a sequence having at least 60%, 65%, 70%, 75%, 80%, 85%, 90%, 91%, 92%, 93%, 94%, 95%, 96%, 97%, 98%, 99% or 100% identity to any one of SEQ ID NOs: 1-5, or (iii) a functional fragment of any of the foregoing. In certain embodiments, such lamin A and/or lamin C nucleotide sequence encodes a protein having a sequence that is at least 90%, 95%, 98%, 99% or 100% identical to the wild type lamin A and/or lamin C protein sequence (e.g., SEQ ID NOs: 12, 13, and/or 21). In certain embodiments, such lamin A and/or lamin C sequence encodes a full length lamin A and/or lamin C protein, e.g., having one or more of SEQ ID NOs: 12, 13, and/or 21.

In one embodiment, a nucleic acid construct of the disclosure comprises a promoter having SEQ ID NO: 44 operably linked to a lamin A and/or lamin C sequence comprising (i) any one of SEQ ID NOs: 1-5, (ii) a sequence having at least 60%, 65%, 70%, 75%, 80%, 85%, 90%, 91%, 92%, 93%, 94%, 95%, 96%, 97%, 98%, 99% or 100% identity to any one of SEQ ID NOs: 1-5, or (iii) a functional fragment of any of the foregoing. In certain embodiments, such lamin A and/or lamin C nucleotide sequence encodes a protein having a sequence that is at least 90%, 95%, 98%, 99% or 100% identical to the wild type lamin A and/or lamin C protein sequence (e.g., SEQ ID NOs: 12, 13, and/or 21). In certain embodiments, such lamin A and/or lamin C sequence encodes a full length lamin A and/or lamin C protein, e.g., having one or more of SEQ ID NOs: 12, 13, and/or 21.

In one embodiment, a nucleic acid construct of the disclosure comprises a promoter having SEQ ID NO: 35 operably linked to a lamin A and/or lamin C sequence comprising (i) any one of SEQ ID NOs: 1-5, (ii) a sequence having at least 60%, 65%, 70%, 75%, 80%, 85%, 90%, 91%, 92%, 93%, 94%, 95%, 96%, 97%, 98%, 99% or 100% identity to any one of SEQ ID NOs: 1-5, or (iii) a functional fragment of any of the foregoing. In certain embodiments, such lamin A and/or lamin C nucleotide sequence encodes a protein having a sequence that is at least 90%, 95%, 98%, 99% or 100% identical to the wild type lamin A and/or lamin C protein sequence (e.g., SEQ ID NOs: 12, 13, and/or 21). In certain embodiments, such lamin A and/or lamin C sequence encodes a full length lamin A and/or lamin C protein, e.g., having one or more of SEQ ID NOs: 12, 13, and/or 21.

In an exemplary embodiment, a nucleic acid construct of the disclosure comprises a promoter having SEQ ID NO: 44 operably linked to a lamin A and/or lamin C sequence comprising (i) SEQ ID NO: 3, (ii) a sequence having at least 80%, 85%, 90%, 91%, 92%, 93%, 94%, 95%, 96%, 97%, 98%, 99% or 100% identity to SEQ ID NO: 3, or (iii) a functional fragment of any of the foregoing. In certain embodiments, such lamin A and/or lamin C nucleotide sequence encodes a protein having a sequence that is at least 90%, 95%, 98%, 99% or 100% identical to the wild type lamin A and/or lamin C protein sequence (e.g., SEQ ID NOs: 12, 13, and/or 21). In certain embodiments, such lamin A and/or lamin C sequence encodes a full length lamin A and/or lamin C protein, e.g., having one or more of SEQ ID NO: 12, 13, and/or 21.

In an exemplary embodiment, a nucleic acid construct of the disclosure comprises a promoter having SEQ ID NO: 44 operably linked to a lamin A and/or lamin C sequence comprising (i) SEQ ID NO: 4, (ii) a sequence having at least 80%, 85%, 90%, 91%, 92%, 93%, 94%, 95%, 96%, 97%, 98%, 99% or 100% identity to SEQ ID NO: 4, or (iii) a functional fragment of any of the foregoing. In certain embodiments, such lamin A and/or lamin C nucleotide sequence encodes a protein having a sequence that is at least 90%, 95%, 98%, 99% or 100% identical to the wild type lamin A and/or lamin C protein sequence (e.g., SEQ ID NOs: 12, 13, and/or 21). In certain embodiments, such lamin A and/or lamin C sequence encodes a full length lamin A and/or lamin C protein, e.g., having one or more of SEQ ID NO: 12, 13, and/or 21.

In an exemplary embodiment, a nucleic acid construct of the disclosure comprises a promoter having SEQ ID NO: 44 operably linked to a lamin A and/or lamin C sequence comprising (i) SEQ ID NO: 5, (ii) a sequence having at least 80%, 85%, 90%, 91%, 92%, 93%, 94%, 95%, 96%, 97%, 98%, 99% or 100% identity to SEQ ID NO: 5, or (iii) a functional fragment of any of the foregoing. In certain embodiments, such lamin A and/or lamin C nucleotide sequence encodes a protein having a sequence that is at least 90%, 95%, 98%, 99% or 100% identical to the wild type lamin A and/or lamin C protein sequence (e.g., SEQ ID NOs: 12, 13, and/or 21). In certain embodiments, such lamin A and/or lamin C sequence encodes a full length lamin A and/or lamin C protein, e.g., having one or more of SEQ ID NO: 12, 13, and/or 21.

In an exemplary embodiment, a nucleic acid construct of the disclosure comprises a promoter having SEQ ID NO: 35 operably linked to a lamin A and/or lamin C sequence comprising (i) SEQ ID NO: 3, (ii) a sequence having at least 80%, 85%, 90%, 91%, 92%, 93%, 94%, 95%, 96%, 97%, 98%, 99% or 100% identity to SEQ ID NO: 3, or (iii) a functional fragment of any of the foregoing. In certain embodiments, such lamin A and/or lamin C nucleotide sequence encodes a protein having a sequence that is at least 90%, 95%, 98%, 99% or 100% identical to the wild type lamin A and/or lamin C protein sequence (e.g., SEQ ID NOs: 12, 13, and/or 21). In certain embodiments, such lamin A and/or lamin C sequence encodes a full length lamin A and/or lamin C protein, e.g., having one or more of SEQ ID NOs: 12, 13, and/or 21.

In an exemplary embodiment, a nucleic acid construct of the disclosure comprises a promoter having SEQ ID NO: 35 operably linked to a lamin A and/or lamin C sequence comprising (i) SEQ ID NO: 4, (ii) a sequence having at least 80%, 85%, 90%, 91%, 92%, 93%, 94%, 95%, 96%, 97%, 98%, 99% or 100% identity to SEQ ID NO: 4, or (iii) a functional fragment of any of the foregoing. In certain embodiments, such lamin A and/or lamin C nucleotide sequence encodes a protein having a sequence that is at least 90%, 95%, 98%, 99% or 100% identical to the wild type lamin A and/or lamin C protein sequence (e.g., SEQ ID NOs: 12, 13, and/or 21). In certain embodiments, such lamin A and/or lamin C sequence encodes a full length lamin A and/or lamin C protein, e.g., having one or more of SEQ ID NOs: 12, 13, and/or 21.

In an exemplary embodiment, a nucleic acid construct of the disclosure comprises a promoter having SEQ ID NO: 35 operably linked to a lamin A and/or lamin C sequence comprising (i) SEQ ID NO: 5, (ii) a sequence having at least 80%, 85%, 90%, 91%, 92%, 93%, 94%, 95%, 96%, 97%, 98%, 99% or 100% identity to SEQ ID NO: 5, or (iii) a functional fragment of any of the foregoing. In certain embodiments, such lamin A and/or lamin C nucleotide sequence encodes a protein having a sequence that is at least 90%, 95%, 98%, 99% or 100% identical to the wild type lamin A and/or lamin C protein sequence (e.g., SEQ ID NOs: 12, 13, and/or 21). In certain embodiments, such lamin A and/or lamin C sequence encodes a full length lamin A and/or lamin C protein, e.g., having one or more of SEQ ID NOs: 12, 13, and/or 21.

In one embodiment, a nucleic acid construct disclosed herein comprises a promoter selected from the group consisting of: the cytomegalovirus (CMV) promoter, the chicken β-actin (CBA) promoter, the CMV enhancer used upstream of a CBA promoter (e.g. SEQ ID NO: 61), the super core promoter (SCP) promoter, the SerpE_TTR promoter (e.g. SEQ ID NO: 63), the Protol promoter (e.g. SEQ ID NO: 64), the minimal CMV (minCMV) promoter, the University College London hybrid liver-specific promoter (UCL-HLP) promoter, the CMV enhancer (CMVe), the CMV early enhancer/CBA (CAG) promoter, the Myh6 promoter, the Desmin promoter, the cardiac troponin T (cTnT) promoter, the alpha-myosin heavy chain (α-MHC) promoter, the myosin light chain 2 (MLC-2) promoter, SEQ ID NO: 102, and the EF1α short (EFS) promoter operably linked to a lamin A and/or lamin C sequence comprising (i) any one of SEQ ID NOs: 1-5, (ii) a sequence having at least 60%, 65%, 70%, 75%, 80%, 85%, 90%, 91%, 92%, 93%, 94%, 95%, 96%, 97%, 98%, 99% or 100% identity to any one of SEQ ID NOs: 1-5, or (iii) a functional fragment of any of the foregoing. In certain embodiments, such lamin A and/or lamin C nucleotide sequence encodes a protein having a sequence that is at least 90%, 95%, 98%, 99% or 100% identical to the wild type lamin A and/or lamin C protein sequence (e.g., SEQ ID NOs: 12, 13, and 21). In certain embodiments, such lamin A and/or lamin C sequence encodes a full length lamin A and/or lamin C protein, e.g., having one or more of SEQ ID NOs: 12, 13, and 21. In one embodiment, a nucleic acid construct disclosed herein comprises a promoter having any one of SEQ ID NOs: 30-58 or 100-102 operably linked to a lamin A and/or lamin C sequence comprising (i) any one of SEQ ID NOs: 1-5, (ii) a sequence having at least 60%, 65%, 70%, 75%, 80%, 85%, 90%, 91%, 92%, 93%, 94%, 95%, 96%, 97%, 98%, 99% or 100% identity to any one of SEQ ID NOs: 1-5, or (iii) a functional fragment of any of the foregoing. In certain embodiments, such lamin A and/or lamin C nucleotide sequence are sequences that encode a protein having a sequence that is at least 90%, 95%, 98%, 99% or 100% identical to the wild type lamin A and/or lamin C protein sequence (e.g., SEQ ID NOs: 12, 13, and/or 21). In certain embodiments, such lamin A and/or lamin C sequences may comprise (i) any one of SEQ ID NOs: 1-5, or (ii) a sequence having at least 60%, 65%, 70%, 75%, 80%, 85%, 90%, 91%, 92%, 93%, 94%, 95%, 96%, 97%, 98%, 99% or 100% identity to any one of SEQ ID NOs: 1-5, wherein such lamin A and/or lamin C sequence encodes a full length lamin A and/or lamin C protein, e.g., having one or more of SEQ ID NOs: 12, 13, and/or 21.

In certain embodiments, a nucleic acid construct disclosed herein comprises a lamin A and/or lamin C nucleotide sequence that has been truncated so as to encode a functional fragment of a lamin A and/or lamin C protein. Exemplary truncated lamin A and/or lamin C nucleotide sequences may comprise a sequence having at least 60%, 65%, 70%, 75%, 80%, 85%, 90%, 91%, 92%, 93%, 94%, 95%, 96%, 97%, 98%, 99% or 100% identity to any one of SEQ ID NOs: 1-5, wherein such lamin A and/or lamin C nucleotide sequence encodes a functional fragment of lamin A and/or lamin C. In certain embodiments, a nucleic acid construct disclosed herein comprises a variant lamin A and/or lamin C nucleotide sequence that has been truncated so as to encode a functional fragment of a lamin A and/or lamin C protein. Exemplary truncated lamin A and/or lamin C nucleotide sequences may a sequence having at least 60%, 65%, 70%, 75%, 80%, 85%, 90%, 91%, 92%, 93%, 94%, 95%, 96%, 97%, 98%, 99% or 100% identity to any one of SEQ ID NOs: 1-5, wherein such truncated variant lamin A and/or lamin C nucleotide sequence encodes a functional fragment of lamin A and/or lamin C protein.

In certain embodiments, the nucleic acid constructs described herein comprise another regulatory element in an addition to a promoter, such as, for example, sequences associated with transcription initiation or termination, enhancer sequences, and efficient RNA processing signals. Exemplary regulatory elements include, for example, an intron, an enhancer, UTR, stability element, WPRE sequence, a Kozak consensus sequence, posttranslational response element, or a polyadenylation (polyA) sequence, or a combination thereof. Regulatory elements can function to modulate gene expression at the transcriptional phase, post-transcriptional phase, or at the translational phase of gene expression. At the RNA level, regulation can occur at the level of translation (e.g., stability elements that stabilize mRNA for translation), RNA cleavage, RNA splicing, and/or transcriptional termination. In various embodiments, regulatory elements can recruit transcription factors to a coding region that increase gene expression selectivity in a cell type of interest, increase the rate at which RNA transcripts are produced, increase the stability of RNA produced, and/or increase the rate of protein synthesis from RNA transcripts.

In one embodiment, the nucleic acid constructs described herein further comprise an enhancer sequence. Exemplary enhancer sequences include, for example, the En34 enhancer (34 bp core enhancer from the human apolipoprotein hepative control region, the EnTTR enhancer (100 bp enhancer sequence from transthyretin), the al-microglobulin/bikunin precursor enhancer, the ABPS enhancer (shortened version of the 100 bp distal enhancer from the al-microglobulin/bikunin precursor to 42 bp), or the ApoE enhancer. See e.g., WO 2018/126116 and Wu et al., Mol Therapy 16(2): 280-289 (2008)). In another embodiment, a suitable enhancer sequence is an intronic sequence comprising SEQ ID NO: 30 or SEQ ID NO: 31. In certain embodiments, an enhancer sequence is positioned upstream of the transgene and the promoter, or between the promoter and the transgene in the nucleic acid constructs described herein.

In certain embodiments, the nucleic acid constructs described herein further comprise a polyA sequence. Suitable polyA sequences include, for example, an artificial polyA that is about 75 bp in length (PA75) (see e.g., WO 2018/126116), the bovine growth hormone polyA, SV40 early polyA signal, SV40 late polyA signal, rabbit beta globin polyA, HSV thymidine kinase polyA, protamine gene polyA, adenovirus 5 EIb polyA, growth hormone polyA, or a PBGD polyA. In certain embodiments, the polyA sequence is positioned downstream of the transgene in the nucleic acid constructs described herein.

In certain embodiments, a regulatory element suitable for use in accordance with the nucleic acid molecules described herein comprises less than 900 bp, 850 bp, 800 bp, 750 bp, 700 bp, 650 bp, 600 bp, 550 bp, 500 bp, 450 bp, 400 bp, 350 bp, 300 bp, 250 bp, 225 bp, 200 bp, 175 bp, 150 bp, 145 bp, 140 bp, 135 bp, 130 bp, 125 bp, 120 bp, 115 bp, 110 bp, 105 bp, 100 bp, 95 bp, 90 bp, 85 bp, 80 bp or 75 bp, or from about 80-300 bp, 80-275 bp, 80-250 bp, 80-200 bp, 80-150 bp, 80-125 bp, 80-120 bp, 80-115 bp, 80-110 bp, 80-105 bp, 80-100 bp, 85-300 bp, 85-275 bp, 85-250 bp, 85-200 bp, 85-150 bp, 85-125 bp, 85-120 bp, 85-115 bp, 85-110 bp, 85-105 bp, 85-100 bp, 90-300 bp, 90-275 bp, 90-250 bp, 90-200 bp, 90-150 bp, 90-125 bp, 90-120 bp, 90-115 bp, 90-110 bp, 90-105 bp, 90-100 bp, 95-300 bp, 95-275 bp, 95-250 bp, 95-200 bp, 95-150 bp, 95-125 bp, 95-120 bp, 95-115 bp, 95-110 bp, 95-105 bp, 95-100 bp, 100-300 bp, 100-275 bp, 100-250 bp, 100-200 bp, 100-150 bp, 100-125 bp, 100-120 bp, 100-115 bp, 100-110 bp, or 100-105 bp. In exemplary embodiments, a regulatory element suitable for use in accordance with the nucleic acid molecules described herein comprises from about 100-120 bp, about 117 bp, or about 100 bp.

In certain embodiments, a nucleic acid construct described herein comprising an lamin A and/or lamin C nucleic acid sequence and a regulatory element is suitable for packaging in an AAV vector, e.g., comprising less than ~4.7 Kb. In certain embodiments, a nucleic acid construct described herein comprising an lamin A and/or lamin C nucleic acid sequence and a regulatory element comprising from about 4,450-4,550 bp, 4,450-4,540 bp, 4,450-4,530 bp, 4,450-4,520 bp, 4,450-4,510 bp, 4,450-4,500 bp, 4,460-4,550 bp, 4,460-4,540 bp, 4,460-4,530 bp, 4,460-4,520 bp, 4,460-4,510 bp, 4,460-4,500 bp, 4,470-4,550 bp, 4,470-4,540 bp, 4,470-4,530 bp, 4,470-4,520 bp, 4,470-4,510 bp, 4,470-4,500 bp, 4,480-4,550 bp, 4,480-4,540 bp, 4,480-4,530 bp, 4,480-4,520 bp, 4,480-4,510 bp, 4,480-4,500 bp, 4,490-4,550 bp, 4,490-4,540 bp, 4,490-4,530 bp, 4,490-4,520 bp, 4,490-4,510 bp, or 4,490-4,500 bp, or comprises about 4,498 bp or about 4,515 bp. In exemplary embodiments, such nucleic acid constructs encode a full length lamin A and/or lamin C protein, e.g., an lamin A and/or lamin C protein having one or more of SEQ ID NOs: 12, 13, and/or 21.

In another embodiment, the transgenes useful herein include reporter sequences, which upon expression produce a detectable signal. Such reporter sequences include, without limitation, DNA sequences encoding β-lactamase, β-galactosidase (LacZ), alkaline phosphatase, thymidine kinase, green fluorescent protein (GFP), red fluorescent protein (RFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (MA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

D. Expression Vectors

In certain embodiments, and of the lamin A and/or lamin C nucleotide sequences or expression constructs described herein may be incorporated into an expression vector.

Expression vectors may be used to deliver the nucleic acid molecule to a target cell via transfection or transduction. A vector may be an integrating or non-integrating vector, referring to the ability of the vector to integrate the expression cassette or transgene into the genome of the host cell. Examples of expression vectors include, but are not limited to, (a) non-viral vectors such as nucleic acid vectors including linear oligonucleotides and circular plasmids; artificial chromosomes such as human artificial chromosomes (HACs), yeast artificial chromosomes (YACs), and bacterial artificial chromosomes (BACs or PACs)); episomal vectors; transposons (e.g., PiggyBac); and (b) viral vectors such as retroviral vectors, lentiviral vectors, adenoviral vectors, and adeno-associated viral vectors.

Expression vectors may be linear oligonucleotides or circular plasmids and can be delivered to a cell via various transfection methods, including physical and chemical methods. Physical methods generally refer to methods of delivery employing a physical force to counteract the cell membrane barrier in facilitating intracellular delivery of genetic material. Examples of physical methods include the use of a needle, ballistic DNA, electroporation, sonoporation, photoporation, magnetofection, and hydroporation. Chemical methods generally refer to methods in which chemical carriers deliver a nucleic acid molecule to a cell and may include inorganic particles, lipid-based vectors, polymer-based vectors and peptide-based vectors.

In some embodiments, an expression vector is administered to a target cell using an inorganic particle. Inorganic particles may refer to nanoparticles, such as nanoparticles that are engineered for various sizes, shapes, and/or porosity to escape from the reticuloendothelial system or to protect an entrapped molecule from degradation. Inorganic nanoparticles can be prepared from metals (e.g., iron, gold, and silver), inorganic salts, or ceramics (e.g, phosphate or carbonate salts of calcium, magnesium, or silicon). The surface of these nanoparticles can be coated to facilitate DNA binding or targeted gene delivery. Magnetic nanoparticles (e.g., supermagnetic iron oxide), fullerenes (e.g., soluble carbon molecules), carbon nanotubes (e.g., cylindrical fullerenes), quantum dots and supramolecular systems may also be used.

In some embodiments, an expression vector is administered to a target cell using a cationic lipid (e.g., cationic liposome). Various types of lipids have been investigated for gene delivery, such as, for example, a lipid nano emulsion (e.g., which is a dispersion of one immiscible liquid in another stabilized by emulsifying agent) or a solid lipid nanoparticle.

In some embodiments, any of the expression vectors disclosed herein is administered to a target cell using a peptide based delivery vehicle. Peptide based delivery vehicles can have advantages of protecting the genetic material to be delivered, targeting specific cell receptors, disrupting endosomal membranes and delivering genetic material into a nucleus. In some embodiments, an expression vector is administered to a target cell using a polymer based delivery vehicle. Polymer based delivery vehicles may comprise natural proteins, peptides and/or polysaccharides or synthetic polymers. In one embodiment, a polymer based delivery vehicle comprises polyethylenimine (PEI). PEI can condense DNA into positively charged particles which bind to anionic cell surface residues and are brought into the cell via endocytosis. In other embodiments, a polymer based delivery vehicle may comprise poly-L-lysine (PLL), poly (DL-lactic acid) (PLA), poly (DL-lactide-co-glycoside) (PLGA), polyornithine, polyarginine, histones, protamines, dendrimers, chitosans, synthetic amino derivatives of dextran, and/or cationic acrylic polymers. In certain embodiments, polymer based delivery vehicles may comprise a mixture of polymers, such as, for example PEG and PLL.

Provided herein are viral vectors comprising any of the nucleic acid constructs and/or polynucleotide sequences disclosed herein. In particular embodiments, the viral vector comprises a nucleotide sequence encoding (a) a lamin A polypeptide; (b) a lamin C polypeptide; (c) a lamin A and lamin C polypeptide; or biologically active variants and/or fragments thereof of any of the foregoing. In particular embodiments, the viral vector comprises a nucleotide sequence encoding (a) a biologically active fragment of a lamin A polypeptide; (b) a biologically active fragment of a lamin C polypeptide; (c) a biologically active fragment of a lamin A and biologically active fragment of a lamin C polypeptide; and/or a fragment thereof. In certain embodiments, the viral vector comprises a nucleotide sequence encoding lamin A or a biologically active variant and/or fragment thereof. In certain embodiments, the viral vector comprises a nucleotide sequence encoding lamin C or a biologically active variant and/or fragment thereof. In certain embodiments, the viral vector comprises a nucleotide sequence encoding lamin A and lamin C or biologically active variants and/or fragments thereof.

In certain embodiments, an expression vector may be a viral vector suitable for gene therapy. Preferred characteristics of viral gene therapy vectors or gene delivery vectors may include the ability to be reproducibly and stably propagated and purified to high titres; to mediate targeted delivery (e.g., to deliver the transgene specifically to the tissue or organ of interest without widespread vector dissemination elsewhere); and to mediate gene delivery and transgene expression without inducing harmful side effects.

Several types of viruses, for example the non-pathogenic parvovirus referred to as adeno-associated virus, have been engineered for the purposes of gene therapy by harnessing the viral infection pathway but avoiding the subsequent expression of viral genes that can lead to replication and toxicity. Such viral vectors can be obtained by deleting all, or some, of the coding regions from the viral genome, but leaving intact those sequences (e.g., terminal repeat sequences) that may be necessary for functions such as packaging the vector genome into the virus capsid or the integration of vector nucleic acid (e.g., DNA) into the host chromatin.

In some cases, the viral vector comprises a transgene operably linked to one or more regulatory elements, wherein the transgene encodes lamin A, lamin C, lamin A and lamin C, or a codon-optimized variant and/or fragment thereof. In certain embodiments, the transgene comprises a nucleotide sequence encoding (a) a lamin A polypeptide; (b) a lamin C polypeptide; (c) a lamin A and lamin C polypeptide; or biologically active variants and/or fragments thereof. In certain embodiments, the transgene comprises a nucleotide sequence encoding lamin C or biologically active variants and/or fragments thereof. In certain embodiments, the transgene comprises a nucleotide sequence encoding lamin A and lamin C or biologically active variants and/or fragments thereof.

In certain embodiments, the viral vector comprises a nucleotide sequence encoding exons 1-12 of a wild-type LMNA gene (e.g. SEQ ID NOs: 81-93) and introns 8-11 of a wild-type LMNA gene (e.g. SEQ ID NOs: 77-80). In certain embodiments, the viral vector comprises a nucleotide sequence encoding exons 1-12 of a wild-type LMNA gene (e.g. SEQ ID NOs: 81-93) and introns 9 and 10 of a wild-type LMNA gene (e.g. SEQ ID NOs: 78 and 79). In certain embodiments, the viral vector comprises a nucleotide sequence encoding exons 1-12 of a wild-type LMNA gene (e.g. SEQ ID NOs: 81-93) and intron 10 of a wild-type LMNA gene (e.g. SEQ ID NO: 79).

In certain embodiments, the viral vector comprises a nucleotide sequence that comprises, consists of, or consists essentially of, the nucleic acid sequence of any one or more of SEQ ID NOs: 1-10, and nucleic acid sequences that are at least 60%, 65%, 70%, 75%, 80%, 82%, 85%, 87%, 90%, 91%, 92%, 93%, 94%, 95%, 96%, 97%, 98%, 99% or 100% identical to any of the foregoing. In certain embodiments, the viral vector comprises a nucleotide sequence that is the sequence of any one or more of SEQ ID NOs: 1-10, or a codon-optimized variant and/or a fragment thereof. In certain embodiments, the viral vector comprises a nucleotide sequence that is at least 60% identical to any one of SEQ ID NOs: 1-10, or codon-optimized variant and/or a fragment thereof. In certain embodiments, the viral vector comprises a nucleotide sequence that is at least 65% identical to any one of SEQ ID NOs: 1-10, or codon-optimized variant and/or a fragment thereof. In certain embodiments, the viral vector comprises a nucleotide sequence that is at least 70% identical to any one of SEQ ID NOs: 1-10, or codon-optimized variant and/or a fragment thereof. In certain embodiments, the viral vector comprises a nucleotide sequence that is at least 75% identical to any one of SEQ ID NOs: 1-10, or codon-optimized variant and/or a fragment thereof. In certain embodiments, the viral vector comprises a nucleotide sequence that is at least 80% identical to any one of SEQ ID NOs: 1-10, or codon-optimized variant and/or a fragment thereof. In certain embodiments, the viral vector comprises a nucleotide sequence that is at least 82% identical to any one of SEQ ID NOs: 1-10, or codon-optimized variant and/or a fragment thereof. In certain embodiments, the viral vector comprises a nucleotide sequence that is at least 85% identical to any one of SEQ ID NOs: 1-10, or codon-optimized variant and/or a fragment thereof. In certain embodiments, the viral vector comprises a nucleotide sequence that is at least 87% identical to any one of SEQ ID NOs: 1-10, or codon-optimized variant and/or a fragment thereof. In certain embodiments, the viral vector comprises a nucleotide sequence that is at least 90% identical to any one of SEQ ID NOs: 1-10, or codon-optimized variant and/or a fragment thereof. In certain embodiments, the viral vector comprises a nucleotide sequence that is at least 91% identical to any one of SEQ ID NOs: 1-10, or codon-optimized variant and/or a fragment thereof. In certain embodiments, the viral vector comprises a nucleotide sequence that is at least 92% identical to any one of SEQ ID NOs: 1-10, or codon-optimized variant and/or a fragment thereof. In certain embodiments, the viral vector comprises a nucleotide sequence that is at least 93% identical to any one of SEQ ID NOs: 1-10, or codon-optimized variant and/or a fragment thereof. In certain embodiments, the viral vector comprises a nucleotide sequence that is at least 94% identical to any one of SEQ ID NOs: 1-10, or codon-optimized variant and/or a fragment thereof. In certain embodiments, the viral vector comprises a nucleotide sequence that is at least 95% identical to any one of SEQ ID NOs: 1-10, or codon-optimized variant and/or a fragment thereof. In certain embodiments, the viral vector comprises a nucleotide sequence that is at least 96% identical to any one of SEQ ID NOs: 1-10, or codon-optimized variant and/or a fragment thereof. In certain embodiments, the viral vector comprises a nucleotide sequence that is at least 97% identical to any one of SEQ ID NOs: 1-10, or codon-optimized variant and/or a fragment thereof. In certain embodiments, the viral vector comprises a nucleotide sequence that is at least 98% identical to any one of SEQ ID NOs: 1-10, or codon-optimized variant and/or a fragment thereof. In certain embodiments, the viral vector comprises a nucleotide sequence that is at least 99% identical to any one of SEQ ID NOs: 1-10, or codon-optimized variant and/or a fragment thereof.

In certain embodiments, the viral vector comprises a nucleotide sequence that is 100% identical to any one of SEQ ID NOs: 1-10, or codon-optimized variant and/or a fragment thereof.

In some embodiments, the viral vector comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 1 that encodes the polypeptide sequence of SEQ ID NO: 12 or 21. In some embodiments, the viral vector comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 6 that encodes the polypeptide sequence of SEQ ID NO: 12 or 21. In some embodiments, the viral vector comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 2 that encodes the polypeptide sequence of SEQ ID NO: 13. In some embodiments, the viral vector comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 7 that encodes the polypeptide sequence of SEQ ID NO: 13. In some embodiments, the viral vector comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 3 that encodes the polypeptide sequence of any one or more of SEQ ID NOs: 12, 13 or 21. In some embodiments, the viral vector comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 4 that encodes the polypeptide sequence of any one or more of SEQ ID NOs: 12, 13 or 21. In some embodiments, the viral vector comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 5 that encodes the polypeptide sequence of any one or more of SEQ ID NOs: 12, 13 or 21. In some embodiments, the viral vector comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 8 that encodes the polypeptide sequence of any one or more of SEQ ID NOs: 12, 13 or 21. In some embodiments, the viral vector comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 9 that encodes the polypeptide sequence of any one or more of SEQ ID NOs: 12, 13 or 21. In some embodiments, the viral vector comprises a nucleotide sequence that is at least 60%, 65%, 70%, 75%, 80%, 85%, 90%, 91%, 92%, 93%, 94%, 95%, 96%, 97%, 98%, 99% or 100% identical to SEQ ID NO: 10 that encodes the polypeptide sequence of any one or more of SEQ ID NOs: 12, 13 or 21.

In certain embodiments, the viral vector comprises a nucleotide sequence that comprises, consists of, or consists essentially of, the nucleic acid sequence of any one of SEQ ID NOs: 3-5, and nucleic acid sequences that are at least 60%, 65%, 70%, 75%, 80%, 82%, 85%, 87%, 90%, 91%, 92%, 93%, 94%, 95%, 96%, 97%, 98%, 99% or 100% identical to any of the foregoing. In certain embodiments, the viral vector comprises a nucleotide sequence that is the sequence of any one of SEQ ID NOs: 3-5, or codon-optimized variant and/or a fragment thereof. In certain embodiments, the viral vector comprises a nucleotide sequence that is at least 60% identical to any one of SEQ ID NOs: 3-5, or a codon-optimized variant and/or a fragment thereof. In certain embodiments, the viral vector comprises a nucleotide sequence that is at least 65% identical to any one of SEQ ID NOs: 3-5, or a codon-optimized variant and/or a fragment thereof. In certain embodiments, the viral vector comprises a nucleotide sequence that is at least 70% identical to any one of SEQ ID NOs: 3-5, or a codon-optimized variant and/or a fragment thereof. In certain embodiments, the viral vector comprises a nucleotide sequence that is at least 75% identical to any one of SEQ ID NOs: 3-5, or a codon-optimized variant and/or a fragment thereof. In certain embodiments, the viral vector comprises a nucleotide sequence that is at least 80% identical to any one of SEQ ID NOs: 3-5, or a codon-optimized variant and/or a fragment thereof. In certain embodiments, the viral vector comprises a nucleotide sequence that is at least 82% identical to any one of SEQ ID NOs: 3-5, or a codon-optimized variant and/or a fragment thereof. In certain embodiments, the viral vector comprises a nucleotide sequence that is at least 85% identical to any one of SEQ ID NOs: 3-5, or a codon-optimized variant and/or a fragment thereof. In certain embodiments, the viral vector comprises a nucleotide sequence that is at least 87% identical to any one of SEQ ID NOs: 3-5, or a codon-optimized variant and/or a fragment thereof. In certain embodiments, the viral vector comprises a nucleotide sequence that is at least 90% identical to any one of SEQ ID NOs: 3-5, or a codon-optimized variant and/or a fragment thereof. In certain embodiments, the viral vector comprises a nucleotide sequence that is at least 91% identical to any one of SEQ ID NOs: 3-5, or a codon-optimized variant and/or a fragment thereof. In certain embodiments, the viral vector comprises a nucleotide sequence that is at least 92% identical to any one of SEQ ID NOs: 3-5, or a codon-optimized variant and/or a fragment thereof. In certain embodiments, the viral vector comprises a nucleotide sequence that is at least 93% identical to any one of SEQ ID NOs: 3-5, or a codon-optimized variant and/or a fragment thereof. In certain embodiments, the viral vector comprises a nucleotide sequence that is at least 94% identical to any one of SEQ ID NOs: 3-5, or a codon-optimized variant and/or a fragment thereof. In certain embodiments, the viral vector comprises a nucleotide sequence that is at least 95% identical to any one of SEQ ID NOs: 3-5, or a codon-optimized variant and/or a fragment thereof. In certain embodiments, the viral vector comprises a nucleotide sequence that is at least 96% identical to any one of SEQ ID NOs: 3-5, or a codon-optimized variant and/or a fragment thereof. In certain embodiments, the viral vector comprises a nucleotide sequence that is at least 97% identical to any one of SEQ ID NOs: 3-5, or a codon-optimized variant and/or a fragment thereof. In certain embodiments, the viral vector comprises a nucleotide sequence that is at least 98% identical to any one of SEQ ID NOs: 3-5, or a codon-optimized variant and/or a fragment thereof. In certain embodiments, the viral vector comprises a nucleotide sequence that is at least 99% identical to any one of SEQ ID NOs: 3-5, or a codon-optimized variant and/or a fragment thereof. In certain embodiments, the viral vector comprises a nucleotide sequence that is 100% identical to any one of SEQ ID NOs: 3-5, or a codon-optimized variant and/or a fragment thereof.

In certain embodiments, the viral vector comprises a nucleotide sequence encoding a polypeptide that comprises, consists of, or consists essentially of, the amino acid sequence of any one or more of SEQ ID NOs: 12-21 and 24, and polypeptides that are at least 60%, 65%, 70%, 75%, 80%, 82%, 85%, 87%, 90%, 91%, 92%, 93%, 94%, 95%, 96%, 97%, 98%, 99% or 100% identical to any of the foregoing. In certain embodiments, the viral vector comprises a nucleotide sequence encoding a polypeptide of any one of SEQ ID NOs: 12-21 or 24, or biologically active variants and/or a fragments thereof. In certain embodiments, the viral vector comprises a nucleotide sequence encoding a polypeptide that is at least 60% identical to any one of SEQ ID NOs: 12-21 or 24, or biologically active variants and/or fragments thereof. In certain embodiments, the viral vector comprises a nucleotide sequence encoding a polypeptide that is at least 65% identical to any one of SEQ ID NOs: 12-21 or 24, or biologically active variants and/or fragments thereof. In certain embodiments, the viral vector comprises a nucleotide sequence encoding a polypeptide that is at least 70% identical to any one of SEQ ID NOs: 12-21 or 24, or biologically active variants and/or fragments thereof. In certain embodiments, the viral vector comprises a nucleotide sequence encoding a polypeptide that is at least 75% identical to any one of SEQ ID NOs: 12-21 or 24, or biologically active variants and/or fragments thereof. In certain embodiments, the viral vector comprises a nucleotide sequence encoding a polypeptide that is at least 80% identical to any one of SEQ ID NOs: 12-21 or 24, or biologically active variants and/or fragments thereof. In certain embodiments, the viral vector comprises a nucleotide sequence encoding a polypeptide that is at least 82% identical to any one of SEQ ID NOs: 12-21 or 24, or biologically active variants and/or fragments thereof. In certain embodiments, the viral vector comprises a nucleotide sequence encoding a polypeptide that is at least 85% identical to any one of SEQ ID NOs: 12-21 or 24, or biologically active variants and/or fragments thereof. In certain embodiments, the viral vector comprises a nucleotide sequence encoding a polypeptide that is at least 87% identical to any one of SEQ ID NOs: 12-21 or 24, or biologically active variants and/or fragments thereof. In certain embodiments, the viral vector comprises a nucleotide sequence encoding a polypeptide that is at least 90% identical to any one of SEQ ID NOs: 12-21 or 24, or biologically active variants and/or fragments thereof. In certain embodiments, the viral vector comprises a nucleotide sequence encoding a polypeptide that is at least 91% identical to any one of SEQ ID NOs: 12-21 or 24, or biologically active variants and/or fragments thereof. In certain embodiments, the viral vector comprises a nucleotide sequence encoding a polypeptide that is at least 92% identical to any one of SEQ ID NOs: 12-21 or 24, or biologically active variants and/or fragments thereof. In certain embodiments, the viral vector comprises a nucleotide sequence encoding a polypeptide that is at least 93% identical to any one of SEQ ID NOs: 12-21 or 24, or biologically active variants and/or fragments thereof. In certain embodiments, the viral vector comprises a nucleotide sequence encoding a polypeptide that is at least 94% identical to any one of SEQ ID NOs: 12-21 or 24, or biologically active variants and/or fragments thereof. In certain embodiments, the viral vector comprises a nucleotide sequence encoding a polypeptide that is at least 95% identical to any one of SEQ ID NOs: 12-21 or 24, or biologically active variants and/or fragments thereof. In certain embodiments, the viral vector comprises a nucleotide sequence encoding a polypeptide that is at least 96% identical to any one of SEQ ID NOs: 12-21 or 24, or biologically active variants and/or fragments thereof. In certain embodiments, the viral vector comprises a nucleotide sequence encoding a polypeptide that is at least 97% identical to any one of SEQ ID NOs: 12-21 or 24, or biologically active variants and/or fragments thereof. In certain embodiments, the viral vector comprises a nucleotide sequence encoding a polypeptide that is at least 98% identical to any one of SEQ ID NOs: 12-21 or 24, or biologically active variants and/or fragments thereof. In certain embodiments, the viral vector comprises a nucleotide sequence encoding a polypeptide that is at least 99% identical to any one of SEQ ID NOs: 12-21 or 24, or biologically active variants and/or fragments thereof. In certain embodiments, the viral vector comprises a nucleotide sequence encoding a polypeptide that is 100% identical to any one of SEQ ID NOs: 12-21 and 24, or biologically active variants and/or fragments thereof.

In certain embodiments, the viral vector comprises a nucleotide sequence encoding lamin A that comprises, consists of, or consists essentially of, an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 12, or biologically active fragments thereof. In certain embodiments, the viral vector comprises a nucleotide sequence encoding lamin A that comprises, consists of, or consists essentially of, an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 21, or biologically active fragments thereof. In certain embodiments, the viral vector comprises a nucleotide sequence encoding lamin C that comprises, consists of, or consists essentially of, an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 13, or biologically active fragments thereof. In certain embodiments, the viral vector comprises a nucleotide sequence encoding lamin A having an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 12 or biologically active fragments thereof, and also encoding lamin C having an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 13 or biologically active fragments thereof. In certain embodiments, the viral vector comprises a nucleotide sequence encoding lamin A having an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 21 or biologically active fragments thereof, and also encoding lamin C having an amino acid sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 13 or biologically active fragments thereof. In certain embodiments, the viral vector comprises a nucleotide sequence encoding lamin A that comprises, consists of, or consists essentially of, the amino acid sequence of SEQ ID NO: 12. In certain embodiments, the viral vector comprises a nucleotide sequence encoding lamin A that comprises, consists of, or consists essentially of, the amino acid sequence of SEQ ID NO: 21. In certain embodiments, the viral vector comprises a nucleotide sequence encoding lamin C that comprises, consists of, or consists essentially of, the amino acid sequence of SEQ ID NO: 13. In certain embodiments, the viral vector comprises a nucleotide sequence encoding lamin A and lamin C that comprises, consists of, or consists essentially of, the amino acid sequence of SEQ ID NO: 12 and/or 13. In certain embodiments, the viral vector comprises a nucleotide sequence encoding lamin A and lamin C that comprises, consists of, or consists essentially of, the amino acid sequence of SEQ ID NO: 21 and/or 13. In certain embodiments, the viral vector comprises a nucleotide sequence encoding lamin A having the amino acid sequence of SEQ ID NO: 12, and also encoding lamin C having the amino acid sequence of SEQ ID NO: 13. In certain embodiments, the viral vector comprises a nucleotide sequence encoding lamin A having the amino acid sequence of SEQ ID NO: 21, and also encoding lamin C having the amino acid sequence of SEQ ID NO: 13.

In some cases, the viral vector comprises a nucleotide sequence encoding lamin A and/or lamin C, wherein the nucleotide sequence does not comprise one or more, two or more, three or more, four or more, five or more, six or more, seven or more, eight or more, nine or more, ten or more, or eleven or more introns from a wild-type LMNA gene. In certain embodiments, the viral vector does not comprise the nucleotide sequence corresponding to introns 1-7 of a wildtype LMNA gene (e.g. SEQ ID NOs: 70-76). In certain embodiments, the viral vector does not comprise the nucleotide sequence corresponding to introns 1-8 and 11 of a wild-type LMNA gene (e.g. SEQ ID NOs: 70-77 and 80). In certain embodiments, the viral vector does not comprise the nucleotide sequence corresponding to introns 1-9 and 11 of a wild-type LMNA gene (e.g. SEQ ID NOs: 70-78 and 80).

In some cases, the viral vector comprises a nucleotide sequence encoding lamin A and/or lamin C, wherein the nucleotide sequence comprises one or more, two or more, three or more, four or more, five or more, six or more, seven or more, eight or more, nine or more, ten or more, or eleven or more introns (e.g. any one or combination of SEQ ID NOs: 70-80). In certain embodiments, the one or more introns correspond to the introns from a wild-type LMNA gene, e.g., a wild-type human LMNA gene. In other embodiments, the one or more introns are synthetic introns. In particular embodiments, the one or more introns are positioned in the nucleotide sequence in the viral vector such that it is capable of encoding both lamin A and lamin C in a splice-dependent manner. In particular embodiments, the one or more introns are positioned in the nucleic acid construct such that the pre-mRNA undergoes alternative splicing to produce mature mRNA encoding lamin A and/or lamin C. In particular embodiments, the one or more introns are positioned in the nucleic acid construct such that the pre-mRNA undergoes alternative splicing to produce more mature mRNA encoding lamin C than mature mRNA encoding lamin A. In particular embodiments, the one or more introns are positioned in the nucleic acid construct such that the pre-mRNA undergoes alternative splicing to produce about the same levels of mature mRNA encoding lamin A and mature mRNA encoding lamin C. In particular embodiments, the one or more introns are positioned in the nucleic acid construct such that the pre-mRNA undergoes alternative splicing to produce more mature mRNA encoding lamin A than mature mRNA encoding lamin C. In certain embodiments, the viral vector comprises nucleotide sequences corresponding to introns 8-11 of a wild-type LMNA gene (e.g. SEQ ID NOs: 77-80). In certain embodiments, the viral vector comprises nucleotide sequences corresponding to introns 9 and 10 of a wild-type LMNA gene (e.g. SEQ ID NOs: 78 and 79). In certain embodiments, the viral vector comprises the nucleotide sequence corresponding to intron 10 of a wild-type LMNA gene (e.g. SEQ ID NO: 79).

In some embodiments, the viral vector comprises a nucleotide sequence comprising at least one, but not all, of the endogenous introns of the wild-type human LMNA gene. In some embodiments, the viral vector comprises a nucleotide sequence comprising at least one intron corresponding to introns 8-11 of the wild-type human LMNA gene (e.g. SEQ ID NOs: 77-80), and lacking at least one intron corresponding to introns 1-7 of the wild-type human LMNA gene (e.g. SEQ ID NOs: 70-76). In some embodiments, the viral vector comprises a nucleotide sequence comprising introns corresponding to introns 8-11 of the wild-type human LMNA gene (e.g. SEQ ID NOs: 77-80), and lacking at least one intron corresponding to introns 1-7 of the wild-type human LMNA gene (e.g. SEQ ID NOs: 70-76). In some embodiments, the viral vector comprises a nucleotide sequence comprising introns corresponding to introns 8-11 of the human wild-type LMNA gene (e.g. SEQ ID NOs: 77-80), and lacking all of the introns corresponding to introns 1-7 of the human wild-type LMNA gene (e.g. SEQ ID NOs: 70-76). In some embodiments, the viral vector comprises a nucleotide sequence comprising introns corresponding to introns 9-10 of the wild-type human LMNA gene (e.g. SEQ ID NOs: 78 and 79), and lacking at least one intron corresponding to introns 1-7 of the wild-type human LMNA gene (e.g. SEQ ID NOs: 70-76). In some embodiments, the viral vector comprises a nucleotide sequence comprising introns corresponding to introns 9-10 of the wild-type human LMNA gene (e.g. SEQ ID NOs: 78 and 79), and lacking all of the introns corresponding to introns 1-7 of the wild-type human LMNA gene (e.g. SEQ ID NOs: 70-76). In some embodiments, the viral vector comprises a nucleotide sequence comprising introns corresponding to introns 9-10 of the wild-type human LMNA gene (e.g. SEQ ID NOs: 78 and 79), and lacking all of the introns corresponding to introns 1-8 and 11 of the wild-type human LMNA gene (e.g. SEQ ID NOs: 70-77 and 80). In some embodiments, the viral vector comprises a nucleotide sequence comprising the intron corresponding to intron 10 of the wild-type human LMNA gene (e.g. SEQ ID NO: 79), and lacking at least one intron corresponding to introns 1-7 of the wild-type human LMNA gene (e.g. SEQ ID NOs: 70-76). In some embodiments, the viral vector comprises a nucleotide sequence comprising the intron corresponding to intron 10 of the wild-type human LMNA gene (e.g. SEQ ID NO: 79), and lacking all of the introns corresponding to introns 1-7 of the wild-type human LMNA gene (e.g. SEQ ID NOs: 70-76). In some embodiments, the viral vector comprises a nucleotide sequence comprising the intron corresponding to intron 10 of the wild-type human LMNA gene (e.g. SEQ ID NO: 79), and lacking all of the introns corresponding to introns 1-9 and 11 of the wild-type human LMNA gene (e.g. SEQ ID NOs: 70-78 and 80). In some embodiments, the intron corresponding to intron 8 of the wild-type human LMNA gene comprises a nucleotide sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 77, or a fragment thereof. In some embodiments, the intron corresponding to intron 9 of the wild-type human LMNA gene comprises a nucleotide sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 78, or a fragment thereof. In some embodiments, the intron corresponding to intron 10 of the wild-type human LMNA gene comprises a nucleotide sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 79 or a fragment thereof. In some embodiments, the intron corresponding to intron 11 of the wild-type human LMNA gene comprises a nucleotide sequence that is at least 60%, 65%, 70%, 75%, 80%, 82%, 85%, 87%, 90%, 91%, 92%, 93%, 94%, 95%, 96%, 97%, 98%, 99% or 100% identical to SEQ ID NO: 80 or a fragment thereof.

In some cases, the viral vector comprises a nucleotide sequence encoding lamin A and/or lamin C (or a biologically active fragment or variant thereof), wherein the nucleotide sequence comprises intron 8 of a wild-type LMNA gene. In some cases, the viral vector comprises a nucleotide sequence encoding lamin A (or a biologically active fragment or variant thereof) and/or lamin C (or a biologically active fragment or variant thereof), wherein the nucleotide sequence comprises intron 9 of a wild-type LMNA gene. In some cases, the viral vector comprises a nucleotide sequence encoding lamin A (or a biologically active fragment or variant thereof) and/or lamin C (or a biologically active fragment or variant thereof), wherein the nucleotide sequence comprises intron 10 of a wild-type LMNA gene. In some cases, the viral vector comprises a nucleotide sequence encoding lamin A (or a biologically active fragment or variant thereof) and/or lamin C (or a biologically active fragment or variant thereof), wherein the nucleotide sequence comprises intron 11 of a wild-type LMNA gene. In some cases, the viral vector comprises a nucleotide sequence encoding lamin A (or a biologically active fragment or variant thereof) and/or lamin C (or a biologically active fragment or variant thereof), wherein the nucleotide sequence comprises introns 9 and 10 of a wild-type LMNA gene. In some cases, the viral vector comprises a nucleotide sequence encoding lamin A (or a biologically active fragment or variant thereof) and/or lamin C (or a biologically active fragment or variant thereof), wherein the nucleotide sequence comprises introns 8, 9, 10, and 11 of a wild-type LMNA gene.

In certain embodiments, the viral vector comprises a nucleotide sequence that comprises, consists of, or consists essentially of, the nucleic acid sequence of any one or more of SEQ ID NO: 77-80, and nucleic acid sequences that are at least 60%, 65%, 70%, 75%, 80%, 82%, 85%, 87%, 90%, 91%, 92%, 93%, 94%, 95%, 96%, 97%, 98%, 99% or 100% identical to any one or more of the foregoing. In certain embodiments, the viral vector comprises a nucleotide sequence that is the sequence of any one of SEQ ID NOs: 77-80, or a biologically active variant and/or a fragment thereof. In certain embodiments, the viral vector comprises a nucleotide sequence that is at least 60% identical to any one or more of SEQ ID NOs: 77-80, or a biologically active variant and/or a fragment thereof. In certain embodiments, the viral vector comprises a nucleotide sequence that is at least 65% identical to any one or more of SEQ ID NOs: 77-80, or a biologically active variant and/or a fragment thereof. In certain embodiments, the viral vector comprises a nucleotide sequence that is at least 70% identical to any one or more of SEQ ID NOs: 77-80, or a biologically active variant and/or a fragment thereof. In certain embodiments, the viral vector comprises a nucleotide sequence that is at least 75% identical to any one or more of SEQ ID NOs: 77-80, or a biologically active variant and/or a fragment thereof. In certain embodiments, the viral vector comprises a nucleotide sequence that is at least 80% identical to any one or more of SEQ ID NOs: 77-80, or a biologically active variant and/or a fragment thereof. In certain embodiments, the viral vector comprises a nucleotide sequence that is at least 82% identical to any one or more of SEQ ID NOs: 77-80, or a biologically active variant and/or a fragment thereof. In certain embodiments, the viral vector comprises a nucleotide sequence that is at least 85% identical to any one or more of SEQ ID NOs: 77-80, or a biologically active variant and/or a fragment thereof. In certain embodiments, the viral vector comprises a nucleotide sequence that is at least 87% identical to any one or more of SEQ ID NOs: 77-80, or a biologically active variant and/or a fragment thereof. In certain embodiments, the viral vector comprises a nucleotide sequence that is at least 90% identical to any one or more of SEQ ID NOs: 77-80, or a biologically active variant and/or a fragment thereof. In certain embodiments, the viral vector comprises a nucleotide sequence that is at least 91% identical to any one or more of SEQ ID NOs: 77-80, or a biologically active variant and/or a fragment thereof. In certain embodiments, the viral vector comprises a nucleotide sequence that is at least 92% identical to any one or more of SEQ ID NOs: 77-80, or a biologically active variant and/or a fragment thereof. In certain embodiments, the viral vector comprises a nucleotide sequence that is at least 93% identical to any one or more of SEQ ID NOs: 77-80, or a biologically active variant and/or a fragment thereof. In certain embodiments, the viral vector comprises a nucleotide sequence that is at least 94% identical to any one or more of SEQ ID NOs: 77-80, or a biologically active variant and/or a fragment thereof. In certain embodiments, the viral vector comprises a nucleotide sequence that is at least 95% identical to any one or more of SEQ ID NOs: 77-80, or a biologically active variant and/or a fragment thereof. In certain embodiments, the viral vector comprises a nucleotide sequence that is at least 96% identical to any one or more of SEQ ID NOs: 77-80, or a biologically active variant and/or a fragment thereof. In certain embodiments, the viral vector comprises a nucleotide sequence that is at least 97% identical to any one or more of SEQ ID NOs: 77-80, or a biologically active variant and/or a fragment thereof. In certain embodiments, the viral vector comprises a nucleotide sequence that is at least 98% identical to any one or more of SEQ ID NOs: 77-80, or a biologically active variant and/or a fragment thereof. In certain embodiments, the viral vector comprises a nucleotide sequence that is at least 99% identical to any one or more of SEQ ID NOs: 77-80, or a biologically active variant and/or a fragment thereof. In certain embodiments, the viral vector comprises a nucleotide sequence that is 100% identical to any one or more of SEQ ID NOs: 77-80, or a biologically active variant and/or a fragment thereof.

In certain embodiments, the viral vectors described herein further comprise a polyadenylation (polyA) sequence. Suitable polyA sequences include, for example, an artificial polyA that is about 75 bp in length (PA75) (see e.g., WO 2018/126116), the bovine growth hormone polyA, SV40 early polyA signal, SV40 late polyA signal, rabbit beta globin polyA, HSV thymidine kinase polyA, protamine gene polyA, adenovirus 5 EIb polyA, growth hormone polyA, or a PBGD polyA. In certain embodiments, the polyA sequence comprises or consists of SEQ ID NO: 11. In certain embodiments, the polyA sequence is positioned downstream of the transgene in the nucleic acid constructs described herein.

E. Viral Vectors

In various embodiments, suitable viral vectors include retroviruses (e.g., A-type, B-type, C-type, and D-type viruses), adenovirus, parvovirus (e.g. adeno-associated viruses or AAV), coronavirus, negative strand RNA viruses such as orthomyxovirus (e.g., influenza virus), rhabdovirus (e.g., rabies and vesicular stomatitis virus), paramyxovirus (e. g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Examples of retroviruses include avian leukosis-sarcoma virus, human T-lymphotrophic virus type 1 (HTLV-1), bovine leukemia virus (BLV), lentivirus, and spumavirus. Other viruses include Norwalk virus, togavirus, flavivirus, reoviruses, papovavirus, hepadnavirus, and hepatitis virus, for example. Viral vectors may be classified into two groups according to their ability to integrate into the host genome—integrating and non-integrating. Oncoretroviruses and lentiviruses can integrate into host cellular chromatin while adenoviruses, adeno-associated viruses, and herpes viruses predominantly persist in the cell nucleus as extrachromosomal episomes.

In certain embodiments, a suitable viral vector is a retroviral vector. Retroviruses refer to viruses of the family Retroviridae. Examples of retroviruses include oncoretroviruses, such as murine leukemia virus (MLV), and lentiviruses, such as human immunodeficiency virus 1 (HIV-1). Retroviral genomes are single-stranded (ss) RNAs and comprise various genes that may be provided in cis or trans. For example, retroviral genome may contain cis-acting sequences such as two long terminal repeats (LTR), with elements for gene expression, reverse transcription and integration into the host chromosomes. Other components include the packaging signal (psi or ψ), for the specific RNA packaging into newly formed virions and the polypurine tract (PPT), the site of the initiation of the positive strand DNA synthesis during reverse transcription. In addition, the retroviral genome may comprise gag, pol and env genes. The gag gene encodes the structural proteins, the pol gene encodes the enzymes that accompany the ssRNA and carry out reverse transcription of the viral RNA to DNA, and the env gene encodes the viral envelope. Generally, the gag, pol and env are provided in trans for viral replication and packaging.

In certain embodiments, a retroviral vector provided herein may be a lentiviral vector. At least five serogroups or serotypes of lentiviruses are recognized. Viruses of the different serotypes may differentially infect certain cell types and/or hosts. Lentiviruses, for example, include primate retroviruses and non-primate retroviruses. Primate retroviruses include HIV and simian immunodeficiency virus (SIV). Non-primate retroviruses include feline immunodeficiency virus (FIV), bovine immunodeficiency virus (BIV), caprine arthritis-encephalitis virus (CAEV), equine infectious anemia virus (EIAV) and visnavirus. Lentiviruses or lentivectors may be capable of transducing quiescent cells. As with oncoretrovirus vectors, the design of lentivectors may be based on the separation of cis- and trans-acting sequences.

In certain embodiments, the disclosure provides expression vectors that have been designed for delivery by an optimized therapeutic retroviral vector. The retroviral vector can be a lentivirus comprising a left (5') LTR; sequences which aid packaging and/or nuclear import of the virus; a regulatory element (such as, for example, a cell-type selective (e.g., cardiomyocyte) promoter and/or enhancer) operably linked to a sequence encoding lamin A and/or lamin C; optionally one or more additional regulatory elements (such as, for example, a polyA sequence); optionally a lentiviral reverse response element (RRE); optionally an insulator; and a right (3') retroviral LTR.

In exemplary embodiments, a viral vector provided herein is an adeno-associated virus (AAV). AAV is a small, replication-defective, non-enveloped animal virus that infects humans and some other primate species. AAV is not known to cause human disease and induces a mild immune response. AAV vectors can also infect both dividing and quiescent cells without integrating into the host cell genome.

The AAV genome consists of a linear single stranded DNA which is ~4.7 kb in length. The genome consists of two open reading frames (ORF) flanked by inverted terminal repeat (ITR) sequences that are about 145 bp in length. The ITR consists of a nucleotide sequence at the 5' end (5' ITR) and a nucleotide sequence located at the 3' end (3' ITR) that contain palindromic sequences. The ITRs function in cis by folding over to form T-shaped hairpin structures by complementary base pairing that function as primers during initiation of DNA replication for second strand synthesis. The two open reading frames encode for rep and cap genes that are involved in replication and packaging of the virion. In an exemplary embodiment, an AAV vector provided herein does not contain the rep or cap genes. Such genes may be provided in trans for producing virions as described further below.

In certain embodiments, an AAV vector may include a stuffer nucleic acid. In some embodiments, the stuffer nucleic acid may encode a green fluorescent protein or antibiotic resistance gene such as kanamycin or ampicillin. In certain embodiments, the stuffer nucleic acid may be located outside of the ITR sequences (e.g., as compared to the lamin A and/or lamin C transgene sequence and regulatory sequences, which are located between the 5' and 3' ITR sequences).

Various serotypes of AAV exist, including AAV1, AAV2, AAV3, AAV4, AAV5, AAV6, AAV7, AAV8, AAV9, AAV10, AAV11, AAV12, and AAV13. These serotypes differ in their tropism, or the types of cells they infect. AAVs may comprise the genome and capsids from multiple serotypes (e.g., pseudotypes). For example, an AAV may comprise the genome of serotype 2 (e.g., ITRs) packaged in the capsid from serotype 5 or serotype 9. Pseudotypes may improve transduction efficiency as well as alter tropism.

In certain embodiments, the viral vectors described herein comprise at a minimum, AAV inverted terminal repeats (ITRs) and a transgene encoding (a) a lamin A polypeptide; (b) a lamin C polypeptide; (c) a lamin A and lamin C polypeptide; or biologically active variants and/or fragments thereof. In certain embodiments, the viral vectors described herein comprise a minigene composed of, at a minimum, AAV inverted terminal repeats (ITRs) and a transgene encoding (a) a biologically active fragment of a lamin A polypeptide; (b) a biologically active fragment of a lamin C polypeptide; (c) a biologically active fragment of a lamin A and biologically active fragment of a lamin C polypeptide; or biologically active variants and/or fragments thereof. In one particular embodiment, the ITRs of AAV serotype 6 or AAV serotype 9 are used. However, ITRs from other suitable serotypes may be selected. The viral vector is packaged into a capsid protein and delivered to a selected host cell. AAV vectors of the present disclosure may be generated from a variety of adeno-associated viruses. The tropism of the vector may be altered by packaging the recombinant genome of one serotype into capsids derived from another AAV serotype. In some embodiments, the ITRs of the rAAV virus may be based on the ITRs of any one of AAV1-12 and may be combined with an AAV capsid selected from any one of AAV1-12, AAV-DJ, AAV-DJ8, AAV-DJ9 or other modified serotypes.

In some embodiments, an AAV vector or an AAV viral particle, or virion, may be used to deliver a construct comprising a regulatory element operably linked to a sequence encoding lamin A and/or lamin C into a cell, cell type, or tissue, and may done either in vivo, ex vivo, or in vitro. In exemplary embodiments, such an AAV vector is replication-deficient. In some embodiments, an AAV virus is engineered or genetically modified so that it can replicate and generate virions only in the presence of helper factors.

In certain embodiments, a viral vector can be selected to produce a virion having high infectivity without selectivity for a particular cell type, while a cardiomyocyte-selective regulatory element confers selective expression of a transgene in cardiomyocytes and not in other muscle cells, even though other muscle cells might be infected with the virus. In certain embodiments, a viral vector can be designed to produce a virion that infects many different cell types but expression of the transgene is enhanced and/or optimized in a cell type of interest (e.g. cardiomyocytes), and expression of the transgene is reduced and/or minimized in other non-target cell types (e.g., non-cardiomyocytes). The differential expression of the transgene in different cell types can be controlled, engineered, or manipulated using different regulatory elements that are selective for one or more cell types. In some cases, one or more regulatory elements operably linked to a transgene enhances selective expression of the transgene in a target cell, cell type, or tissue, while the one or more regulatory elements suppress transgene expression in off-target cells, cell type, or tissue, or confers significantly lower, de minimis, or statistically lower gene expression in one or more off-target cells, cell types, or tissue. For gene therapy, selective expression of a transgene in a target cell type (e.g., cardiomyocyte) and/or minimized expression of the transgene in a non-target cell type can be desired. Expression of the transgene in an unintended cell-type (e.g., non-target cell type) may result in an adverse effect to the subject. Expression of the transgene in an unintended cell-type can counteract the therapeutic effect of the transgene in the intended cell type.

In exemplary embodiments, the disclosure provides expression vectors that have been designed for delivery by an AAV. The AAV can be any serotype, for examples, AAV1, AAV2, AAV3, AAV3b, AAV4, AAV5, AAV6, AAV7, AAV8, AAV9, AAV10, AAV11, AAV12, AAV-DJ, or a chimeric, hybrid, or variant AAV. The AAV can also be a self-complementary AAV (scAAV). In certain embodiments, an expression vector designed for delivery by an AAV comprises a 5' ITR and a 3' ITR. In certain embodiments, an expression vector designed for delivery by an AAV comprises a 5' ITR, a promoter, a construct comprising a regulatory element (such as, for example, a cell-type selective (e.g. cardiomyocyte) promoter and/or enhancer) operably linked to a sequence encoding lamin A and/or lamin C, and a 3' ITR. In certain embodiments, an expression vector designed for delivery by an AAV comprises a 5' ITR, an enhancer, a promoter, a construct comprising a regulatory element (such as, for example, a cell-type selective (e.g. cardiomyocyte) promoter and/or enhancer) operably linked to a sequence encoding lamin A and/or lamin C, a polyA sequence, and a 3' ITR. In exemplary embodiments, an expression vector designed for delivery by an AAV comprises a 5' ITR, a regulatory element comprising any one of SEQ ID NOs: 30-69 or 100-102 or a variant or functional fragment thereof, a sequence encoding lamin A and/or lamin C, and a 3' ITR. In one embodiment, an expression vector designed for delivery by an AAV comprises a 5' ITR, a promoter comprising any one or more of SEQ ID NOs: 31, 33, 60, or 61 or a variant or functional fragment thereof, a sequence encoding lamin A and/or lamin C, and a 3' ITR. In another embodiment, an expression vector designed for delivery by an AAV comprises a 5' ITR, a regulatory element comprising SEQ ID NO: 31 or a variant or functional fragment thereof, a sequence encoding lamin A and/or lamin C, and a 3' ITR. In another embodiment, an expression vector designed for delivery by an AAV comprises a 5' ITR, a regulatory element comprising SEQ ID NO: 33 or a variant or functional fragment thereof, a sequence encoding lamin A and/or lamin C, and a 3' ITR. In another embodiment, an expression vector designed for delivery by an AAV comprises a 5' ITR, a regulatory element comprising SEQ ID NO: 60 or a variant or functional fragment thereof, a sequence encoding lamin A and/or lamin C, and a 3' ITR. In another embodiment, an expression vector designed for delivery by an AAV comprises a 5' ITR, a regulatory element comprising SEQ ID NO: 61 or a variant or functional fragment thereof, a sequence encoding lamin A and/or lamin C, and a 3' ITR. Exemplary AAV expression vectors are illustrated in FIGS. 1-5 and 11A-C.

F. Viral Particle

In certain embodiments, the disclosure provides viral particles comprising a viral vector comprising a nucleotide sequence encoding (a) a lamin A polypeptide; (b) a lamin C polypeptide; (c) a lamin A and lamin C polypeptide; or biologically active variants and/or fragments thereof. In certain embodiments, the disclosure provides viral particles comprising a viral vector comprising a nucleotide sequence encoding (a) a biologically active fragment of a lamin A polypeptide; (b) a biologically active fragment of a lamin C polypeptide; (c) a biologically active fragment of a lamin A and biologically active fragment of a lamin C polypeptide; or biologically active variants and/or fragments thereof. The terms "viral particle", and "virion" are used herein interchangeably and relate to an infectious and typically replication-defective virus particle comprising the viral genome (e.g., the viral expression vector) packaged within a capsid and, as the case may be e.g., for retroviruses, a lipidic envelope surrounding the capsid. A "capsid" refers to the structure in which the viral genome is packaged. A capsid consists of several oligomeric structural subunits made of proteins. For example, AAV have an icosahedral capsid formed by the interaction of three capsid proteins: VP1, VP2 and VP3. In one embodiment, a virion provided herein is a recombinant AAV virion or rAAV virion obtained by packaging an AAV vector comprising a regulatory element (including for example, a cell-type (e.g., cardiomyocyte) selective regulatory element) operably linked to a sequence encoding lamin A and/or lamin C as described herein in a protein shell.

In certain embodiments, a recombinant AAV virion provided herein may be prepared by encapsidating an AAV genome derived from a particular AAV serotype in a viral particle formed by natural Cap proteins corresponding to an AAV of the same particular serotype. In other embodiments, an AAV viral particle provided herein comprises a viral vector comprising ITR(s) of a given AAV serotype packaged into proteins from a different serotype. See e.g., Bunning H et al. J Gene Med 2008; 10: 717-733. For example, a viral vector having ITRs from a given AAV serotype may be package into: a) a viral particle constituted of capsid proteins derived from a same or different AAV serotype (e.g. AAV2 ITRs and AAV9 capsid proteins; AAV2 ITRs and AAV8 capsid proteins; etc.); b) a mosaic viral particle constituted of a mixture of capsid proteins from different AAV serotypes or mutants (e.g. AAV2 ITRs with AAV1 and AAV9 capsid proteins); c) a chimeric viral particle constituted of capsid proteins that have been truncated by domain swapping between different AAV serotypes or variants (e.g. AAV2 ITRs with AAV8 capsid proteins with AAV9 domains); or d) a targeted viral particle engineered to display selective binding domains, enabling stringent interaction with target cell specific receptors (e.g. AAV5 ITRs with AAV9 capsid proteins genetically truncated by insertion of a peptide ligand; or AAV9 capsid proteins non-genetically modified by coupling of a peptide ligand to the capsid surface).

The skilled person will appreciate that an AAV virion provided herein may comprise capsid proteins of any AAV serotype. In one embodiment, the viral particle comprises capsid proteins from an AAV serotype selected from the group consisting of an AAV1, an AAV2, an AAV5, an AAV6, an AAV8, and an AAV9, which are more suitable for delivery to myocardium (M. Hocquemiller et al., Hum Gene Ther 27(7): 478-496 (2016)). In some embodiments, the viral vector comprises capsid proteins from an AAV6 serotype. In some embodiments, the viral vector comprises capsid proteins from an AAV9 serotype.

Numerous methods are known in the art for production of rAAV virions, including transfection, stable cell line production, and infectious hybrid virus production systems which include adenovirus-AAV hybrids, herpesvirus-AAV hybrids (Conway, J E et al., (1997) J. Virology 71(11):8780-8789) and baculovirus-AAV hybrids. rAAV production cultures for the production of rAAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions; 3) AAV rep and cap genes and gene products; 4) a transgene (e.g., a sequence encoding lamin A and/or lamin C as described herein) flanked by AAV ITR sequences; and 5) suitable media and media components to support rAAV production.

In various embodiments, the host cells described herein comprise the following three components: (1) a rep gene and a cap gene, (2) genes providing helper functions, and (3) a transgene (e.g., a sequence encoding lamin A and/or lamin C described herein flanked by ITRs). The AAV rep gene, AAV cap gene, and genes providing helper functions can be introduced into the cell by incorporating said genes into a vector such as, for example, a plasmid, and introducing said vector into the host cell. The rep, cap and helper function genes can be incorporated into the same plasmid or into different plasmids. In a preferred embodiment, the AAV rep and cap genes are incorporated into one plasmid and the genes providing helper functions are incorporated into another plasmid. The various plasmids for creation of a host cell for virion production (e.g., comprising AAV rep and cap genes, helper functions, or a transgene) can be introduced into the cell by using any suitable method well known in the art. Examples of transfection methods include, but are not limited to, co-precipitation with calcium phosphate, DEAE-dextran, polybrene, electroporation, microinjection, liposome-mediated fusion, lipofection, retrovirus infection and biolistic transfection. In certain embodiments, the plasmids providing the rep and cap genes, the helper functions and the transgene (e.g., a sequence encoding lamin A and/or lamin C disclosed herein flanked by ITRs) can be introduced into the cell simultaneously. In another embodiment, the plasmids providing the rep and cap genes and the helper functions can be introduced in the cell before or after the introduction of plasmid comprising the transgene. In an exemplary embodiment, the cells are transfected simultaneously with three plasmids (e.g., a triple transfection method): (1) a plasmid comprising the transgene (e.g., a sequence encoding lamin A and/or lamin C disclosed herein flanked by ITRs), (2) a plasmid comprising the AAV rep and cap genes, and (3) a plasmid comprising the genes providing the helper functions. Exemplary host cells may be 293, A549 or HeLa cells.

In other embodiments, one or more of (1) the AAV rep and cap genes, (2) genes providing helper functions, and (3) the transgene, may be carried by the packaging cell, either episomally and/or integrated into the genome of the packaging cell. In one embodiment, host cells may be packaging cells in which the AAV rep and cap genes and helper functions are stably maintained in the host cell and the host cell is transiently transfected with a plasmid containing a transgene (e.g., a sequence encoding lamin A and/or lamin C disclosed herein flanked by ITRs). In another embodiment, host cells are packaging cells in which the AAV rep and cap genes are stably maintained in the host cell and the host cell is transiently transfected with a plasmid containing a transgene (e.g., a sequence encoding lamin A and/or lamin C disclosed herein flanked by ITRs) and a plasmid containing the helper functions. In another embodiment, host cells may be packaging cells in which the helper functions are stably maintained in the host cell and the host cell is transiently transfected with a plasmid containing a transgene (e.g., a sequence encoding lamin A and/or lamin C disclosed herein flanked by ITRs) and a plasmid containing rep and cap genes. In another embodiment, host cells may be producer cell lines that are stably transfected with rep and cap genes, helper functions and the transgene sequence (e.g., a sequence encoding lamin A and/or lamin C disclosed herein flanked by ITRs). Exemplary packaging and producer cells may be derived from 293, A549 or HeLa cells.

In another embodiment, the producer cell line is an insect cell line (typically Sf9 cells) that is infected with baculovirus expression vectors that provide Rep and Cap proteins. This system does not require adenovirus helper genes (Ayuso E, et al., Curr. Gene Ther. 2010, 10:423-436).

The term “cap protein”, as used herein, refers to a polypeptide having at least one functional activity of a native AAV Cap protein (e.g. VP1, VP2, VP3). Examples of functional activities of cap proteins include the ability to induce formation of a capsid, facilitate accumulation of single-stranded DNA, facilitate AAV DNA packaging into capsids (i.e. encapsidation), bind to cellular receptors, and facilitate entry of the virion into host cells. In principle, any Cap protein can be used in the context of the present invention.

Cap proteins have been reported to have effects on host tropism, cell, tissue, or organ specificity, receptor usage, infection efficiency, and immunogenicity of AAV viruses. Accordingly, an AAV cap for use in an rAAV may be selected taking into consideration, for example, the subject’s species (e.g. human or non-human), the subject’s immunological state, the subject’s suitability for long or short-term treatment, or a particular therapeutic application (e.g. treatment of a particular disease or disorder, or delivery to particular cells, tissues, or organs). In certain embodiments, the cap protein is derived from the AAV of the group consisting of AAV1, AAV2, AAV5, AAV6, AAV8, and AAV9 serotypes. In some embodiments, the cap protein is derived from AAV6. In some embodiments, the cap protein is derived from AAV9.

In some embodiments, an AAV Cap for use in the method of the invention can be generated by mutagenesis (i.e. by insertions, deletions, or substitutions) of one of the aforementioned AAV caps or its encoding nucleic acid. In some embodiments, the AAV cap is at least 70%, 75%, 80%, 85%, 90%, 95%, 98%, or 99% or more similar to one or more of the aforementioned AAV caps.

In some embodiments, the AAV cap is chimeric, comprising domains from two, three, four, or more of the aforementioned AAV caps. In some embodiments, the AAV cap is a mosaic of VP1, VP2, and VP3 monomers originating from two or three different AAV or a recombinant AAV. In some embodiments, a rAAV composition comprises more than one of the aforementioned caps.

In some embodiments, an AAV cap for use in a rAAV virion is engineered to contain a heterologous sequence or other modification. For example, a peptide or protein sequence that confers selective targeting or immune evasion may be engineered into a cap protein. Alternatively or in addition, the cap may be chemically modified so that the surface of the rAAV is polyethylene glycolated (i.e., pegylated), which may facilitate immune evasion. The cap protein may also be mutagenized (e.g., to remove its natural receptor binding, or to mask an immunogenic epitope).

The term "rep protein", as used herein, refers to a polypeptide having at least one functional activity of a native AAV rep protein (e.g. rep 40, 52, 68, 78). Examples of functional activities of a rep protein include any activity associated with the physiological function of the protein, including facilitating replication of DNA through recognition, binding and nicking of the AAV origin of DNA replication as well as DNA helicase activity. Additional functions include modulation of transcription from AAV (or other heterologous) promoters and site-specific integration of AAV DNA into a host chromosome. In a particular embodiment, AAV rep genes may be from the serotypes AAV1, AAV2, AAV4, AAV5, AAV6, AAV7, AAV8, AAV9, AAV10 or AAVrh10. In some embodiments, the AAV rep genes are from AAV6. In some embodiments, the AAV rep genes are from AAV9.

In some embodiments, an AAV rep protein for use in the method of the invention can be generated by mutagenesis (i.e. by insertions, deletions, or substitutions) of one of the aforementioned AAV reps or its encoding nucleic acid. In some embodiments, the AAV rep is at least 70%, 75%, 80%, 85%, 90%, 95%, 98%, or 99% or more similar to one or more of the aforementioned AAV reps.

The expressions "helper functions" or "helper genes", as used herein, refer to viral proteins upon which AAV is dependent for replication. The helper functions include those proteins required for AAV replication including, without limitation, those proteins involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus. Helper functions include, without limitation, adenovirus E1, E2a, VA, and E4 or herpesvirus UL5, ULB, UL52, and UL29, and herpesvirus polymerase. In a preferred embodiment, the proteins upon which AAV is dependent for replication are derived from adenovirus.

In some embodiments, a viral protein upon which AAV is dependent for replication for use in the method of the invention can be generated by mutagenesis (i.e. by insertions, deletions, or substitutions) of one of the aforementioned viral proteins or its encoding nucleic acid. In some embodiments, the viral protein is at least 70%, 75%, 80%, 85%, 90%, 95%, 98%, or 99% or more similar to one or more of the aforementioned viral proteins.

Methods for assaying the functions of cap proteins, rep proteins and viral proteins upon which AAV is dependent for replication are well known in the art.

G. Host Cell

In another aspect, the invention relates to a host cell comprising a viral vector or viral particle which comprises a nucleotide sequence encoding (a) a lamin A polypeptide; (b) a lamin C polypeptide; (c) a lamin A and lamin C polypeptide; or biologically active variants and/or fragments thereof. In another embodiment, the invention relates to a host cell comprising a viral vector or viral particle which comprises a nucleotide sequence encoding (a) a biologically active fragment of a lamin A polypeptide; (b) a biologically active fragment of a lamin C polypeptide; (c) a biologically active fragment of a lamin A and a biologically active fragment of a lamin C polypeptide; or biologically active variants and/or fragments thereof. Host cells may be a bacterial cell, a yeast cell, an insect cell or a mammalian cell. In an exemplary embodiment, a host cell refers to any cell line that is susceptible to infection by a virus of interest, and amenable to culture in vitro.

In certain embodiments, a host cell provided herein may be used for ex vivo gene therapy purposes. In such embodiments, the cells are transfected with a nucleic acid molecule or expression vector comprising a sequence encoding lamin A and/or lamin C and subsequently transplanted into the patient or subject. Transplanted cells can have an autologous, allogenic or heterologous origin. For clinical use, cell isolation will generally be carried out under Good Manufacturing Practices (GMP) conditions. Before transplantation, cell quality and absence of microbial or other contaminants is typically checked and preconditioning, such as with radiation and/or an immunosuppressive treatment, may be carried out. Furthermore, the host cells may be transplanted together with growth factors to stimulate cell proliferation and/or differentiation.

In certain embodiments, a host cell may be used for ex vivo gene therapy into the heart or other tissue(s) of interest. Preferably, said cells are eukaryotic cells such as mammalian cells, these include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like. A person skilled in the art will choose the more appropriate cells according to the patient or subject to be transplanted.

In certain embodiments, a host cell provided herein may be a cell with self-renewal and pluripotency properties, such as stem cells or induced pluripotent stem cells. Stem cells are preferably mesenchymal stem cells. Mesenchymal stem cells (MSCs) are capable of differentiating into at least one of an osteoblast, a chondrocyte, an adipocyte, or a myocyte and may be isolated from any type of tissue. Generally, MSCs will be isolated from bone marrow, adipose tissue, umbilical cord, or peripheral blood. Methods for obtaining thereof are well known to a person skilled in the art. Induced pluripotent stem cells (also known as iPS cells or iPSCs) are a type of pluripotent stem cell that can be generated directly from adult cells. Yamanaka et al. induced iPS cells by transferring the Oct3/4, Sox2, Klf4 and c-Myc genes into mouse and human fibroblasts, and forcing the cells to express the genes (WO 2007/069666). Thomson et al. subsequently produced human iPS cells using Nanog and Lin28 in place of Klf4 and c-Myc (WO 2008/118820).

In an exemplary embodiment, a host cell provided herein is a packaging cell. Said cells can be adherent or suspension cells. The packaging cell, and helper vector or virus or DNA construct(s) provide together in trans all the missing functions which are required for the complete replication and packaging of the viral vector.

Preferably, said packaging cells are eukaryotic cells such as mammalian cells, including simian, human, dog and rodent cells. Examples of human cells are PER.C6 cells (WO01/38362), MRC-5 (ATCC CCL-171), WI-38 (ATCC CCL-75), HEK-293 cells (ATCC CRL-1573), HeLa cells (ATCC CCL2), and fetal rhesus lung cells (ATCC CL-160). Examples of non-human primate cells are Vero cells (ATCC CCL81), COS-1 cells (ATCC CRL-1650) or COS-7 cells (ATCC CRL-1651). Examples of dog cells are MDCK cells (ATCC CCL-34). Examples of rodent cells are hamster cells, such as BHK21-F, HKCC cells, or CHO cells.

As an alternative to mammalian sources, cell lines for use in the invention may be derived from avian sources such as chicken, duck, goose, quail or pheasant. Examples of avian cell lines include avian embryonic stem cells (WO01/85938 and WO03/076601), immortalized duck retina cells (WO2005/042728), and avian embryonic stem cell derived cells, including chicken cells (WO2006/108846) or duck cells, such as EB66 cell line (WO2008/129058 & WO2008/142124).

In another embodiment, said host cell are insect cells, such as SF9 cells (ATCC CRL-1711), Sf21 cells (IPLB-Sf21), MG1 cells (BTI-TN-MG1) or High Five™ cells (BTI-TN-5B1-4).

In certain embodiments, the host cells provided herein comprising a viral vector or viral particle which comprises a nucleotide sequence encoding (a) a lamin A polypeptide; (b) a lamin C polypeptide; (c) a lamin A and lamin C polypeptide; or biologically active variants and/or fragments thereof, may further comprise one or more additional nucleic acid constructs, such as, for example (i) a nucleic acid construct (e.g., an AAV helper plasmid) that encodes rep and cap genes, but does not carry ITR sequences; and/or (ii) a nucleic acid construct (e.g., a plasmid) providing the adenoviral functions necessary for AAV replication. In an exemplary embodiment, a host cell provided herein comprises: i) any of the nucleic acid constructs or a viral vectors disclosed herein (e.g., any of the nucleic acid constructs or vectors disclosed herein comprising a nucleotide sequence encoding (a) a lamin A polypeptide; (b) a lamin C polypeptide; (c) a lamin A and lamin C polypeptide; or biologically active variants and/or fragments thereof; ii) a nucleic acid construct encoding AAV rep and cap genes which does not carry the ITR sequences; and iii) a nucleic acid construct comprising adenoviral helper genes (as described further below).

In certain embodiments, the rep, cap, and adenoviral helper genes can be combined on a single plasmid (Blouin V et al. J Gene Med. 2004; 6(suppl): S223-S228; Grimm D. et al. Hum. Gene Ther. 2003; 7: 839-850). Thus, in another exemplary embodiment, a host cell provided herein comprises: i) a nucleic acid molecule or an expression vector comprising a sequence encoding lamin A and/or lamin C (i.e., the recombinant AAV genome); and ii) a plasmid encoding AAV rep and cap genes which does not carry the ITR sequences and further comprising adenoviral helper genes.

In another embodiment, a host cell provided herein comprises: a) any of the nucleic acid constructs or a viral vectors disclosed herein (e.g., any of the nucleic acid constructs or viral vectors disclosed herein comprising a nucleotide sequence encoding (a) a lamin A polypeptide; (b) a lamin C polypeptide; (c) a lamin A and lamin C polypeptide; or biologically active variants and/or fragments thereof; b) a plasmid encoding AAV rep and cap genes which does not carry the ITR sequences; and c) a plasmid comprising adenoviral helper genes E2a, E4, and VA RNAs; wherein co-transfection is performed in cells, preferably mammalian cells, that constitutively express and transcomplement the adenoviral E1 gene, like HEK-293 cells (ATCC CRL-1573).

In certain embodiments, a host cell suitable for large-scale production of AAV vectors is an insect cell that can be infected with a combination of recombinant baculoviruses (Urabe et al. Hum. Gene Ther. 2002; 13: 1935-1943). For example, SF9 cells may be co-infected with three baculovirus vectors respectively expressing AAV rep, AAV cap and the AAV vector to be packaged. The recombinant baculovirus vectors will provide the viral helper gene functions required for virus replication and/or packaging.

Further guidance for the construction and production of virions for gene therapy according to the invention can be found in: Viral Vectors for Gene Therapy, Methods and Protocols. Series: Methods in Molecular Biology, Vol. 737. Merten and Al-Rubeai (Eds.); 2011 Humana Press (Springer); Gene Therapy. M. Giacca. 2010 Springer-Verlag; Heilbronn R. and Weger S. Viral Vectors for Gene Transfer: Current Status of Gene Therapeutics. In: Drug Delivery, Handbook of Experimental Pharmacology 197; M. Schafer-Korting (Ed.). 2010 Springer-Verlag; pp. 143-170; Adeno-Associated Virus: Methods and Protocols. R. O. Snyder and P. Moulllier (Eds). 2011 Humana Press (Springer); Bunning H. et al. Recent developments in adeno-associated virus technology. J. Gene Med. 2008; 10:717-733; and Adenovirus: Methods and Protocols. M. Chillon and A. Bosch (Eds.); Third. Edition. 2014 Humana Press (Springer).

Host cells for expressing a transgene of interest (e.g., a sequence encoding a lamin A and/or lamin C) may be grown under conditions adequate for assembly of the AAV virions. In certain embodiments, host cells are grown for a suitable period of time in order to promote the assembly of the AAV virions and the release of virions into the media. Generally, cells may be grown for about 24 hours, about 36 hours, about 48 hours, about 72 hours, about 4 days, about 5 days, about 6 days, about 7 days, about 8 days, about 9 days, or up to about 10 days. After about 10 days (or sooner, depending on the culture conditions and the particular host cell used), the level of production generally decreases significantly. Generally, time of culture is measured from the point of viral production. For example, in the case of AAV, viral production generally begins upon supplying helper virus function in an appropriate host cell as described herein. Generally, cells are harvested about 48 to about 100, preferably about 48 to about 96, preferably about 72 to about 96, preferably about 68 to about 72 hours after helper virus infection (or after viral production begins).

rAAV production cultures can be grown under a variety of conditions (over a wide temperature range, for varying lengths of time, and the like) suitable to the particular host cell being utilized. rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

Suitable media known in the art may be used for the production of rAAV virions. These media include, without limitation, media produced by Hyclone Laboratories and JRH including Modified Eagle Medium (MEM), Dulbecco's Modified Eagle Medium (DMEM), each of which is incorporated herein by reference in its entirety. In certain embodiments, rAAV production culture media may be supplemented with serum or serum-derived recombinant proteins at a level of 0.5%-20% (v/v or w/v). Alternatively, rAAV vectors may be produced in serum-free conditions which may also be referred to as media with no animal-derived products.

After culturing the host cells to allow AAV virion production, the resulting virions may be then be harvested and purified. In certain embodiments, the AAV virions can be obtained from (1) the host cells of the production culture by lysis of the host cells, and/or (2) the culture medium of said cells after a period of time post-transfection, preferably 72 hours. The rAAV virions may be harvested from the spent media from the production culture, provided the cells are cultured under conditions that cause release of rAAV virions into the media from intact cells (see e.g., U.S. Pat. No. 6,566,118). Suitable methods of lysing cells are also known in the art and include for example multiple freeze/thaw cycles, sonication, microfluidization, and treatment with chemicals, such as detergents and/or proteases.

After harvesting, the rAAV virions may be purified. The term "purified" as used herein includes a preparation of rAAV virions devoid of at least some of the other components that may also be present where the rAAV virions naturally occur or are initially prepared from. Thus, for example, purified rAAV virions may be prepared using an isolation technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

In certain embodiments, the rAAV production culture harvest may be clarified to remove host cell debris. In some embodiments, the production culture harvest may be clarified using a variety of standard techniques, such as, centrifugation or filtration through a filter of 0.2 μm or greater pore size (e.g., a cellulose acetate filter or a series of depth filters).

In certain embodiments, the rAAV production culture harvest is further treated with Benzonase™ to digest any high molecular weight DNA present in the production culture. In some embodiments, the Benzonase™ digestion is performed under standard conditions, for example, a final concentration of 1-2.5 units/ml of Benzonase™ at a temperature ranging from ambient to 37° C. for a period of 30 minutes to several hours.

In certain embodiments, the rAAV virions may be isolated or purified using one or more of the following purification steps: equilibrium centrifugation; flow-through anionic exchange filtration; tangential flow filtration (TFF) for concentrating the rAAV particles; rAAV capture by apatite chromatography; heat inactivation of helper virus; rAAV capture by hydrophobic interaction chromatography; buffer exchange by size exclusion chromatography (SEC); nanofiltration; and rAAV capture by anionic exchange chromatography, cationic exchange chromatography, or affinity chromatography. These steps may be used alone, in various combinations, or in different orders. Methods to purify rAAV particles are found, for example, in Xiao et al., (1998) Journal of Virology 72:2224-2232; U.S. Pat. Nos. 6,989,264 and 8,137,948; and WO 2010/148143.

In certain embodiments, purified AAV virions can be dialyzed against PBS, filtered and stored at −80° C. Titers of viral genomes can be determined by quantitative PCR using linearized plasmid DNA as standard curve (see e.g., Lock M, et al., Hum. Gene Ther. 2010; 21:1273-1285).

H. Pharmaceutical Composition

In certain embodiments, the disclosure provides compositions comprising any of the nucleic acid constructs, expression vectors, viral vectors, viral particles or host cells disclosed herein. In some embodiments, the disclosure provides compositions comprising a viral vector or viral particle which comprises a nucleotide sequence encoding (a) a lamin A polypeptide; (b) a lamin C polypeptide; (c) a lamin A and lamin C polypeptide; or biologically active variants and/or fragments thereof and a pharmaceutically acceptable carrier. In some embodiments, the disclosure provides compositions comprising a viral vector or viral particle which comprises a nucleotide sequence encoding (a) a biologically active fragment of a lamin A polypeptide; (b) a biologically active fragment of a lamin C polypeptide; (c) a biologically active fragment of a lamin A and a biologically active fragment of a lamin C polypeptide; or biologically active variants and/or fragments thereof and a pharmaceutically acceptable carrier. In other embodiments, the disclosure provides host cells which comprise a viral vector or viral particle comprising a nucleotide sequence encoding (a) a lamin A polypeptide; (b) a lamin C polypeptide; (c) a lamin A and lamin C polypeptide; or biologically active variants and/or fragments thereof and a pharmaceutically acceptable carrier. In particular embodiments, such compositions are suitable for gene therapy applications. Pharmaceutical compositions are preferably sterile and stable under conditions of manufacture and storage. Sterile solutions may be accomplished, for example, by filtration through sterile filtration membranes.

Acceptable carriers and excipients in the pharmaceutical compositions are preferably nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. Pharmaceutical compositions of the disclosure can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water and physiological saline.

The pharmaceutical compositions of the disclosure may be prepared in microcapsules, such as hydroxylmethylcellulose or gelatin-microcapsules and polymethylmethacrylate microcapsules. The pharmaceutical compositions of the disclosure may also be prepared in other drug delivery systems such as liposomes, albumin microspheres, microemulsions, nano-particles, and nanocapsules. The pharmaceutical composition for gene therapy can be in an acceptable diluent, or can comprise a slow release matrix in which the gene delivery vehicle is imbedded.

Pharmaceutical compositions provided herein may be formulated for parenteral administration, subcutaneous administration, intravenous administration, systemic administration, intramuscular administration, intra-arterial administration, intraparenchymal administration, intrathecal administration, intra-cisterna *magna* administration, intracerebroventricular administration, or intraperitoneal administration. In one embodiment, the pharmaceutical composition is formulated for intravenous administration. In one embodiment, the pharmaceutical composition is formulated for systemic administration. The pharmaceutical composition may also be formulated for, or administered via, nasal, spray, oral, aerosol, rectal, or vaginal administration. In one embodiment, a pharmaceutical composition provided herein is administered to the muscle, i.e. by intramuscular injection. The tissue target may be specific, for example the heart, or it may be a combination of several tissues, for example the heart and liver tissues. Exemplary tissue or other targets may include liver, skeletal muscle, heart muscle, adipose deposits, kidney, lung, vascular endothelium, epithelial, hematopoietic cells, CNS and/or CSF. In a particular embodiment, a pharmaceutical composition provided herein is administered to the heart, i.e. by intracardiac injection, intravenous injection or systemically. One or more of these methods may be used to administer a pharmaceutical composition of the disclosure.

In certain embodiments, a pharmaceutical composition provided herein comprises an "effective amount" or a "therapeutically effective amount." As used herein, such amounts refer to an amount effective, at dosages and for periods of time necessary to achieve the desired therapeutic result, such as increasing the level of LMNA expression and/or increasing ventricular output.

The dosage of the pharmaceutical compositions of the disclosure depends on factors including the route of administration, the disease to be treated, and physical characteristics (e.g., age, weight, general health) of the subject. Dosage may be adjusted to provide the optimum therapeutic response. Typically, a dosage may be an amount that effectively treats the disease without inducing significant toxicity. In one embodiment, an AAV vector provided herein can be administered to the patient for the treatment of a laminopathy (including for example, dilated cardiomyopathy) in an amount or dose within a range of $5\times10^{11}$ to $1\times10^{14}$ gc/kg (genome copies per kilogram of patient body weight (gc/kg)). In a more particular embodiment, the AAV vector is administered in an amount comprised within a range of about $5\times10^{11}$ gc/kg to about $3\times10^{13}$ gc/kg, or about $1\times10^{12}$ to about $1\times10^{14}$ gc/kg, or about $1\times10^{12}$ to about $1\times10^{13}$ gc/kg, or about $5\times10^{11}$ gc/kg, $1\times10^{12}$ gc/kg, $1.5\times10^{12}$ gc/kg, $2.0\times10^{12}$ gc/kg, $2.5\times10^{12}$ gc/kg, $3\times10^{12}$ gc/kg, $3.5\times10^{12}$ gc/kg, $4\times10^{12}$ gc/kg, $4.5\times10^{12}$ gc/kg, $5\times10^{12}$ gc/kg, $5.5\times10^{12}$ gc/kg, $6\times10^{12}$ gc/kg, $6.5\times10^{12}$ gc/kg, $7\times10^{12}$ gc/kg, $7.5\times10^{12}$ gc/kg, $8\times10^{12}$ gc/kg, $8.5\times10^{12}$ gc/kg, $9\times10^{12}$ gc/kg or $9.5\times10^{12}$ gc/kg. The gc/kg may be determined, for example, by qPCR or digital droplet PCR (ddPCR) (see e.g., M. Lock et al, Hum Gene Ther Methods. 2014 April; 25(2): 115-25). In another embodiment, an AAV vector provided herein can be administered to the patient for the treatment of a laminopathy (including for example, dilated cardiomyopathy) in an amount or dose within a range of $1\times10^{9}$ to $1\times10^{11}$ iu/kg (infective units of the vector (iu)/subject's or patient's body weight (kg)). In certain embodiments, the pharmaceutical composition may be formed in a unit dose as needed. Such single dosage units may contain about $1\times10^{9}$ gc to about $1\times10^{15}$ gc.

Pharmaceutical compositions of the disclosure may be administered to a subject in need thereof, for example, one or more times (e.g., 1-10 times or more) daily, weekly, monthly, biannually, annually, or as medically necessary. In an exemplary embodiment, a single administration is sufficient. In one embodiment, the pharmaceutical composition is suitable for use in human subjects and is administered by intramuscular injection. In one embodiment, the pharmaceutical composition is suitable for use in human subjects and is administered by intracardiac injection, intravenous injection, or systemic administration. In one embodiment, the pharmaceutical composition is delivered via a peripheral vein by bolus injection. In other embodiments, the pharmaceutical composition is delivered via a peripheral vein by infusion over about 10 minutes (±5 minutes), over about 20 minutes (±5 minutes), over about 30 minutes (±5 minutes), over about 60 minutes (±5 minutes), or over about 90 minutes (±10 minutes).

In another aspect, the disclosure further provides a kit comprising a nucleic acid construct, viral vector, viral particle, host cell, or pharmaceutical composition as described herein in one or more containers. A kit may include instructions or packaging materials that describe how to administer a nucleic acid molecule, vector, host cell or virion contained within the kit to a patient. Containers of the kit can be of any suitable material, e.g., glass, plastic, metal, etc., and of any suitable size, shape, or configuration. In certain embodiments, the kits may include one or more ampoules or syringes that contain a nucleic acid construct, viral vector, viral particle, host cell, or pharmaceutical composition in a suitable liquid or solution form.

I. Methods of Treatment

The nuclear lamina, that underlies the inner nuclear membrane, is a meshwork of type V intermediate filament proteins consisting primarily of the A and B type lamins. Mammalian somatic cells express four major and three minor types of lamins. The LMNA gene encodes A-type lamins, including two major isoforms, A and C, and two minor isoforms AΔ10 and C2. The B type lamins major isoforms B1 and B2 are encoded by LMNB1 and LMNB2, respectively. LMNB2 further encodes the minor isoform B3. In addition to providing mechanical strength to the nucleus, recent discoveries in nuclear-lamina associated human diseases have established that lamins contribute to at least three pathways: (a) gene expression and differentiation by contributing to subnuclear localization and epigenetic regulation of genes; (b) DNA damage repair and genome stability; and (c) regulation of transcription factors and signaling components controlling various differentiation pathways.

Some 15 different diseases/anomalies, called laminopathies or nuclear envelopathies, are linked to mutations within lamins and lamin-binding proteins. More than 500 mutations have been reported within LMNA, which result in aberrant folding, instability, and misassembly of the lamin polypeptide, or they can affect the biochemical properties of protein domain surfaces, resulting in disturbed lamin A/C interactions. These mutations give rise to multiple disease phenotypes in four major disease types: striated muscle diseases, lipodystrophic syndromes, peripheral neuropathy, and accelerating aging disorders. These disease phenotypes range from cardiac and skeletal myopathies, lipodystrophies, peripheral neuropathies, to premature aging with early death.

Dilated cardiomyopathy is a type of striated muscle disease characterized by dilation and impaired contraction of the left ventricle or both ventricles and impaired systolic function. The prevalence of dilated cardiomyopathy ranges from 1:2500 individuals to 1:250 individuals. Despite being a rare disease, dilated cardiomyopathy represents a serious health burden, often leading to arrhythmias (i.e. bradyarrhthmias and tachyarrhthmias), atrioventricular block, thromboembolism and sudden death at any stage of disease. As of 2014, 165 dilated cardiomyopathy associated mutations had been identified in the LMNA gene (Tesson F. Cardiol J. 2014; 21(4):331-42). These mutations included missense/nonsense mutations, splicing mutations, small deletions, small insertions, small indel, gross deletions, or gross insertions. The majority of LMNA mutations leading to dilated cardiomyopathy are autosomal dominant missense mutations found throughout the gene that generate mutated lamin A/C proteins.

In certain embodiments, the disclosure provides methods for treating laminopathies. Laminopathies appropriate for treatment include, but are not limited to, Charcot-Marie-Tooth disease, Emery-Dreifuss Muscular Dystrophy (EDMD), familial partial lipodystrophy, Hutchinson-Gilford Progeria syndrome (HGPS), limb-girdle muscular dystrophy, LMNA-related congenital muscular dystrophy, mandibuloacral dysplasia, arrhythmogenic right ventricular cardiomyopathy, familial atrial fibrillation, left ventricular noncompaction, dilated cardiomyopathy, Atypical Werner syndrome, Barraquer-Simons syndrome, Buschke-Ollendorff syndrome, Familial partial lipodystrophy of the Dunnigan type (FPLD), Greenberg dysplasia, leukodystrophy, limb-girdle muscular dystrophy type 1B, lipoatrophy with diabetes, hepatic steatosis, hypertrophic cardiomyopathy, and leukomelanodermic papules (LDHCP), Mandibuloacral dysplasia with type A lipodystrophy (MADA), Mandibuloacral dysplasia with type B lipodystrophy (MADB), Pelger-Huet anomaly (PHA), Pelizaeus-Merzbacher disease and Tight skin contracture syndrome.

In some embodiments, the laminopathy may be a laminopathic lipodystrophy disorder, systemic laminopathy, laminopathic neurological disorder, or muscle laminopathy. By "laminopathic" lipodystrophy disorders and "laminopathic" neurological disorders is meant lypodystrophy and neurological disorders resulting from or associated with abnormal nuclear envelope morphology. Lipodystrophy disorders are characterized by abnormal distribution of adipose tissue, optionally associated with metabolic disorders such as diabetes and hypertriglyceridemia. Lipodystrophy patients often experience selective loss and/or excessive accumulation of adipose tissue in certain regions of the body (e.g., loss in the limbs accompanied by excessive deposit in the upper back). Examples of laminopathic lipodystrophy disorders include, for instance, familial partial lipodystrophy (Dunnigan type), acquired partial lipodystrophy, type A insulin resistance syndrome, generalized lipoatrophy syndrome, and familial partial lipodystrophy (Kobberling).

Systemic laminopathies affect a variety of tissue types and include, e.g., atypical Werner syndrome, progeria (e.g., Hutchinson-Gilford progeria syndrome), restrictive dermopathy, and mandibuloacral dysplasia. The symptoms associated with systemic laminopathies are diverse. Atypical Werner syndrome patients prematurely exhibit features commonly associated with aging such as short stature, osteoporosis, thinning hair, athlerosclerosis, and cataracts. Restrictive dermopathy, on the other hand, is commonly associated with skin and joint contracture, abnormal skull mineralization, and pulmonary defects. Laminopathic neurological disorders, or laminopathies with peripheral nerve involvement, also are suitable for treatment by the inventive method. Neurological laminopathies include, e.g., Charcot-Marie-Tooth disease type 2B1, autosomal dominant leukodystrophy, and autosomal dominant spinal muscular dystrophy.

A majority of laminopathies caused by lamin A/C mutations involve striated muscle. Emery-Dreifuss muscular dystrophy (EDMD), limb-girdle muscular dystrophy type 1B, congenital muscular dystrophy, multisystem dystrophy syndrome, dilated cardiomyopathy 1A, familial dilated cardiomyopathy, and dilated cardiomyopathy with conduction system defects are diagnosed as muscle laminopathies. Patients suffering from muscle laminopathies exhibit, for example, muscle weakness or wasting, hypertrophy of select muscles (e.g., calf), muscle or tendon contractures, cardiomyopathy, impaired cardiac conduction, and mental retardation.

In certain embodiments, the disclosure provides methods for treating a laminopathy in a subject comprising administering a therapeutically effective amount of any of the nucleic acid constructs, viral vectors, viral particles, host cells, and/or pharmaceutical compositions disclosed herein. In certain embodiments, the disclosure provides methods for expressing (a) a lamin A polypeptide or biologically active fragment thereof; (b) a lamin C or biologically active fragment thereof polypeptide; (c) a lamin A polypeptide or biologically active fragment thereof and a lamin C polypeptide or biologically active fragment thereof; or biologically active variants and/or fragments thereof in a subject comprising administering to said subject a viral vector, viral particle, host cell, or pharmaceutical composition disclosed herein. In certain embodiments, the disclosure provides methods for increasing expression of (a) a functional lamin A polypeptide; (b) a functional lamin C polypeptide; (c) a functional lamin A polypeptide and a functional lamin C polypeptide; or biologically active variants and/or fragments thereof in a subject comprising administering a viral vector, viral particle, host cell, or pharmaceutical composition disclosed herein. In some embodiments, such subject has been diagnosed with or is at risk for a laminopathy, wherein the laminopathy is any one or more of: Charcot-Marie-Tooth disease, Emery-Dreifuss muscular dystrophy, familial partial lipodystrophy, Hutchinson-Gilford progeria syndrome, limb-girdle muscular dystrophy, LMNA-related congenital muscular dystrophy, mandibuloacral dysplasia, arrhythmogenic right ventricular cardiomyopathy, familial atrial fibrillation, left ventricular noncompaction, and dilated cardiomyopathy. In some cases, a nucleotide sequence encoding a polypeptide encoding (a) a lamin A polypeptide; (b) a lamin C polypeptide; (c) a lamin A polypeptide and a lamin C polypeptide; or biologically active variants and/or fragments thereof is delivered using a virus or a viral vector, such as AAV6 or AAV9. In some cases, the subject in need thereof has an insufficient gene expression or a mutation in any one or more of LMNA, LMNB1, and LMNB2.

In some cases, treatment using a nucleic acid construct, viral vector, viral particle, host cell, or pharmaceutical composition described herein results in improved heart function, improved heart muscle contractions, increased expression of lamin A and/or lamin C, or in reduced mTOR activity. In certain embodiments, the disclosure provides a method for treating a subject with, or at risk of developing, dilated cardiomyopathy. Symptoms associated with dilated cardiomyopathy include shortness of breath, swelling in the legs, fatigue, weight gain, fainting, palpitations, dizziness, blood clots, chest pain, and/or sudden death. Furthermore, dilated cardiomyopathy arising from LMNA mutations results in hyperactivated mTOR signaling in the heart. Treatment with a nucleic acid construct, viral vector, viral particle, host cell, or pharmaceutical composition described herein can result in an improvement of one or more symptoms, such as a reduction in mTOR signaling. Administration of a therapy as described herein to a subject at risk of developing dilated cardiomyopathy can prevent the development of or slow the progression of one or more symptoms.

In certain embodiments, treatment with a nucleic acid construct, viral vector, viral particle, host cell, or pharmaceutical composition described herein reduces mTOR signaling, by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 45%, 50%, 55%, 60%, 65%, 70%, 75%, 80%, 85%, 90%, or 95% as compared to an untreated control or as compared to the level before treatment.

In certain embodiments, treatment with a nucleic acid construct, viral vector, viral particle, host cell, or pharmaceutical composition described herein increases lamin A and/or lamin C expression, by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 45%, 50%, 55%, 60%, 65%, 70%, 75%, 80%, 85%, 90%, or 95% as compared to an untreated control or as compared to the level before treatment.

In certain embodiments, treatment with a nucleic acid construct, viral vector, viral particle, host cell, or pharmaceutical composition described herein is combined with one or more additional therapies selected from the group consisting of: beta blockers, angiotensin-converting enzyme (ACE) inhibitors, angiotensin receptor blocker (ARB), niprilysin inhibitors, diuretics, aldosterone antagonist, isosorbide dinitrate, hydralazine, digoxin, ivabradine, cardiac resynchronization therapy (CRT), implantable cardioverter defibrillators (ICD), surgery, heart transplant, and/or combinations thereof.

In certain embodiments, methods and compositions of this disclosure can be used to treat a subject who has been diagnosed with a disease, for example, a laminopathy. In various embodiments, the laminopathy can be caused by a known genetic event (e.g., any of the LMNA mutations known in the art) or may have an unknown cause. The subject can be a patient suffering from a muscle laminopathy. In some instances, the subject is a patient with dilated cardiomyopathy.

In certain embodiments, methods and compositions of this disclosure can be used to treat a subject who is at risk of developing a disease. The subject can be known to be predisposed to a disease, for example, a laminopathy (i.e. dilated cardiomyopathy). The subject can be predisposed to a disease due to a genetic event, or due to known risk factors. For example, a subject can carry a mutation in LMNA which is associated with dilated cardiomyopathy.

In certain embodiments, treatments provided herein can result in a decrease or cessation of symptoms, e.g., any of the laminopathy symptoms disclosed herein. For example, treatment can result in improved heart function, improved ECG readings, ERK1/2 downregulation, decreased mTOR signaling, and increased survival times. Measurements of heart function, ECG readings, ERK1/2 downregulation, mTOR signaling, increased survival times, and other relevant parameters can be performed in a specific disease model of a laminopathy. For instance, several mouse models of laminopathies (e.g. muscular dystrophy or dilated cardiomyopathy) have been developed. In particular, the H222P LMNA mouse model contains a point mutation (H222P) resulting in muscular dystrophy and dilated cardiomyopathy with conduction-system disease. While heterozygous mice (LMNA$^{'2221}$ do not show any phenotypes as neonates or adults, adult homozygous mutant mice (LMNA$^{H222P/H222P}$) develop muscular dystrophy and dilated cardiomyopathy with conduction-system disease similar to the clinical features of human laminopathies affecting striated muscles. See, e.g., Arimura T, et al. *Human Molecular Genetics,* 2005; 14(1):155-169. The LMNA$^{flox/flox}$ mouse model displays more severe defects in a range of tissues, with skeletal muscles being the most impaired. See, e.g., Kim Y, Biochem Biophys Res Commun. 2013; 440(1):8-13. The LMNA$^{flox/flox}$ mouse model has loxP sites flanking the second exon of Lmna, effectively creating a conditional Lmna knockout mouse. Germline Cre expression results in Lmna homozygous mutants with postnatal lethality at postnatal days 16-18. In some embodiments, the animal model is a H222P LMNA mutant mouse. In some embodiments, the animal model is an LMNA$^{flox/flox}$ mutant mouse (e.g. Jackson laboratories stock number 026284). Such disease model systems can be used for discovery of specific nucleic acid constructs, viral vectors, viral particles, host cells, or pharmaceutical compositions to treat the laminopathy.

In certain embodiments, a nucleic acid construct, viral vector, viral particle, host cell, or pharmaceutical composition described herein is administered to the subject intravenously or systemically. Other forms of administration that may be useful in the methods described herein include, but are not limited to, direct delivery to the desired organ (e.g., the heart), orally, intravenously, intramuscularly, intrathecally, subcutaneously, sublingually, nasally, inhalation, nebulization, cutaneously, topically, systemically, intramyocardially, transdermally, and other parental routes of administration. Routes of administration may be combined, if desired.

J. Examples

The disclosure now being generally described, it will be more readily understood by reference to the following examples, which are included merely for purposes of illustration of certain embodiments and embodiments of the present disclosure, and are not intended to limit the disclosure.

Example 1: LMNA minigene construct 1 production of Lamin A and Lamin C

HEK293T cells (Fujifilm) were seeded in 6-well plates at a density of 900,000 cells/well and incubated at 37 degrees Centigrade overnight. The next day, cells were transiently transfected with 3 micrograms of plasmid DNA encoding LMNA under the control of the chicken beta actin (CB) promoter (Minigene 1), or a GFP control. The CB regulatory element incorporates the chicken beta actin promoter and corresponds to SEQ ID NO: 102. Cells were transfected according to standard methods using Fugene® transfection reagent (Promega). Two days post transfection, cells were trypsinized, centrifuged, and processed for protein analysis. Samples were prepared for Western blot analysis by lysing cells in Laemli 4× buffer with beta-mercaptoethanol (Biorad) and boiling for 5 minutes at 95 degrees Centigrade. Protein lysates were then separated by TGX gel and transferred to a nitrocellulose membrane. Membranes were blocked and washed using a standard western blot protocol, and blotted with a primary antibody overnight at 4 degrees Centigrade. Mouse anti-Lamin A/C (CST #4777, 1:1000) and mouse anti-GAPDH (GeneTex #GT239, 1:2000) were used as the primary antibodies. Anti-mouse IgG HRP (Invitrogen A16078, 1:5000) was used as a secondary antibody for chemiluminescence detection. Lamin C and Lamin A, were detected at 65 kDa and 72 kDa, respectively, while GAPDH was detected at 37 kDa.

Figure 6:
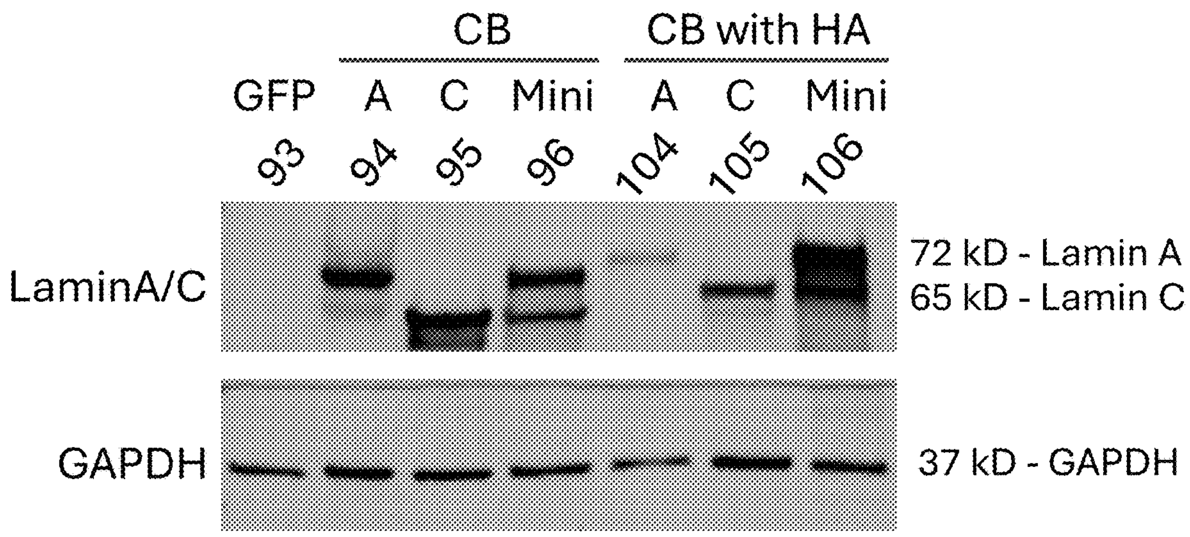
FIG. 6 is a western blot showing that Lamin A and Lamin C isoforms are both produced from LMNA minigene construct 1 in HEK293 cells.

HEK293T cells transfected with a construct encoding only Lamin A or Lamin C showed production of each respective protein, as expected. HEK293T cells transfected with LMNA minigene construct 1 showed production of both Lamin A and Lamin C, indicating that the single construct was capable of generating both isoforms (FIG. 6). Minigenes 2 and 3 did not produce both Lamin isoforms under the tested conditions.

Example 2: Lamin A and Lamin C mRNA Expression

HEK293T cells were grown and transiently transfected as described above. iPS cardiomyocytes (Fujifilm) were also transiently transfected. Cardiomyocytes were seeded at 500,000 cells/well in 6-well plates and incubated at 37 degrees Centigrade for two days. Two days post-transfection, cells were trypsinized, centrifuged, and processed for RNA-based analysis. RNA was extracted from cell pellets using the RNAeasy mini kit (Qiagen) following the manufacturer's instructions, and used to synthesize cDNA with SuperScript IV Reverse Transcriptase (Invitrogen). Quantitative PCR was performed using Lamin A/C, Lamin A or Lamin C-specific primer sets (Table 5), to evaluate expression levels of the respective genes.

Figure 7:
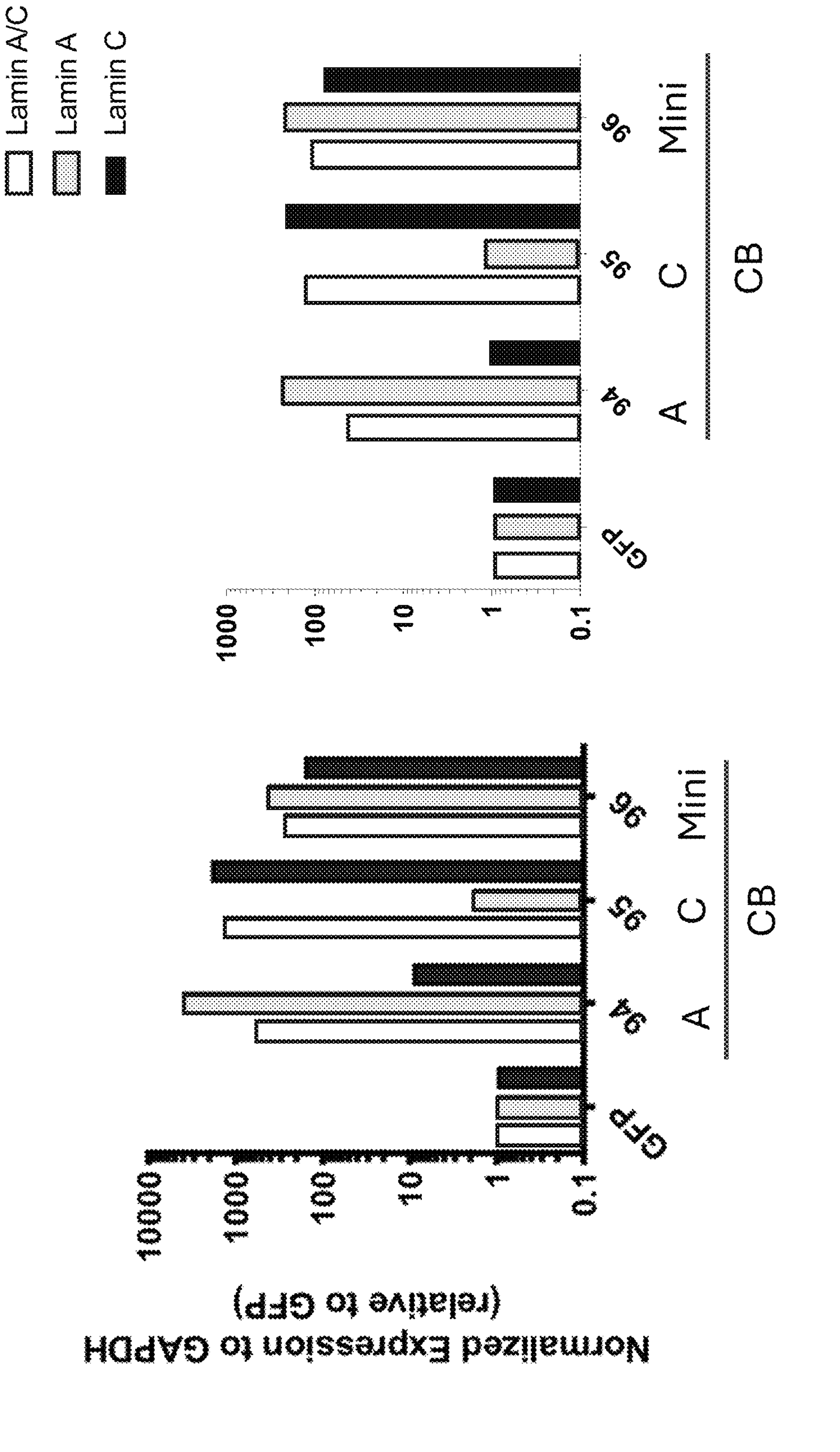
FIG. 7 is a graph of mRNA expression levels demonstrating that the LMNA minigene construct is able to express both Lamin A and Lamin C in both HEK293T cells (left) and iPS cardiomyocytes (right).

Cells transfected with a construct encoding only Lamin A or Lamin C showed mRNA transcription for each respective gene, as expected. HEK293T cells transfected with minigene construct 1, however, showed transcription of both Lamin A and Lamin C mRNA, indicating that the single construct was capable of transcribing both isoforms (FIG. 7).

TABLE 5

Primers used for quantitative PCR experiments

| SEQ ID NO: | Gene | Primer | Sequence |
|---|---|---|---|
| 94 | Human Lamin A | Forward | GCTCTTCTGCCTCCAGTGTC |
| 95 | | Reverse | ATGATGCTGCAGTTCTGGGG |
| 96 | Human Lamin C | Forward | CCTGGTGTGGAAGGCACAGAAC |
| 97 | | Reverse | GGCTACCACTCACGTGGTGGTG |
| 98 | Human Lamin A/C | Forward | ACCAAGAAGGAGGGTGACCT |
| 99 | | Reverse | AGCCTGTTCTCAGCATCCAC |

Figure 8:
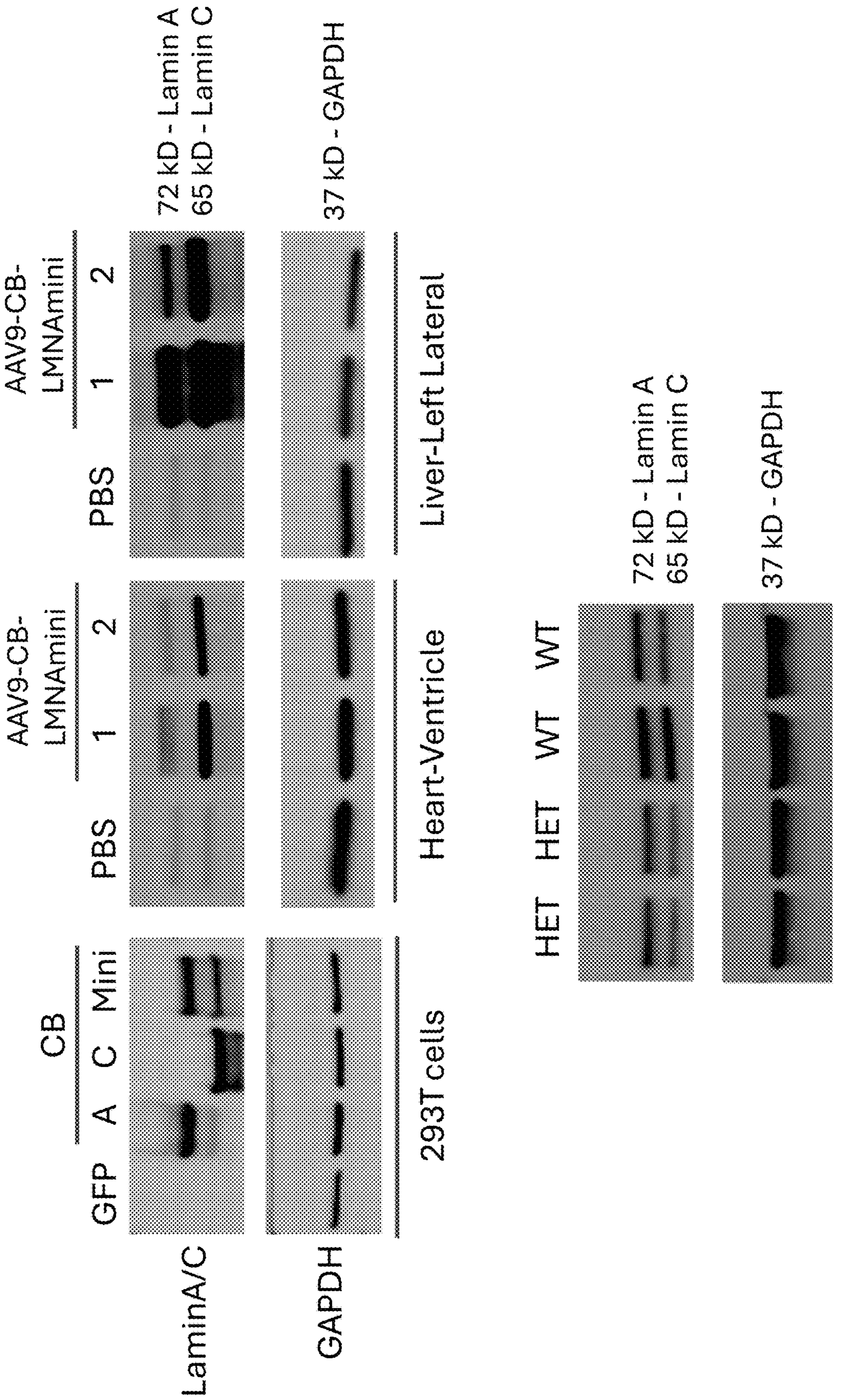
FIG. 8 is a western blot showing that Lamin A and Lamin C isoforms are both produced from minigene construct 1 in vitro (293T cells), and in vivo in heart and liver tissues (bottom panels heart tissue from wildtype and heterozygous $Lmna^{-/-}$ male mouse model animals at 24 weeks old).

Example 3: Minigene Construct 1 Production of Lamin a and Lamin C in Heart and Liver Tissue Lamin A and Lamin C production was measured in vitro in HEK293T cells. Cells were grown, transiently transfected, and processed for Western blot analysis as described above. Lamin A and Lamin C production was also measured in vivo in 12 week old wild-type (FIG. 8, top) mice, and 24 week old mice heterozygous for the LMNA gene (LMNA$^{+/-}$) (FIG. 8, bottom). Both mouse strains were administered the AAV9 virus carrying minigene construct 1. Tissue samples were collected and snap-frozen post extraction and stored at −80 degree Centigrade until needed. They were then thawed, homogenized using bead homogenizer in RIPA buffer containing protease inhibitor cocktail, and resuspended in Laemli 4× buffer with beta-mercaptoethanol (Biorad). Western blot analysis was performed as described above.

HEK293T cells transfected with a construct encoding only Lamin A or Lamin C showed protein for each respective protein, as expected (FIG. 8, top). HEK293T cells transfected with minigene construct 1 showed production of both Lamin A and Lamin C, indicating that the single construct was capable of generating both isoforms (FIG. 8 top). Lamin A and Lamin C isoforms are both detected in wild-type and heterozygous LMNA$^{+/-}$ mice when dosed with AAV9 virus carrying the minigene construct 1 (FIG. 8, top and bottom). Endogenous LMNA levels are detectable in both wild-type and heterozygous LMNA$^{+/-}$ mice.

Example 4: Rescue of Disease Phenotype in LMNA$^{-/-}$ KO Mice

LMNA$^{-/-}$ KO animals were generated by mating LMNA$^{+/-}$ males and females. LMNA$^{+/-}$×LMNA$^{+/-}$ litters underwent facial vein injections at p1. Facial vein injections were performed as generally described in Lampe et al. (*J Vis Exp.* 2014; (93):e52037). Mice were dosed with 10 microliters of AAV9 virus carrying minigene construct 1 (2E11 virus genomes per mouse), or PBS. Pups were left with their mother for three weeks to wean with no pup manipulation.

Figure 9:
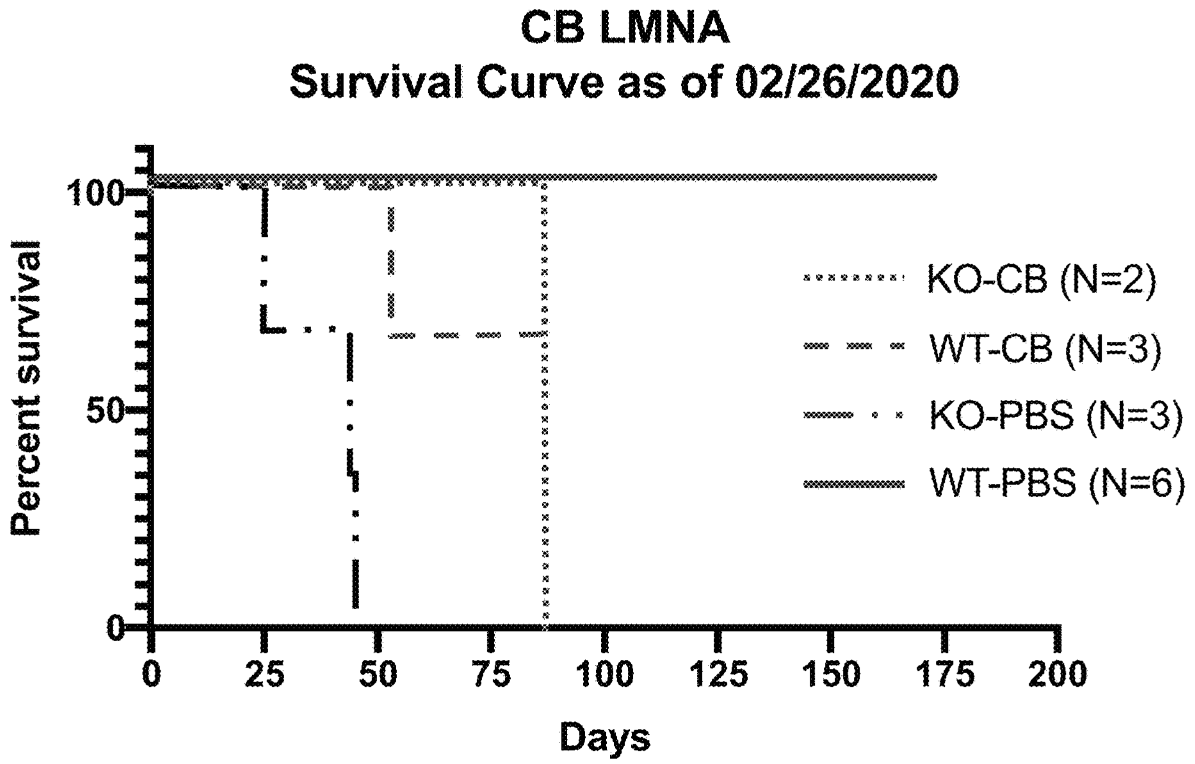
FIG. 9 is a graph showing rescue of disease phenotype in $LMNA^{-/-}$ KO mice when dosed with AAV virus carrying minigene construct 1.

LMNA$^{-/-}$ KO mice treated with PBS control survived less than 50 days (FIG. 9). However, mice dosed with AAV9 carrying minigene construct 1 survived more than 80 days, indicating that minigene construct 1 substantially mitigated the severe disease phenotype normally observed in LMNA$^{-/-}$ KO mice.

Example 5: In Vivo Expression of Lamin A and Lamin C Isoforms in Mice 12 week old C57BL/6 wild-type, male mice underwent a systemic administration of AAV9 carrying minigene construct 1, or PBS via tail vein of approximately 200 microliters. AAV9 preparations included AAV9 carrying minigene construct 1, using a ubiquitous promoter, AAV9 carrying a LMNA construct under the control of a heart-specific promoter (cTNT), or AAV9 carrying GFP under a ubiquitous promoter. A low dose of 4E11 vg/mouse or a high dose of 2E12 vg/mouse were used. All animals were processed and samples taken at six weeks post injection. Heart and liver tissue was harvested and stored using standard methods for later experimentation.

Tissues were kept in RNAlater post extraction and stored at −80 degrees Centigrade until needed. They were then thawed and homogenized in RLT buffer using bead homogenizer. RNA was extracted using the RNAeasy mini kit (Qiagen) following the manufacturer's instructions. cDNA libraries were produced from RNA extracts using TRUseq cDNA library preparation kit (Illumina), and underwent NGS sequencing on a Nextseq 500 platform and analyzed.

Figure 10A:
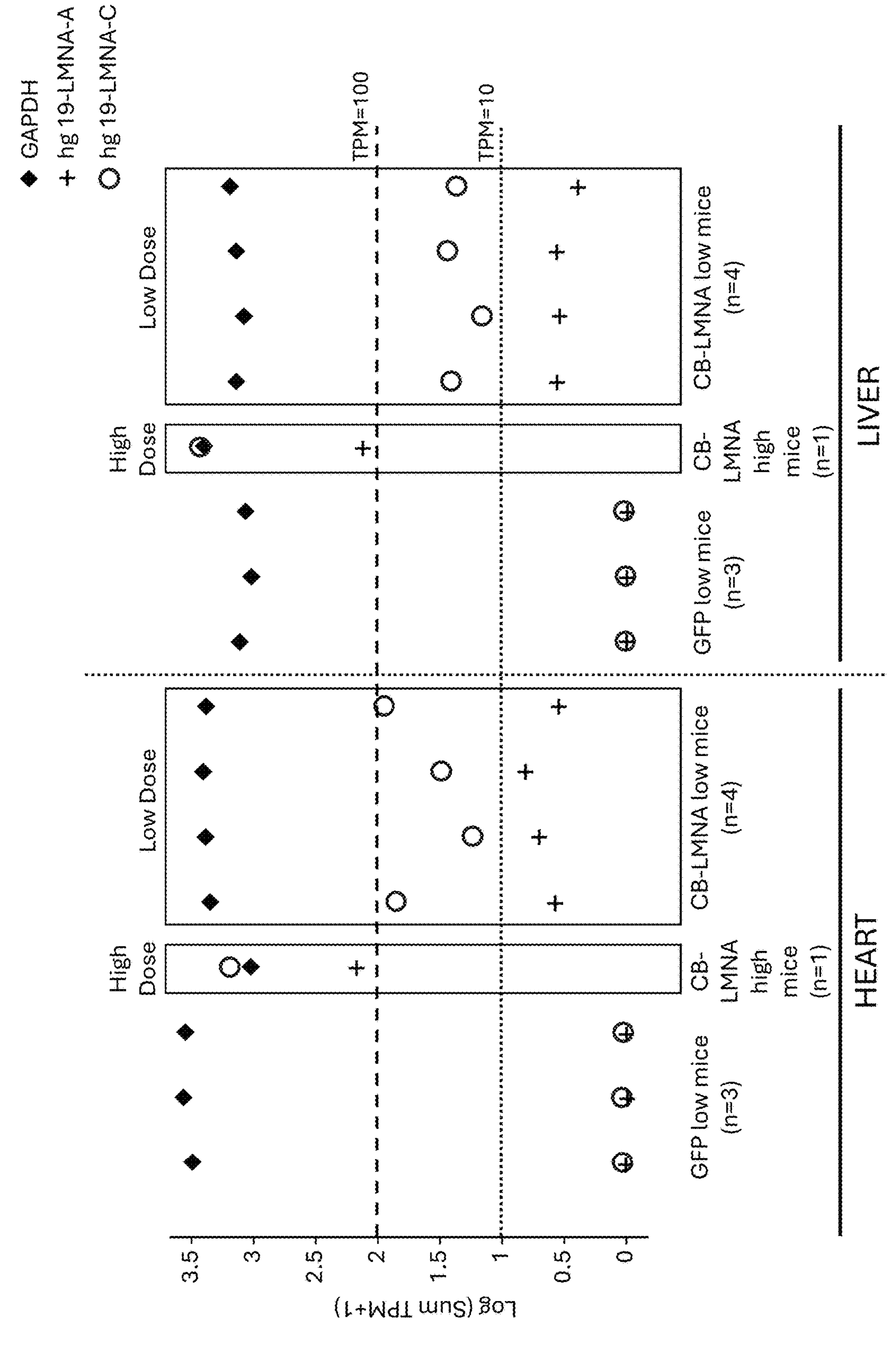
FIG. 10A and FIG. 10B show in vivo expression of Lamin A and Lamin C isoforms in mice treated with AAV9 carrying minigene construct 1 when measured by RNAseq.
Figure 10B:
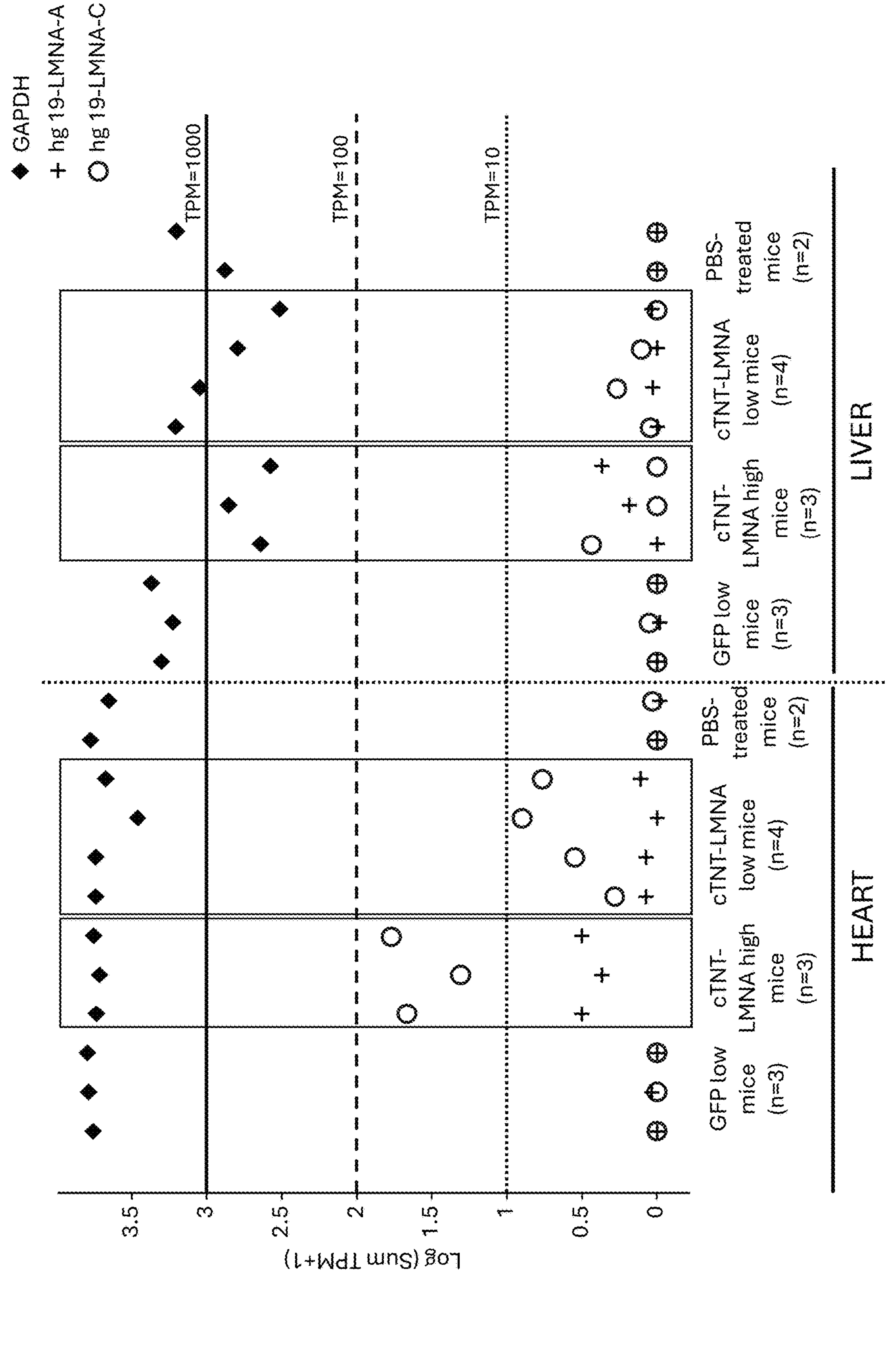
Figure 11A:
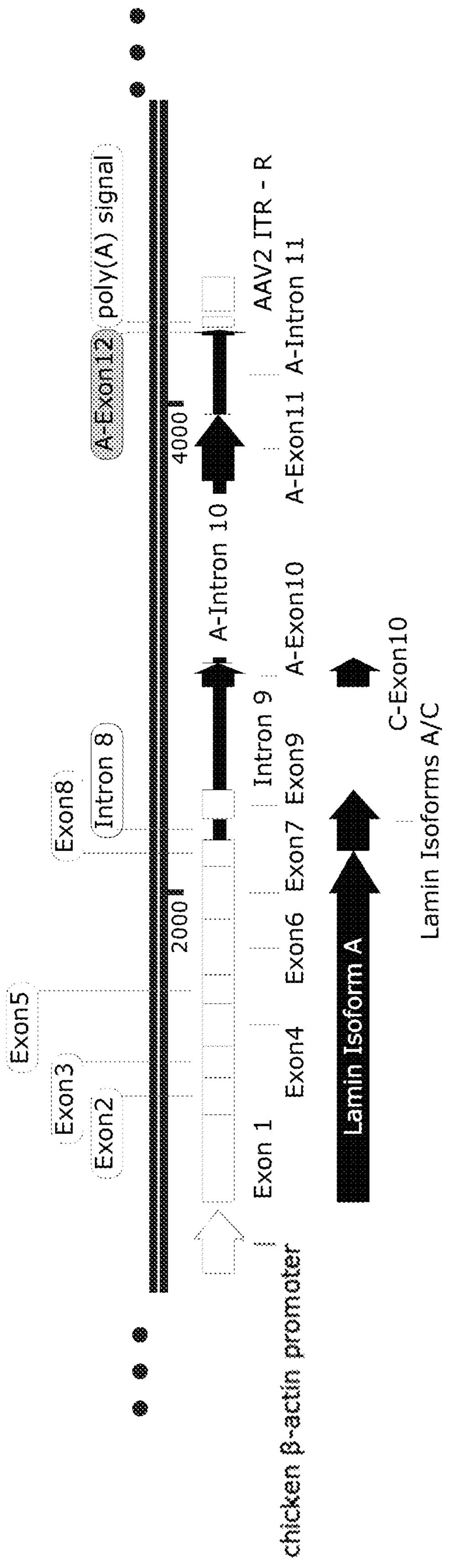
FIG. 11A-11C are simplified schematics of several different constructs each incorporating the chicken beta actin promoter.
Figure 11B:
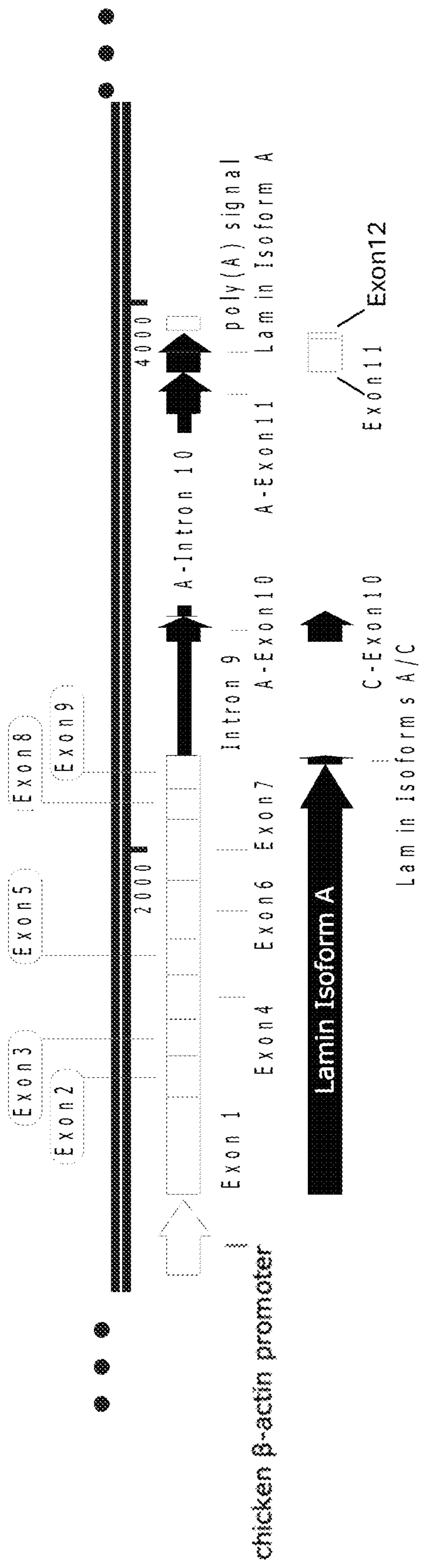
Figure 11C:
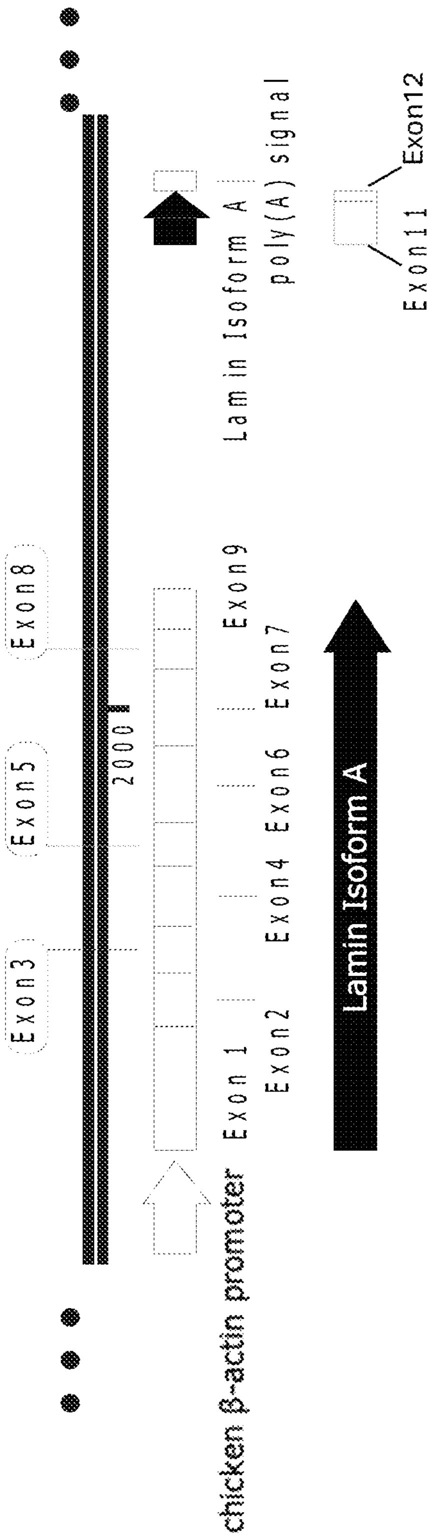

Mice dosed with AAV9 carrying minigene construct 1 (ubiquitous promoter) showed expression of Lamin A and Lamin C in both heart and liver (FIG. 10A). As expected, mice dosed with LMNA under the control of a heart-specific promoter (cTNT) showed expression of Lamin A and Lamin C in the heart, but not the liver (FIG. 10B). High doses of LMNA under the control of a ubiquitous promoter showed some liver toxicity in mice, and was separately confirmed by measurement of serum biomarkers (AST, ALT, ALP, bilirubin, creatine, etc.). Low dose animals were healthy.

Example 6: Expression of Lamin A and/or Lamin C in HEK293T Cells with CMV Promoter HEK293T cells were incubated at 37 degrees Centigrade overnight. The next day, cells were transiently transfected with DNA encoding LMNA under the control of the CMV promoter, or a GFP control. Cells were transfected according to standard methods. Cells were cultured and later trypsinized, centrifuged, and processed for protein analysis.

Samples were prepared for Western blot analysis by lysing cells and boiling at 95 degrees Centigrade. Protein lysates were then gel separated and transferred to a nitrocellulose membrane. Membranes were blocked and washed using a standard western blot protocol and blotted with primary antibody overnight at 4 degrees Centigrade. Mouse anti-Lamin A/C and mouse anti-GAPDH were used as the primary antibodies. Anti-mouse IgG HRP was used as a secondary antibody for chemiluminescence detection. Lamin C and A were detected at 65 kDa and 72 kDa, respectively, while GAPDH was detected at 37 kDa.

Figure 12:
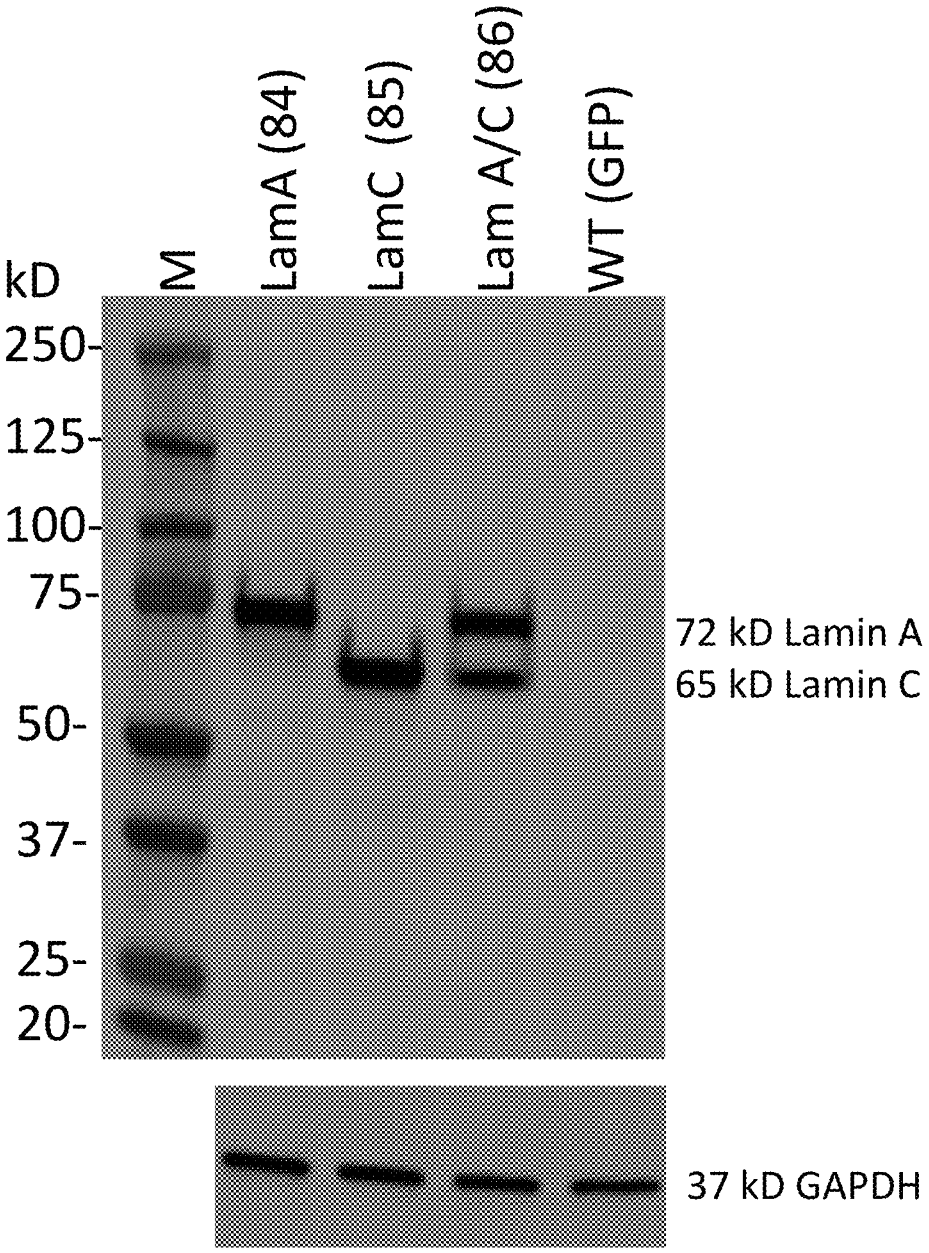
FIG. 12 is a western blot showing expression of Lamin A and Lamin C isoforms in LMNA minigene constructs encoding Lamin A and/or Lamin C in HEK293 cells.
Figure 13:
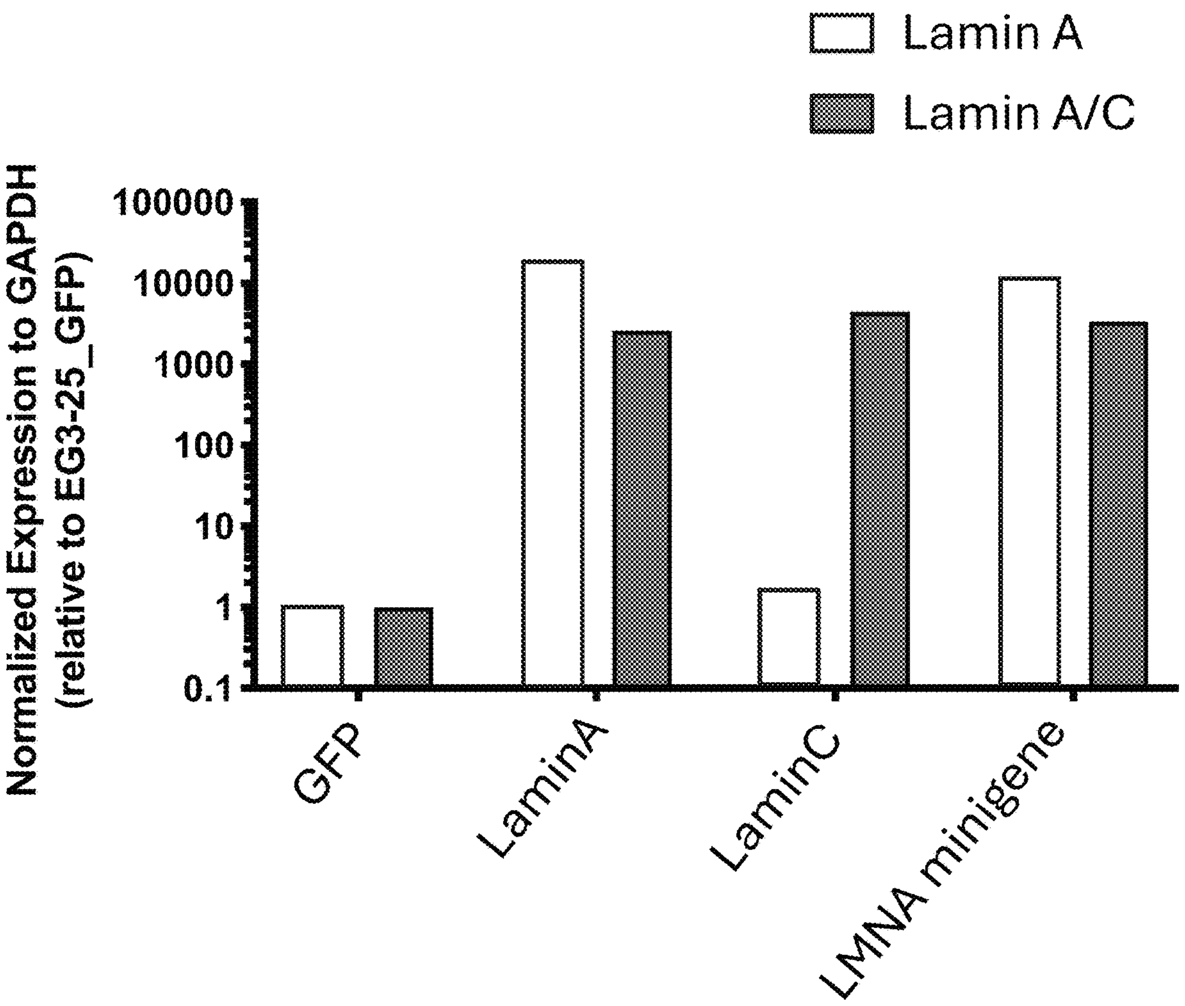
FIG. 13 is a graph of mRNA expression levels demonstrating that an LMNA minigene construct encoding Lamin A and/or Lamin C under the CMV promoter is able to express Lamin A and/or Lamin C in HEK293T cells. In particular an LMNA minigene encoding Lamin A and Lamin C expressed both Lamin A and Lamin C in HEK293T cells.

HEK293T cells transfected with a construct encoding only Lamin A or only Lamin C showed protein for each respective protein (FIG. 12). HEK293T cells transfected with an LMNA minigene construct having a Lamin A/C sequence (see the Lamin A/C sequence of minigene construct 1), indicating that the single construct was capable of generating both isoforms (FIG. 12).

Example 7: Lamin A and Lamin C mRNA Expression

HEK293T cells were grown and transiently transfected as described in Example 6. Two days post transfection, cells were trypsinized, centrifuged, and processed for RNA-based analysis. RNA was extracted from cell pellets using the standard extraction, and used to synthesize cDNA with reverse transcriptase. Quantitative PCR was performed using Lamin A/C, Lamin A specific primer sets, to evaluate expression levels of the respective genes.

Cells transfected with a construct encoding only Lamin A or only Lamin C showed mRNA transcription for each respective gene. HEK293T cells transfected with an LMNA minigene construct having a Lamin A/C sequence (see the Lamin A/C sequence of minigene construct 1), however, showed transcription of both Lamin A and Lamin C mRNA, indicating that the single construct was capable of transcribing both isoforms.

K. Sequences

TABLE 1

List of exemplary Lamin A and/or Lamin C nucleic acid sequences.

| SEQ ID NO: | Nucleic Acid Sequence | Name |
|---|---|---|
| 1 | ATGGAGACCCCGTCCCAGCGGCGCGCCACCCGCAGCGGG<br>GCGCAGGCCAGCTCCACTCCGCTGTCGCCCACCCGCATCA<br>CCCGGCTGCAGGAGAAGGAGGACCTGCAGGAGCTCAATG<br>ATCGCTTGGCGGTCTACATCGACCGTGTGCGCTCGCTGGA<br>AACGGAGAACGCAGGGCTGCGCCTTCGCATCACCGAGTCT<br>GAAGAGGTGGTCAGCCGCGAGGTGTCCGGCATCAAGGCC<br>GCCTACGAGGCCGAGCTCGGGGATGCCCGCAAGACCCTTG<br>ACTCAGTAGCCAAGGAGCGCGCCCGCCTGCAGCTGGAGCT<br>GAGCAAAGTGCGTGAGGAGTTTAAGGAGCTGAAAGCGCG<br>CAATACCAAGAAGGAGGGTGACCTGATAGCTGCTCAGGC<br>TCGGCTGAAGGACCTGGAGGCTCTGCTGAACTCCAAGGAG<br>GCCGCACTGAGCACTGCTCTCAGTGAGAAGCGCACGCTGG<br>AGGGCGAGCTGCATGATCTGCGGGGCCAGGTGGCCAAGC<br>TTGAGGCAGCCCTAGGTGAGGCCAAGAAGCAACTTCAGG<br>ATGAGATGCTGCGGCGGGTGGATGCTGAGAACAGGCTGC<br>AGACCATGAAGGAGGAACTGGACTTCCAGAAGAACATCT<br>ACAGTGAGGAGCTGCGTGAGACCAAGCGCCGTCATGAGA<br>CCCGACTGGTGGAGATTGACAATGGGAAGCAGCGTGAGT<br>TTGAGAGCCGGCTGGCGGATGCGCTGCAGGAACTGCGGG<br>CCCAGCATGAGGACCAGGTGGAGCAGTATAAGAAGGAGC<br>TGGAGAAGACTTATTCTGCCAAGCTGGACAATGCCAGGCA<br>GTCTGCTGAGAGGAACAGCAACCTGGTGGGGGCTGCCCA<br>CGAGGAGCTGCAGCAGTCGCGCATCCGCATCGACAGCCTC<br>TCTGCCCAGCTCAGCCAGCTCCAGAAGCAGCTGGCAGCCA<br>AGGAGGCGAAGCTTCGAGACCTGGAGGACTCACTGGCCC<br>GTGAGCGGGACACCAGCCGGCGGCTGCTGGCGGAAAAGG<br>AGCGGGAGATGGCCGAGATGCGGGCAAGGATGCAGCAGC<br>AGCTGGACGAGTACCAGGAGCTTCTGGACATCAAGCTGGC<br>CCTGGACATGGAGATCCACGCCTACCGCAAGCTCTTGGAG<br>GGCGAGGAGGAGAGGCTACGCCTGTCCCCCAGCCCTACCT<br>CGCAGCGCAGCCGTGGCCGTGCTTCCTCTCACTCATCCCA<br>GACACAGGGTGGGGGCAGCGTCACCAAAAAGCGCAAACT<br>GGAGTCCACTGAGAGCCGCAGCAGCTTCTCACAGCACGCA<br>CGCACTAGCGGGCGCGTGGCCGTGGAGGAGGTGGATGAG<br>GAGGGCAAGTTTGTCCGGCTGCGCAACAAGTCCAATGAG<br>GACCAGTCCATGGGCAATTGGCAGATCAAGCGCCAGAAT<br>GGAGATGATCCCTTGCTGACTTACCGGTTCCCACCAAAGT<br>TCACCCTGAAGGCTGGGCAGGTGGTGACGATCTGGGCTGC<br>AGGAGCTGGGGCCACCCACAGCCCCCCTACCGACCTGGTG<br>TGGAAGGCACAGAACACCTGGGGCTGCGGGAACAGCCTG | Lamin A sequence |

TABLE 1-continued

List of exemplary Lamin A and/or Lamin C nucleic acid sequences.

| SEQ ID NO: | Nucleic Acid Sequence | Name |
|---|---|---|
| | CGTACGGCTCTCATCAACTCCACTGGGGAAGAAGTGGCCA<br>TGCGCAAGCTGGTGCGCTCAGTGACTGTGGTTGAGGACGA<br>CGAGGATGAGGATGGAGATGACCTGCTCCATCACCACCAC<br>GGCTCCCACTGCAGCAGCTCGGGGACCCCGCTGAGTACA<br>ACCTGCGCTCGCGCACCGTGCTGTGCGGGACCTGCGGGCA<br>GCCTGCCGACAAGGCATCTGCCAGCGGCTCAGGAGCCCA<br>GGTGGGCGGACCCATCTCCTCTGGCTCTTCTGCCTCCAGTG<br>TCACGGTCACTCGCAGCTACCGCAGTGTGGGGGGCAGTGG<br>GGGTGGCAGCTTCGGGGACAATCTGGTCACCCGCTCCTAC<br>CTCCTGGGCAACTCCAGCCCCCGAACCCAGAGCCCCCAGA<br>ACTGCAGCATCATGTAA | |
| 2 | ATGGAGACCCCGTCCCAGCGGCGCGCCACCCGCAGCGGG<br>GCGCAGGCCAGCTCCACTCCGCTGTCGCCCACCCGCATCA<br>CCCGGCTGCAGGAGAAGGAGGACCTGCAGGAGCTCAATG<br>ATCGCTTGGCGGTCTACATCGACCGTGTGCGCTCGCTGGA<br>AACGGAGAACGCAGGGCTGCGCCTTCGCATCACCGAGTCT<br>GAAGAGGTGGTCAGCCGCGAGGTGTCCGGCATCAAGGCC<br>GCCTACGAGGCCGAGCTCGGGGATGCCCGCAAGACCCTTG<br>ACTCAGTAGCCAAGGAGCGCGCCCGCCTGCAGCTGGAGCT<br>GAGCAAAGTGCGTGAGGAGTTTAAGGAGCTGAAAGCGCG<br>CAATACCAAGAAGGAGGGTGACCTGATAGCTGCTCAGGC<br>TCGGCTGAAGGACCTGGAGGCTCTGCTGAACTCCAAGGAG<br>GCCGCACTGAGCACTGCTCTCAGTGAGAAGCGCACGCTGG<br>AGGGCGAGCTGCATGATCTGCGGGGCCAGGTGGCCAAGC<br>TTGAGGCAGCCCTAGGTGAGGCCAAGAAGCAACTTCAGG<br>ATGAGATGCTGCGGCGGGTGGATGCTGAGAACAGGCTGC<br>AGACCATGAAGGAGGAACTGGACTTCCAGAAGAACATCT<br>ACAGTGAGGAGCTGCGTGAGACCAAGCGCCGTCATGAGA<br>CCCGACTGGTGGAGATTGACAATGGGAAGCAGCGTGAGT<br>TTGAGAGCCGGCTGGCGGATGCGCTGCAGGAACTGCGGG<br>CCCAGCATGAGGACCAGGTGGAGCAGTATAAGAAGGAGC<br>TGGAGAAGACTTATTCTGCCAAGCTGGACAATGCCAGGCA<br>GTCTGCTGAGAGGAACAGCAACCTGGTGGGGGCTGCCCA<br>CGAGGAGCTGCAGCAGTCGCGCATCCGCATCGACAGCCTC<br>TCTGCCCAGCTCAGCCAGCTCCAGAAGCAGCTGGCAGCCA<br>AGGAGGCGAAGCTTCGAGACCTGGAGGACTCACTGGCCC<br>GTGAGCGGGACACCAGCCGGCGGCTGCTGGCGGAAAAGG<br>AGCGGGAGATGGCCGAGATGCGGGCAAGGATGCAGCAGC<br>AGCTGGACGAGTACCAGGAGCTTCTGGACATCAAGCTGGC<br>CCTGGACATGGAGATCCACGCCTACCGCAAGCTCTTGGAG<br>GGCGAGGAGGAGAGGCTACGCCTGTCCCCCAGCCCTACCT<br>CGCAGCGCAGCCGTGGCCGTGCTTCCTCTCACTCATCCCA<br>GACACAGGGTGGGGGCAGCGTCACCAAAAAGCGCAAACT<br>GGAGTCCACTGAGAGCCGCAGCAGCTTCTCACAGCACGCA<br>CGCACTAGCGGGCGCGTGGCCGTGGAGGAGGTGGATGAG<br>GAGGGCAAGTTTGTCCGGCTGCGCAACAAGTCCAATGAG<br>GACCAGTCCATGGGCAATTGGCAGATCAAGCGCCAGAAT<br>GGAGATGATCCCTTGCTGACTTACCGGTTCCCACCAAAGT<br>TCACCCTGAAGGCTGGGCAGGTGGTGACGATCTGGGCTGC<br>AGGAGCTGGGGCCACCCACAGCCCCCCTACCGACCTGGTG<br>TGGAAGGCACAGAACACCTGGGGCTGCGGGAACAGCCTG<br>CGTACGGCTCTCATCAACTCCACTGGGGAAGAAGTGGCCA<br>TGCGCAAGCTGGTGCGCTCAGTGACTGTGGTTGAGGACGA<br>CGAGGATGAGGATGGAGATGACCTGCTCCATCACCACCAC<br>GTGAGTGGTAGCCGCCGCTGA | Lamin C sequence |
| 3 | ATGGAGACCCCGTCCCAGCGGCGCGCCACCCGCAGCGGG<br>GCGCAGGCCAGCTCCACTCCGCTGTCGCCCACCCGCATCA<br>CCCGGCTGCAGGAGAAGGAGGACCTGCAGGAGCTCAATG<br>ATCGCTTGGCGGTCTACATCGACCGTGTGCGCTCGCTGGA<br>AACGGAGAACGCAGGGCTGCGCCTTCGCATCACCGAGTCT<br>GAAGAGGTGGTCAGCCGCGAGGTGTCCGGCATCAAGGCC<br>GCCTACGAGGCCGAGCTCGGGGATGCCCGCAAGACCCTTG<br>ACTCAGTAGCCAAGGAGCGCGCCCGCCTGCAGCTGGAGCT<br>GAGCAAAGTGCGTGAGGAGTTTAAGGAGCTGAAAGCGCG<br>CAATACCAAGAAGGAGGGTGACCTGATAGCTGCTCAGGC<br>TCGGCTGAAGGACCTGGAGGCTCTGCTGAACTCCAAGGAG<br>GCCGCACTGAGCACTGCTCTCAGTGAGAAGCGCACGCTGG<br>AGGGCGAGCTGCATGATCTGCGGGGCCAGGTGGCCAAGC<br>TTGAGGCAGCCCTAGGTGAGGCCAAGAAGCAACTTCAGG<br>ATGAGATGCTGCGGCGGGTGGATGCTGAGAACAGGCTGC<br>AGACCATGAAGGAGGAACTGGACTTCCAGAAGAACATCT<br>ACAGTGAGGAGCTGCGTGAGACCAAGCGCCGTCATGAGA<br>CCCGACTGGTGGAGATTGACAATGGGAAGCAGCGTGAGT | Lamin A/C sequence from minigene 1 |

TABLE 1-continued

List of exemplary Lamin A and/or Lamin C nucleic acid sequences.

| SEQ ID NO: | Nucleic Acid Sequence | Name |
|---|---|---|
| | TTGAGAGCCGGCTGGCGGATGCGCTGCAGGAACTGCGGG | |
| | CCCAGCATGAGGACCAGGTGGAGCAGTATAAGAAGGAGC | |
| | TGGAGAAGACTTATTCTGCCAAGCTGGACAATGCCAGGCA | |
| | GTCTGCTGAGAGGAACAGCAACCTGGTGGGGGCTGCCCA | |
| | CGAGGAGCTGCAGCAGTCGCGCATCCGCATCGACAGCCTC | |
| | TCTGCCCAGCTCAGCCAGCTCCAGAAGCAGCTGGCAGCCA | |
| | AGGAGGCGAAGCTTCGAGACCTGGAGGACTCACTGGCCC | |
| | GTGAGCGGGACACCAGCCGGCGGCTGCTGGCGGAAAAGG | |
| | AGCGGGAGATGGCCGAGATGCGGGCAAGGATGCAGCAGC | |
| | AGCTGGACGAGTACCAGGAGCTTCTGGACATCAAGCTGGC | |
| | CCTGGACATGGAGATCCACGCCTACCGCAAGCTCTTGGAG | |
| | GGCGAGGAGGAGAGGCTACGCCTGTCCCCCAGCCCTACCT | |
| | CGCAGCGCAGCCGTGGCCGTGCTTCCTCTCACTCATCCCA | |
| | GACACAGGGTGGGGGCAGCGTCACCAAAAAGCGCAAACT | |
| | GGAGTCCACTGAGAGCCGCAGCAGCTTCTCACAGCACGCA | |
| | CGCACTAGCGGGCGCGTGGCCGTGGAGGAGGTGGATGAG | |
| | GAGGGCAAGTTTGTCCGGCTGCGCAACAAGTCCAATGAG | |
| | GACCAGTCCATGGGCAATTGGCAGATCAAGCGCCAGAAT | |
| | GGAGATGATCCCTTGCTGACTTACCGGTTCCCACCAAAGT | |
| | TCACCCTGAAGGCTGGGCAGGTGGTGACGGTGAGTGGCA | |
| | GGGCGCTTGGGACTCTGGGGAGGCCTTGGGTGGCGATGG | |
| | GAGCGCTGGGGTAAGTGTCCTTTTCTCCTCTCCAGATCTGG | |
| | GCTGCAGGAGCTGGGGCCACCCACAGCCCCCCTACCGACC | |
| | TGGTGTGGAAGGCACAGAACACCTGGGGCTGCGGGAACA | |
| | GCCTGCGTACGGCTCTCATCAACTCCACTGGGGAAGTAAG | |
| | TAGGCCTGGGCCTGGCTGCTTGCTGGACGAGGCTCCCCCT | |
| | GATGGCCAACATCGGAGCCAGCTGCCCCCAACCCAAGTTT | |
| | GCCAATTCAGGGCCCCTTTCTAGAGCTCTCTGTTGCAGGCT | |
| | CCAGACTTCTCCACCCAGTAGGCAAACCAAAAGATGCTTC | |
| | CTCAACAGCACAAGGGGTGGAAGTTAGACAGTGAGGATT | |
| | GTTAAAGGCAGAGCCATACTCCTACCCGGAGAGCTTGACA | |
| | GTGTCCCTCTGGGGTGGAAATGAGTTCCTTAGCTCCATCA | |
| | CCACAGAGGACAGAGTAAGCAGCAGGCCGGACAAAGGGC | |
| | AGGCCACAAGAAAAGTTGCAGGTGGTCACTGGGGTAGAC | |
| | ATGCTGTACAACCCTTCCCTGGCCCTGACCCTTGGACCTG | |
| | GTTCCATGTCCCCACCAGGAAGTGGCCATGCGCAAGCTGG | |
| | TGCGCTCAGTGACTGTGGTTGAGGACGACGAGGATGAGG | |
| | ATGGAGATGACCTGCTCCATCACCACCACGTGAGTGGTAG | |
| | CCGCCGCTGAGGCCGAGCCTGCACTGGGGCCACCCAGCCA | |
| | GGCCTGGGGGCAGCCTCTCCCCAGCCTCCCCGTGCCAAAA | |
| | ATCTTTTCATTAAAGAATGTTTTGGAACTTTACTCGCTGGC | |
| | CTGGCCTTTCTTCTCTCTCCTCCCTATACCTTGAACAGGGA | |
| | ACCCAGGTGTCTGGGTGCCCTACTCTGGTAAGGAAGGGAG | |
| | TGGGAACTTTCTGATGCCATGGAATATTCCTGTGGGAGCA | |
| | GTGGACAAGGGTCTGGATTTGTCTTCTGGGAAAGGGAGGG | |
| | GAGGACAGACGTGGGGCATGCCCGCCCTGCCTCTCTCCCC | |
| | CATTCTTGTTGCATGCATATCCTCTCATTTCCCTCATTTTTC | |
| | CTGCAAGAATGTTCTCTCTCATTCCTGACCGCCCCTCCACT | |
| | CCAATTAATAGTGCATGCCTGCTGCCCTACAAGCTTGCTC | |
| | CCGTTCTCTCTTCTTTTCCTCTTAAGCTCAGAGTAGCTAGA | |
| | ACAGAGTCAGAGTCACTGCTCTGGTTCTCTGTCCCCAAGT | |
| | CTTCCTGAGCCTTCTCCCCTTTTATGTCTTCCCTCTCCTCCT | |
| | CCGGGCCCCTAGCCTCCCAAACCCCCATTGCCCGCTGGCT | |
| | CCTTGGGCACAGAACCACACCTTCCTGCCTGGCGGCTGGG | |
| | AGCCTGCAGGAGCCTGGAGCCTGGTTGGGCCTGAGTGGTC | |
| | AGTCCCAGACTCGCCGTCCCGCCTGAGCCTTGTCTCCCTTC | |
| | CCAGGGCTCCCACTGCAGCAGCTCGGGGGACCCCGCTGAG | |
| | TACAACCTGCGCTCGCGCACCGTGCTGTGCGGGACCTGCG | |
| | GGCAGCCTGCCGACAAGGCATCTGCCAGCGGCTCAGGAG | |
| | CCCAGGTGGGCGGACCCATCTCCTCTGGCTCTTCTGCCTCC | |
| | AGTGTCACGGTCACTCGCAGCTACCGCAGTGTGGGGGGCA | |
| | GTGGGGGTGGCAGCTTCGGGGACAATCTGGTCACCCGCTC | |
| | CTACCTCCTGGGCAACTCCAGCCCCCGAACCCAGGTGAGT | |
| | TGTCTCTGCTTTGTCTCCAAATCCTGCAGGCGGGTCCCTGG | |
| | TCATCGAGGGGTAGGACGAGGTGGCCTTGCAGGGGGGAG | |
| | AGCCTGCCTTCTCTTCCGCAGCCCGGGGGAGTGGGAGCCT | |
| | CCTCCCCACAGCCTGAGTCCTAGACAGCCCACCTCTGCAT | |
| | CCTGCCCCTCTTGTCTGAGCCCCAGACTGGAGGGCAGGGG | |
| | CAGGGCTGGAGTGTGAGGGATGGGGGAGATGCTACCTCC | |
| | CTTCTAGGGGCCAGGGGAGGGAGGGTCTGGGTCCAGGCC | |
| | CTGCTGCTCACACCTCTCTCCTCTGTTTTCTCTCTTAGAGC | |
| | CCCCAGAACTGCAGCATCATGTAA | |

TABLE 1-continued

| List of exemplary Lamin A and/or Lamin C nucleic acid sequences. | | |
|---|---|---|
| SEQ ID NO: | Nucleic Acid Sequence | Name |
| 4 | ATGGAGACCCCGTCCCAGCGGCGCGCCACCCGCAGCGGG<br>GCGCAGGCCAGCTCCACTCCGCTGTCGCCCACCCGCATCA<br>CCCGGCTGCAGGAGAAGGAGGACCTGCAGGAGCTCAATG<br>ATCGCTTGGCGGTCTACATCGACCGTGTGCGCTCGCTGGA<br>AACGGAGAACGCAGGGCTGCGCCTTCGCATCACCGAGTCT<br>GAAGAGGTGGTCAGCCGCGAGGTGTCCGGCATCAAGGCC<br>GCCTACGAGGCCGAGCTCGGGGATGCCCGCAAGACCCTTG<br>ACTCAGTAGCCAAGGAGCGCGCCCGCCTGCAGCTGGAGCT<br>GAGCAAAGTGCGTGAGGAGTTTAAGGAGCTGAAAGCGCG<br>CAATACCAAGAAGGAGGGTGACCTGATAGCTGCTCAGGC<br>TCGGCTGAAGGACCTGGAGGCTCTGCTGAACTCCAAGGAG<br>GCCGCACTGAGCACTGCTCTCAGTGAGAAGCGCACGCTGG<br>AGGGCGAGCTGCATGATCTGCGGGGCCAGGTGGCCAAGC<br>TTGAGGCAGCCCTAGGTGAGGCCAAGAAGCAACTTCAGG<br>ATGAGATGCTGCGGCGGGTGGATGCTGAGAACAGGCTGC<br>AGACCATGAAGGAGGAACTGGACTTCCAGAAGAACATCT<br>ACAGTGAGGAGCTGCGTGAGACCAAGCGCCGTCATGAGA<br>CCCGACTGGTGGAGATTGACAATGGGAAGCAGCGTGAGT<br>TTGAGAGCCGGCTGGCGGATGCGCTGCAGGAACTGCGGG<br>CCCAGCATGAGGACCAGGTGGAGCAGTATAAGAAGGAGC<br>TGGAGAAGACTTATTCTGCCAAGCTGGACAATGCCAGGCA<br>GTCTGCTGAGAGGAACAGCAACCTGGTGGGGGCTGCCCA<br>CGAGGAGCTGCAGCAGTCGCGCATCCGCATCGACAGCCTC<br>TCTGCCCAGCTCAGCCAGCTCCAGAAGCAGCTGGCAGCCA<br>AGGAGGCGAAGCTTCGAGACCTGGAGGACTCACTGGCCC<br>GTGAGCGGGACACCAGCCGGCGGCTGCTGGCGGAAAAGG<br>AGCGGGAGATGGCCGAGATGCGGGCAAGGATGCAGCAGC<br>AGCTGGACGAGTACCAGGAGCTTCTGGACATCAAGCTGGC<br>CCTGGACATGGAGATCCACGCCTACCGCAAGCTCTTGGAG<br>GGCGAGGAGGAGAGGCTACGCCTGTCCCCCAGCCCTACCT<br>CGCAGCGCAGCCGTGGCCGTGCTTCCTCTCACTCATCCCA<br>GACACAGGGTGGGGGCAGCGTCACCAAAAAGCGCAAACT<br>GGAGTCCACTGAGAGCCGCAGCAGCTTCTCACAGCACGCA<br>CGCACTAGCGGGCGCGTGGCCGTGGAGGAGGTGGATGAG<br>GAGGGCAAGTTTGTCCGGCTGCGCAACAAGTCCAATGAG<br>GACCAGTCCATGGGCAATTGGCAGATCAAGCGCCAGAAT<br>GGAGATGATCCCTTGCTGACTTACCGGTTCCCACCAAAGT<br>TCACCCTGAAGGCTGGGCAGGTGGTGACGATCTGGGCTGC<br>AGGAGCTGGGGCCACCCACAGCCCCCCTACCGACCTGGTG<br>TGGAAGGCACAGAACACCTGGGGCTGCGGGAACAGCCTG<br>CGTACGGCTCTCATCAACTCCACTGGGGAAGTAAGTAGGC<br>CTGGGCCTGGCTGCTTGCTGGACGAGGCTCCCCCTGATGG<br>CCAACATCGGAGCCAGCTGCCCCCAACCCAAGTTTGCCAA<br>TTCAGGGCCCCTTTCTAGAGCTCTCTGTTGCAGGCTCCAGA<br>CTTCTCCACCCAGTAGGCAAACCAAAAGATGCTTCCTCAA<br>CAGCACAAGGGGTGGAAGTTAGACAGTGAGGATTGTTAA<br>AGGCAGAGCCATACTCCTACCCGGAGAGCTTGACAGTGTC<br>CCTCTGGGGTGGAAATGAGTTCCTTAGCTCCATCACCACA<br>GAGGACAGAGTAAGCAGCAGGCCGGACAAAGGGCAGGCC<br>ACAAGAAAAGTTGCAGGTGGTCACTGGGGTAGACATGCT<br>GTACAACCCTTCCCTGGCCCTGACCCTTGGACCTGGTTCCA<br>TGTCCCCACCAGGAAGTGGCCATGCGCAAGCTGGTGCGCT<br>CAGTGACTGTGGTTGAGGACGACGAGGATGAGGATGGAG<br>ATGACCTGCTCCATCACCACCACGTGAGTGGTAGCCGCCG<br>CTGAGGCCGAGCCTGCACTGGGGCCACCCAGCCAGGCCTG<br>GGGGCAGCCTCTCCCCAGCCTCCCCGTGCCAAAAATCTTT<br>TCATTAAAGAATGTTTTGGAACTTTACTCGCTGGCCTGGCC<br>TTTCTTCTCTCTCCTCCCTATACCTTGAACAGGGAACCCAG<br>GTGTCTGGGTGCCCTACTCTGGTAAGGAAGGGAGTGGGAA<br>CTTTCTGATGCCATGGAATATTCCTGTGGGAGCAGTGGAC<br>AAGGGTCTGGATTTGTCTTCTGGGAAAGGGAGGGGAGGA<br>CAGACGTGGGGCATGCCCGCCCTGCCTCTCTCCCCCATTCT<br>TGTTGCATGCATATCCTCTCATTTCCCTCATTTTTCCTGCA<br>AGAATGTTCTCTCTCATTCCTGACCGCCCCTCCACTCCAAT<br>TAATAGTGCATGCCTGCTGCCCTACAAGCTTGCTCCCGTTC<br>TCTCTTCTTTTCCTCTTAAGCTCAGAGTAGCTAGAACAGAG<br>TCAGAGTCACTGCTCTGGTTCTCTGTCCCCAAGTCTTCCTG<br>AGCCTTCTCCCCTTTTATGTCTTCCCTCTCCTCCTCCGGGCC<br>CCTAGCCTCCCAAACCCCCATTGCCCGCTGGCTCCTTGGG<br>CACAGAACCACACCTTCCTGCCTGGCGGCTGGGAGCCTGC<br>AGGAGCCTGGAGCCTGGTTGGGCCTGAGTGGTCAGTCCCA<br>GACTCGCCGTCCCGCCTGAGCCTTGTCTCCCTTCCCAGGGC<br>TCCCACTGCAGCAGCTCGGGGGACCCCGCTGAGTACAACC<br>TGCGCTCGCGCACCGTGCTGTGCGGGACCTGCGGGCAGCC | Lamin A/C sequence from minigene 2 |

TABLE 1-continued

List of exemplary Lamin A and/or Lamin C nucleic acid sequences.

| SEQ ID NO: | Nucleic Acid Sequence | Name |
|---|---|---|
| | TGCCGACAAGGCATCTGCCAGCGGCTCAGGAGCCCAGGT<br>GGGCGGACCCATCTCCTCTGGCTCTTCTGCCTCCAGTGTCA<br>CGGTCACTCGCAGCTACCGCAGTGTGGGGGGCAGTGGGG<br>GTGGCAGCTTCGGGGACAATCTGGTCACCCGCTCCTACCT<br>CCTGGGCAACTCCAGCCCCCGAACCCAGAGCCCCCAGAAC<br>TGCAGCATCATGTAA | |
| 5 | ATGGAGACCCCGTCCCAGCGGCGCGCCACCCGCAGCGGG<br>GCGCAGGCCAGCTCCACTCCGCTGTCGCCCACCCGCATCA<br>CCCGGCTGCAGGAGAAGGAGGACCTGCAGGAGCTCAATG<br>ATCGCTTGGCGGTCTACATCGACCGTGTGCGCTCGCTGGA<br>AACGGAGAACGCAGGGCTGCGCCTTCGCATCACCGAGTCT<br>GAAGAGGTGGTCAGCCGCGAGGTGTCCGGCATCAAGGCC<br>GCCTACGAGGCCGAGCTCGGGGATGCCCGCAAGACCCTTG<br>ACTCAGTAGCCAAGGAGCGCGCCCGCCTGCAGCTGGAGCT<br>GAGCAAAGTGCGTGAGGAGTTTAAGGAGCTGAAAGCGCG<br>CAATACCAAGAAGGAGGGTGACCTGATAGCTGCTCAGGC<br>TCGGCTGAAGGACCTGGAGGCTCTGCTGAACTCCAAGGAG<br>GCCGCACTGAGCACTGCTCTCAGTGAGAAGCGCACGCTGG<br>AGGGCGAGCTGCATGATCTGCGGGGCCAGGTGGCCAAGC<br>TTGAGGCAGCCCTAGGTGAGGCCAAGAAGCAACTTCAGG<br>ATGAGATGCTGCGGCGGGTGGATGCTGAGAACAGGCTGC<br>AGACCATGAAGGAGGAACTGGACTTCCAGAAGAACATCT<br>ACAGTGAGGAGCTGCGTGAGACCAAGCGCCGTCATGAGA<br>CCCGACTGGTGGAGATTGACAATGGGAAGCAGCGTGAGT<br>TTGAGAGCCGGCTGGCGGATGCGCTGCAGGAACTGCGGG<br>CCCAGCATGAGGACCAGGTGGAGCAGTATAAGAAGGAGC<br>TGGAGAAGACTTATTCTGCCAAGCTGGACAATGCCAGGCA<br>GTCTGCTGAGAGGAACAGCAACCTGGTGGGGGCTGCCCA<br>CGAGGAGCTGCAGCAGTCGCGCATCCGCATCGACAGCCTC<br>TCTGCCCAGCTCAGCCAGCTCCAGAAGCAGCTGGCAGCCA<br>AGGAGGCGAAGCTTCGAGACCTGGAGGACTCACTGGCCC<br>GTGAGCGGGACACCAGCCGGCGGCTGCTGGCGGAAAAGG<br>AGCGGGAGATGGCCGAGATGCGGGCAAGGATGCAGCAGC<br>AGCTGGACGAGTACCAGGAGCTTCTGGACATCAAGCTGGC<br>CCTGGACATGGAGATCCACGCCTACCGCAAGCTCTTGGAG<br>GGCGAGGAGGAGAGGCTACGCCTGTCCCCCAGCCCTACCT<br>CGCAGCGCAGCCGTGGCCGTGCTTCCTCTCACTCATCCCA<br>GACACAGGGTGGGGGCAGCGTCACCAAAAAGCGCAAACT<br>GGAGTCCACTGAGAGCCGCAGCAGCTTCTCACAGCACGCA<br>CGCACTAGCGGGCGCGTGGCCGTGGAGGAGGTGGATGAG<br>GAGGGCAAGTTTGTCCGGCTGCGCAACAAGTCCAATGAG<br>GACCAGTCCATGGGCAATTGGCAGATCAAGCGCCAGAAT<br>GGAGATGATCCCTTGCTGACTTACCGGTTCCCACCAAAGT<br>TCACCCTGAAGGCTGGGCAGGTGGTGACGATCTGGGCTGC<br>AGGAGCTGGGGCCACCCACAGCCCCCCTACCGACCTGGTG<br>TGGAAGGCACAGAACACCTGGGGCTGCGGGAACAGCCTG<br>CGTACGGCTCTCATCAACTCCACTGGGGAAGAAGTGGCCA<br>TGCGCAAGCTGGTGCGCTCAGTGACTGTGGTTGAGGACGA<br>CGAGGATGAGGATGGAGATGACCTGCTCCATCACCACCAC<br>GTGAGTGGTAGCCGCCGCTGAGGCCGAGCCTGCACTGGG<br>GCCACCCAGCCAGGCCTGGGGGCAGCCTCTCCCCAGCCTC<br>CCCGTGCCAAAAATCTTTTCATTAAAGAATGTTTTGGAAC<br>TTTACTCGCTGGCCTGGCCTTTCTTCTCTCTCCTCCCTATAC<br>CTTGAACAGGGAACCCAGGTGTCTGGGTGCCCTACTCTGG<br>TAAGGAAGGGAGTGGGAACTTTCTGATGCCATGGAATATT<br>CCTGTGGGAGCAGTGGACAAGGGTCTGGATTTGTCTTCTG<br>GGAAAGGGAGGGGAGGACAGACGTGGGGCATGCCCGCCC<br>TGCCTCTCTCCCCCATTCTTGTTGCATGCATATCCTCTCATT<br>TCCCTCATTTTTCCTGCAAGAATGTTCTCTCTCATTCCTGA<br>CCGCCCCTCCACTCCAATTAATAGTGCATGCCTGCTGCCCT<br>ACAAGCTTGCTCCCGTTCTCTCTTCTTTTCCTCTTAAGCTC<br>AGAGTAGCTAGAACAGAGTCAGAGTCACTGCTCTGGTTCT<br>CTGTCCCCAAGTCTTCCTGAGCCTTCTCCCCTTTTATGTCTT<br>CCCTCTCCTCCTCCGGGCCCCTAGCCTCCCAAACCCCCATT<br>GCCCGCTGGCTCCTTGGGCACAGAACCACACCTTCCTGCC<br>TGGCGGCTGGGAGCCTGCAGGAGCCTGGAGCCTGGTTGG<br>GCCTGAGTGGTCAGTCCCAGACTCGCCGTCCCGCCTGAGC<br>CTTGTCTCCCTTCCCAGGGCTCCCACTGCAGCAGCTCGGG<br>GGACCCCGCTGAGTACAACCTGCGCTCGCGCACCGTGCTG<br>TGCGGGACCTGCGGGCAGCCTGCCGACAAGGCATCTGCCA<br>GCGGCTCAGGAGCCCAGGTGGGCGGACCCATCTCCTCTGG<br>CTCTTCTGCCTCCAGTGTCACGGTCACTCGCAGCTACCGCA | Lamin A/C sequence from minigene 3 |

TABLE 1-continued

List of exemplary Lamin A and/or Lamin C nucleic acid sequences.

| SEQ ID NO: | Nucleic Acid Sequence | Name |
| --- | --- | --- |
| | GTGTGGGGGGCAGTGGGGGTGGCAGCTTCGGGGACAATC<br>TGGTCACCCGCTCCTACCTCCTGGGCAACTCCAGCCCCCG<br>AACCCAGAGCCCCCAGAACTGCAGCATCATG | |
| 6 | GTGATGCGGTTTTGGCAGTACATCAATGGGCGTGGATAGC<br>GGTTTGACTCACGGGGATTTCCAAGTCTCCACCCCATTGA<br>CGTCAATGGGAGTTTGTTTTGGCACCAAAATCAACGGGAC<br>TTTCCAAAATGTCGTAACAACTCCGCCCCATTGACGCAAA<br>TGGGCGGTAGGCGTGTACGGTGGGAGGTCTATATAAGCA<br>GAGCTGGTACCGTGTGTATGCTCAGGGGCTGGGAAAGGA<br>GGGGAGGGAGCTCCGGCTCAGGAATTCGCCACCATGGAG<br>ACCCCGTCCCAGCGGCGCGCCACCCGCAGCGGGGCGCAG<br>GCCAGCTCCACTCCGCTGTCGCCCACCCGCATCACCCGGC<br>TGCAGGAGAAGGAGGACCTGCAGGAGCTCAATGATCGCT<br>TGGCGGTCTACATCGACCGTGTGCGCTCGCTGGAAACGGA<br>GAACGCAGGGCTGCGCCTTCGCATCACCGAGTCTGAAGAG<br>GTGGTCAGCCGCGAGGTGTCCGGCATCAAGGCCGCCTACG<br>AGGCCGAGCTCGGGGATGCCCGCAAGACCCTTGACTCAGT<br>AGCCAAGGAGCGCGCCCGCCTGCAGCTGGAGCTGAGCAA<br>AGTGCGTGAGGAGTTTAAGGAGCTGAAAGCGCGCAATAC<br>CAAGAAGGAGGGTGACCTGATAGCTGCTCAGGCTCGGCT<br>GAAGGACCTGGAGGCTCTGCTGAACTCCAAGGAGGCCGC<br>ACTGAGCACTGCTCTCAGTGAGAAGCGCACGCTGGAGGG<br>CGAGCTGCATGATCTGCGGGGCCAGGTGGCCAAGCTTGAG<br>GCAGCCCTAGGTGAGGCCAAGAAGCAACTTCAGGATGAG<br>ATGCTGCGGCGGGTGGATGCTGAGAACAGGCTGCAGACC<br>ATGAAGGAGGAACTGGACTTCCAGAAGAACATCTACAGT<br>GAGGAGCTGCGTGAGACCAAGCGCCGTCATGAGACCCGA<br>CTGGTGGAGATTGACAATGGGAAGCAGCGTGAGTTTGAG<br>AGCCGGCTGGCGGATGCGCTGCAGGAACTGCGGGCCCAG<br>CATGAGGACCAGGTGGAGCAGTATAAGAAGGAGCTGGAG<br>AAGACTTATTCTGCCAAGCTGGACAATGCCAGGCAGTCTG<br>CTGAGAGGAACAGCAACCTGGTGGGGGCTGCCCACGAGG<br>AGCTGCAGCAGTCGCGCATCCGCATCGACAGCCTCTCTGC<br>CCAGCTCAGCCAGCTCCAGAAGCAGCTGGCAGCCAAGGA<br>GGCGAAGCTTCGAGACCTGGAGGACTCACTGGCCCGTGA<br>GCGGGACACCAGCCGGCGGCTGCTGGCGGAAAAGGAGCG<br>GGAGATGGCCGAGATGCGGGCAAGGATGCAGCAGCAGCT<br>GGACGAGTACCAGGAGCTTCTGGACATCAAGCTGGCCCTG<br>GACATGGAGATCCACGCCTACCGCAAGCTCTTGGAGGGCG<br>AGGAGGAGAGGCTACGCCTGTCCCCCAGCCCTACCTCGCA<br>GCGCAGCCGTGGCCGTGCTTCCTCTCACTCATCCCAGACA<br>CAGGGTGGGGGCAGCGTCACCAAAAAGCGCAAACTGGAG<br>TCCACTGAGAGCCGCAGCAGCTTCTCACAGCACGCACGCA<br>CTAGCGGGCGCGTGGCCGTGGAGGAGGTGGATGAGGAGG<br>GCAAGTTTGTCCGGCTGCGCAACAAGTCCAATGAGGACCA<br>GTCCATGGGCAATTGGCAGATCAAGCGCCAGAATGGAGA<br>TGATCCCTTGCTGACTTACCGGTTCCCACCAAAGTTCACCC<br>TGAAGGCTGGGCAGGTGGTGACGATCTGGGCTGCAGGAG<br>CTGGGGCCACCCACAGCCCCCCTACCGACCTGGTGTGGAA<br>GGCACAGAACACCTGGGGCTGCGGGAACAGCCTGCGTAC<br>GGCTCTCATCAACTCCACTGGGGAAGAAGTGGCCATGCGC<br>AAGCTGGTGCGCTCAGTGACTGTGGTTGAGGACGACGAG<br>GATGAGGATGGAGATGACCTGCTCCATCACCACCACGGCT<br>CCCACTGCAGCAGCTCGGGGGACCCCGCTGAGTACAACCT<br>GCGCTCGCGCACCGTGCTGTGCGGGACCTGCGGGCAGCCT<br>GCCGACAAGGCATCTGCCAGCGGCTCAGGAGCCCAGGTG<br>GGCGGACCCATCTCCTCTGGCTCTTCTGCCTCCAGTGTCAC<br>GGTCACTCGCAGCTACCGCAGTGTGGGGGGCAGTGGGGG<br>TGGCAGCTTCGGGGACAATCTGGTCACCCGCTCCTACCTC<br>CTGGGCAACTCCAGCCCCCGAACCCAGAGCCCCCAGAACT<br>GCAGCATCATGTAAACTAGTAATAAAAGATCTTTATTTTC<br>ATTAGATCTGTGTGTTGGTTTTTTGTGTG | Lamin A construct |
| 7 | GTGATGCGGTTTTGGCAGTACATCAATGGGCGTGGATAGC<br>GGTTTGACTCACGGGGATTTCCAAGTCTCCACCCCATTGA<br>CGTCAATGGGAGTTTGTTTTGGCACCAAAATCAACGGGAC<br>TTTCCAAAATGTCGTAACAACTCCGCCCCATTGACGCAAA<br>TGGGCGGTAGGCGTGTACGGTGGGAGGTCTATATAAGCA<br>GAGCTGGTACCGTGTGTATGCTCAGGGGCTGGGAAAGGA<br>GGGGAGGGAGCTCCGGCTCAGGAATTCGCCACCATGGAG<br>ACCCCGTCCCAGCGGCGCGCCACCCGCAGCGGGGCGCAG<br>GCCAGCTCCACTCCGCTGTCGCCCACCCGCATCACCCGGC<br>TGCAGGAGAAGGAGGACCTGCAGGAGCTCAATGATCGCT<br>TGGCGGTCTACATCGACCGTGTGCGCTCGCTGGAAACGGA | Lamin C construct |

TABLE 1-continued

List of exemplary Lamin A and/or Lamin C nucleic acid sequences.

| SEQ ID NO: | Nucleic Acid Sequence | Name |
|---|---|---|
| | GAACGCAGGGCTGCGCCTTCGCATCACCGAGTCTGAAGAG<br>GTGGTCAGCCGCGAGGTGTCCGGCATCAAGGCCGCCTACG<br>AGGCCGAGCTCGGGGATGCCCGCAAGACCCTTGACTCAGT<br>AGCCAAGGAGCGCGCCCGCCTGCAGCTGGAGCTGAGCAA<br>AGTGCGTGAGGAGTTTAAGGAGCTGAAAGCGCGCAATAC<br>CAAGAAGGAGGGTGACCTGATAGCTGCTCAGGCTCGGCT<br>GAAGGACCTGGAGGCTCTGCTGAACTCCAAGGAGGCCGC<br>ACTGAGCACTGCTCTCAGTGAGAAGCGCACGCTGGAGGG<br>CGAGCTGCATGATCTGCGGGGCCAGGTGGCCAAGCTTGAG<br>GCAGCCCTAGGTGAGGCCAAGAAGCAACTTCAGGATGAG<br>ATGCTGCGGCGGGTGGATGCTGAGAACAGGCTGCAGACC<br>ATGAAGGAGGAACTGGACTTCCAGAAGAACATCTACAGT<br>GAGGAGCTGCGTGAGACCAAGCGCCGTCATGAGACCCGA<br>CTGGTGGAGATTGACAATGGGAAGCAGCGTGAGTTTGAG<br>AGCCGGCTGGCGGATGCGCTGCAGGAACTGCGGGCCCAG<br>CATGAGGACCAGGTGGAGCAGTATAAGAAGGAGCTGGAG<br>AAGACTTATTCTGCCAAGCTGGACAATGCCAGGCAGTCTG<br>CTGAGAGGAACAGCAACCTGGTGGGGGCTGCCCACGAGG<br>AGCTGCAGCAGTCGCGCATCCGCATCGACAGCCTCTCTGC<br>CCAGCTCAGCCAGCTCCAGAAGCAGCTGGCAGCCAAGGA<br>GGCGAAGCTTCGAGACCTGGAGGACTCACTGGCCCGTGA<br>GCGGGACACCAGCCGGCGGCTGCTGGCGGAAAAGGAGCG<br>GGAGATGGCCGAGATGCGGGCAAGGATGCAGCAGCAGCT<br>GGACGAGTACCAGGAGCTTCTGGACATCAAGCTGGCCCTG<br>GACATGGAGATCCACGCCTACCGCAAGCTCTTGGAGGGCG<br>AGGAGGAGAGGCTACGCCTGTCCCCCAGCCCTACCTCGCA<br>GCGCAGCCGTGGCCGTGCTTCCTCTCACTCATCCCAGACA<br>CAGGGTGGGGGCAGCGTCACCAAAAAGCGCAAACTGGAG<br>TCCACTGAGAGCCGCAGCAGCTTCTCACAGCACGCACGCA<br>CTAGCGGGCGCGTGGCCGTGGAGGAGGTGGATGAGGAGG<br>GCAAGTTTGTCCGGCTGCGCAACAAGTCCAATGAGGACCA<br>GTCCATGGGCAATTGGCAGATCAAGCGCCAGAATGGAGA<br>TGATCCCTTGCTGACTTACCGGTTCCCACCAAAGTTCACCC<br>TGAAGGCTGGGCAGGTGGTGACGATCTGGGCTGCAGGAG<br>CTGGGGCCACCCACAGCCCCCCTACCGACCTGGTGTGGAA<br>GGCACAGAACACCTGGGGCTGCGGGAACAGCCTGCGTAC<br>GGCTCTCATCAACTCCACTGGGGAAGAAGTGGCCATGCGC<br>AAGCTGGTGCGCTCAGTGACTGTGGTTGAGGACGACGAG<br>GATGAGGATGGAGATGACCTGCTCCATCACCACCACGTGA<br>GTGGTAGCCGCCGCTGAACTAGTAATAAAAGATCTTTATT<br>TTCATTAGATCTGTGTGTTGGTTTTTTGTGTG | |
| 8 | GTGATGCGGTTTTGGCAGTACATCAATGGGCGTGGATAGC<br>GGTTTGACTCACGGGGATTTCCAAGTCTCCACCCCATTGA<br>CGTCAATGGGAGTTTGTTTTGGCACCAAAATCAACGGGAC<br>TTTCCAAAATGTCGTAACAACTCCGCCCCATTGACGCAAA<br>TGGGCGGTAGGCGTGTACGGTGGGAGGTCTATATAAGCA<br>GAGCTGGTACCGTGTGTATGCTCAGGGGCTGGGAAAGGA<br>GGGGAGGGAGCTCCGGCTCAGGAATTCGCCACCATGGAG<br>ACCCCGTCCCAGCGGCGCGCCACCCGCAGCGGGGCGCAG<br>GCCAGCTCCACTCCGCTGTCGCCCACCCGCATCACCCGGC<br>TGCAGGAGAAGGAGGACCTGCAGGAGCTCAATGATCGCT<br>TGGCGGTCTACATCGACCGTGTGCGCTCGCTGGAAACGGA<br>GAACGCAGGGCTGCGCCTTCGCATCACCGAGTCTGAAGAG<br>GTGGTCAGCCGCGAGGTGTCCGGCATCAAGGCCGCCTACG<br>AGGCCGAGCTCGGGGATGCCCGCAAGACCCTTGACTCAGT<br>AGCCAAGGAGCGCGCCCGCCTGCAGCTGGAGCTGAGCAA<br>AGTGCGTGAGGAGTTTAAGGAGCTGAAAGCGCGCAATAC<br>CAAGAAGGAGGGTGACCTGATAGCTGCTCAGGCTCGGCT<br>GAAGGACCTGGAGGCTCTGCTGAACTCCAAGGAGGCCGC<br>ACTGAGCACTGCTCTCAGTGAGAAGCGCACGCTGGAGGG<br>CGAGCTGCATGATCTGCGGGGCCAGGTGGCCAAGCTTGAG<br>GCAGCCCTAGGTGAGGCCAAGAAGCAACTTCAGGATGAG<br>ATGCTGCGGCGGGTGGATGCTGAGAACAGGCTGCAGACC<br>ATGAAGGAGGAACTGGACTTCCAGAAGAACATCTACAGT<br>GAGGAGCTGCGTGAGACCAAGCGCCGTCATGAGACCCGA<br>CTGGTGGAGATTGACAATGGGAAGCAGCGTGAGTTTGAG<br>AGCCGGCTGGCGGATGCGCTGCAGGAACTGCGGGCCCAG<br>CATGAGGACCAGGTGGAGCAGTATAAGAAGGAGCTGGAG<br>AAGACTTATTCTGCCAAGCTGGACAATGCCAGGCAGTCTG<br>CTGAGAGGAACAGCAACCTGGTGGGGGCTGCCCACGAGG<br>AGCTGCAGCAGTCGCGCATCCGCATCGACAGCCTCTCTGC<br>CCAGCTCAGCCAGCTCCAGAAGCAGCTGGCAGCCAAGGA<br>GGCGAAGCTTCGAGACCTGGAGGACTCACTGGCCCGTGA<br>GCGGGACACCAGCCGGCGGCTGCTGGCGGAAAAGGAGCG | Minigene 1 construct |

TABLE 1-continued

List of exemplary Lamin A and/or Lamin C nucleic acid sequences.

| SEQ ID NO: | Nucleic Acid Sequence | Name |
|---|---|---|
| | GGAGATGGCCGAGATGCGGGCAAGGATGCAGCAGCAGCT<br>GGACGAGTACCAGGAGCTTCTGGACATCAAGCTGGCCCTG<br>GACATGGAGATCCACGCCTACCGCAAGCTCTTGGAGGGCG<br>AGGAGGAGAGGCTACGCCTGTCCCCCAGCCCTACCTCGCA<br>GCGCAGCCGTGGCCGTGCTTCCTCTCACTCATCCCAGACA<br>CAGGGTGGGGGCAGCGTCACCAAAAAGCGCAAACTGGAG<br>TCCACTGAGAGCCGCAGCAGCTTCTCACAGCACGCACGCA<br>CTAGCGGGCGCGTGGCCGTGGAGGAGGTGGATGAGGAGG<br>GCAAGTTTGTCCGGCTGCGCAACAAGTCCAATGAGGACCA<br>GTCCATGGGCAATTGGCAGATCAAGCGCCAGAATGGAGA<br>TGATCCCTTGCTGACTTACCGGTTCCCACCAAAGTTCACCC<br>TGAAGGCTGGGCAGGTGGTGACGGTGAGTGGCAGGGCGC<br>TTGGGACTCTGGGGAGGCCTTGGGTGGCGATGGGAGCGCT<br>GGGGTAAGTGTCCTTTTCTCCTCTCCAGATCTGGGCTGCAG<br>GAGCTGGGGCCACCCACAGCCCCCCTACCGACCTGGTGTG<br>GAAGGCACAGAACACCTGGGGCTGCGGGAACAGCCTGCG<br>TACGGCTCTCATCAACTCCACTGGGGAAGTAAGTAGGCCT<br>GGGCCTGGCTGCTTGCTGGACGAGGCTCCCCCTGATGGCC<br>AACATCGGAGCCAGCTGCCCCCAACCCAAGTTTGCCAATT<br>CAGGGCCCCTTTCTAGAGCTCTCTGTTGCAGGCTCCAGAC<br>TTCTCCACCCAGTAGGCAAACCAAAAGATGCTTCCTCAAC<br>AGCACAAGGGGTGGAAGTTAGACAGTGAGGATTGTTAAA<br>GGCAGAGCCATACTCCTACCCGGAGAGCTTGACAGTGTCC<br>CTCTGGGGTGGAAATGAGTTCCTTAGCTCCATCACCACAG<br>AGGACAGAGTAAGCAGCAGGCCGGACAAAGGGCAGGCCA<br>CAAGAAAAGTTGCAGGTGGTCACTGGGGTAGACATGCTGT<br>ACAACCCTTCCCTGGCCCTGACCCTTGGACCTGGTTCCATG<br>TCCCCACCAGGAAGTGGCCATGCGCAAGCTGGTGCGCTCA<br>GTGACTGTGGTTGAGGACGACGAGGATGAGGATGGAGAT<br>GACCTGCTCCATCACCACCACGTGAGTGGTAGCCGCCGCT<br>GAGGCCGAGCCTGCACTGGGGCCACCCAGCCAGGCCTGG<br>GGGCAGCCTCTCCCCAGCCTCCCCGTGCCAAAAATCTTTT<br>CATTAAAGAATGTTTTGGAACTTTACTCGCTGGCCTGGCCT<br>TTCTTCTCTCTCCTCCCTATACCTTGAACAGGGAACCCAGG<br>TGTCTGGGTGCCCTACTCTGGTAAGGAAGGGAGTGGGAAC<br>TTTCTGATGCCATGGAATATTCCTGTGGGAGCAGTGGACA<br>AGGGTCTGGATTTGTCTTCTGGGAAAGGGAGGGGAGGAC<br>AGACGTGGGGCATGCCCGCCCTGCCTCTCTCCCCCATTCTT<br>GTTGCATGCATATCCTCTCATTTCCCTCATTTTTCCTGCAA<br>GAATGTTCTCTCTCATTCCTGACCGCCCCTCCACTCCAATT<br>AATAGTGCATGCCTGCTGCCCTACAAGCTTGCTCCCGTTCT<br>CTCTTCTTTTCCTCTTAAGCTCAGAGTAGCTAGAACAGAGT<br>CAGAGTCACTGCTCTGGTTCTCTGTCCCCAAGTCTTCCTGA<br>GCCTTCTCCCCTTTTATGTCTTCCCTCTCCTCCTCCGGGCCC<br>CTAGCCTCCCAAACCCCCATTGCCCGCTGGCTCCTTGGGC<br>ACAGAACCACACCTTCCTGCCTGGCGGCTGGGAGCCTGCA<br>GGAGCCTGGAGCCTGGTTGGGCCTGAGTGGTCAGTCCCAG<br>ACTCGCCGTCCCGCCTGAGCCTTGTCTCCCTTCCCAGGGCT<br>CCCACTGCAGCAGCTCGGGGGACCCCGCTGAGTACAACCT<br>GCGCTCGCGCACCGTGCTGTGCGGGACCTGCGGGCAGCCT<br>GCCGACAAGGCATCTGCCAGCGGCTCAGGAGCCCAGGTG<br>GGCGGACCCATCTCCTCTGGCTCTTCTGCCTCCAGTGTCAC<br>GGTCACTCGCAGCTACCGCAGTGTGGGGGGCAGTGGGGG<br>TGGCAGCTTCGGGGACAATCTGGTCACCCGCTCCTACCTC<br>CTGGGCAACTCCAGCCCCCGAACCCAGGTGAGTTGTCTCT<br>GCTTTGTCTCCAAATCCTGCAGGCGGGTCCCTGGTCATCG<br>AGGGGTAGGACGAGGTGGCCTTGCAGGGGGGAGAGCCTG<br>CCTTCTCTTCCGCAGCCCGGGGGAGTGGGAGCCTCCTCCC<br>CACAGCCTGAGTCCTAGACAGCCCACCTCTGCATCCTGCC<br>CCTCTTGTCTGAGCCCCAGACTGGAGGGCAGGGGCAGGGC<br>TGGAGTGTGAGGGATGGGGGAGATGCTACCTCCCTTCTAG<br>GGGCCAGGGGAGGGAGGGTCTGGGTCCAGGCCCTGCTGC<br>TCACACCTCTCTCCTCTGTTTTCTCTCTTAGAGCCCCCAGA<br>ACTGCAGCATCATGTAAACTAGTAATAAAAGATCTTTATT<br>TTCATTAGATCTGTGTGTTGGTTTTTTGTGTG | |
| 9 | GTGATGCGGTTTTGGCAGTACATCAATGGGCGTGGATAGC<br>GGTTTGACTCACGGGGATTTCCAAGTCTCCACCCCATTGA<br>CGTCAATGGGAGTTTGTTTTGGCACCAAAATCAACGGGAC<br>TTTCCAAAATGTCGTAACAACTCCGCCCCATTGACGCAAA<br>TGGGCGGTAGGCGTGTACGGTGGGAGGTCTATATAAGCA<br>GAGCTGGTACCGTGTGTATGCTCAGGGGCTGGGAAAGGA<br>GGGGAGGGAGCTCCGGCTCAGGAATTCGCCACCATGGAG<br>ACCCCGTCCCAGCGGCGCGCCACCCGCAGCGGGGCGCAG<br>GCCAGCTCCACTCCGCTGTCGCCCACCCGCATCACCCGGC | Minigene 2 construct |

TABLE 1-continued

List of exemplary Lamin A and/or Lamin C nucleic acid sequences.

| SEQ ID NO: | Nucleic Acid Sequence | Name |
| --- | --- | --- |
| | TGCAGGAGAAGGAGGACCTGCAGGAGCTCAATGATCGCT<br>TGGCGGTCTACATCGACCGTGTGCGCTCGCTGGAAACGGA<br>GAACGCAGGGCTGCGCCTTCGCATCACCGAGTCTGAAGAG<br>GTGGTCAGCCGCGAGGTGTCCGGCATCAAGGCCGCCTACG<br>AGGCCGAGCTCGGGGATGCCCGCAAGACCCTTGACTCAGT<br>AGCCAAGGAGCGCGCCCGCCTGCAGCTGGAGCTGAGCAA<br>AGTGCGTGAGGAGTTTAAGGAGCTGAAAGCGCGCAATAC<br>CAAGAAGGAGGGTGACCTGATAGCTGCTCAGGCTCGGCT<br>GAAGGACCTGGAGGCTCTGCTGAACTCCAAGGAGGCCGC<br>ACTGAGCACTGCTCTCAGTGAGAAGCGCACGCTGGAGGG<br>CGAGCTGCATGATCTGCGGGGCCAGGTGGCCAAGCTTGAG<br>GCAGCCCTAGGTGAGGCCAAGAAGCAACTTCAGGATGAG<br>ATGCTGCGGCGGGTGGATGCTGAGAACAGGCTGCAGACC<br>ATGAAGGAGGAACTGGACTTCCAGAAGAACATCTACAGT<br>GAGGAGCTGCGTGAGACCAAGCGCCGTCATGAGACCCGA<br>CTGGTGGAGATTGACAATGGGAAGCAGCGTGAGTTTGAG<br>AGCCGGCTGGCGGATGCGCTGCAGGAACTGCGGGCCCAG<br>CATGAGGACCAGGTGGAGCAGTATAAGAAGGAGCTGGAG<br>AAGACTTATTCTGCCAAGCTGGACAATGCCAGGCAGTCTG<br>CTGAGAGGAACAGCAACCTGGTGGGGGCTGCCCACGAGG<br>AGCTGCAGCAGTCGCGCATCCGCATCGACAGCCTCTCTGC<br>CCAGCTCAGCCAGCTCCAGAAGCAGCTGGCAGCCAAGGA<br>GGCGAAGCTTCGAGACCTGGAGGACTCACTGGCCCGTGA<br>GCGGGACACCAGCCGGCGGCTGCTGGCGGAAAAGGAGCG<br>GGAGATGGCCGAGATGCGGGCAAGGATGCAGCAGCAGCT<br>GGACGAGTACCAGGAGCTTCTGGACATCAAGCTGGCCCTG<br>GACATGGAGATCCACGCCTACCGCAAGCTCTTGGAGGGCG<br>AGGAGGAGAGGCTACGCCTGTCCCCCAGCCCTACCTCGCA<br>GCGCAGCCGTGGCCGTGCTTCCTCTCACTCATCCCAGACA<br>CAGGGTGGGGGCAGCGTCACCAAAAAGCGCAAACTGGAG<br>TCCACTGAGAGCCGCAGCAGCTTCTCACAGCACGCACGCA<br>CTAGCGGGCGCGTGGCCGTGGAGGAGGTGGATGAGGAGG<br>GCAAGTTTGTCCGGCTGCGCAACAAGTCCAATGAGGACCA<br>GTCCATGGGCAATTGGCAGATCAAGCGCCAGAATGGAGA<br>TGATCCCTTGCTGACTTACCGGTTCCCACCAAAGTTCACCC<br>TGAAGGCTGGGCAGGTGGTGACGATCTGGGCTGCAGGAG<br>CTGGGGCCACCCACAGCCCCCCTACCGACCTGGTGTGGAA<br>GGCACAGAACACCTGGGGCTGCGGGAACAGCCTGCGTAC<br>GGCTCTCATCAACTCCACTGGGGAAGTAAGTAGGCCTGGG<br>CCTGGCTGCTTGCTGGACGAGGCTCCCCCTGATGGCCAAC<br>ATCGGAGCCAGCTGCCCCCAACCCAAGTTTGCCAATTCAG<br>GGCCCCTTTCTAGAGCTCTCTGTTGCAGGCTCCAGACTTCT<br>CCACCCAGTAGGCAAACCAAAAGATGCTTCCTCAACAGCA<br>CAAGGGGTGGAAGTTAGACAGTGAGGATTGTTAAAGGCA<br>GAGCCATACTCCTACCCGGAGAGCTTGACAGTGTCCCTCT<br>GGGGTGGAAATGAGTTCCTTAGCTCCATCACCACAGAGGA<br>CAGAGTAAGCAGCAGGCCGGACAAAGGGCAGGCCACAAG<br>AAAAGTTGCAGGTGGTCACTGGGGTAGACATGCTGTACAA<br>CCCTTCCCTGGCCCTGACCCTTGGACCTGGTTCCATGTCCC<br>CACCAGGAAGTGGCCATGCGCAAGCTGGTGCGCTCAGTG<br>ACTGTGGTTGAGGACGACGAGGATGAGGATGGAGATGAC<br>CTGCTCCATCACCACCACGTGAGTGGTAGCCGCCGCTGAG<br>GCCGAGCCTGCACTGGGGCCACCCAGCCAGGCCTGGGGG<br>CAGCCTCTCCCCAGCCTCCCCGTGCCAAAAATCTTTTCATT<br>AAAGAATGTTTTGGAACTTTACTCGCTGGCCTGGCCTTTCT<br>TCTCTCTCCTCCCTATACCTTGAACAGGGAACCCAGGTGTC<br>TGGGTGCCCTACTCTGGTAAGGAAGGGAGTGGGAACTTTC<br>TGATGCCATGGAATATTCCTGTGGGAGCAGTGGACAAGGG<br>TCTGGATTTGTCTTCTGGGAAAGGGAGGGGAGGACAGAC<br>GTGGGGCATGCCCGCCCTGCCTCTCTCCCCCATTCTTGTTG<br>CATGCATATCCTCTCATTTCCCTCATTTTTCCTGCAAGAAT<br>GTTCTCTCTCATTCCTGACCGCCCCTCCACTCCAATTAATA<br>GTGCATGCCTGCTGCCCTACAAGCTTGCTCCCGTTCTCTCT<br>TCTTTTCCTCTTAAGCTCAGAGTAGCTAGAACAGAGTCAG<br>AGTCACTGCTCTGGTTCTCTGTCCCCAAGTCTTCCTGAGCC<br>TTCTCCCCTTTTATGTCTTCCCTCTCCTCCTCCGGGCCCCTA<br>GCCTCCCAAACCCCCATTGCCCGCTGGCTCCTTGGGCACA<br>GAACCACACCTTCCTGCCTGGCGGCTGGGAGCCTGCAGGA<br>GCCTGGAGCCTGGTTGGGCCTGAGTGGTCAGTCCCAGACT<br>CGCCGTCCCGCCTGAGCCTTGTCTCCCTTCCCAGGGCTCCC<br>ACTGCAGCAGCTCGGGGGACCCCGCTGAGTACAACCTGCG<br>CTCGCGCACCGTGCTGTGCGGGACCTGCGGGCAGCCTGCC<br>GACAAGGCATCTGCCAGCGGCTCAGGAGCCCAGGTGGGC<br>GGACCCATCTCCTCTGGCTCTTCTGCCTCCAGTGTCACGGT<br>CACTCGCAGCTACCGCAGTGTGGGGGGCAGTGGGGGTGG | |

TABLE 1-continued

List of exemplary Lamin A and/or Lamin C nucleic acid sequences.

| SEQ ID NO: | Nucleic Acid Sequence | Name |
|---|---|---|
| | CAGCTTCGGGGACAATCTGGTCACCCGCTCCTACCTCCTG GGCAACTCCAGCCCCCGAACCCAGAGCCCCCAGAACTGC AGCATCATGTAAACTAGTAATAAAAGATCTTTATTTTCATT AGATCTGTGTGTTGGTTTTTTGTGTG | |
| 10 | GTGATGCGGTTTTGGCAGTACATCAATGGGCGTGGATAGC GGTTTGACTCACGGGGATTTCCAAGTCTCCACCCCATTGA CGTCAATGGGAGTTTGTTTTGGCACCAAAATCAACGGGAC TTTCCAAAATGTCGTAACAACTCCGCCCCATTGACGCAAA TGGGCGGTAGGCGTGTACGGTGGGAGGTCTATATAAGCA GAGCTGGTACCGTGTGTATGCTCAGGGGCTGGGAAAGGA GGGGAGGGAGCTCCGGCTCAGGAATTCGCCACCATGGAG ACCCCGTCCCAGCGGCGCGCCACCCGCAGCGGGGCGCAG GCCAGCTCCACTCCGCTGTCGCCCACCCGCATCACCCGGC TGCAGGAGAAGGAGGACCTGCAGGAGCTCAATGATCGCT TGGCGGTCTACATCGACCGTGTGCGCTCGCTGGAAACGGA GAACGCAGGGCTGCGCCTTCGCATCACCGAGTCTGAAGAG GTGGTCAGCCGCGAGGTGTCCGGCATCAAGGCCGCCTACG AGGCCGAGCTCGGGGATGCCCGCAAGACCCTTGACTCAGT AGCCAAGGAGCGCGCCCGCCTGCAGCTGGAGCTGAGCAA AGTGCGTGAGGAGTTTAAGGAGCTGAAAGCGCGCAATAC CAAGAAGGAGGGTGACCTGATAGCTGCTCAGGCTCGGCT GAAGGACCTGGAGGCTCTGCTGAACTCCAAGGAGGCCGC ACTGAGCACTGCTCTCAGTGAGAAGCGCACGCTGGAGGG CGAGCTGCATGATCTGCGGGGCCAGGTGGCCAAGCTTGAG GCAGCCCTAGGTGAGGCCAAGAAGCAACTTCAGGATGAG ATGCTGCGGCGGGTGGATGCTGAGAACAGGCTGCAGACC ATGAAGGAGGAACTGGACTTCCAGAAGAACATCTACAGT GAGGAGCTGCGTGAGACCAAGCGCCGTCATGAGACCCGA CTGGTGGAGATTGACAATGGGAAGCAGCGTGAGTTTGAG AGCCGGCTGGCGGATGCGCTGCAGGAACTGCGGGCCCAG CATGAGGACCAGGTGGAGCAGTATAAGAAGGAGCTGGAG AAGACTTATTCTGCCAAGCTGGACAATGCCAGGCAGTCTG CTGAGAGGAACAGCAACCTGGTGGGGGCTGCCCACGAGG AGCTGCAGCAGTCGCGCATCCGCATCGACAGCCTCTCTGC CCAGCTCAGCCAGCTCCAGAAGCAGCTGGCAGCCAAGGA GGCGAAGCTTCGAGACCTGGAGGACTCACTGGCCCGTGA GCGGGACACCAGCCGGCGGCTGCTGGCGGAAAAGGAGCG GGAGATGGCCGAGATGCGGGCAAGGATGCAGCAGCAGCT GGACGAGTACCAGGAGCTTCTGGACATCAAGCTGGCCCTG GACATGGAGATCCACGCCTACCGCAAGCTCTTGGAGGGCG AGGAGGAGAGGCTACGCCTGTCCCCCAGCCCTACCTCGCA GCGCAGCCGTGGCCGTGCTTCCTCTCACTCATCCCAGACA CAGGGTGGGGGCAGCGTCACCAAAAAGCGCAAACTGGAG TCCACTGAGAGCCGCAGCAGCTTCTCACAGCACGCACGCA CTAGCGGGCGCGTGGCCGTGGAGGAGGTGGATGAGGAGG GCAAGTTTGTCCGGCTGCGCAACAAGTCCAATGAGGACCA GTCCATGGGCAATTGGCAGATCAAGCGCCAGAATGGAGA TGATCCCTTGCTGACTTACCGGTTCCCACCAAAGTTCACCC TGAAGGCTGGGCAGGTGGTGACGATCTGGGCTGCAGGAG CTGGGGCCACCCACAGCCCCCCTACCGACCTGGTGTGGAA GGCACAGAACACCTGGGGCTGCGGGAACAGCCTGCGTAC GGCTCTCATCAACTCCACTGGGGAAGAAGTGGCCATGCGC AAGCTGGTGCGCTCAGTGACTGTGGTTGAGGACGACGAG GATGAGGATGGAGATGACCTGCTCCATCACCACCACGTGA GTGGTAGCCGCCGCTGAGGCCGAGCCTGCACTGGGGCCAC CCAGCCAGGCCTGGGGGCAGCCTCTCCCCAGCCTCCCCGT GCCAAAAATCTTTTCATTAAAGAATGTTTTGGAACTTTACT CGCTGGCCTGGCCTTTCTTCTCTCTCCTCCCTATACCTTGA ACAGGGAACCCAGGTGTCTGGGTGCCCTACTCTGGTAAGG AAGGGAGTGGGAACTTTCTGATGCCATGGAATATTCCTGT GGGAGCAGTGGACAAGGGTCTGGATTTGTCTTCTGGGAAA GGGAGGGGAGGACAGACGTGGGGCATGCCCGCCCTGCCT CTCTCCCCCATTCTTGTTGCATGCATATCCTCTCATTTCCCT CATTTTTCCTGCAAGAATGTTCTCTCTCATTCCTGACCGCC CCTCCACTCCAATTAATAGTGCATGCCTGCTGCCCTACAA GCTTGCTCCCGTTCTCTCTTCTTTTCCTCTTAAGCTCAGAGT AGCTAGAACAGAGTCAGAGTCACTGCTCTGGTTCTCTGTC CCCAAGTCTTCCTGAGCCTTCTCCCCTTTTATGTCTTCCCTC TCCTCCTCCGGGCCCCTAGCCTCCCAAACCCCCATTGCCCG CTGGCTCCTTGGGCACAGAACCACACCTTCCTGCCTGGCG GCTGGGAGCCTGCAGGAGCCTGGAGCCTGGTTGGGCCTGA GTGGTCAGTCCCAGACTCGCCGTCCCGCCTGAGCCTTGTC TCCCTTCCCAGGGCTCCCACTGCAGCAGCTCGGGGGACCC CGCTGAGTACAACCTGCGCTCGCGCACCGTGCTGTGCGGG | Minigene 3 construct |

TABLE 1-continued

List of exemplary Lamin A and/or Lamin C nucleic acid sequences.

| SEQ ID NO: | Nucleic Acid Sequence | Name |
|---|---|---|
| | ACCTGCGGGCAGCCTGCCGACAAGGCATCTGCCAGCGGCT<br>CAGGAGCCCAGGTGGGCGGACCCATCTCCTCTGGCTCTTC<br>TGCCTCCAGTGTCACGGTCACTCGCAGCTACCGCAGTGTG<br>GGGGGCAGTGGGGGTGGCAGCTTCGGGGACAATCTGGTC<br>ACCCGCTCCTACCTCCTGGGCAACTCCAGCCCCCGAACCC<br>AGAGCCCCCAGAACTGCAGCATCATGTAAACTAGTAATAA<br>AAGATCTTTATTTTCATTAGATCTGTGTGTTGGTTTTTTGT<br>GTG | |
| 11 | AATAAAAGATCTTTATTTTCATTAGATCTGTGTGTTGGTTT<br>TTTGTGTG | Polyadenyl-<br>ation<br>signal<br>sequence |
| 70 | GTGAGTTCGCCCAGGTGGCTGCGTGCCTGGCGGGGAGTGG<br>AGAGGGCGGCGGGCCGGCGCCCCTGGCCGGCCGCAGGAA<br>GGGAGTGAGAGGGCCTGGAGGCCGATAACTTTGCCATAG<br>TCTCCTCCCTCCCCGGAACTGCCCCCAGCGGGTGACTGGC<br>AGTGTCAAGGGGAATTGTCAAGACAGGACAGAGAGGGAA<br>GTGGTGGTCTCTGGGAGAGGGTCGGGGAGGATATAAGGA<br>ATGGTGGGGGTATCAGGGACAAGTTGGGGCTGGGGCCGG<br>CCTGAATTCGGTCAGATTGGGATTTGCCAACTATTTGGAG<br>CCGGGGGGAGGGGCTTGAGCAAAACAGAACTAGCCCTGC<br>CAGCTCGAAGAACTCTGGGCACCCAGGACACATCGGAGT<br>GGCAGAAAGGGTCCTGTTAGAACTTTGTTAGCGGGCTTGG<br>CACTGTGCTAGCTTTGCCCAAGCTGGCTCTGAACACATGA<br>TGCCCACTAAGACATAACTCTCAAGTTGGCATCTGTCCAG<br>CGTGTTGGAGCGAGGTCAGGAAGGCAGGGCAATCCCCCTT<br>TTCCCTCCCAAGGGCTTGGCGGTGGCCCCCCCTCAGCATG<br>ACCTTGTCCTGGGTTCTAAGGGTTGGGAAGTTCTCCCTCAC<br>TCTGCCACTCTGCGTGTCTGGGACCTTCCTTGGGCTCTGAC<br>AGGCCCACCAAAAGAGCTCCGGGAGATGAGAGATCGGCT<br>CCCCCGCAGCTCCCACAGCCCTTGGCCTGCTTGGCCCAGG<br>AATGCAAGGGAGGGAGGGAGGCAGAGGGCAGAGGCTCCC<br>AGCTCAGGAAGTTGTGTTATGCCCAGGTCTGGCCGCACTC<br>CTCCCTTGGCCCTCTGCCTAGTGTCTTCGAGGGTTGGGGGC<br>ACTGTCCTTCCCTCCTTGGGGTGAGCCACTTTCATTTTCCC<br>AGCGGGGCCAGGCAGTCTTTGCTCGGGCCCATCCTCTTAG<br>CTGCTGACGTTTTGATCTTTGTCTTATTGAAGTGCTGGAAT<br>ACAGTGACATTTTTGAAATCCAGCCGTTGGAAGATTCAGG<br>CCACTCCCACTTTACCCACCCCTGCCCCACCCTACCCCACC<br>CTACTCAACTGCACCTTCTTCTTTTCTAAAAAAGCCTTTGG<br>GAGCTTGGAAGTATAGGCCCTCTCTTCCAGCCCCATCAAA<br>ATTTGTTTCCCTTCTTCCTGCCTTCCCTTTCTCTATGCAGAC<br>CCAGGCCAAGAGCACTAAGGGTGCTTGGAGATCCGTAAA<br>GGGCTGTTGGCTTTGACTTCTTCTCTCTCTTTTATCATCTAC<br>TCCAAACTTCTGCTCTTCCTAGAACCCTTTGCTAGGTGTGG<br>TTTTGTTGCCCAGGCTGGAGTGCAATGGCACAATCTCGGC<br>TCACTGCAACCTCCGCCTCCCAGGTTCAAGTGATTCTCCTG<br>CCTCAGCCTCCCGAATAGCTGAGATTACAGGCATGTGCCA<br>CCATGCCGGGCTAATTTTGTATTTCTAGTAGAGATGGGGT<br>TTCTCCATGTTCGTCAGGCTAGTCTTGAACTCCCAACCTCA<br>GGTGATCCACCCGCCTCAGCCTCCCAAAGTGCTAGGATTA<br>CAGGCATGAGCCACCACGCTGGGCCCATCACCCTTCTTTC<br>TGAAGAGTCAATGGAAGTTGTGTGTAGGAAGACAGGCTT<br>AACGGTTTTTTTTTGAGACAGGGTCTTACTCTGTCACCCAG<br>ACTGGAGTGAAGTGGTGCGATCTTGGCTCACCACAACCTC<br>TGCCTCCCAGGCTCAAAAGATTCTCCTGCCTCAGCCTCCTG<br>AGTAGCTGGGATTATAAGTGTGTGCCACCACACATGGCTA<br>TTTTTTTTTTTTTTTTTTTTTTTAATTTTTAGTAGAGATGGG<br>GTTTCACCATGTTGGCTAGGCTGGTCTCAAACTCCTGACTT<br>CAAATGATCCACCTGCCTCGGCCTCCCAAAGTGCTGGGAT<br>TACAGGTGTGAGCTACCATGCCCGGCCATCAACCTTTATT<br>TTGTTTTTTTGAGACGGAGTCTTGCTTTGTTGCCCAGGCTG<br>GAGTACAGTAGTGTGACCTCAGGTCACTGCAACCTCTGCC<br>TCCCAGGTTCAAGCCATGCTCCTGCCTCAGCCTCCCAAGT<br>AGCTGGGACTATAGGTGCCTGCCACCACGCCCGGCTACTT<br>TTTATATTTTTAGTAGAGACGGGGTTTCACCATGTTGGCCA<br>GGGTGATCTCGAACTCCTGACCTCAAGTGATCTGCCTGCC<br>TCAGCCTCCCAAAGTGTTGGGATTAGAGACGGGAGCCACT<br>GCGCCTGGCTTCTTTTTTTCTTGAGATAGGGTTTCACTCTG<br>TTACCCAGGCTGGAGTGCAGTGGCAAGGTCATGGCTCACT<br>GCAGCCTCTACCTCTCTGGCTCAAGCCATCCTCCCGCCTCA<br>GCCTCCTGAGTAGCTGGGACCACAGGCAGGCACCACCACC<br>CACAGCTAATGTTTTTGTATTATTTTGTAGAGATGGGGTTT | Intron 1 of<br>lamin A<br>and lamin<br>C |

TABLE 1-continued

List of exemplary Lamin A and/or Lamin C nucleic acid sequences.

| SEQ ID NO: | Nucleic Acid Sequence | Name |
|---|---|---|
| | TGCCATGTTGCCCACAGTCTTGAACTCCTGGGTTCATTCTG<br>CTGAAAGAGACCACACCTGTCCTTTTCTTTATTTTTATTAT<br>ATTTTTCAGAGACAGGGCCTTGCCCTGTTGCTCAGGCTAG<br>AGTGCAATGGTACAATCATAACTTGCTGCAGCCTGGAACT<br>CCTCCTGGGCTCAAGCGATCCTACCGTCTCACCTTCCGGA<br>ATAGCTGAGACTAAGGGCAGGCACCACCACGCTTGGCTA<br>ATTTTTTTTTTTTTTTTTTTTTTTTTGCTTTTTGTTTGTAAAG<br>ATGGAAACTTGCTATGTTGCTCAGCTGGTTCCGAAGTTTTG<br>GCCTCAAGCAATCCTCCTGCCTCGGCCTCCGGAAGCACTG<br>GGATTACAGGCATAAGCCACCAGGCCTGACGCCAGGCCT<br>GTCTTTTTTCTACTAGTGATATGAACAATTTAGTTAGCAAG<br>ACAGATAGGAAGCAAGGAAGGGGAGACCCAGAGAATTCG<br>TTGCATTCTAAACTAGTCCACTCATCTACCAAAGCCCTGTG<br>AAGGACATTTTTAGCAGTTTTAGCAGTTTTCTGGTCAAAA<br>CTTTGATCGAGAAACAGATTGAGTGGATTCGATATTCTCT<br>TGCTCACCCAGCCACGCCAGTTTGTCTCCTCTGCCTCCTAG<br>TGCAGCTGTCCAGGCCTGGGACACCAGGCGGGTATGTGCG<br>CATGTGGGGCAGGGCGGAGGTGGTGTGTGTACTTGTTATA<br>TTTAGCCACCTCCCTCTGTTCTCCCCCACTGATCCTGGCTG<br>GAAAGGCTGGGCTTCCGGAAAAGAGAGGTGGATTTGCAC<br>ACCTGGATCCCAAGCTGATAGAAAGTGGGGTGAAGACAA<br>AGGGGACTCAGACTGGGGTGTCTGTCCTCTTCTATGCCCA<br>CAGTAGGAGGAGCCAGGATTGGTTACTCCCTGCTGGGTCT<br>GCTGTGCTCAGAGTGAGGTAGAGAAGTGGGTAGAGTAAA<br>GAATTTGGGAGAGGAAAAAAGGCATTTTCCCAACCCCTCC<br>CACCAAAGCCTAGAGAGAAGGTGTTGTCTGGTTTAATGTT<br>TAATTAGAGCTCAGAGTTCAGGGCCAGATTTGGAGTTGGG<br>ATGGAAAGTTGTTTTTAAGACCCTGTAGCAATTTTTGACCC<br>AGCCTGGGTACCTCAACCACACTCAGGAGTTTGGGGGACC<br>TTCTGTTGGGCTGGATTATAGGCTCCAAGAAGAAACCCCT<br>TTCGCCAATACTCTCTCTCTCTTCTTTTTTTGAGACAGGGT<br>CTTGTTCTGTTGCCCAGGCTGGGGTGCAGTGGCATGATCA<br>CAGCTCACTGCAACGTCAGCCTCACAGGCTCTGGTGATTC<br>TCCCACCTCAGCCTCCTGAGTAGCTGGGATTACAAGTGTG<br>TGCCACCATGCCCAGCTAATTTTTTTTTTCTTTTTTTTTTTT<br>TGAGACGGAGTCTTGTTCTGTTGCCAGGCTGGAGTGCAGT<br>GGTGCGATCTCGGCTCATTGCAACCTCCACCTCCCAGGTT<br>CAAGCGATTCTCCTGCCTCAGCCTCCCGAGTAGCTGGGAC<br>TACAGGCACATGCCATCACGCCCAGTTAATTTTTGTATTTT<br>TAGTAGAGTTGGGGTTTCACCATGTTGGCCAGGATGGTCT<br>TGATCTCTTGACCTCGTGATCCGTCCACCTTGGCCTCCCAA<br>AGTGCTGGGATTACAGGTGTGAGCCACCGTACCCGGCCAC<br>TAATTTTTATATATTTTGTAGAGATGGGGTTTCACCGTGTT<br>GCCCAAGCTGGTCTCGAACTCCTAGGCTCAAGTAATCCAC<br>CTGCCTTGGCCTTGGCCTCCCAAAGTGCTGGGATGTATAG<br>GCATGAGCTACCGCACCTGGTACCCCCTGCCCCTTCTCTGT<br>CTCTTTCTAGTCTGTAGCCCAAGGGATTTGGATACCCAAG<br>TGCAGGCAGAATGGGAAGGTTGTAAGCACCAGGGAAGCC<br>TGTCTGGAGTCCAGGCTTGCAGCTGGGCCCCACCCCAGGC<br>AAGGCAGCTGGGTGGATGACTCAGATGCTGCCCCCCTCCC<br>TCCCACCCTGGTGGCTTTACAGAAGACAGCAGGAGACAG<br>GGTGGAGACAGCAGTTGTCTTAAAGGGAGGAGTGGTGGT<br>CTGAATGTCTACCTCTTCTGCCCCCCTCCCCATTGCATCCT<br>GGAGTCCCTTGCCTGGCTCCTTCCTGAGACCCTCTGGTGGT<br>GTCTGGACACATAGCTCTCTCTGGACAGGTAACATGCACA<br>AGTAATTAGAATCCAGAGTTGAGTTCAGAGTTATGGATTG<br>GGCTGCAGGATAGTGCCAGGGTCTGTGCCTTCCCATGTGA<br>AACTGATGGAGGAAGGCTGAGTCAGAAGTGGGGAGATCC<br>GAGGCCCACAAAGCAGAAGCGCTACTTCCACTCCAAAAA<br>GGCCCTGGTGCTTGACAACTTCCTGGATTGCCCACTGTTGC<br>AGCCCCAGTGTGGACAGGCAGGGAGATGCAGGCTCCAGT<br>TCATGTAGGCTCTGATCAAGACAAGAACAGCAAAGGCCA<br>CAGAGGCACAGATGCTTGTCCCATGTCACACAATAAAGGG<br>GTCAGCACTTGATCACAGGCCTTATGACTTCCAGCTGGGT<br>GTGCTCTTACCATTAAGCCTCACTTCTCTAGCTTGGGGGAC<br>AGGTTGGAGGGAGGATCTAGAGGGTGAGGTAAGGTGAAG<br>TCAGGTAGCTGAGGCTCACTTCTGCAGCCTGGAAACTCTG<br>CTCTGGGGCCAGTGACACCTTAGTGCTCTATGGCCATACT<br>TCGTGGCTCATGCCTGTAATCCCAGTGCTTTGGGAGGCTA<br>AGGCAGGAGGATCACTTGAGGCCAGGAGTTTGAGACCAG<br>TCTGGGCAACATAGCAAGACCCCCTTCTGTACAAAAAAAT<br>TAGCCGGTCAACACCTGTAGTCCAGCTGCTTGGGAAGCTG<br>AGGCGGGAGGATCACCTGAAGCCAGGAGTTTGAGGCTAT<br>TGTGAGCTATGACTGCACTACTGCACTCTAGCCTGGGAGA<br>GAGAAAGACCCTGTCTCTGAAAAAGAAAAAAACAAAACA | |

TABLE 1-continued

List of exemplary Lamin A and/or Lamin C nucleic acid sequences.

| SEQ ID NO: | Nucleic Acid Sequence | Name |
|---|---|---|
| | AAACTCTGCTGTCCTGCAGGGCCTGTTAGCATATGATCGA<br>TAGCCTTTGCTCCAGCCTATACCTGGACCCAGGACCCCTG<br>CCAGCCCCTCAATCGTGAGACGGTCAGAGCTCTGGGAGGC<br>TGGTGATTCTTGTCTTGAGACTATCTTGAGACTTGTCATGG<br>GAATTGTCCACCCGGATTGAAAGGAAGCTGTGCCTTTTGG<br>CAGACCCATTAGGTTAATGGGGTTGGAGACCTTTGAGGAT<br>GCATGGGCCCTGGGCTTTATCTGAGGGTATCTCCTGGTGTT<br>ACCTCTCCAACCCTCCACCACCAAATCCATTCTTTTTTTTT<br>TTTTTTTTTTTTTTTTGACAGTCTCGCTCCCTGGCCCAGGCT<br>GGAGTGCAGTGGCATGATCTTGGCTTACTGCAATCTCCAC<br>CTCCCAGGCTCAAGTGATCCTCCCACCTCAGCCTCCCAAG<br>AAGCTGGGACTATAGGCACGTGCCACATGCTCGGCTAATT<br>TTTCTATTTTTAGTAGAGACCAGGTTTCACCATGTTACTCA<br>GGCTGGTCTTGAACTCTGGGGCTTAAGCAGTCCACCCACC<br>TTGACCTCCCAAAGTGCTGAGAGCCACTGAGCCTAGCCCA<br>AATCCACGTTCTGATTCAAAGGGAAAGAAGAAGGGTGCA<br>GCTAAACCTGGGGGGTGAGAAGTACTTAAAAAGCCCAAG<br>AGAAACAAAAGAGAGAATAATTCCTCACTAGGACCCCCT<br>ATTGCCTTCCCACTATTGGTGCCCTTGCTTGGCACTTCCCC<br>TGGCCTCCAGGAGTCTGAGACTTACTCTTCCATGGATGTG<br>CCCATTGCCCCCACTTCCAGGTCCACCCCCCAGTGATTCG<br>GTAGCTTAGTGTCTGCGCTGAAGCCCAGGACAGCTGGATG<br>GACAACTGGTAGATCCCTTCACCTACCAACTGTGCTTTCTG<br>CTCCCCTCCCCCTTGCTTCCCTCCTCCCCAGCCCCTCGCCA<br>CCCCTAGCAGCTGCAGCAGCCAAGACCAAGTCTTCAGAGA<br>CCCAGACACAAGGGCAGGGTTCATTCCATTCTCACCTCCT<br>TGGGGTCCCAGTGTACTGATAGGCCGAACTCTAATATTAT<br>AGGAGATCTCTGGAAGATTGCAGGGTCTCTTATCCCTCAA<br>TAAGGGGCAAGGCAAGCCGGGCGCAGTGGCTCACGCCTG<br>TAATCCCAGCACTTTGAGAAGCCGAGGGGAACAGATCACT<br>TCAGGTCAGGAGTTAAGAGACCAGCCTGGCCAACATGGT<br>GAAACCCTGTCTCTACTAAAAATACAAAAATTAACCAGAA<br>ATCGCTTGAACCCAGGAGGCAGATGTTGCAGTGAGCCGA<br>GATCACGCCACTGCACTCCAGCCAGGGCGACAGAGCAAG<br>ATTCCGTCTCAAAAAAATAATACTAATAATAAATAAATAA<br>ATAAGGGGCAAGGTAGTCCACCAACAAAATGACAGGCAG<br>TGTGATATAGTGGACACCCTAGCCCTCGGTGCCCTTAGTT<br>CTGTGTGTGGCCCTTTCACTAAATTGCTGTGTGACCTTGAG<br>CAAATCGCCTCCCCTTTCTGGCTTTCCTTAGCTGTAAAAGA<br>AAGGGATTGGAGCGGAAAGTCTCCAGAGACCTTTTAGGTT<br>CCAAAGTAGTACAGTGACCCACAAAGTGAGAAAACAGTC<br>TTCTAAAATACCAAGTTATTAATAGTAAAATCAAATATAA<br>ATAATGTGAATATAGTTAATAGCTAATGTTGTTCTCAATA<br>GAAATGTTTCCCACAAGCTGTGGAATTAAACATACTACCA<br>CATTTCTCTATTTCCCCGTGAAAGTTTGTTAGAAATGGTTA<br>AATTGTGACATTACCCTCTTGGCAAATGTTTTGTTTTCATT<br>GCTACTAGGAAAGGGCAACTCGTTTTCGATGCCTCTCCCT<br>TCTGGACGGTGGAAAGGGCTGTGTCATAGAGTAGGAACG<br>GGAGATGCGGCACAGGAATGGCTCCCATTGACCCGGGTTG<br>GGGGCTAGGGCGAAGGCCTAGGAGAGGCAGAACTGTTAC<br>CTTAGAGCTGGCCAGGATTAGAGAACAGTGCCTGGAACC<br>GGGGGGAGGGGCACGGTGACCTTGGGCTGCCCACCTTCTA<br>CCCTTCCAGCACCCATACTGGCTCCCCCAACCTGCGGCTG<br>GGCTGGGAGGAGGTCTTGGCCCCTACCAATCCCTTAAGGA<br>AGGGGAAAGAGTTTGGGAAGGGGAGTCCTCCCTTCACCCC<br>TGCCTCCCCCAAGTTGTGAGAGAGGAAGCCGGAATCCTGC<br>CTGCTGAAGCCAGGAATAATTCTGGCTGAGATCCCAGGCC<br>CGGCAGGGGCGCTGAGTCATGGTAGAGGGCAGAGTGGAG<br>AGTGGACAGGAGACCCTAAGCTTGTCCAGTCAGAAAAGC<br>AGAGGCTGAGGGGTGGCCTTTTCTTGAGAACTACATTCAA<br>GTTGCAGCAAGAAGGACAGTGGTCTGAATTTGACGGGGA<br>CAAATGGAAGGGAGATAGGACACATGAGTTCCTTTAGGTC<br>TGGCTCAGGGGAGCTAGACTTCATTTCAAGGGGTCTAGGT<br>TCTGGGCAGTTGAGAAGGAGGCTATTTGGGGTCACCAAGG<br>CTCCCCTTTCTTCCCAAAGCTCTAACACTGCCACCTTCTGC<br>TGGCTAGGAGAGAGCTGTGTCTTCTGAGGCTAGAGCTGGA<br>ATGCAGTGAGACCAGACTGCCTAGGTCCTCCCTCACTTCT<br>TCTCCTGACCTTGGGGTGTGGCTCCCACTCTCTCCCAGTGT<br>CCTCAGGGTTAATAACTATGTGCCACCAGATAGAGAGTTA<br>AGGGGCTGCTGAATTGGCTTCTTGTGAAGGGAATCCCCTA<br>AATGTCCCTCGTTTTGGTCACTGGCCTCCCTCCCGCCCCCT<br>TCAGGACATTCTACTATCTTCTTAGGCCATCCCTCCCTCCT<br>CCAGGCACTACTTCTTTTGCTCTATCCCCAAGCCCCACCCC<br>TGCATTTTTGTGACAACACCGGAATGATTTCTAGAGAGAG<br>AGGCCAGGAAGAAGGAAAGTGGCACTTGGCAGGAGACCT | |

TABLE 1-continued

List of exemplary Lamin A and/or Lamin C nucleic acid sequences.

| SEQ ID NO: | Nucleic Acid Sequence | Name |
|---|---|---|
| | TGCAGGGGGCGGCTGGTGAGGAAGCCAGCCGCCCATTGT | |
| | CCAGGACCCCAGTGCCCTGGCCTCCGGCCTCAGGCTTCTC | |
| | CTGCCTCTGTACAATGCCACGTTGATACGCCCAGCAGCTG | |
| | TGACTCAGGCCTGGCCCCCTGCCAGGCCCAGCACTTCTAC | |
| | TGGAGTTGCGTCTGAACATGTCAACAGGCTTCCTATCCCT | |
| | CTCTCAGCACCAGTTCTCCCCACTTCAGCCCCTCCCTCTGC | |
| | CTGGAATTAAAACCTGGCTTTGTCTTAGGGAAGGACAGCT | |
| | GGGAGCCTAGTGGCTCTGGTAGGGGATCTGAGAGGCCTCA | |
| | GACCCTAGGCATATTTGGCTGTTTGGCAGGTGTCACGCCC | |
| | AAGGGAAGCGTGTGGAAGCAGAGCCATGCCTGCTGTGGG | |
| | TGCACATGCCCGCGTGAGGGAGTCGGGGTGTTTCATCCTG | |
| | GGGCACCTGTGGGCTTTTGAGGTGTATGATATTCAGAACT | |
| | TCACAGGTTGGGGTTTGGGGAAGGCTCAAGGGGCTTCTAA | |
| | GTCCCTGGAACAGCTGCCCCCCTCAGTTCCTCTCTCTCTCT | |
| | CTCTTTTTTTTTGAGATGGAGTCTCGCTCTGTTGCCCAGGC | |
| | TAGAATGCAGTGGCGCGATCTTGGCTCACTGCAAACTCCG | |
| | CCTCCTGGGTTCAAGTGATTCTCCTGCCTCAGCCTCCCAAG | |
| | TAGCTGGGACTATAGGTGCCCGCCACCATGCCTGGCTAAT | |
| | TTTTGTATTTTTAGTAGAAATGGGGTTTCACCATGCTGGCC | |
| | AGGATGGTCTCAAACTCCTGACCTCGTGATCCACCCACCT | |
| | TGGCCTCCCAAAGTGCTGGGATTACAGGCGTGAGCCACTG | |
| | CGCCCAGCCTCAGTTCCTCTCTTTAAGGTCTCCTTTCCAGA | |
| | GAGGGATAGCACCTCAAATGCCAGGGAGGGGAATTCTCC | |
| | ACATCCTGCCCTTACCCGAGTTGTGGCAGACCCACAGACT | |
| | AGCCAAGAAACCAAGCAGTGGTTACTTTGCCGGGTTGGGG | |
| | GGGAGGTAGGGGCTATCAAACCTCATGATTGGCCGCACAC | |
| | AAAGGTGTGAGTATGTGTATATTTGAGGGTGGGTGGGAGT | |
| | GGCACTTTCACTAGGCCTCCGTATCACTCTCTGACTGGGGT | |
| | ATCTCCCAGCAAGCGAGACAGAGGCAGACACGCTTCCCA | |
| | GACTGTCTTACTGGGTCTCTCTGTGTTATTCTCTGCAGTGT | |
| | CTGTGTGTATCGTGCCATTTTCTATGTTTTGCACCAATCTG | |
| | CTGTGAGTGTCCTCAGGTGACCTGGGGGCAGGTTTTTAGT | |
| | GCCTGAGCCTACCCGTCTCCAGGCTTTAGTTTCCCCCTGTA | |
| | AAAGTATAGGAGTTGGTTCAAGAGAAGGTTCCTCTAGAAG | |
| | CCTTGAGCCTGTGAACCGTCTAGTCTCCGGGTATTTGTGG | |
| | GACACACAGAAAAAGCCCCACGACCCAACAGGTAGAACA | |
| | CTGGCTGAAATCAGCAGGGCAGAGCTGAGACAGGCTCAA | |
| | GTAGGCTGAGGGGTAGGGAGGTTTTGGGTGAATGGGAGG | |
| | GAGGGACAGAGAGAAGGAGGATATATTGCAGTAGGAGGA | |
| | GTTGCTGGAACAAAAGGAGGGGTGGTAGGAGTGGCTTGG | |
| | GGTGGCAGCAGAAGACGCCCTGTCACATGGCGGGAAGTC | |
| | AGCCTGGGCAGAGGTCTAGGTGTCCAGGAGGGGCTGGGT | |
| | GTGGTGGCTCACGCCTGTAATCCCAGGACTTTGGGAGGCT | |
| | GATGCAGGAGGATCACGTGAGGTCAGGAGTTCAAGACCA | |
| | GCCTGGCCAACATGGCGAAACCCTATCTCTACTAAAAATG | |
| | CCAAAAATTAGCTGGGTGTGGTGGCAGGCGCCTGTAATCC | |
| | CAGCTACTCTGGAGGCTGAGGCACAAGAATTGCTTGAACC | |
| | TGGGAGGTGGAGGTTGCAGGGAGCCGAGATCGCGCCACT | |
| | CTACTCTAGCCTGGGCAACACAGTGAGACTCTGTCTCAAA | |
| | AATAATAATAATAGGGGCTGGGCGCGGTGGCTCATGACTG | |
| | TAATCCCAGCATTTTGGGAGGTGGAGGCGGGTGGATCACC | |
| | TGAGGTCAGGAGTCCGAGACCAGCCTGGCCAACATGGCA | |
| | AAACTCCGTCTCTACTAAAAATAGAAAAATTAGCTAGGCA | |
| | TGGTGGTGCAGGCCTGTAATCCAGCTACTCGGGAGGCTGA | |
| | GAAGCAGGAGAATCACTTGAACCTGGGAGGTGAAGGTTG | |
| | CAGTGAGATCACCTGGGCGACAGAATGAGACTCCACCTCA | |
| | AAATAATAATAATAGTAATAATAATAAATGAAAAATTTTA | |
| | AAATTAAACAATTAAAAATTTTAAATTAAAATTAAACAAA | |
| | TTAGATGCCCAGGAGGATACAGGAGAGCATTTGCCACCA | |
| | GGCGGACTCCCTGTACCCACCCGGCCACAGGGGGCGATGT | |
| | TCCTGGGAGACAGGAAATGCCCAGGGGCTGGGAGACCCT | |
| | CTGCTCTTCTGCTCCCTTCCTGTGTGCTGCCTGGCAATGGG | |
| | GAACTCTGAGGGCTGGTGAGCAGGGCTGCTGAGGAGTGG | |
| | GTCTAAGGAGTCCCTGCAGGGCTGGGCCAGCTCCTCCACC | |
| | TCCCCTTTGTCTTCCCCTCCCACTTGTTATTTTTAGCTACAG | |
| | TGTCTGTCCCTCTTGCTTCTCCCCCAGATTGGGAGAGGAA | |
| | ACGGAGGCCTCTCCCTCCGGGCCTAGCCTGTTGCCCCCAG | |
| | CAACCGGGCCCAAACAGGCCTGTGGCCGGCCCTGGCTTCC | |
| | ATATCTGGCATCAGAGTTGGGCTGAGCAGGGTGACTCAGA | |
| | GGGTGGGTCAGCGCCTGGCCCGGTGCCCACCTAGCCCCTT | |
| | TGCTGTGCTGGTGCCTTTCTTCCCCAAACAGCCCCAAGGG | |
| | CCCGGGCCTGCTGCAGCTGGGGAGCCGGACTTCCTTGTCC | |
| | CACCAGGCACAGCTCTTCAGACCCCTGCCTTGGGTCACAT | |
| | TTGCAAGTGCCAACTCTCATTTCTACCTTATTCTTTTCCTCT | |
| | CTGTTCCCCTCCCCACCCCCTCTCTTCCCTCTTTCTGAGATC | |

TABLE 1-continued

List of exemplary Lamin A and/or Lamin C nucleic acid sequences.

| SEQ ID NO: | Nucleic Acid Sequence | Name |
|---|---|---|
| | AGATTTGCCAGTGATGGGAAGAGTTAGAAACAGGATGCC | |
| | CAGCCCTTCTCGCCTCAAGAGGCCACTGGGATGCAGCCAC | |
| | TCCTGTGCTTGGGGAACCTGGAGGATGCAAGGGAAAGGA | |
| | CTGGCACTCTGCTGGCACAGCACCCGGCCTGGGGCAGGAC | |
| | ACGGGCGAAGCCAGGGTCTCCCCTGTGAGCACTAGAGGA | |
| | TTTCCCGACCCCTGCCCGGGTATTGTGTGCCTGAGCATGA | |
| | GTCACCTGAGGGGCCCAGGTTCCCACCCTTCCCAGCTCCT | |
| | CTGGCCTGCCCCACCCTGTCCTCCCTGCCAACCCAGCACG | |
| | GGGACGGCACTCAGCGTGTGCTCAGCTTTCCTGATGCCAA | |
| | CCCCCAGTGGAGTGGGCTGCACCACCACCCTGGGACCGAA | |
| | TGCCTGGCTAGGGTCTACTTTGGTCCCTGCTAGGTCTGAG | |
| | GACCCCTCCTAGGAAGGAAATGGCACTTGGGGGCGGGGG | |
| | CAGGGAGGAGGGAGGAGAGACACTGGGCTCTACTGTACC | |
| | CCTAGTCATCTCTTGGGGTGTGCGTGTGGCTCCCTGGCCAC | |
| | AGAGCTCCCAAGGTCTGAGTCATGAGCCCATGGGTGATAG | |
| | TGGCTTCTTCCCCGCAGATGGGAGCTCCCCGTGCCTAAGA | |
| | AAACCACAAAGGTTCTTCCTCACTTCCCTCTCTGCTCGTGG | |
| | TTTTTCTCATCTGCAGGGTGTGTCTTAGTCCTTTAATCTCCT | |
| | CTCTTTGCAGTGCTAGTCAAAACCTCCACCAGGGAAAGAC | |
| | AAATAACCCCCTTACTGTTTTTTTTTTTTTTTTTTTTTTTTT | |
| | TGAGATGGAGTCTCGCTCTGTCACCCATGCTGTAGTGCAG | |
| | TGGCACAATCTCGGCTCACTGCAACCTCCGCCTCCCAAGT | |
| | TCAAGTGATCCTCCTACCTCAGCCTCCTCAGTAGCTGGGA | |
| | CTACAGGTGCACACCACCGTACCCAGCTAAATTTTTTTTT | |
| | TTTTTTTTGAGATAGAGTCTCACTCTGTCACCCAGGCTGGA | |
| | GTACAGTGGTACAATCTCAACTCACTACAATCTCCGCCTC | |
| | CCAGGCTCAAGCAATTCTCGTGTCTCAGCCTCCCAAGTTG | |
| | CTGGGACTATGGACGTGCACCACCTTGCCCGACTAATTTT | |
| | TGTATTTTTGATAGAGTCAGAGTTTCACCATGTTGGCAGG | |
| | CTGGTCTCGAACTCCTGGCCTCAAGTGATCCACCTGCCTTG | |
| | GCCTCCCAAAGTGCTGGGATTACAGGTGTGAGCCACCACA | |
| | CTCAGCCAGCCCCCTTACTTTCCTTGGAGACCATATACTGT | |
| | GGCTTGTGCCAAAGTGGTACAGCATGGATTTCCAGCTCCC | |
| | CTATCTACTTGCTGCGGGACCCTAGATATAGCTTTCTGTGC | |
| | CTATTTCCTCAATTGCATAGGAATAGCACCTATCGCATAG | |
| | GGTAGCTGTGAAGATGACGTGAGTTAACATAATATTTAGA | |
| | GCAGTGCTTGGTACCTAATAAGCTCTATATAAGTGTTTGCT | |
| | ATTATATTATTATTATCACTGCCACCACCGCTTTTGCAAGC | |
| | AGCAGAAGGTGAAGAGGTTAGACTGAAGAAAAAACTTCT | |
| | GTGCTCATCAGCCCATAAGCTCGCAGAGCACAGGGATCAT | |
| | GCATCTATGTTTTCCTCAGTCAGTGTCTGCCAGGCACTGGC | |
| | AAGGAAAGGCTGTTACCAGGGGGAACTCCAGGAATTCCT | |
| | CCTGGCACCTAAGGAGGCTGGGGAGACAGGACTAGGGAA | |
| | AAGGTGCCCTTGAGACACCTTCTGAAATCATCCCATTGCC | |
| | TTCCAGCTTCTTTCAGCTCAGGCTGGCTGGTCAGGGAAAC | |
| | GCTTTGTGCCATAGTGTCTGCCCTCTTCCTCCTCCTGGCTT | |
| | CTCCATTCTCTCTGGAACTTGTGGCTTAGGAAAGCAGTGA | |
| | GGTGGAGGAGGAGGAACCCTAGATCAGCAGCTAGAATTG | |
| | ACTGGAATGCTGCTGCTGGCTTTCGGTAATTGACACTGGG | |
| | CCATTCACCTTCCTCCTTTGCACCTCAGTTTCCTCATCTAT | |
| | AAAAGGGAGAGGGTTGAGCTGAATCAACTCTAAGCTCCTT | |
| | CTAGTTCTCTAAATTCTGAGAGCCTCCTAGTACAGCCAGC | |
| | AGCAGCCATTAGCCTTCAGGGTAGAGAGGCCTCTTCTGGG | |
| | AAGCCCCAGCCAGCCTGGGGGTCAGCCCAAGGAGCTCGG | |
| | AATCTAAGTTGCCCCAGTTGCTTCACTTTACCAGCGGTTTT | |
| | TCTTCATTTTCCCTCCTCCCCCTGCAGCTGCTTCAGCTTCG | |
| | GAAAAGTTCTGAAGTCATGGAAAGTTGGGGCTGTGCTCCC | |
| | AGCCAGGGGCTAGGCCGGATGGCAGCCAAAACCTGAGCT | |
| | GGGTTTTGACTTTATTTTTAGCTTTTCTGACTGAGACAGAG | |
| | GAGGGAATACATTCTCCGGTTCTGGAAGGGGCTCTTTTTT | |
| | GCAGGAGACAGACACTTACATTAAACAACTTGTTCTGAGG | |
| | TGTGGCCAGAGGCCTGGACTGAGCAAGTGTGCAGGCTGG | |
| | GGGAGCTTCCTCTGGCTTCTCATGTCCTTCCCCTGCCCCTC | |
| | TGAGTGTCACTCTATCCTCCTCCCTGCCTGGTGGGGGGAG | |
| | GTGGGGGTGACTCCTTTTTTGGACTCTCCTAAGCAGAACA | |
| | CTGCCTGGGTCTCGTCCTCCAGAGCTTCTGCAAATCTAGCC | |
| | TTCCCTATCCCTCTTCACAGTGAATTGCTGGGCCTCTTGGA | |
| | GTTTAGGACTTTTGTGGTAGAAGAAAAATGTTGGCAGGGC | |
| | TGCTTTTCTCCTTTCCAGGATAGATTTTTCCTTCTGCCCAC | |
| | GCTTGGTTTTCCTTTTTTCCATCTGCTGTGGTGGGCTCATG | |
| | CTTAAGCACTGATGAGTTACAGATGGCAGCTGGAACCAGG | |
| | TCCTCTGGATCTTTCCCTCCGCTCCCTGGGTCTGCTGCTTT | |
| | CTCTCACCCTATATTTGTGAAGCAATTGTAACATCTAGAA | |
| | AGTTCTTGGGTTCTCTGGAGGTTTTTAAGAAAATAGGACC | |
| | TTTCTATTTCTCCAGTCCACTAGCAAAAATAATCAGGGGC | |

TABLE 1-continued

List of exemplary Lamin A and/or Lamin C nucleic acid sequences.

| SEQ ID NO: | Nucleic Acid Sequence | Name |
|---|---|---|
| | CCAGAAAAGGTGAGGGAGGTGGCAGAGGCAGCGCTGTTC GACTGGTTATAGCTAAAGCTTTACCCACTTTGAGGAGCAG GGAGGCTTAAAGCTGGGGCCCAGATGGACCTGGAGGCCT GGGATCCACATCTGGAACCAGATGCTGAGGCTATGGTAGA TGGGTAGGGCTCAGCCTTCTCCCAGGGCACGGATGAGGCA GGAGGGAGGGAGGCAGGGACCCCTCTGTTCAGTGCAGAT CAGGGCACCCAGACTGGGTCCTGAGAAAGGAAAGGGTCA ATATTGTGCCTGGTCATCCTTGTCTGAGGTCCCTCTGAGCT CTAACCAGACTTTCCTTCCCCACAGTCCCACATGTGTAAA AGGGACTAGGAGAGGTGACCAGTACCTTTGGGGCTCAGA TCGAGAAGTGCTAGGGACATGTGGGCCATGAGCTTAGTTG TCAGGCTCCTCAGAGGGAGGGAAGCTTGGCCAAAGGGAA GTGAGTAGAGTCCAGGGAGAAGGCTAAGTAAGGCCCTGT GTGGGAAGGGGCAGGAGACAAAGGTACCCCTGTCTCTTTG GGAAAGAATGGGAGGAGAGAGAGGGAAAAGCATTCATAT CACGGGGTAGAGCTCTGCCCTTGGCCCCAGGCACGTTCCT GAGCCCTGAGTCATGGGAAGGGTGGAGAAGCAGGAAGGG GGTTTTCAAGGACCTTGGGGAGGTGGGAGCCCAGCCCCAG AGGCAAGCAGATGCAAACCAACCTAATGCAAGGATGCCC TCTCCTGGTAATTGCAGGCATAGCAGCGCCAGCCCCCATG GCTGACCTCCTGGGAGCCTGGCACTGTCTAGGCACACAGA CTCCTTCTCTTAAATCTACTCTCCCCTCTCTTCTTTAG | |
| 71 | GTGAGGCCACCCTGCAGGGCCCACCCATGGCCCCACCTAA CACATGTACACTCACTCTTCTACCTAGGCCCTCCCCCATGT GGTGCCTGGTCTGACCTGTCACCTGATTTCAGAGCCATTC ACCTGTCCTAGAGTCATTTTACCCACTGAGGTCACATCTTA TCCTAATTTGGCTGCCAATGGGATCTACCACAGTGAATTT AAAATAATCCAGGAGGCCGGGCATGGTGGTTCACGCCTGT AATCCCAGCACTTTAGGAGGCCGAGGTGGGCCGATCACG AGGTCAGGAGATCGAGATCATCCTGACTAACATGGTGAA ACCCCGTCTCTACTAAAAATACAAAAAATTAGCCTGGCAT GGTGGCGGGCGCCTGTAGTCCCAACTACTCGGGAGGCTGA GGCAGGAGAATGGCGTGAGCCTGCGAGGCAGAGCTTGCA GTGAGCTGAGATCATGCCACTGCACTCCAGCCTGGGCAAC AGAGTGAGACTCCGTCTCAAAAAAATAATAATAATAATA ATAAAAATAATCCAGGCCATGTGTGGTGGCTCATGCCTGT AATCCCAGCATTTTGGGAGGCCAAGGAGGCAGGATTGCTT GAGTCCAGGAGTTTGAGACCAGCCTGGGCAACACAGACC CCATCTCTAGAAAATAAAAATTTAAAGAAATTAGCTGGGC ATGGTGGTGTGCACCTATAGTCCCAGCTACTTGGGAGGCT GAGGCAGGAGGATGGCTTGAACCTGAGAGGTCGAGGATA CAGTGAGCTGTGATTGCACCACTGCACTTCAGCCTGGGTG ACAGAGGGAAACCCTGTCTCTACATAAATAAATACATAAA ATAAAATAATCCACAAGCCATTTCTACTTAACTTTGCAAT GAACTGTACCTGACCCTAGATCCCTCCCAGTTTGGCCCTCC GGTATACAAGGGCCTCCTATAGGCCCTTGTGATTTCTCTG GGGAAAAGGAGGACTGGAGTTGATCATTTATTGAGGCCAT CAGAAGCGGATGGCTAATTACATATGGGACATGTGTTAAT AATGCTTTGTGTATATAGAGTGGCCTTTACTTTCAAAACAC TCTTCTCCAATTTATCATGTTAAAAGCTAGGAATTGGGCTG GGTGCAGTGGCTCACGCCTATAATCCCAGCACTTTGGGAG GCCAAGGCGGGTGGATCATTTGAGGTCAGGAGTTTGAGAC CAGTCTGACCAACATGGTTAAACTCCGTCTCTACTAAAAA TACAAAATTAGCCAGGCGTGGTGGCACACACCTGTAGTCC CAACAACTACTTGTGAGGCTGAGGCAGGAAAATCATTTGA ACCCAGGATCAGAGGTTGTGGTGAACTGAGATTGCACCAT TGCACTCCAGCCTGGGCAACAAGAGCAAAACTCTATCTCA AAAAAAATAAAAAATAGCCAGGCACGGTGGCTCATGCCT GTAATCCTAGCACTTTGGGAGGCAGAGGTGGGCAGATCAC CTGAGGTTAGGAGTTCGAGACTAGCCTGGCCAACATGGTG AAACCCCATCTCTACTACAAATACAAAAATTAGCTAGGCA TGGTGGCAGCCACCTGTAATCCCAGCTACTTGGGAGGCTG AGGCAGGAGAATCGCTTGAACCCGGGAGGTGGAGGTTGC AGTGAGCCAAGATCGGGTCACAGCACTCCAGCCTAGGCA ACAGAGCGAGACTCCATCTCAAAAAAACATAAATAAATA AAAATAAAAATAAATAATAAATAAAAGCTAAGAATCAAA GAAGCAGTTTATTCCTAATTTCACAGTCTCATCTGTTCATA GTGGGGCCAGGATTAGAGTCAGTGGCCAAGCTTCCATCCT GGGTTCTTTCCCTTCCCAGGCCCTACCATCATAGTATACCA GGGAAAGACCTGGAGAAGCCAGCAGGTTGACCACCGAAC CAAGGCTGGGCCACCTTCCTCCTGGGTCTGGTCTCCAGCC TCCCAGTTGTACCCTTCCCCCAGCCCTTCCTGGATGCACTG ATCAGCCTGTGCTTCCTTGCCCTGTTTTTCTTTATAAATAG AGCCATGTTCTCCTCTCTCTCTCTCTCTTTTTTTTTTTTTTT | Intron 2 of lamin A and lamin C |

TABLE 1-continued

List of exemplary Lamin A and/or Lamin C nucleic acid sequences.

| SEQ ID NO: | Nucleic Acid Sequence | Name |
|---|---|---|
| | TTTTGAGATGGAGTCTTACTCTGTCACCCAGGCTGGAGTG<br>CAATGGCACGATCTCAGCTCACTGCAACCTCTGTCTCCCA<br>GGTTCAAGCAATTCTCCTGCCTCAGCCTCCCGAGTAGCTG<br>GGATTACAGGTGCCCACCACCATGCCCAGCTACTTTTTGG<br>ATTTTTAGTAGAGACAGGGTTTCACCATGTTGGTCAGGCT<br>GGTCTTGAACTCCTGACCTTAGGTGTTCTGCCCGCCTCAGC<br>CTCCCAAAGTGCTGGGATTACAGGCGTGAGCCACCACGCC<br>TGGCAAGACGTGTTCTCTCTATGTTGTTGAGGCTGGTCTTG<br>AACTCCTGGCTGCAAGAGATCTTCCTGCCTCAGCCTCCCA<br>ATGTGCTGGGATTATAGGCATGAGCCACCACACTTAGCCC<br>AGCCTGTGCTTTCTTAAATGAAAATCTAAGCATACGGCTG<br>GGTGTGGTGGCTCACGCCTGTAATCCCAGCATTTTGGGAG<br>GCCAAGGTGGGCAGATCACGAGGTCAGGAGATCGAGACT<br>ATCCTGGCCAACATGGTGAAACCCTGTCTCTACTAAAGAT<br>ACAAAAATTAGCTGGGTGTGGTGGCCCATGTCTGTAGTCC<br>CAGCTACTCGGGAGACTGAGGCAGGAGAATGGCATGAAC<br>CTGGGAGGCAGAGCTTGCAGTGAGCTGAGATCGCGCCACT<br>GCTCTCCAGCCTAGGTGACAGAGCGAGACTCCATCTCAAA<br>AAAAAAATAAAAATAAAAAAAAGAAAATCTAAGCGTGGT<br>GCTCCCCTGCTCAAACATCCTCAGGTTCTTTTCATGGCAGA<br>TAAGGGCATCTCTTCATGAGCCAGCCCCTGCCTACTGACC<br>CAGCCACCTCTCCCATCCCTTCCCACCCCGTACTTCAGGCT<br>TCAGCAGTACTGATCTTTCCAAAGACCCCAGAACACACAT<br>GCCTTCATACCTCTGTGCCTGTACATGCTTGTTTCTGCCCT<br>TGAAATCATGACAGTAGCTCTCTGTAGGCCCCGCTAGCCT<br>GTCCCTTGGGTCTTAGCCTCTTGGAGGCCTTCCCAGAGCCC<br>CCCAAAAGTACCCCAGGCATACTTTGGTTCCTTCTCTCATG<br>TCCCCTCAGTACTTTGCACATACCTCCTTTATAGCAGTTGC<br>TATGTTGTGCCAGAGAAGGGAGTCCTGTGGCTGGGGGGCA<br>TATATCTTTTCTTTTTGAGACAGAGTCTAGCTGTGTCACCC<br>AGGCTGGAGTGCAGTAGTGCGATCTCGGCTCACTGCAACC<br>TCCACCTCCTGGATTCAAGCGATTCTTGTGCCTCAGCCTCC<br>TGAGTAGCTGGGACTACAGGCGTGTGCCACCATCATGCCT<br>GGCTACTTTTTTGTATTAGATATATATATTTTCTCTCTTAGCA<br>CAGTACCTACCAAGAGTGAGTGAGTAGATGTCCTGACCCC<br>TGCAGGCATCCAAGGCCCTCCTTCCCTGGACCTGTTTCCAC<br>ATGTGTGAAGGGGTGCACAGGCAGCAGCCCACCTCTCAGC<br>TTCCTTCCAGTTCTTGTGTTCTGTGACCCCTTTTCCTCATCT<br>CTGCCTGCTTCCTCACAG | |
| 72 | GTGGGGACTGTGCTTTGCAAGCCAGAGGGCTGGGGCTGG<br>GTGATGACAGACTTGGGCTGGGCTAGGGGGGACCAGCTG<br>TGTGCAGAGCTCGCCTTCCTGAGTCCCTTGCCCTAGTGGA<br>CAGGGAGTTGGGGGTGGCCAGCACTCAGCTCCCAGGTTAA<br>AGTGGGGCTGGTAGTGGCTCATGGAGTAGGGCTGGGCAG<br>GGAGCCCCGCCCCTGGGTCTTGGCCTCCCAGGAACTAATT<br>CTGATTTTGGTTTCTGTGTCCTTCCTCCAACCCTTCCAG | Intron 3 of lamin A and lamin C |
| 73 | GTGCTTGCTCTCGATTGGTTCCCTCACTGCCTCTGCCCTTG<br>GCAGCCCTACCCTTACCCACGCTGGGCTATGCCTTCTGGG<br>GATCAGGCAGATGGTGGCAGGGAGCTCAGGGTGGCCCAG<br>GACCTGGGGCTGTAGCAGTGATGCCCAACTCAGGCCTGTG<br>CCTCCACCCCTCCCAGTCACCACAGTCCTAACCCTTTGTCC<br>TCCCCTCCAG | Intron 4 of lamin A and lamin C |
| 74 | GTGATACCCCACCTCACCCCTCTCTCCAGGGGCCTAGAGT<br>CTGGGCCGGATGCAGGCTGGAAGCCCAGGGTTGGGGGTG<br>GGGGTGGGGGTGGGAGGTTCCTGAGGAGGAGAGGGATGA<br>AAAGTGTCCCCACAACCACAGAGAAGGGTCGCAGGATGT<br>GGAGTCAGATGGCCTGTGTGCTGTTTCTGTACACTCTTACC<br>TCACCTTCACTTCTCAGGGCTTTGGTTTTCCCATTCGAAAA<br>TGGAGGCTGTTCTTAATCTCCCTAACTCAGAGTTGCCACA<br>GGACTCTGCAATGTGAGGTGTTAAAAGCATCAGTATTTTT<br>CTAGTTGGCTGTGCTATTTGTGACAGGAGAAAAAGTCTAG<br>CCTCAGAACGAGAGGTTTCAGTTAGACAAGGGGAAGGAC<br>TTCCCAGTTGCCAGCCAAGACTATGTTTAGAGCTTGTGAT<br>GTTCAGAGCTGGCTCTGATGAGGGCTCTGGGGAAGCTCTG<br>ATTGCAGATCCTGGAGAGAGTAGCCAGGTGTCTCCTACAC<br>CGACCCACGTCCCTCCTTCCCCATACTTAGGGCCCTTGGG<br>AGCTCACCAAACCCTCCCACCCCCCTTCAG | Intron 5 of lamin A and lamin C |

TABLE 1-continued

List of exemplary Lamin A and/or Lamin C nucleic acid sequences.

| SEQ ID NO: | Nucleic Acid Sequence | Name |
|---|---|---|
| 75 | GTGGGCTGGGGAGACGTCGGGGAGGTGCTGGCAGTGTCC TCTGGCCGGCAACTGGCCTTGACTAGACCCCCACTTGGTC TCCCTCTCCCCAG | Intron 6 of lamin A and lamin C |
| 76 | GTAGGCTCCTGCTCAGGGTCTAAGGGGATACAGCTGCATC AGGGAGAGAGTGGCAAGACAGAAGGATGGCATGTGGAGA GAGGAACATCCTTGCCCTCAGAGGGTGGACCAGGGTGAG CCTGTATATCTCCTCCACACTCTGGTTCCAGGCCTGGCTCC TGGACTCTTTGGCTGTGAGACCTTGAGCAGGTTATTTAAC CTCTCAGAGCATCAGTTTCCTCATCTGTAAAATGGGGATG AATACTGATCCCTAAGTCTTTGAGTTGTCAGGAAGATGAA AGATAAGGTATCCGTGTGCCTGGTGCTGCGTATGTGTCCA CAGATCATGGCTATTATCCCCGGGGGAAGGGCAGTGACA GGGGTGTGTGTAGATGGAAGGAGAGGCCTCAATTGCAGG CAGGCAGAGGGCTGGGCCTTTGAGCAAGATACACCCAAG AGCCTGGGTGAGCCTCCCCGACCTTCCTCTTCCCTATCTTC CCGGCAG | Intron 7 of lamin A and lamin C |
| 77 | GTGAGTGGCAGGGCGCTTGGGACTCTGGGGAGGCCTTGG GTGGCGATGGGAGCGCTGGGGTAAGTGTCCTTTTCTCCTC TCCAG | Intron 8 of lamin A and lamin C |
| 78 | GTAAGTAGGCCTGGGCCTGGCTGCTTGCTGGACGAGGCTC CCCCTGATGGCCAACATCGGAGCCAGCTGCCCCCAACCCA AGTTTGCCAATTCAGGGCCCCTTTCTAGAGCTCTCTGTTGC AGGCTCCAGACTTCTCCACCCAGTAGGCAAACCAAAAGAT GCTTCCTCAACAGCACAAGGGGTGGAAGTTAGACAGTGA GGATTGTTAAAGGCAGAGCCATACTCCTACCCGGAGAGCT TGACAGTGTCCCTCTGGGGTGGAAATGAGTTCCTTAGCTC CATCACCACAGAGGACAGAGTAAGCAGCAGGCCGGACAA AGGGCAGGCCACAAGAAAAGTTGCAGGTGGTCACTGGGG TAGACATGCTGTACAACCCTTCCCTGGCCCTGACCCTTGG ACCTGGTTCCATGTCCCCACCAG | Intron 9 of lamin A and lamin C |
| 79 | GTGAGTGGTAGCCGCCGCTGAGGCCGAGCCTGCACTGGG GCCACCCAGCCAGGCCTGGGGGCAGCCTCTCCCCAGCCTC CCCGTGCCAAAAATCTTTTCATTAAAGAATGTTTTGGAAC TTTACTCGCTGGCCTGGCCTTTCTTCTCTCTCCTCCCTATAC CTTGAACAGGGAACCCAGGTGTCTGGGTGCCCTACTCTGG TAAGGAAGGGAGTGGGAACTTTCTGATGCCATGGAATATT CCTGTGGGAGCAGTGGACAAGGGTCTGGATTTGTCTTCTG GGAAAGGGAGGGGAGGACAGACGTGGGGCATGCCCGCCC TGCCTCTCTCCCCCATTCTTGTTGCATGCATATCCTCTCATT TCCCTCATTTTTCCTGCAAGAATGTTCTCTCTCATTCCTGA CCGCCCCTCCACTCCAATTAATAGTGCATGCCTGCTGCCCT ACAAGCTTGCTCCCGTTCTCTCTTCTTTTCCTCTTAAGCTC AGAGTAGCTAGAACAGAGTCAGAGTCACTGCTCTGGTTCT CTGTCCCCAAGTCTTCCTGAGCCTTCTCCCCTTTTATGTCTT CCCTCTCCTCCTCCGGGCCCCTAGCCTCCCAAACCCCCATT GCCCGCTGGCTCCTTGGGCACAGAACCACACCTTCCTGCC TGGCGGCTGGGAGCCTGCAGGAGCCTGGAGCCTGGTTGG GCCTGAGTGGTCAGTCCCAGACTCGCCGTCCCGCCTGAGC CTTGTCTCCCTTCCCAG | Intron 10 of lamin A |
| 80 | GTGAGTTGTCTCTGCTTTGTCTCCAAATCCTGCAGGCGGGT CCCTGGTCATCGAGGGGTAGGACGAGGTGGCCTTGCAGG GGGGAGAGCCTGCCTTCTCTTCCGCAGCCCGGGGGAGTGG GAGCCTCCTCCCCACAGCCTGAGTCCTAGACAGCCCACCT CTGCATCCTGCCCCTCTTGTCTGAGCCCCAGACTGGAGGG CAGGGGCAGGGCTGGAGTGTGAGGGATGGGGGAGATGCT ACCTCCCTTCTAGGGGCCAGGGGAGGGAGGGTCTGGGTCC AGGCCCTGCTGCTCACACCTCTCTCCTCTGTTTTCTCTCTT AG | Intron 11 of lamin A |
| 81 | ATGGAGACCCCGTCCCAGCGGCGCGCCACCCGCAGCGGG GCGCAGGCCAGCTCCACTCCGCTGTCGCCCACCCGCATCA CCCGGCTGCAGGAGAAGGAGGACCTGCAGGAGCTCAATG ATCGCTTGGCGGTCTACATCGACCGTGTGCGCTCGCTGGA AACGGAGAACGCAGGGCTGCGCCTTCGCATCACCGAGTCT GAAGAGGTGGTCAGCCGCGAGGTGTCCGGCATCAAGGCC | Exon 1 of lamin A and lamin C |

TABLE 1-continued

List of exemplary Lamin A and/or Lamin C nucleic acid sequences.

| SEQ ID NO: | Nucleic Acid Sequence | Name |
|---|---|---|
| | GCCTACGAGGCCGAGCTCGGGGATGCCCGCAAGACCCTTG ACTCAGTAGCCAAGGAGCGCGCCCGCCTGCAGCTGGAGCT GAGCAAAGTGCGTGAGGAGTTTAAGGAGCTGAAAGCGCG | |
| 82 | CAATACCAAGAAGGAGGGTGACCTGATAGCTGCTCAGGC TCGGCTGAAGGACCTGGAGGCTCTGCTGAACTCCAAGGAG GCCGCACTGAGCACTGCTCTCAGTGAGAAGCGCACGCTGG AGGGCGAGCTGCATGATCTGCGGGGCCAGGTGGCCAAG | Exon 2 of of lamin A and lamin C |
| 83 | CTTGAGGCAGCCCTAGGTGAGGCCAAGAAGCAACTTCAG GATGAGATGCTGCGGCGGGTGGATGCTGAGAACAGGCTG CAGACCATGAAGGAGGAACTGGACTTCCAGAAGAACATC TACAGTGAG | Exon 3 of lamin A and lamin C |
| 84 | GAGCTGCGTGAGACCAAGCGCCGTCATGAGACCCGACTG GTGGAGATTGACAATGGGAAGCAGCGTGAGTTTGAGAGC CGGCTGGCGGATGCGCTGCAGGAACTGCGGGCCCAGCAT GAGGACCAGGTGGAGCAGTATAAGAAGGAGCTGGAGAAG ACTTATTCTGCCAAG | Exon 4 of of lamin A and lamin C |
| 85 | CTGGACAATGCCAGGCAGTCTGCTGAGAGGAACAGCAAC CTGGTGGGGGCTGCCCACGAGGAGCTGCAGCAGTCGCGC ATCCGCATCGACAGCCTCTCTGCCCAGCTCAGCCAGCTCC AGAAGCAG | Exon 5 of of lamin A and lamin C |
| 86 | CTGGCAGCCAAGGAGGCGAAGCTTCGAGACCTGGAGGAC TCACTGGCCCGTGAGCGGGACACCAGCCGGCGGCTGCTGG CGGAAAAGGAGCGGGAGATGGCCGAGATGCGGGCAAGG ATGCAGCAGCAGCTGGACGAGTACCAGGAGCTTCTGGAC ATCAAGCTGGCCCTGGACATGGAGATCCACGCCTACCGCA AGCTCTTGGAGGGCGAGGAGGAGAG | Exon 6 of of lamin A and lamin C |
| 87 | GCTACGCCTGTCCCCCAGCCCTACCTCGCAGCGCAGCCGT GGCCGTGCTTCCTCTCACTCATCCCAGACACAGGGTGGGG GCAGCGTCACCAAAAAGCGCAAACTGGAGTCCACTGAGA GCCGCAGCAGCTTCTCACAGCACGCACGCACTAGCGGGCG CGTGGCCGTGGAGGAGGTGGATGAGGAGGGCAAGTTTGT CCGGCTGCGCAACAAGTCCAATGAG | Exon 7 of of lamin A and lamin C |
| 88 | GACCAGTCCATGGGCAATTGGCAGATCAAGCGCCAGAAT GGAGATGATCCCTTGCTGACTTACCGGTTCCCACCAAAGT TCACCCTGAAGGCTGGGCAGGTGGTGACG | Exon 8 of of lamin A and lamin C |
| 89 | ATCTGGGCTGCAGGAGCTGGGGCCACCCACAGCCCCCCTA CCGACCTGGTGTGGAAGGCACAGAACACCTGGGGCTGCG GGAACAGCCTGCGTACGGCTCTCATCAACTCCACTGGGGA A | Exon 9 of of lamin A and lamin C |
| 90 | GAAGTGGCCATGCGCAAGCTGGTGCGCTCAGTGACTGTGG TTGAGGACGACGAGGATGAGGATGGAGATGACCTGCTCC ATCACCACCAC | Exon 10 of lamin A |
| 91 | GAAGTGGCCATGCGCAAGCTGGTGCGCTCAGTGACTGTGG TTGAGGACGACGAGGATGAGGATGGAGATGACCTGCTCC ATCACCACCACGTGAGTGGTAGCCGCCGCTGA | Exon 10 of lamin C |
| 92 | GGCTCCCACTGCAGCAGCTCGGGGGACCCCGCTGAGTACA ACCTGCGCTCGCGCACCGTGCTGTGCGGGACCTGCGGGCA GCCTGCCGACAAGGCATCTGCCAGCGGCTCAGGAGCCCA GGTGGGCGGACCCATCTCCTCTGGCTCTTCTGCCTCCAGTG TCACGGTCACTCGCAGCTACCGCAGTGTGGGGGGCAGTGG GGGTGGCAGCTTCGGGGACAATCTGGTCACCCGCTCCTAC CTCCTGGGCAACTCCAGCCCCCGAACCCAG | Exon 11 of lamin A |
| 93 | AGCCCCCAGAACTGCAGCATCATGTAA | Exon 12 of lamin A |

TABLE 2

List of certain amino acid sequences disclosed herein.

| SEQ ID NO: | Amino Acid Sequence | Name |
|---|---|---|
| 12 | METPSQRRATRSGAQASSTPLSPTRITRLQEKEDLQELNDRL AVYIDRVRSLETENAGLRLRITESEEVVSREVSGIKAAYEAEL GDARKTLDSVAKERARLQLELSKVREEFKELKARNTKKEGD LIAAQARLKDLEALLNSKEAALSTALSEKRTLEGELHDLRGQ VAKLEAALGEAKKQLQDEMLRRVDAENRLQTMKEELDFQK NIYSEELRETKRRHETRLVEIDNGKQREFESRLADALQELRA QHEDQVEQYKKELEKTYSAKLDNARQSAERNSNLVGAAHE ELQQSRIRIDSLSAQLSQLQKQLAAKEAKLRDLEDSLARERD TSRRLLAEKEREMAEMRARMQQQLDEYQELLDIKLALDMEI HAYRKLLEGEEERLRLSPSPTSQRSRGRASSHSSQTQGGGSV TKKRKLESTESRSSFSQHARTSGRVAVEEVDEEGKFVRLRNK SNEDQSMGNWQIKRQNGDDPLLTYRFPPKFTLKAGQVVTIW AAGAGATHSPPTDLVWKAQNTWGCGNSLRTALINSTGEEV AMRKLVRSVTVVEDDEDEDGDDLLHHHHGSHCSSSGDPAE YNLRSRTVLCGTCGQPADKASASGSGAQVGGPISSGSSASSV TVTRSYRSVGGSGGGSFGDNLVTRSYLLGNSSPRTQSPQNCS IM | Pre-lamin A sequence |
| 13 | METPSQRRATRSGAQASSTPLSPTRITRLQEKEDLQELNDRL AVYIDRVRSLETENAGLRLRITESEEVVSREVSGIKAAYEAEL GDARKTLDSVAKERARLQLELSKVREEFKELKARNTKKEGD LIAAQARLKDLEALLNSKEAALSTALSEKRTLEGELHDLRGQ VAKLEAALGEAKKQLQDEMLRRVDAENRLQTMKEELDFQK NIYSEELRETKRRHETRLVEIDNGKQREFESRLADALQELRA QHEDQVEQYKKELEKTYSAKLDNARQSAERNSNLVGAAHE ELQQSRIRIDSLSAQLSQLQKQLAAKEAKLRDLEDSLARERD TSRRLLAEKEREMAEMRARMQQQLDEYQELLDIKLALDMEI HAYRKLLEGEEERLRLSPSPTSQRSRGRASSHSSQTQGGGSV TKKRKLESTESRSSFSQHARTSGRVAVEEVDEEGKFVRLRNK SNEDQSMGNWQIKRQNGDDPLLTYRFPPKFTLKAGQVVTIW AAGAGATHSPPTDLVWKAQNTWGCGNSLRTALINSTGEEV AMRKLVRSVTVVEDDEDEDGDDLLHHHHVSGSRR | Lamin C sequence |
| 14 | METPSQRRATRSGAQASSTPLSPTRITRLQEKEDLQELNDRL AVYIDRVRSLETENAGLRLRITESEEVVSREVSGIKAAYEAEL GDARKTLDSVAKERARLQLELSKVREEFKELKARNTKKEGD LIAAQARLKDLEALLNSKEAALSTALSEKRTLEGELHDLRGQ VAKLEAALGEAKKQLQDEMLRRVDAENRLQTMKEELDFQK NIYSEELRETKRRHETRLVEIDNGKQREFESRLADALQELRA QHEDQVEQYKKELEKTYSAKLDNARQSAERNSNLVGAAHE ELQQSRIRIDSLSAQLSQLQKQLAAKEAKLRDLEDSLARERD TSRRLLAEKEREMAEMRARMQQQLDEYQELLDIKLALDMEI HAYRKLLEGEEERLRLSPSPTSQRSRGRASSHSSQTQGGGSV TKKRKLESTESRSSFSQHARTSGRVAVEEVDEEGKFVRLRNK SNEDQSMGNWQIKRQNGDDPLLTY | Minigene 1 Lamin isoform A/C (exons 1-8) |
| 15 | RFPPKFTLKAGQVVTIWAAGAGATHSPPTDLVWKAQNTWG CGNSLRTALINSTGE | Minigene 1 Lamin isoforms A/C (exon 9) |
| 16 | EVAMRKLVRSVTVVEDDEDEDGDDLLHHHHVSGSRR | Minigene 1 Lamin isoform C (exon 10) |
| 17 | EVAMRKLVRSVTVVEDDEDEDGDDLLHHHH | Minigene 1 Lamin Isoform A (exon 10) |
| 18 | GSHCSSSGDPAEYNLRSRTVLCGTCGQPADKASASGSGAQV GGPISSGSSASSVTVTRSYRSVGGSGGGSFGDNLVTRSYLLG NSSPRTQ | Minigene 1 Lamin A exon 11 |
| 19 | SPQNCSIM | Minigene 1 Lamin A exon 12 |
| 20 | METPSQRRATRSGAQASSTPLSPTRITRLQEKEDLQELNDRL AVYIDRVRSLETENAGLRLRITESEEVVSREVSGIKAAYEAEL GDARKTLDSVAKERARLQLELSKVREEFKELKARNTKKEGD LIAAQARLKDLEALLNSKEAALSTALSEKRTLEGELHDLRGQ VAKLEAALGEAKKQLQDEMLRRVDAENRLQTMKEELDFQK NIYSEELRETKRRHETRLVEIDNGKQREFESRLADALQELRA | Minigene 2 Lamin Isoform A/C (exons 1-9) |

TABLE 2-continued

List of certain amino acid sequences disclosed herein.

| SEQ ID NO: | Amino Acid Sequence | Name |
|---|---|---|
| | QHEDQVEQYKKELEKTYSAKLDNARQSAERNSNLVGAAHE ELQQSRIRIDSLSAQLSQLQKQLAAKEAKLRDLEDSLARERD TSRRLLAEKEREMAEMRARMQQQLDEYQELLDIKLALDMEI HAYRKLLEGEEERLRLSPSPTSQRSRGRASSHSSQTQGGGSV TKKRKLESTESRSSFSQHARTSGRVAVEEVDEEGKFVRLRNK SNEDQSMGNWQIKRQNGDDPLLTYRFPPKFTLKAGQVVTIW AAGAGATHSPPTDLVWKAQNTWGCGNSLTALINSTGE | |
| 21 | METPSQRRATRSGAQASSTPLSPTRITRLQEKEDLQELNDRL AVYIDRVRSLETENAGLRLRITESEEVVSREVSGIKAAYEAEL GDARKTLDSVAKERARLQLELSKVREEFKELKARNTKKEGD LIAAQARLKDLEALLNSKEAALSTALSEKRTLEGELHDLRGQ VAKLEAALGEAKKQLQDEMLRRVDAENRLQTMKEELDFQK NIYSEELRETKRRHETRLVEIDNGKQREFESRLADALQELRA QHEDQVEQYKKELEKTYSAKLDNARQSAERNSNLVGAAHE ELQQSRIRIDSLSAQLSQLQKQLAAKEAKLRDLEDSLARERD TSRRLLAEKEREMAEMRARMQQQLDEYQELLDIKLALDMEI HAYRKLLEGEEERLRLSPSPTSQRSRGRASSHSSQTQGGGSV TKKRKLESTESRSSFSQHARTSGRVAVEEVDEEGKFVRLRNK SNEDQSMGNWQIKRQNGDDPLLTYRFPPKFTLKAGQVVTIW AAGAGATHSPPTDLVWKAQNTWGCGNSLRTALINSTGEEV AMRKLVRSVTVVEDDEDEDGDDLLHHHHGSHCSSSGDPAE YNLRSRTVLCGTCGQPADKASASGSGAQVGGPISSGSSASSV TVTRSYRSVGGSGGGSFGDNLVTRSY | Mature Lamin A Sequence |
| 22 | [Reserved] | |
| 23 | [Reserved] | |
| 24 | GSHCSSSGDPAEYNLRSRTVLCGTCGQPADKASASGSGAQV GGPISSGSSASSVTVTRSYRSVGGSGGGSFGDNLVTRSYLLG NSSPRTQSPQNCSIM | Minigene 2 Lamin Isoform A (exon 11-12) |
| 25 | [Reserved] | |
| 26 | [Reserved] | |
| 27 | [Reserved] | |
| 28 | [Reserved] | |
| 29 | [Reserved] | |

TABLE 3

List of exemplary regulatory element nucleic acid sequences

| SEQ ID NO: | Nucleic Acid Sequence | Length |
|---|---|---|
| 30 | GTAAGGTAAGAATTGAATTTCTCAGTTGAAGGATGCTTAC ACTCTTGTCCATCTAG | 56 bp |
| 31 | GTGTGTATGCTCAGGGGCTGGGAAAGGAGGGGAGGGAGC TCCGGCTCAG | 49 bp |
| 32 | GTGATGCGGTTTTGGCAGTACATCAATGGGCGTGGATAGC GGTTTGACTCACGGGGATTTCCAAGTCTCCACCCCATTGA CGTCAATGGGAGTTTGTTTTGGCACCAAAATCAACGGGAC TTTCCAAAATGTCGTAACAACTCCGCCCCATTGACGCAAA TGGGCGGTAGGCGTGTACGGTGGGAGGTCTATATAAGCA GAGCTGGTACCGTAAGGTAAGAATTGAATTTCTCAGTTGA AGGATGCTTACACTCTTGTCCATCTAG | 266 bp |
| 33 | GTGATGCGGTTTTGGCAGTACATCAATGGGCGTGGATAGC GGTTTGACTCACGGGGATTTCCAAGTCTCCACCCCATTGA CGTCAATGGGAGTTTGTTTTGGCACCAAAATCAACGGGAC TTTCCAAAATGTCGTAACAACTCCGCCCCATTGACGCAAA TGGGCGGTAGGCGTGTACGGTGGGAGGTCTATATAAGCA GAGCTGGTACCGTGTGTATGCTCAGGGGCTGGGAAAGGA GGGGAGGGAGCTCCGGCTCAG | 259 bp |

TABLE 3-continued

List of exemplary regulatory element nucleic acid sequences

| SEQ ID NO: | Nucleic Acid Sequence | Length |
|---|---|---|
| 34 | GTGATGACGTGTCCCATAAGGCCCCTCGGTCTAAGGCTTC CCTATTTCCTGGTTCGCCGGCGGCCATTTTGGGTGGAAGC GATAGCTGAGTGGCGGCGGCTGCTGATTGTGTTCTAG | 117 bp |
| 35 | GTGATGACGTGTCCCATACTTCCGGGTCAGGTGGGCCGGC TGTCTTGACCTTCTTTGCGGCTCGGCCATTTTGTCCCAGTC AGTCCGGAGGCTGCGGCTGCAGAAGTACCGCCTGCG | 117 bp |
| 36 | GTGATGACGTGTCCCATATTTTCATCTCGCGAGACTTGTGA GCGGCCATCTTGGTCCTGCCCTGACAGATTCTCCTATCGG GGTCACAGGGACGCTAAGATTGCTACCTGGACTTTC | 117 bp |
| 37 | GTGATGACGTGTCCCATGGCCTCATTGGATGAGAGGTCCC ACCTCACGGCCCGAGGCGGGGCTTCTTTGCGCTTAAAAGC CGAGCCGGGCCAATGTTCAAATGCGCAGCTCTTAGTC | 117 bp |
| 38 | GTGATGACGTGTCCCATCCCCCCTCCACCCCCTAGCCCGC GGAGCACGCTGGGATTTGGCGCCCCCCTCCTCGGTGCAAC CTATATAAGGCTCACAGTCTGCGCTCCTGGTACACGC | 117 bp |
| 39 | CCCCCCTCCACCCCCTAGCCCGCGGAGCACGCTGGGATTT GGCGCCCCCCTCCTCGGTGCAACCTATATAAGGCTCACAG TCTGCGCTCCTGGTACACGC | 100 bp |
| 40 | GGCCTCATTGGATGAGAGGTCCCACCTCACGGCCCGAGGC GGGGCTTCTTTGCGCTTAAAAGCCGAGCCGGGCCAATGTT CAAATGCGCAGCTCTTAGTC | 100 bp |
| 41 | GGGTGGGGCCCGCGCGTATAAAGGGGGCGCAGGCGGGCT GGGCGTTCCACAGGCCAAGTGCGCTGTGCTCGAGGGGTGC CGGCCAGGCCTGAGCGAGCGA | 100 bp |
| 42 | GGTGCGATATTCGGATTGGCTGGAGTCGGCCATCACGCTC CAGCTACGCCACTTCCTTTTCGTGGCACTATAAAGGGTGC TGCACGGCGCTTGCATCTCT | 100 bp |
| 43 | ACTTCCGGGTCAGGTGGGCCGGCTGTCTTGACCTTCTTTGC GGCTCGGCCATTTTGTCCCAGTCAGTCCGGAGGCTGCGGC TGCAGAAGTACCGCCTGCG | 100 bp |
| 44 | GCTGAGCGCGCGCGATGGGGCGGGAGGTTTGGGGTCAAG GAGCAAACTCTGCACAAGATGGCGGCGGTAGCGGCAGTG GCGGCGCGTAGGAGGCGGTGAG | 100 bp |
| 45 | ATTTTCATCTCGCGAGACTTGTGAGCGGCCATCTTGGTCCT GCCCTGACAGATTCTCCTATCGGGGTCACAGGGACGCTAA GATTGCTACCTGGACTTTC | 100 bp |
| 46 | TGGGACCCCCGGAAGGCGGAAGTTCTAGGGCGGAAGTGG CCGAGAGGAGAGGAGAATGGCGGCGGAAGGCTGGATTTG GCGTTGGGGCTGGGGCCGGCGG | 100 bp |
| 47 | AAGGCCCCTCGGTCTAAGGCTTCCCTATTTCCTGGTTCGCC GGCGGCCATTTTGGGTGGAAGCGATAGCTGAGTGGCGGC GGCTGCTGATTGTGTTCTAG | 100 bp |
| 48 | AGTGACCCGGAAGTAGAAGTGGCCCTTGCAGGCAAGAGT GCTGGAGGGCGGCAGCGGCGACCGGAGCGGTAGGAGCAG CAATTTATCCGTGTGCAGCCCC | 100 bp |
| 49 | GGGAGGGGCGCGCTGGGGAGCTTCGGCGCATGCGCGCTG AGGCCTGCCTGACCGACCTTCAGCAGGGCTGTGGCTACCA TGTTCTCTCGCGCGGGTGTCG | 100 bp |
| 50 | ACTGCGCACGCGCGCGGTCGCACCGATTCACGCCCCCTTC CGGCGCCTAGAGCACCGCTGCCGCCATGTTGAGGGGGGG ACCGCGACCAGCTGGGCCCCT | 100 bp |
| 51 | CCCTCGAGGGGCGGAGCAAAAAGTGAGGCAGCAACGCCT CCTTATCCTCGCTCCCGCTTTCAGTTCTCAATAAGGTCCGA TGTTCGTGTATAAATGCTCG | 100 bp |

TABLE 3-continued

List of exemplary regulatory element nucleic acid sequences

| SEQ ID NO: | Nucleic Acid Sequence | Length |
|---|---|---|
| 52 | CTTGGTGACCAAATTTGAAAAAAAAAAAAAACCGCGCCA ACTCATGTTGTTTTCAATCAGGTCCGCCAAGTTTGTATTTA AGGAACTGTTTCAGTTCATA | 100 bp |
| 53 | GGCTGAGCTATCCTATTGGCTATCGGGACAAAATTTGCTT GAGCCAATCAAAGTGCTCCGTGGACAATCGCCGTTCTGTC TATAAAAAGGTGAAGCAGCG | 100 bp |
| 54 | GGAAGTGCCAGACCGGAGGTGCGTCATTCACCGGCGACG CCGATACGGTTCCTCCACCGAGGCCCATGCGAAGCTTTCC ACTATGGCTTCCAGCACTGTC | 100 bp |
| 55 | CCCTCGAGGGGCGGAGCAAAAAGTGAGGCAGCAACGCCT CCTTATCCTCGCTCCCGCTTTCAGTTCTCAATAAGGTCCGA TGTTCGTGTATAAATGCTCG | 100 bp |
| 56 | CTTGGTGACCAAATTTGAAAAAAAAAAAAAACCGCGCCA ACTCATGTTGTTTTCAATCAGGTCCGCCAAGTTTGTATTTA AGGAACTGTTTCAGTTCATA | 100 bp |
| 57 | GGCTGAGCTATCCTATTGGCTATCGGGACAAAATTTGCTT GAGCCAATCAAAGTGCTCCGTGGACAATCGCCGTTCTGTC TATAAAAAGGTGAAGCAGCG | 100 bp |
| 58 | GGAAGTGCCAGACCGGAGGTGCGTCATTCACCGGCGACG CCGATACGGTTCCTCCACCGAGGCCCATGCGAAGCTTTCC ACTATGGCTTCCAGCACTGTC | 100 bp |
| 102 | GCGTTACATAACTTACGGTAAATGGCCCGCCTGGCTGACC GCCCAACGACCCCCGCCCATTGACGTCAATAATGACGTAT GTTCCCATAGTAACGCCAATAGGGACTTTCCATTGACGTC AATGGGTGGAGTATTTACGGTAAACTGCCCACTTGGCAGT ACATCAAGTGTATCATATGCCAAGTACGCCCCCTATTGAC GTCAATGACGGTAAATGGCCCGCCTGGCATTATGCCCAGT ACATGACCTTATGGGACTTTCCTACTTGGCAGTACATCTAC GTATTAGTCATCGCTATTACCATGGTCGAGGTGAGCCCCA CGTTCTGCTTCACTCTCCCCATCTCCCCCCCCTCCCCACCC CCAATTTTGTATTTATTTATTTTTTAATTATTTTGTGCAGCG ATGGGGGCGGGGGGGGGGGGGGGGCGCGCGCCAGGCGG GGCGGGGCGGGGCGAGGGGCGGGGCGGGGCGAGGCGGA GAGGTGCGGCGGCAGCCAATCAGAGCGGCGCGCTCCGAA AGTTTCCTTTTATGGCGAGGCGGCGGCGGCGGCGGCCCTA TAAAAAGCGAAGCGCGCGGCGGGCG | 584 bp |

TABLE 4

Additional nucleic acid sequences disclosed herein

| SEQ ID NO: | Nucleic Acid Sequence | Source/Genomic Location |
|---|---|---|
| 59 | GTGATGCGGTTTTGGCAGTACATCAATGGGCGTGGATAGC GGTTTGACTCACGGGGATTTCCAAGTCTCCACCCCATTGA CGTCAATGGGAGTTTGTTTTGGCACCAAAATCAACGGGAC TTTCCAAAATGTCGTAACAACTCCGCCCCATTGACGCAAA TGGGCGGTAGGCGTGTACGGTGGGAGGTCTATATAAGCA GAGCT | CMV Promoter |
| 60 | TCGAGGTGAGCCCCACGTTCTGCTTCACTCTCCCCATCTCC CCCCCCTCCCCACCCCCAATTTTGTATTTATTTATTTTTTAA TTATTTTGTGCAGCGATGGGGGCGGGGGGGGGGGGGGGG CGCGCGCCAGGCGGGGCGGGGCGGGGCGAGGGGCGGGGC GGGGCGAGGCGGAGAGGTGCGGCGGCAGCCAATCAGAGC GGCGCGCTCCGAAAGTTTCCTTTTATGGCGAGGCGGCGGC GGCGGCGGCCCTATAAAAAGCGAAGCGCGCGGCGGGCG | CBA Promoter |
| 61 | GCGTTACATAACTTACGGTAAATGGCCCGCCTGGCTGACC GCCCAACGACCCCCGCCCATTGACGTCAATAATGACGTAT GTTCCCATAGTAACGCCAATAGGGACTTTCCATTGACGTC AATGGGTGGAGTATTTACGGTAAACTGCCCACTTGGCAGT ACATCAAGTGTATCATATGCCAAGTACGCCCCCTATTGAC | CMV enhancer used upstream of CBA promoter |

TABLE 4-continued

| Additional nucleic acid sequences disclosed herein | | |
|---|---|---|
| SEQ ID NO: | Nucleic Acid Sequence | Source/Genomic Location |
| | GTCAATGACGGTAAATGGCCCGCCTGGCATTATGCCCAGT ACATGACCTTATGGGACTTTCCTACTTGGCAGTACATCTAC GTATTAGTCATCGCTATTACCATG | |
| 62 | GTACTTATATAAGGGGGTGGGGGCGCGTTCGTCCTCAGTC GCGATCGAACACTCGAGCCGAGCAGACGTGCCTACGGAC C | SCP |
| 63 | GGGGAGGCTGCTGGTGAATATTAACCAAGGTCACCCCAGT TATCGGAGGAGCAAACAGGGGCTAAGTCCACGCTAGCGT CTGTCTGCACATTTCGTAGAGCGAGTGTTCCGATACTCTA ATCTCCCTAGGCAAGGTTCATATTTGTGTAGGTTACTTATT CTCCTTTTGTTGACTAAGTCAATAATCAGAATCAGCAGGT TTGGAGTCAGCTTGGCAGGGATCAGCAGCCTGGGTTGGAA GGAGGGGGTATAAAAGCCCCTTCACCAGGAGAAGCCGTC | SerpE_TTR |
| 64 | GTTTGCTGCTTGCAATGTTTGCCCATTTTAGGGTGGACACA GGACGCTGTGGTTTCTGAGCCAGGGCTAGCGGGCGACTCA GATCCCAGCCAGTGGACTTAGCCCCTGTTTGCTCCTCCGAT AACTGGGGTGACCTTGGTTAATATTCACCAGCAGCCTCCC CCGTTGCCCCTCTGGATCCACTGCTTAAATACGGACGAGG ACAGGGCCCTGTCTCCTCAGCTTCAGGCACCACCACTGAC CTGGGACAGTGAATCGCCAC | Proto1 |
| 65 | TGATGCGGTTTTGGCAGTACATCAATGGGCGTGGATAGCG GTTTGACTCACGGGGATTTCCAAGTCTCCACCCCATTGAC GTCAATGGGAGTTTGTTTTGGCACCAAAATCAACGGGACT TTCCAAAATGTCGTAACAACTCCGCCCCATTGACGCAAAT GGGCGGTAGGCGTGTACGGTGGGAGGTCTATATAAGCAG AGCT | minCMV |
| 66 | GTTTGCTGCTTGCAATGTTTGCCCATTTTAGGGTGGACACA GGACGCTGTGGTTTCTGAGCCAGGGGGCGACTCAGATCCC AGCCAGTGGACTTAGCCCCTGTTTGCTCCTCCGATAACTG GGGTGACCTTGGTTAATATTCACCAGCAGCCTCCCCCGTT GCCCCTCTGGATCCACTGCTTAAATACGGACGAGGACAGG GCCCTGTCTCCTCAGCTTCAGGCACCACCACTGACCTGGG ACAGTGAATC | UCL-HLP |
| 67 | CGTTACATAACTTACGGTAAATGGCCCGCCTGGCTGACCG CCCAACGACCCCCGCCCATTGACGTCAATAATGACGTATG TTCCCATAGTAACGCCAATAGGGACTTTCCATTGACGTCA ATGGGTGGAGTATTTACGGTAAACTGCCCACTTGGCAGTA CATCAAGTGTATCATATGCCAAGTACGCCCCCTATTGACG TCAATGACGGTAAATGGCCCGCCTGGCATTATGCCCAGTA CATGACCTTATGGGACTTTCCTACTTGGCAGTACATCTACG TATTAGTCATCGCTATTACCATG | CMVe |
| 68 | GTTACATAACTTACGGTAAATGGCCCGCCTGGCTGACCGC CCAACGACCCCCGCCCATTGACGTCAATAATGACGTATGT TCCCATAGTAACGCCAATAGGGACTTTCCATTGACGTCAA TGGGTGGAGTATTTACGGTAAACTGCCCACTTGGCAGTAC ATCAAGTGTATCATATGCCAAGTACGCCCCCTATTGACGT CAATGACGGTAAATGGCCCGCCTGGCATTATGCCCAGTAC ATGACCTTATGGGACTTTCCTACTTGGCAGTACATCTACGT ATTAGTCATCGCTATTACCATGGGTCGAGGTGAGCCCCAC GTTCTGCTTCACTCTCCCCATCTCCCCCCCCTCCCCACCCC CAATTTTGTATTTATTTATTTTTTAATTATTTTGTGCAGCGA TGGGGGCGGGGGGGGGGGGGGCGCGCGCCAGGCGGGGC GGGGCGGGGCGAGGGGCGGGGCGGGGCGAGGCGGAGAG GTGCGGCGGCAGCCAATCAGAGCGGCGCGCTCCGAAAGT TTCCTTTTATGGCGAGGCGGCGGCGGCGGCGGCCCTATAA AAAGCGAAGCGCGCGGCGGGCGGGAGTCGCTGCGTTGCC TTCGCCCCGTGCCCCGCTCCGCGCCGCCTCGCGCCGCCCG CCCCGGCTCTGACTGACCGCGTTACTCCCACAGGTGAGCG GGCGGGACGGCCCTTCTCCTCCGGGCTGTAATTAGCGCTT GGTTTAATGACGGCTCGTTTCTTTTCTGTGGCTGCGTGAAA GCCTTAAAGGGCTCCGGGAGGGCCCTTTGTGCGGGGGGG AGCGGCTCGGGGGGTGCGTGCGTGTGTGTGTGCGTGGGGA GCGCCGCGTGCGGCCCGCGCTGCCCGGCGGCTGTGAGCGC | CAG |

TABLE 4-continued

Additional nucleic acid sequences disclosed herein

| SEQ ID NO: | Nucleic Acid Sequence | Source/Genomic Location |
|---|---|---|
| | TGCGGGCGCGGCGCGGGGCTTTGTGCGCTCCGCGTGTGCG CGAGGGGAGCGCGGCCGGGGGCGGTGCCCCGCGGTGCGG GGGGGCTGCGAGGGGAACAAAGGCTGCGTGCGGGGTGTG TGCGTGGGGGGGTGAGCAGGGGGTGTGGGCGCGGCGGTC GGGCTGTAACCCCCCCCTGCACCCCCCTCCCCGAGTTGCT GAGCACGGCCCGGCTTCGGGTGCGGGGCTCCGTGCGGGG CGTGGCGCGGGGCTCGCCGTGCCGGGCGGGGGGTGGCGG CAGGTGGGGGTGCCGGGCGGGGCGGGGCCGCCTCGGGCC GGGGAGGGCTCGGGGGAGGGGCGCGGCGGCCCCGGAGCG CCGGCGGCTGTCGAGGCGCGGCGAGCCGCAGCCATTGCCT TTTATGGTAATCGTGCGAGAGGGCGCAGGGACTTCCTTTG TCCCAAATCTGGCGGAGCCGAAATCTGGGAGGCGCCGCC GCACCCCCTCTAGCGGGCGCGGGCGAAGCGGTGCGGCGC CGGCAGGAAGGAAATGGGCGGGGAGGGCCTTCGTGCGTC GCCGCGCCGCCGTCCCCTTCTCCATCTCCAGCCTCGGGGCT GCCGCAGGGGGACGGCTGCCTTCGGGGGGGACGGGGCAG GGCGGGGTTCGGCTTCTGGCGTGTGACCGGCGGCTCTAGA GCCTCTGCTAACCATGTTCATGCCTTCTTCTTTTTCCTACA GCTCCTGGGCAACGTGCTGGTTGTTGTGCTGTCTCATCATT TTGGCAAAGAATT | |
| 69 | GCTCCGGTGCCCGTCAGTGGGCAGAGCGCACATCGCCCAC AGTCCCCGAGAAGTTGGGGGGAGGGGTCGGCAATTGAAC CGGTGCCTAGAGAAGGTGGCGCGGGGTAAACTGGGAAAG TGATGTCGTGTACTGGCTCCGCCTTTTTCCCGAGGGTGGG GGAGAACCGTATATAAGTGCAGTAGTCGCCGTGAACGTTC TTTTTCGCAACGGGTTTGCCGCCAGAACACAGG | EFS |
| 100 | GAGTGGGTAAGTGTGAAAAATCTGCATGTGTGGCTGAAG ATGGGCACAGACACGGTCAAGTCTGTATGTGAGAGTGCTG AACTGGGGTTCTGTGTGAAAATCTGCCTGAGGCGGCAGGG AGAATCACTGCCATTGCGTGAGCAGGTTGGATGTTGGCCA CTCTATCAGGAGCATTAGGGAAGGGGTGGGGACTCCAGA CGTGTCCCCAAACCAGGGTGGCCTCAAGACCTTGGGAGAA CACTTGTCTGAAGACTTGGGGAACAGAAGGAGACCAGGC ATGGCACTTATGCAGACTGAGGCCAGGACAGAATTTCCTG ACAAAAGAAAACTGAGCCATGGAGATGGACAACAGATCC CTTCCCTGGGCACCATACTGCAGCTTTTAGTCCCTAGCACT GGGGGCTCCAGTACTAACAGCAGGAAGATGCTCCCAGCCT GGGACTGTGTGAGGGAGGTCAGAATGGGAAGGAGAGGCT GGGGAACAGGGGAGGAAAGCCCATGGTTGGGAGGCGGAG GACAGGCATTTGGCCTGCAGGAGAAGGTGACCCTCACCCA TGTTTTCAGTTCACCCTTCGGGTTAAAAATAACTGAGGTA AGGGCCATGGCAGGGTGGGAGAGGCGGTGTGAGAAGGTC CTGTCTTCCCACTATCTGCTCATCAGCCCTTTGAAGGGGAG GAATGTGCCCAAGGACTAAAAAAAGGCCGTGGAGCCAGA GAGGCTGGGGCAGCAGACCTTTCTTGGGCAAATCAGGGG GCCCTGCTGTCCTCCTGTCACCTCCAGAGCCAAAGGATCA AAGGAGGAGGAGCCAGGAGGGGAGAGAGGTGGGAGGGA GGGTCCCTCCGGAAGGACTCCAAATTTAGACAGAGGGTG GGGGAAACGGGATATAAAGGAACTGGAGCTTTGAGGACA GATAGAGAGACTCCTGCGGCCCAGGTAAGAGGAGGTTTG GGGT | Myh6 |
| 101 | AGCAGTCTGGGCTTTCACATGACAGCATCTGGGGCTGCGG CAGAGGGTCGGGTCCGAAGCGCTGCCTTATCAGCGTCCCC AGCCCTGGGAGGTGACAGCTGGCTGGCTTGTGTCAGCCCC TCGGGCACTCACGTATCTCCATCCGACGGGTTTAAAATAG CAAAACTCTGAGGCCACACAATAGCTTGGGCTTATATGGG CTCCTGTGGGGGAAGGGGGAGCACGGAGGGGGCCGGGGC CGCTGCTGCCAAAATAGCAGCTCACAAGTGTTGCATTCCT CTCTGGGCGCCGGGCACATTCCTGCTGGCTCTGCCCGCCC CGGGGTGGGCGCCGGGGGGACCTTAAAGCCTCTGCCCCCC AAGGAGCCCTTCCCAGACAGCCGCCGGCACCCACCGCTCC GTGGGAC | cTnT |

INCORPORATION BY REFERENCE

All publications, patents, and patent applications mentioned in this specification are herein incorporated by reference to the same extent as if each individual publication, patent, or patent application was specifically and individually indicated to be incorporated by reference.

What is claimed is:

1. A nucleic acid construct comprising a nucleotide sequence encoding a lamin A polypeptide and a lamin C polypeptide, wherein said construct comprises introns 8-11 of the wildtype human LMNA gene and lacks introns 1-7 of the wildtype-human LMNA gene, wherein the lamin A polypeptide comprises an amino acid sequence that is at least 95% identical to the amino acid sequence of SEQ ID NO: 12 or SEQ ID NO: 21, and wherein said lamin C polypeptide comprises an amino acid sequence that is at least 95% identical to the amino acid sequence of SEQ ID NO: 13.

2. The nucleic acid construct of claim 1, wherein intron 8 comprises a nucleotide sequence that is at least 95% identical to the nucleotide sequence of SEQ ID NO: 77.

3. The nucleic acid construct of claim 1, wherein intron 11 comprises a nucleotide sequence that is at least 95% identical to the nucleotide sequence of SEQ ID NO: 80.

4. The nucleic acid construct of claim 1, wherein the nucleic acid construct further comprises a regulatory element and wherein the regulatory element has less than or equal to 800 base pairs (bp), 700 bp, 600 bp, 500 bp, 400 bp, 300 bp, 250 bp, 200 bp, 150 bp, 140 bp, 130 bp, 120 bp, 110 bp, 100 bp, 70 bp, or 50 bp.

5. The nucleic acid construct of claim 1, wherein the regulatory element comprises any one of or a combination of: any one of SEQ ID NOs: 30-58, SEQ ID NO: 102, a cytomegalovirus (CMV) promoter, a chicken β-actin (CBA) promoter, a CMV enhancer used upstream of a CBA promoter, a super core promoter (SCP) promoter, a SerpE TTR promoter, a Protol promoter, a minimal CMV (minCMV) promoter, a University College London hybrid liver-specific promoter (UCL-HLP) promoter, a CMV enhancer (CMVe), a CMV early enhancer/CBA (CAG) promoter, a Myh6 promoter, a Desmin promoter, a cardiac troponin T (cTNT) promoter, an alpha-myosin heavy chain (a-MHC) promoter, a myosin light chain 2 (MLC-2) promoter, and an EF1α short (EFS) promoter.

6. The nucleic acid construct of claim 5, wherein the regulatory element is cell-type selective.

7. The nucleic acid construct of claim 6, wherein the regulatory element is selectively expressed in cardiomyocytes.

8. The nucleic acid construct of claim 7, wherein the regulatory element is any one of or combination of: the Myh6 promoter, the Desmin promoter, the cTNT promoter, the α-MHC promoter, or the MLC-2 promoter.

9. The nucleic acid construct of claim 6, wherein the regulatory element is the cTNT promoter.

10. The nucleic acid construct of claim 9, wherein the cTNT promoter comprises SEQ ID NO: 101.

11. The nucleic acid construct of claim 1, wherein the nucleic acid construct comprises a nucleotide sequence that is at least 95% identical to the nucleotide sequence of SEQ ID NO: 3 or SEQ ID NO: 8.

12. The nucleic acid construct of claim 1, wherein the lamin A polypeptide comprises SEQ ID NO: 12 or SEQ ID NO: 21 and the lamin C polypeptide comprises SEQ ID NO: 13.

13. The nucleic acid construct of claim 1, wherein the nucleic acid construct comprises SEQ ID NO: 3 or SEQ ID NO: 8.

14. The nucleic acid construct of claim 1, wherein the nucleotide sequence further comprises a polyadenylation signal.

15. A viral vector comprising the nucleic acid construct of claim 1.

16. The viral vector of claim 15, wherein the viral vector is an adeno-associated virus (AAV) vector.

17. The viral vector of claim 16, wherein the AAV vector is AAV1, AAV2, AAV5, AAV6, AAV8, AAV9, scAAV1, scAAV2, scAAV5, scAAV6, scAAV8, or scAAV9.

18. The viral vector of claim 16, wherein the nucleotide sequence further comprises a 5' AAV inverted terminal repeat (ITR) sequence and a 3' AAV ITR sequence.

19. A viral particle comprising the viral vector of claim 15.

20. The viral particle of claim 19, wherein the viral particle comprises capsid proteins of an AAV.

21. The viral particle of claim 20, wherein the AAV is an AAV6 or AAV9.

22. A host cell comprising one of the following: the nucleic acid construct of claim 1, or the viral vector of claim 15, 16, 17 or 18, or the viral particle of claim 19, 20 or 21.

23. A pharmaceutical composition comprising one or more pharmaceutically acceptable excipients, and one of the following: the nucleic acid construct of claim 1, or the viral vector of claim 15, 16, 17 or 18, or the viral particle of claim 19, 20 or 21.

24. A method for treating a laminopathy in a subject comprising administering a therapeutically effective amount of the pharmaceutical composition of claim 23 to a subject in need thereof.

25. The method of claim 24, wherein the laminopathy is any one or more of: Charcot-Marie-Tooth disease, Emery-Dreifuss muscular dystrophy, familial partial lipodystrophy, Hutchinson-Gilford progeria syndrome, limb-girdle muscular dystrophy, LMNA-related congenital muscular dystrophy, mandibuloacral dysplasia, arrhythmogenic right ventricular cardiomyopathy, familial atrial fibrillation, left ventricular noncompaction, or dilated cardiomyopathy.

26. The method of claim 24, wherein said pharmaceutical composition is administered intramyocardially, intravenously, intramuscularly, intrathecally, subcutaneously, systemically, or locally into the myocardium.

27. A method for expressing a lamin A polypeptide and a lamin C polypeptide in a subject comprising administering to said subject a therapeutically effective amount of one of the following: the nucleic acid construct of claim 1, or the viral vector of claim 15, 16, 17 or 18, or the viral particle of claim 19, 20 or 21.

28. A method for increasing expression of a functional lamin A polypeptide and a functional lamin C polypeptide in a subject comprising administering to said subject a therapeutically effective amount of one of the following: the nucleic acid construct of claim 1, or the viral vector of claim 15, 16, 17 or 18, or the viral particle of claim 19, 20 or 21.

29. The method of claim 28, wherein the subject is suffering from a laminopathy.

* * * * *